United States Patent
Stockwell et al.

(10) Patent No.: US 9,695,133 B2
(45) Date of Patent: Jul. 4, 2017

(54) QUINAZOLINONE-BASED ONCOGENIC-RAS-SELECTIVE LETHAL COMPOUNDS AND THEIR USE

(71) Applicant: THE TRUSTEES OF COLUMBIA UNIVERSITY IN THE CITY OF NEW YORK, New York, NY (US)

(72) Inventors: Brent R Stockwell, New York, NY (US); Matthew Welsch, New York, NY (US); Wan Seok Yang, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/414,669

(22) PCT Filed: Jul. 12, 2013

(86) PCT No.: PCT/US2013/050244
§ 371 (c)(1),
(2) Date: Jan. 13, 2015

(87) PCT Pub. No.: WO2014/011973
PCT Pub. Date: Jan. 16, 2014

(65) Prior Publication Data
US 2015/0175558 A1 Jun. 25, 2015

Related U.S. Application Data

(60) Provisional application No. 61/671,602, filed on Jul. 13, 2012.

(51) Int. Cl.
*C07D 239/91* (2006.01)
*C07D 403/06* (2006.01)
*C07D 213/61* (2006.01)

(52) U.S. Cl.
CPC ......... *C07D 239/91* (2013.01); *C07D 213/61* (2013.01); *C07D 403/06* (2013.01)

(58) Field of Classification Search
CPC .................................................. C07D 403/02
See application file for complete search history.

(56) References Cited

U.S. PATENT DOCUMENTS

2006/0211683 A1* 9/2006 Selliah ................. A61K 31/495
514/218
2011/0288052 A1 11/2011 Townsend et al.

OTHER PUBLICATIONS

Vippagunta et al. (2001).*
McMahon et al. (2000).*
Pinedo et al (2000).*
Babij, C. et al. STK33 kinase activity is nonessential in KRAS-dependent cancer cells. *Cancer Res* 71, 5818-5826(2011).
Barbie, D. A. et al. Systematic RNA interference reveals that oncogenic KRAS-driven cancers require TBK1. *Nature* 462, 108-112(2009).
Boden, S. E., Bertsche, T., Ammon, H. P. & Safayhi, H. MEK-1/2 inhibition prevents 5-lipoxygenase translocation in N-formylpeptide-challenged human neutrophils. *Int J Biochem Cell Biol* 32, 1069-1074 (2000).
Chen, B. K., Liu, Y. W., Yamamoto, S. & Chang, W. C. Overexpression of Ha-ras enhances the transcription of human arachidonate 12-lipoxygenase promoter in A431 cells. *Biochim Biophys Acta* 1344, 270-277 (1997).
Chen, X. S. & Funk, C. D. The N-terminal "beta-barrel" domain of 5-lipoxygenase is essential for nuclear membrane translocation. *J Biol Chem* 276, 811-818(2001).
Chuang, J. I., Chang, T. Y. & Liu, H. S. Glutathione depletion-induced apoptosis of Ha-ras-transformed NIH3T3 cells can be prevented by melatonin. *Oncogene* 22, 1349-1357(2003).
Colles, S. M. & Chisolm, G. M. Lysophosphatidylcholine-induced cellular injury in cultured fibroblasts involves oxidative events. *J Lipid Res* 41, 1188-1198 (2000).
Dixon, S. J., Costanzo, M., Baryshnikova, A., Andrews, B. & Boone, C. Systematic mapping of genetic interaction networks. *Annu Rev Genet* 43, 601-625 (2009).
Dixon, Scott J. et al. Ferroptosis: An Iron-Dependent Form of Nonapoptotic Cell Death. *Cell* 149, 1060-1072 (2012).
Dolma, S., Lessnick, S. L., Hahn, W. C. & Stockwell, B. R. Identification of genotype-selective antitumor agents using synthetic lethal chemical screening in engineered human tumor cells. *Cancer Cell* 3, 285-296 (2003).

(Continued)

*Primary Examiner* — Paul V Ward
(74) *Attorney, Agent, or Firm* — Bryan Cave LLP

(57) ABSTRACT

The present invention provides, inter alia, compounds having the structure (1) compositions containing such compounds are also provided. Methods for using such compounds or compositions for treating or ameliorating the effects of a cancer having a cell that harbors an oncogenic RAS mutation, for modulating a lipoxygenase in a ferroptosis cell death pathway, and for depleting reduced glutathione (GSH) in a cell harboring an oncogenic RAS mutation are further provided.

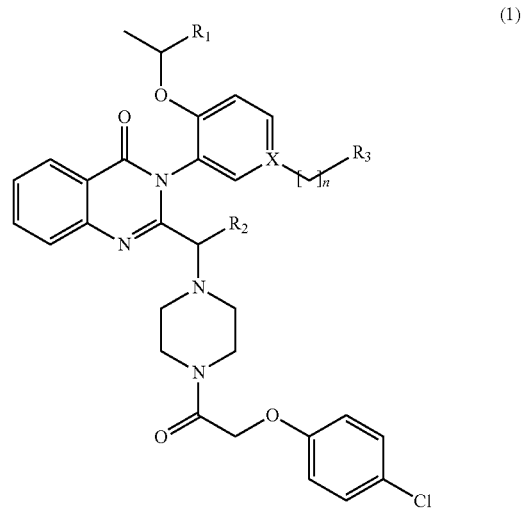

(1)

28 Claims, 62 Drawing Sheets
(47 of 62 Drawing Sheet(s) Filed in Color)

(56) References Cited

OTHER PUBLICATIONS

Downward, J. Targeting RAS signalling pathways in cancer therapy. *Nat Rev Cancer* 3, 11-22 (2003).

Fanelus, I. & Desrosiers, R. R. Reactive oxygen species generated by thiol-modifying phenylarsine oxide stimulate the expression of protein L-isoaspartyl methyltransferase. *Biochem Biophys Res Commun* 371, 203-208 (2008).

Haeggstrom, J. Z. & Funk, C. D. Lipoxygenase and leukotriene pathways: biochemistry, biology, and roles in disease. *Chemical reviews* 111, 5866-5898 (2011).

Hartwell, L. H., Szankasi, P., Roberts, C. J., Murray, A. W. & Friend, S. H. Integrating genetic approaches into the discovery of anticancer drugs. *Science* 278, 1064-1068 (1997).

Hussain, S. P., Hofseth, L. J. & Harris, C. C. Radical causes of cancer. *Nat Rev Cancer* 3, 276-285 (2003).

Imai, H. & Nakagawa, Y. Biological significance of phospholipid hydroperoxide glutathione peroxidase (PHGPx, GPx4) in mammalian cells. *Free Radic Biol Med* 34, 145-169 (2003).

International Search Report for PCT/US2013/050244, mailed Dec. 9, 2013.

Irani, K. et al. Mitogenic signaling mediated by oxidants in Ras-transformed fibroblasts. *Science* 275, 1649-1652 (1997).

Ji, Z. et al. Chemical genetic screening of KRAS-based synthetic lethal inhibitors for pancreatic cancer. *Frontiers in bioscience : a journal and virtual library* 14, 2904-2910 (2009).

Kaelin, W. G., Jr. The concept of synthetic lethality in the context of anticancer therapy. *Nat Rev Cancer* 5, 689-698 (2005).

Kamphorst, J. J., Fan, J., Lu, W., White, E. & Rabinowitz, J. D. Liquid chromatography-high resolution mass spectrometry analysis of fatty acid metabolism. *Analytical chemistry* 83, 9114-9122 (2011).

Kang, Y. J. & Enger, M. D. Buthionine sulfoximine-induced cytostasis does not correlate with glutathione depletion. *Am J Physiol* 262, C122-127 (1992).

Kumar, M. S. et al. The GATA2 Transcriptional Network is Requisite for RAS Oncogene-Driven Non-Small Cell Lung Cancer. *Cell* 149, 642-655 (2012).

Lebeau, A., Terro, F., Rostene, W. & Pelaprat, D. Blockade of 12-lipoxygenase expression protects cortical neurons from apoptosis induced by beta-amyloid peptide. *Cell Death Differ* 11, 875-884 (2004).

Li, Y., Maher, P. & Schubert, D. A role for 12-lipoxygenase in nerve cell death caused by glutathione depletion. *Neuron* 19, 453-463 (1997).

Luo, J. et al. A genome-wide RNAi screen identifies multiple synthetic lethal interactions with the Ras oncogene. *Cell* 137, 835-848 (2009).

Luo, T. et al. STK33 kinase inhibitor BRD-8899 has no effect on KRAS-dependent cancer cell viability. *Proc Natl Acad Sci U S A* 109, 2860-2865 (2012).

Malumbres, M. & Barbacid, M. RAS oncogenes: the first 30 years. *Nat Rev Cancer* 3, 459-465 (2003).

McGarry, S. J. & Williams, A. J. Digoxin activates sarcoplasmic reticulum Ca(2+)-release channels: a possible role in cardiac inotropy. *Br J Pharmacol* 108, 1043-1050 (1993).

Patel, N. S. et al. Reduction of renal ischemia-reperfusion injury in 5-lipoxygenase knockout mice and by the 5-lipoxygenase inhibitor zileuton. *Mol Pharmacol* 66, 220-227 (2004).

Price, B. D., et al. Stimulation of phosphatidylcholine hydrolysis, diacylglycerol release, and arachidonic acid production by oncogenic ras is a consequence of protein kinase C activation. *J Biol Chem* 264, 16638-16643 (1989).

Ran, Q. et al. Embryonic fibroblasts from Gpx4+/− mice: a novel model for studying the role of membrane peroxidation in biological processes. *Free Radic Biol Med* 35, 1101-1109 (2003).

Root, D. E., Flaherty, S. P., Kelley, B. P. & Stockwell, B. R. Biological mechanism profiling using an annotated compound library. *Chemistry & biology* 10, 881-892 (2003).

Scholl, C. et al. Synthetic lethal interaction between oncogenic KRAS dependency and STK33 suppression in human cancer cells. *Cell* 137, 821-834 (2009).

Seiler, A. et al. Glutathione peroxidase 4 senses and translates oxidative stress into 12/15-lipoxygenase dependent- and AIF-mediated cell death. *Cell Metab* 8, 237-248 (2008).

Shaw, A. T. et al. Selective killing of K-ras mutant cancer cells by small molecule inducers of oxidative stress. *Proc Natl Acad Sci U S A* 108, 8773-8778 (2011).

Shornick, L. P. & Holtzman, M. J. A cryptic, microsomal-type arachidonate 12-lipoxygenase is tonically inactivated by oxidation-reduction conditions in cultured epithelial cells. *J Biol Chem* 268, 371-376 (1993).

Szatrowski, T. P. & Nathan, C. F. Production of large amounts of hydrogen peroxide by human tumor cells. *Cancer Res* 51, 794-798 (1991).

Trachootham, D. et al. Selective killing of oncogenically transformed cells through a ROS-mediated mechanism by beta-phenylethyl isothiocyanate. *Cancer Cell* 10, 241-252 (2006).

Wang, B., et al. An inhibitor of arachidonate 5-lipoxygenase, Nordy, induces differentiation and inhibits self-renewal of glioma stem-like cells. *Stem Cell Rev.* Jun.;7(2):458-70 (2011).

Weiss, W. A. Taylor, S. S. & Shokat, K. M. Recognizing and exploiting differences between RNAi and small-molecule inhibitors. *Nat Chem Biol* 3, 739-744 (2007).

Weiwer, M. et al. Development of small-molecule probes that selectively kill cells induced to express mutant RAS. *Bioorg Med Chem Lett* 22, 1822-1826 (2012).

Wolpaw, A. J. et al. Modulatory profiling identifies mechanisms of small molecule-induced cell death. *Proc Natl Acad Sci U S A* 108, E771-780 (2011).

Written Opinion of the Searching Authority for PCT/US2013/050244, mailed Dec. 9, 2013.

Yagoda, N. et al. RAS-RAF-MEK-dependent oxidative cell death involving voltage-dependent anion channels. *Nature* 447, 864-868 (2007).

Yang, W. S. & Stockwell, B. R. Synthetic Lethal Screening Identifies Compounds Activating Iron-Dependent, Nonapoptotic Cell Death in Oncogenic-RAS-Harboring Cancer Cells. *Chemistry & biology* 15, 234-245 (2008a).

Yang, W. S. & Stockwell, B. R. Inhibition of casein kinase 1-epsilon induces cancer-cell-selective, PERIOD2-dependent growth arrest. *Genome biology* 9, R92 (2008b).

Yang, W. S. et al. Identification of Simple Compounds with Microtubule-Binding Activity That Inhibit Cancer Cell Growth with High Potency. *ACS Med Chem Lett* 3, 35-38 (2012).

Yu, Z., Schneider, C., Boeglin, W. E., Marnett, L. J. & Brash, A. R. The lipoxygenase gene ALOXE3 implicated in skin differentiation encodes a hydroperoxide isomerase. *Proc Natl Acad Sci U S A* 100, 9162-9167 (2003).

* cited by examiner e

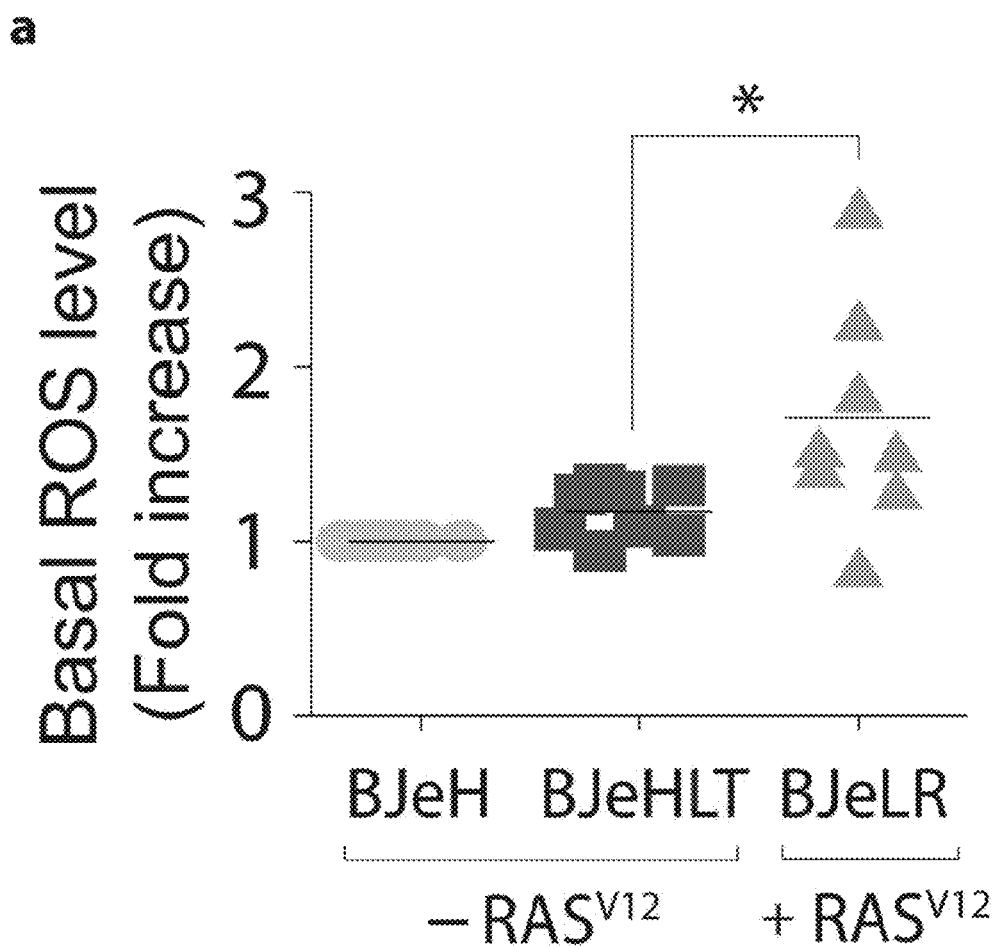

b

GFP-ALOX5 location: [RSL3] = 0.4 µM e d

PE (piperazine erastin)

| Abbreviation | Full name | Mechanism | Concentration (μM) | Incubation time (hour) |
|---|---|---|---|---|
| 9-AA | 9-Aminoacridine | DNA intercalating agent | 51.5 | 12 |
| CAN | Cantharidin | Protein phosphatase inhibitor | 51 | 30 |
| CAM | Camptothecin | Topoisomerase I inhibitor | 28.7 | 24 |
| COL | Colchicine | Microtubule depolymerizing agent | 2.5 | 30 |
| CCD | Cytochalasin D | Binds to actin and inhibits cytoskeletal function | 2 | 12 |
| DIG | Digoxin | Inhibits Na/K ATPase pump | 12.8 | 24 |
| ECH | Echinomycin | DNA intercalating agent | 0.9 | 30 |
| EMT | Emetine | Inhibits protein synthesis | 1.8 | 24 |
| ETO | Etoposide | Topoisomerase II inhibitor | 68 | 24 |
| PAO | Phenylarsine oxide | Metabolic poison, protein phosphatase inhibitor | 6 | 30 |
| STS | Staurosporine | Protein kinase inhibitor | 1 | 12 | b

| Abbreviation | Full name | Concentration (µM) | Incubation time (day) |
|---|---|---|---|
| DPI2 | - | 40 | 1 |
| DPI6 | - | 12 | 0.5 |
| DPI7 | - | 0.2 | 0.5 |
| DPI9 | - | 2.2 | 0.5 |
| DPI10 | - | 10 | 1 |
| DPI12 | - | 3.3 | 0.5 |
| DPI13 | - | 13.9 | 0.5 |
| DPI17 | - | 2 | 0.5 |
| DPI18 | - | 3.6 | 0.5 |
| DPI19 | - | 3.5 | 0.5 |
| IONO | Ionomycin | 10 | 0.5 |
| STS | Staurosporine | 1 | 0.5 |
| 9-AA | 9-aminoacridine | 25.75 | 1 |
| CAN | Cantharidin | 25.5 | 1 |
| CAM | Camptothecin | 14.35 | 2 |
| COL | Colchicine | 0.5 | 1 |
| CCD | Cytochalasin D | 0.8 | 1 |
| DIG | Digoxin | 1.28 | 1 |
| ECH | Echinomycin | 0.09 | 1 |
| EMT | Emetine | 0.72 | 1 |
| ETO | Etoposide | 68 | 2 |
| PAO | Phenylarsine oxide | 0.6 | 1 | c a b a b

| Property | Metric | Erastin | PE |
|---|---|---|---|
| Potency | GI₅₀ in BJeLR | 1.8 μM | 0.9 μM |
| Selectivity | GI₅₀ in BJeLR/GI₅₀ in BJeH | 7.2 | 7.3 |
| Stability | T₁/₂ in mouse liver microsome | < 15 min | > 45 min |
| Solubility | Water solubility | 86 μM | 1400 μM | c

Mice Blank Plasma

Blank Plasma Spiked by IS (Tolbutamide)

Plasma Sample from animal 108-1 Hour Following Intravenous and Oral Administration g h Y = 0.000951x+0.00065 (correlation coefficient = 0.9966)

Blank Brain Spiked by IS (Tolbutamide)

Brain Sample from animal 104-0.5 Hours Following Intravenous and Oral Administration g h Y = 0.000202x + 0.000483(correlation coefficient = 0.9942)

QUINAZOLINONE-BASED ONCOGENIC-RAS-SELECTIVE LETHAL COMPOUNDS AND THEIR USE

CROSS-REFERENCE TO RELATED APPLICATIONS

This application is a U.S. National Stage Application of International Application No. PCT/US2013/050244, which was filed on Jul. 12, 2013, and which claims priority to U.S. Provisional Patent Application No. 61/671,602, which was filed on Jul. 13, 2012, which applications are incorporated by reference in their entireties as if recited in full herein.

GOVERNMENT FUNDING

This invention was made with government support under grant no. R01CA097061 awarded by the National Institutes of Health. The government has certain rights in the invention.

FIELD OF INVENTION

The present invention provides, inter alia, quinazolinone-based oncogenic-RAS-selective lethal compounds and compositions containing such compounds. Methods for using such compounds or compositions are also provided.

BACKGROUND OF THE INVENTION

Synthetic lethality describes a genetic interaction in which simultaneous mutations in two genes lead to synergistic cell death compared to individual mutations in the same genes (Kaelin, 2005; Yang et al., 2008a). The concept of synthetic lethality was originally used to study the buffering capacity of cells and organisms upon genetic variations, through which many gene-gene interactions have been discovered in multiple organisms, including bacteria, yeasts, and nematodes (Dixon et al., 2009; Malumbres, 2003). Soon after, it was recognized that this concept can be used as a framework for discovering anti-cancer drug leads with high therapeutic indices (Kaelin, 2005; Hartwell, 1997): one can search for small molecules that are only lethal in the presence of a specific oncogenic mutation.

Oncogenic RAS proteins have been targeted using this synthetic lethal screening approach, due to the widespread importance of mutant RAS proteins in the genesis and maintenance of human cancers (Malumbres et al., 2003), as well as the challenge of targeting oncogenic RAS proteins directly (Downward, 2003). Several synthetic lethal screens using RNA-interference-based (RNAi) libraries reported genes with synthetic lethal relationships with KRAS, such as PLK1 (Luo et al., 2009), TBK1 (Barbie et al., 2009), STK33 (Scholl et al., 2009), and GATA2 (Kumar et al., 2012). Some of these results may require further verification, because some follow-up studies did not support the originally postulated roles (Babij et al., 2011; Luo et al., 2012). The mechanism of synthetic lethality was attributed to increased dependence on mitotic function, NF-κB signaling, S6 kinase activity, and the GATA2 transcriptional network, respectively. The specific death-initiating mechanisms were different in these cases; however, cancer cells with oncogenic RAS mutations invariably died via apoptosis upon treatment with these RNAi reagents.

A different approach to targeting oncogenic RAS uses synthetic lethal screening with small molecules. Several RAS-synthetic-lethal (RSL) compounds were identified using this strategy (Yang et al., 2009; Yagoda et al., 2007; Weiwer et al., 2012; Shaw et al., 2011; Ji et al., 2009). The lethality of these RSL compounds, such as erastin and RSL3, was significantly enhanced upon activation of RAS-RAF-MEK signaling. In contrast to the results of RNAi screens, the small molecule approach yielded compounds that induced a distinct form of oxidative, non-apoptotic cell death. This mode of cell death was distinct from necrosis, and is a regulated form of oxidative cell death termed ferroptosis due to its unique morphology, inhibitor sensitivity and strict dependency on iron (Dixon et al., 2012). Thus, ferroptosis may be an efficient means of inducing synthetic lethality with small molecules in tumor cells harboring oncogenic RAS proteins. Defining the molecular pathways governing ferroptosis could aid in targeting RAS mutant tumors.

To define the core effectors of ferroptosis, erastin and RSL3 were further investigated, because both of these RSL compounds induce ferroptotic cell death via different triggering mechanisms. Erastin binds to VDAC2/3 (Yagoda et al., 2007), and inhibits system xc- (Dixon et al., 2012) to induce ferroptotic cell death. In contrast, RSL3 is not dependent on these proteins (Yang et al., 2008a), and its target has not been reported. Metabolomic profiling was used to evaluate comprehensively changes in metabolism upon erastin treatment, and it was found that a common lipoxygenase-mediated pathway executing ferroptotic cell death in response to RSL compounds.

RAS genes are among the most commonly mutated in human cancers, but their protein products have remained intractable to therapeutic agents. Thus, there is a need for, inter alia, anti-cancer drugs with high therapeutic indices that selectively target tumor cells, such as those harboring oncogenic RAS mutations. The present invention is directed to meeting these and other needs.

SUMMARY OF THE INVENTION

One embodiment of the present invention is a compound that has the structure (1):

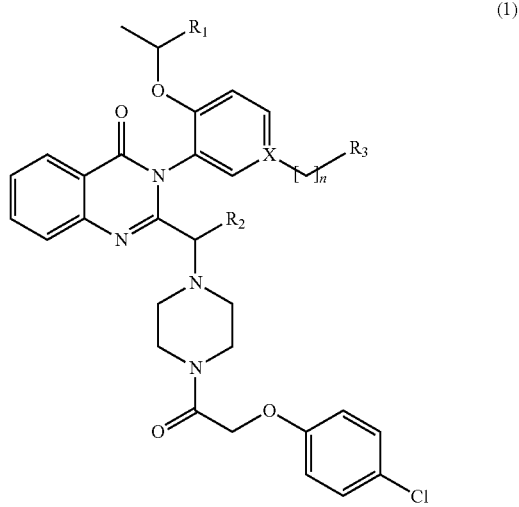

wherein $R_1$ is selected from the group consisting of H, $C_{1-4}$ alkyl, $C_{1-4}$ alkoxy, hydroxy, and halogen;

R₂ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;

R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, with the proviso that when X is C, n=0, and R₃ is nothing, R₁ cannot be H when R₂ is CH₃, or an N-oxide, crystalline form, hydrate, or pharmaceutically acceptable salt thereof.

Another embodiment of the present invention is a compound that has the structure (30):

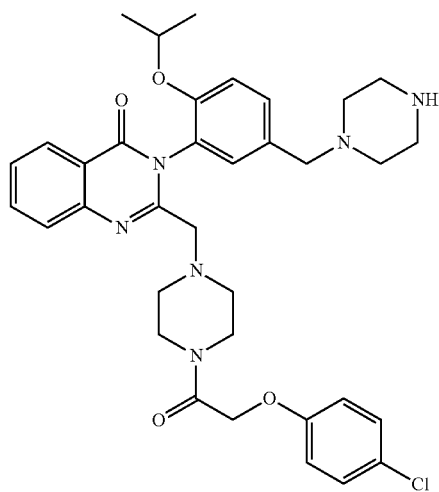
(30)

or an N-oxide, crystalline form, hydrate, or pharmaceutically acceptable salt thereof.

An additional embodiment of the present invention is a composition. This composition comprises a pharmaceutically acceptable carrier and a compound having the structure (1):

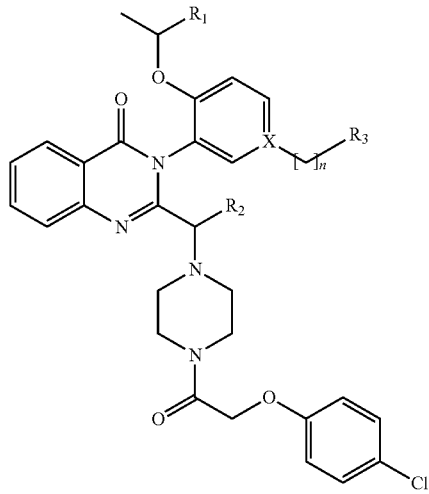
(1)

wherein

R₁ is selected from the group consisting of H, $C_{1-4}$ alkyl, $C_{1-4}$ alkoxy, hydroxy, and halogen;

R₂ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;

R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, with the proviso that when X is C, n=0, and R₃ is nothing, R₁ cannot be H when R₂ is CH₃, or an N-oxide, crystalline form, hydrate, or pharmaceutically acceptable salt thereof.

A further embodiment of the present invention is another composition. This composition comprises a pharmaceutically acceptable carrier and a compound having the structure (30):

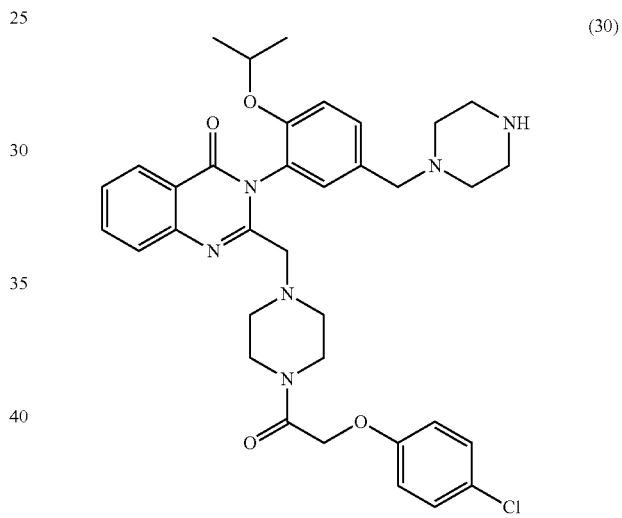
(30)

or an N-oxide, crystalline form, hydrate, or pharmaceutically acceptable salt thereof.

Another embodiment of the present invention is a method for treating or ameliorating the effects of a cancer comprising a cell that harbors an oncogenic RAS mutation. This method comprises administering to a subject in need thereof a therapeutically effective amount of any compound disclosed herein.

A further embodiment of the present invention is a method for treating or ameliorating the effects of a cancer comprising a cell that harbors an oncogenic RAS mutation. The method comprises administering to a subject in need thereof a therapeutically effective amount of any composition disclosed herein.

Another embodiment of the present invention is a method for treating or ameliorating the effects of a cancer comprising a cell that harbors an oncogenic RAS mutation. This method comprises administering to a subject in need thereof a therapeutically effective amount of a composition comprising a pharmaceutically acceptable carrier and a compound having the structure (30):

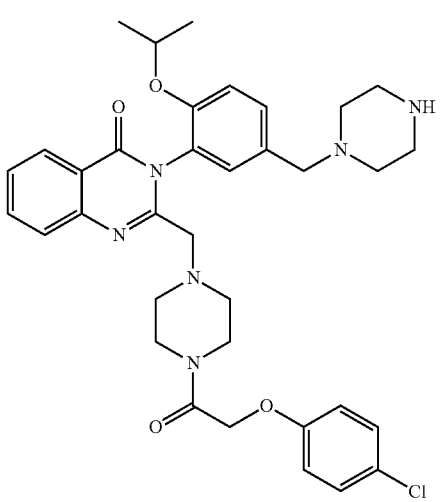

(30)

or an N-oxide, crystalline form, hydrate, or pharmaceutically acceptable salt thereof.

An additional embodiment of the present invention is a method for modulating a lipoxygenase in a ferroptosis cell death pathway. This method comprises administering to a cell an effective amount of a compound having the structure (1):

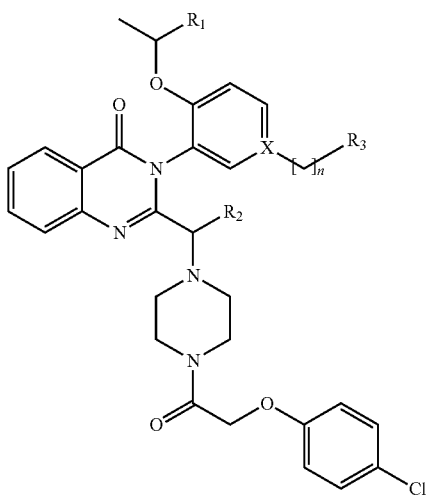

(1)

wherein $R_1$ is selected from the group consisting of H, $C_{1-4}$ alkyl, $C_{1-4}$ alkoxy, hydroxy, and halogen;

$R_2$ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;

$R_3$ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, with the proviso that when X is C, n=0, and $R_3$ is nothing, $R_1$ cannot be H when $R_2$ is $CH_3$, or an N-oxide, crystalline form, hydrate, or pharmaceutically acceptable salt thereof.

A further embodiment of the present invention is a method for depleting reduced glutathione (GSH) in a cell harboring an oncogenic RAS mutation comprising administering to the cell an effective amount of a compound having the structure (1):

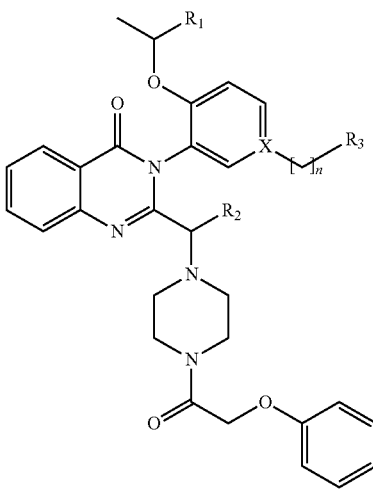

(1)

wherein $R_1$ is selected from the group consisting of H, $C_{1-4}$ alkyl, $C_{1-4}$ alkoxy, hydroxy, and halogen;

$R_2$ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;

$R_3$ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, with the proviso that when X is C, n=0, and $R_3$ is nothing, $R_1$ cannot be H when $R_2$ is $CH_3$, or an N-oxide, crystalline form, hydrate, or pharmaceutically acceptable salt thereof.

Another embodiment of the present invention is a compound having the structure (100):

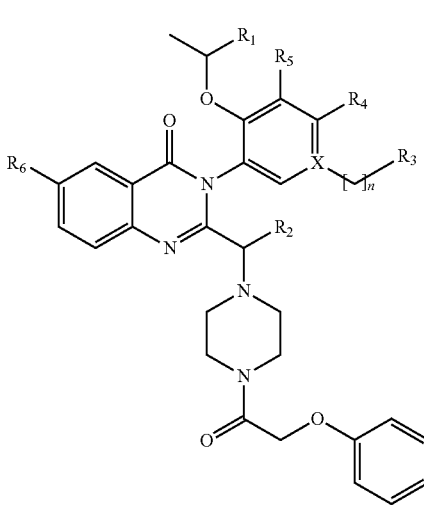

(100)

wherein
R₁ is selected from the group consisting of H, $C_{1-4}$ alkyl, $C_{1-4}$ alkoxy, hydroxy, and halogen;
R₂ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;
R₃ is selected from the group consisting of nothing, H, $C_{1-4}$ alkyl, $C_{1-4}$ alkoxy, carbonyl, $C_{3-8}$ cycloalkyl, and $C_{3-8}$ heterocycloalkyl;
R₄ and R₅ are independently selected from the group consisting of H, $C_{3-8}$ cycloalkyl, and $C_{3-8}$ heterocycloalkyl;
R₆ is selected from the group consisting of H, —NH₂, $C_{1-4}$ alkyl, $C_{1-4}$ alkoxy, carbonyl, aryl, heteraryl, $C_{3-8}$ cycloalkyl, and $C_{3-8}$ heterocycloalkyl;
X is selected from the group consisting of C, N, and O; and
n is an integer from 0-6,
with the proviso that when X is C, n=0, and R₃ is nothing, R₁ cannot be H when R₂ is CH₃,
or an N-oxide, crystalline form, hydrate, or pharmaceutically acceptable salt thereof.

An additional embodiment of the present invention is a composition. This composition comprises a pharmaceutically acceptable carrier and any compound disclosed herein.

Another embodiment of the present invention is a method for treating or ameliorating the effects of a cancer comprising a cell that harbors an oncogenic RAS mutation. This method comprises administering to a subject in need thereof a therapeutically effective amount of a compound selected from the group consisting of:

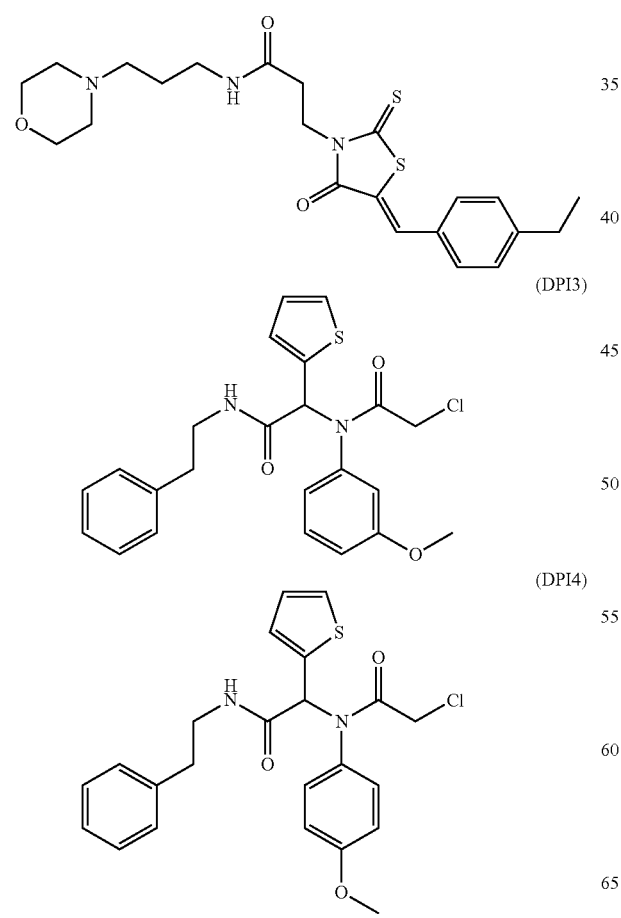

(DPI2)

(DPI3)

(DPI4)

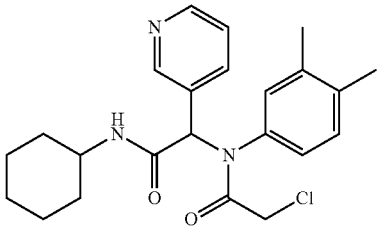

(DPI6)

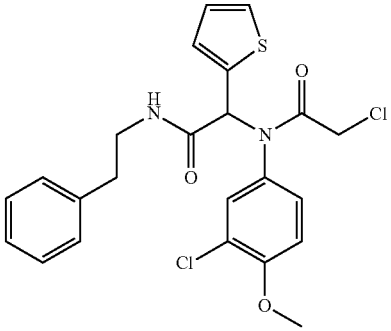

(DPI7)

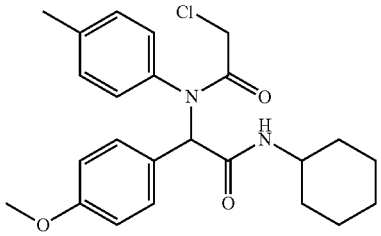

(DPI8)

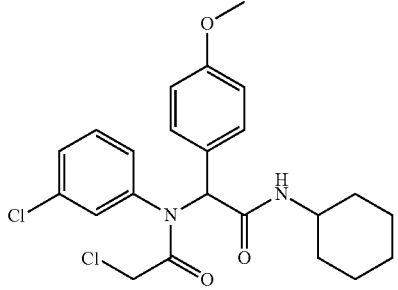

(DPI9)

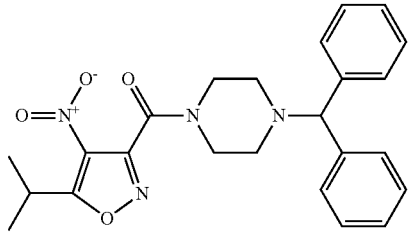

(DPI10)

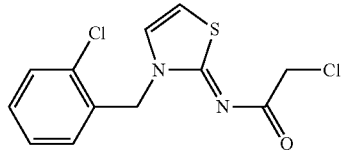

(DPI12)

(DPI13)
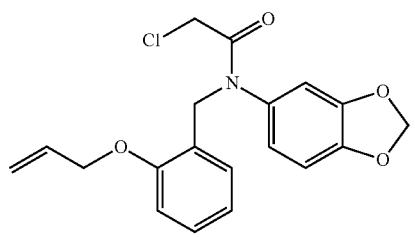
(DPI15)
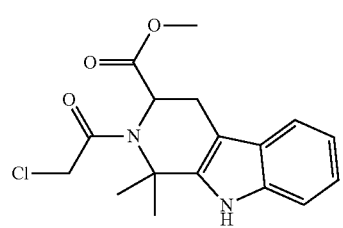
(DPI17)
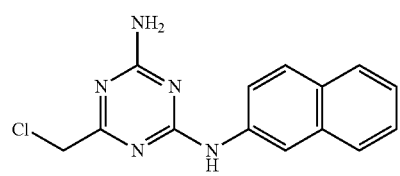
(DPI18)
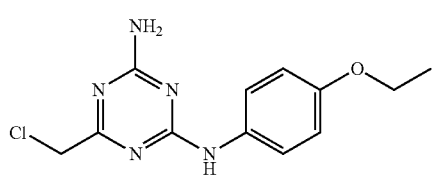
(DPI19)
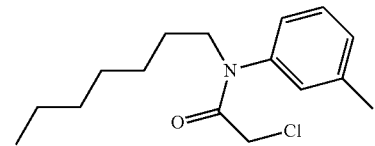
(51)
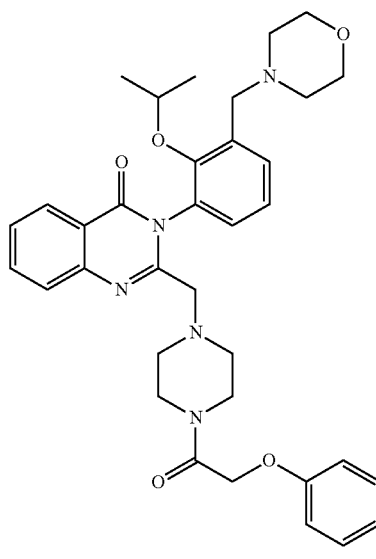
(52)
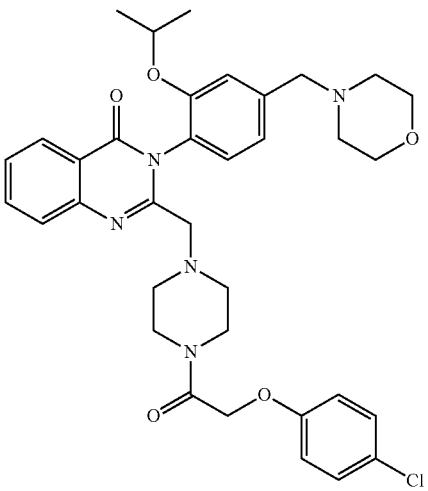
(40)
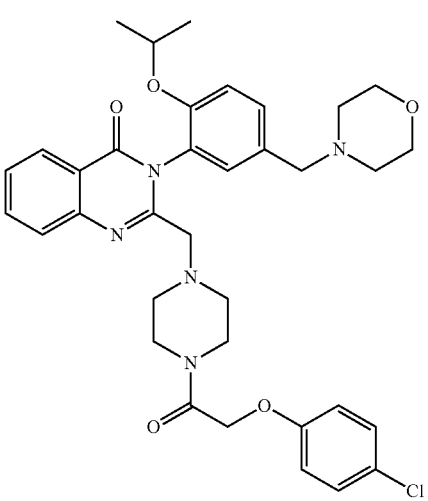
(15)
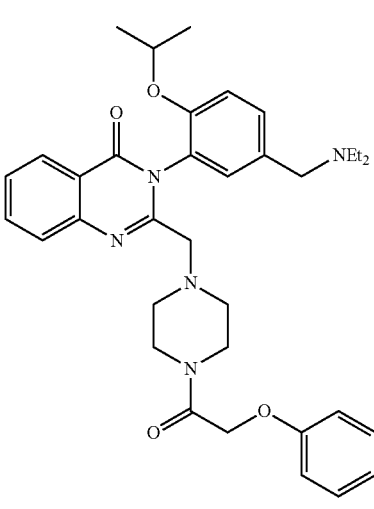

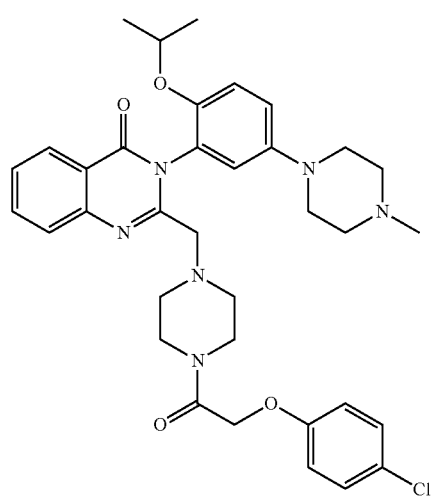
(17)
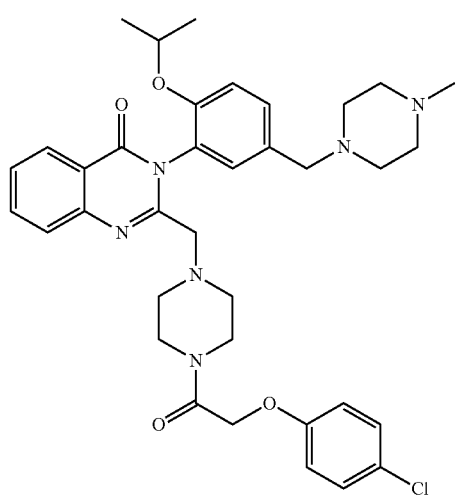
(60)
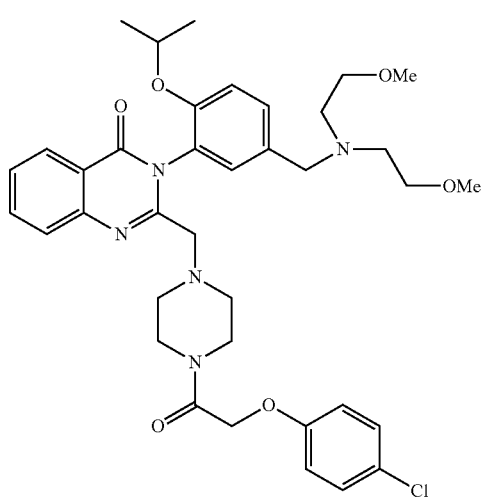
(18)
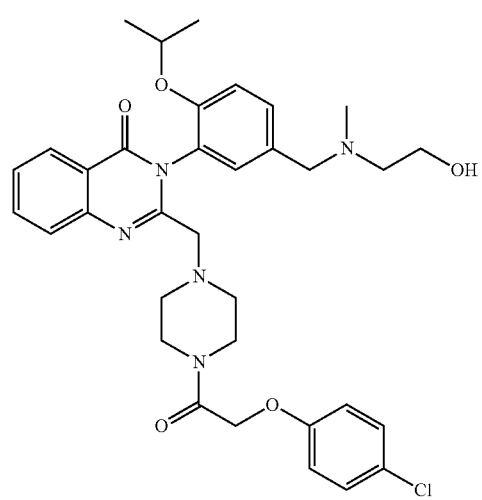
(21)
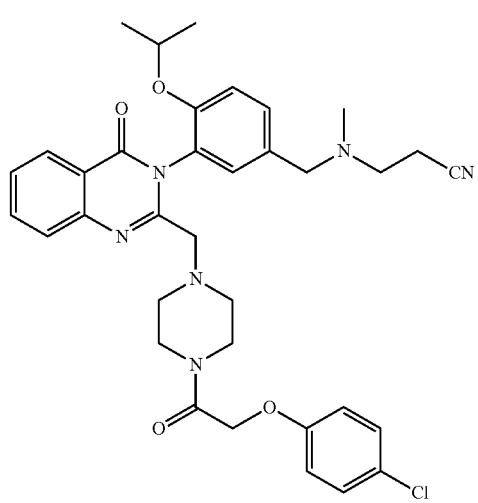
(19)
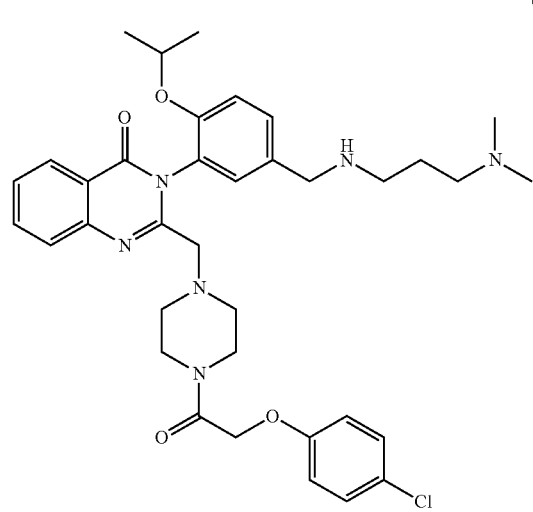
(22)

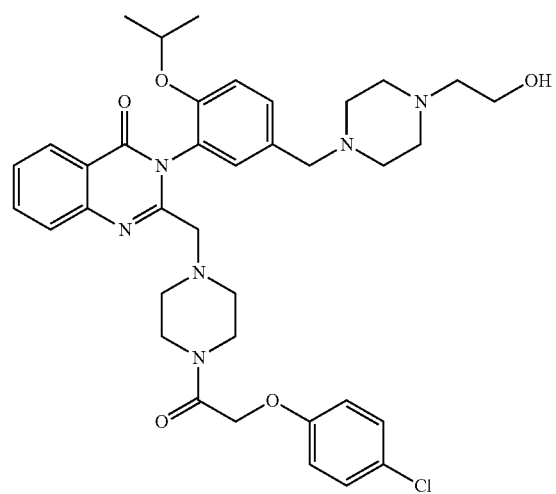
(23)
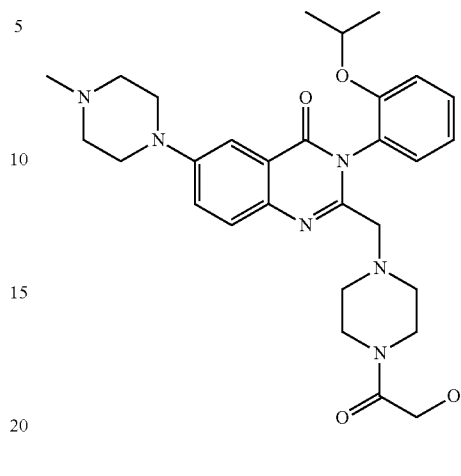
(2)
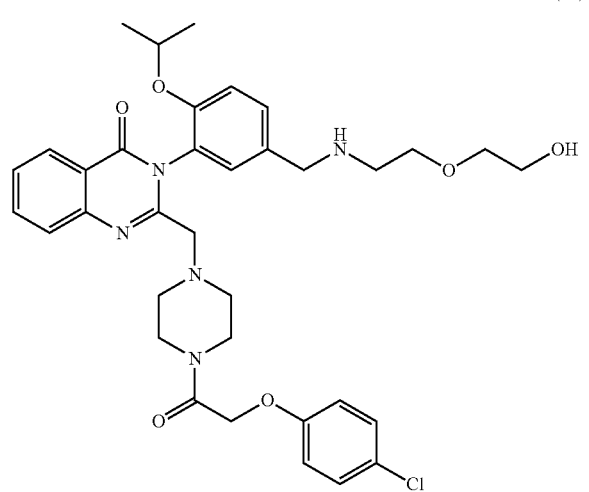
(24)
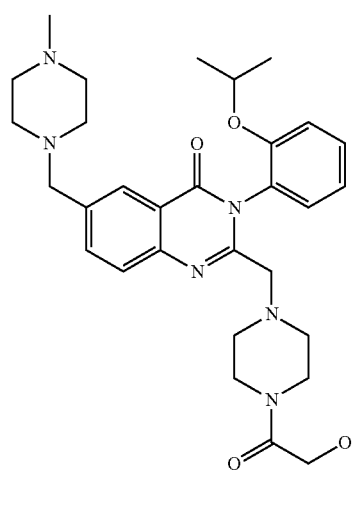
(3)
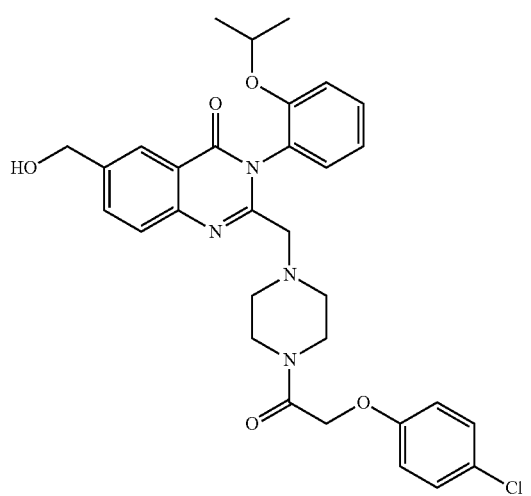
(1a)
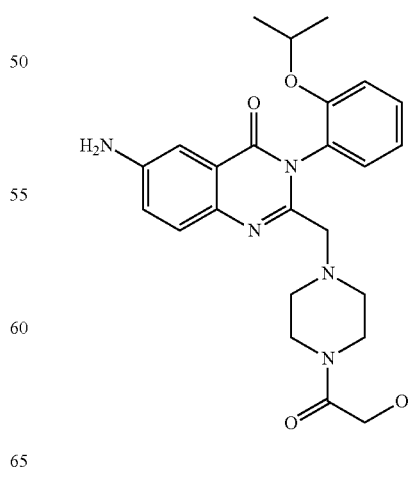
(4)

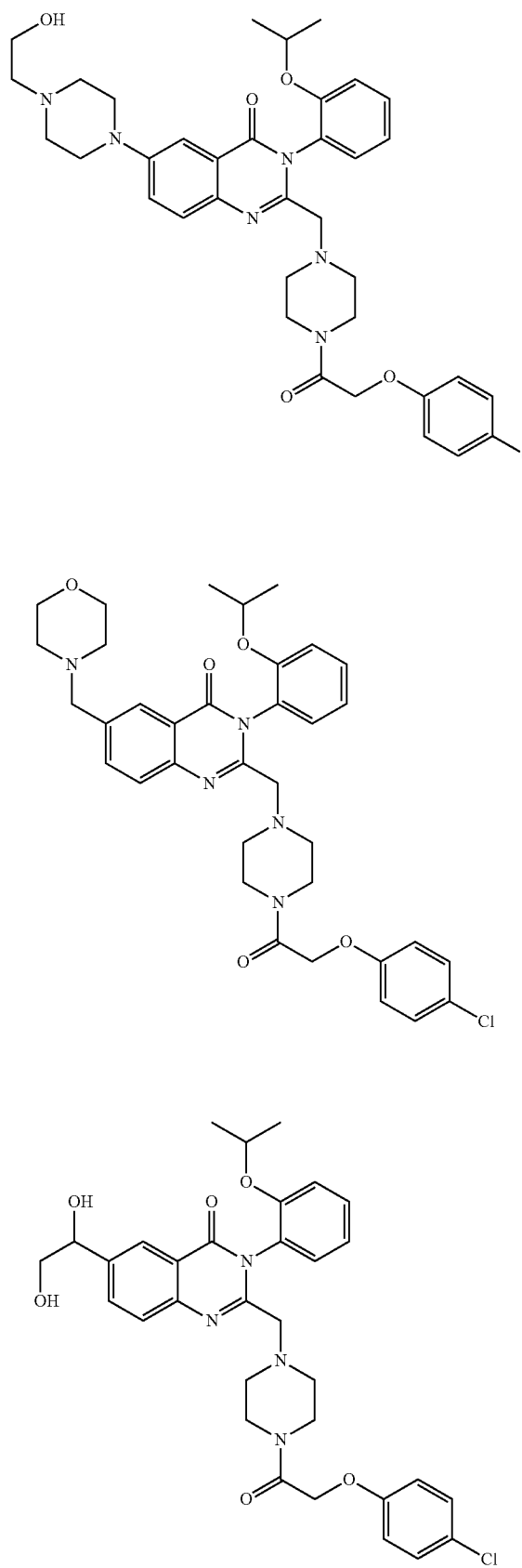
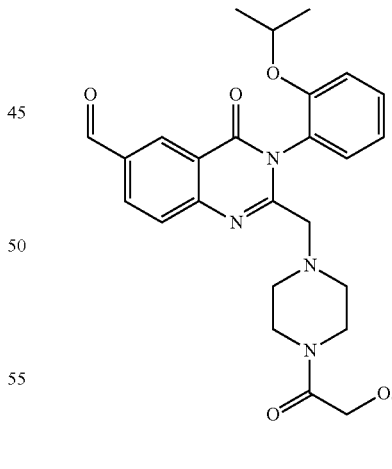
or an N-oxide, crystalline form, hydrate, or pharmaceutically acceptable salt thereof.
Another embodiment of the present invention is a method for modulating a lipoxygenase in a ferroptosis cell death pathway. This method comprises administering to a cell an effective amount of any compound or composition disclosed herein.

An additional embodiment of the present invention is a method for modulating a lipoxygenase in a ferroptosis cell death pathway. This method comprises administering to a cell an effective amount of a compound selected from the group consisting of:
(DPI2)
(DPI3)
(DPI4)
(DPI6)
(DPI7)
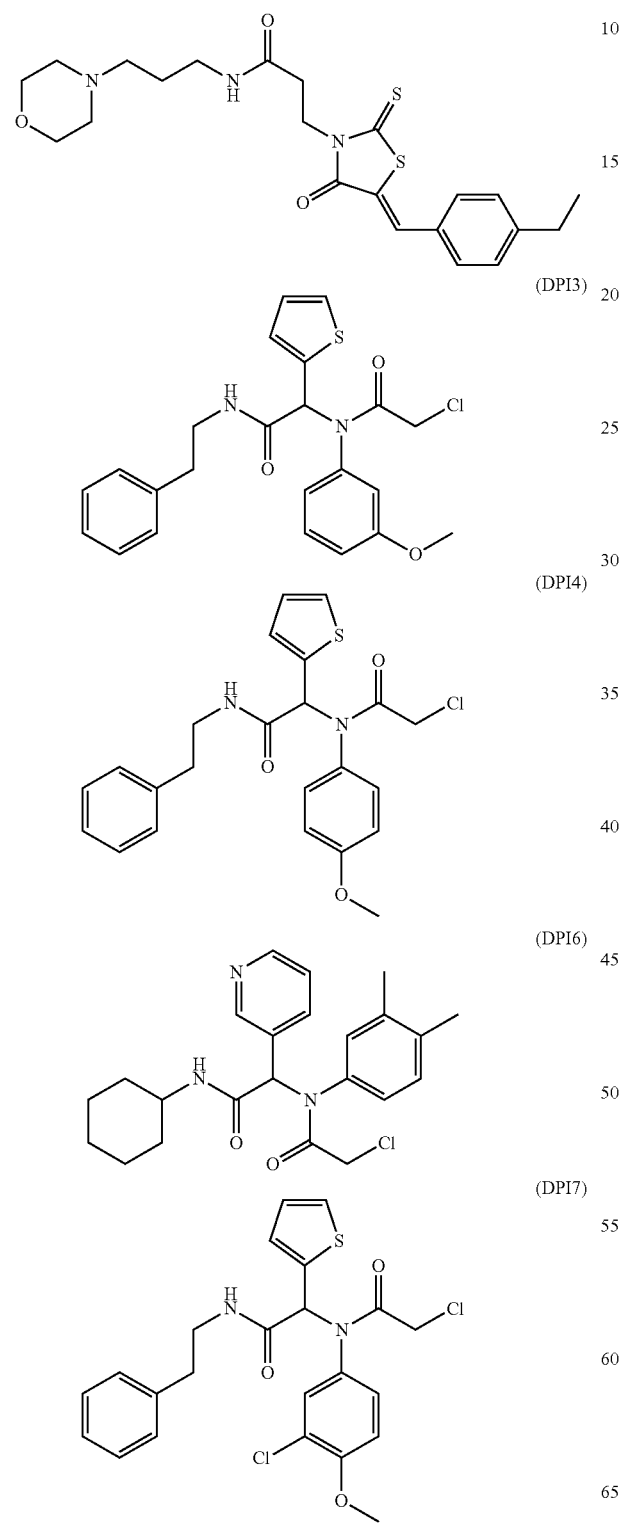
(DPI8)
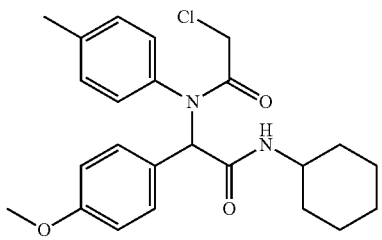
(DPI9)
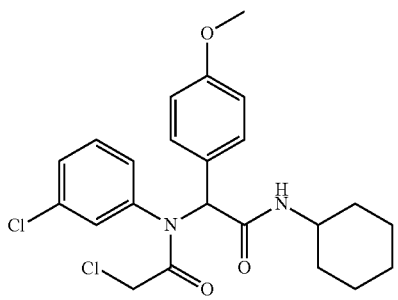
(DPI10)
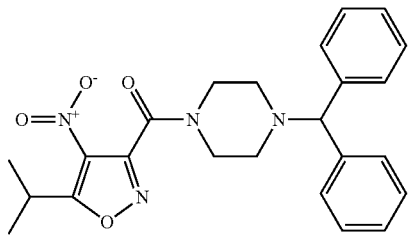
(DPI12)
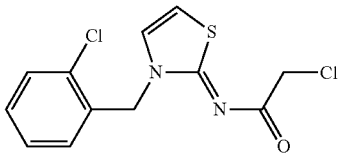
(DPI13)
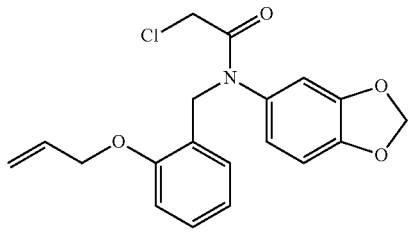
(DPI15)
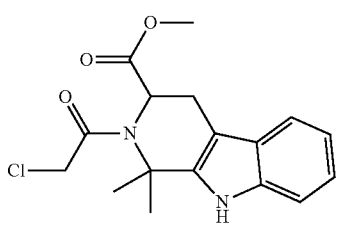
(DPI17)
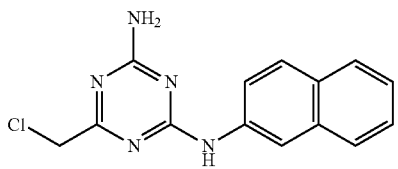

(DPI18)
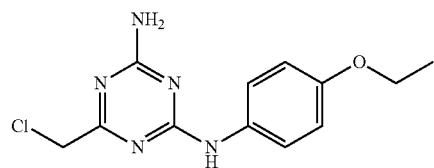
(DPI19)
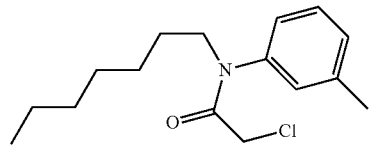
(51)
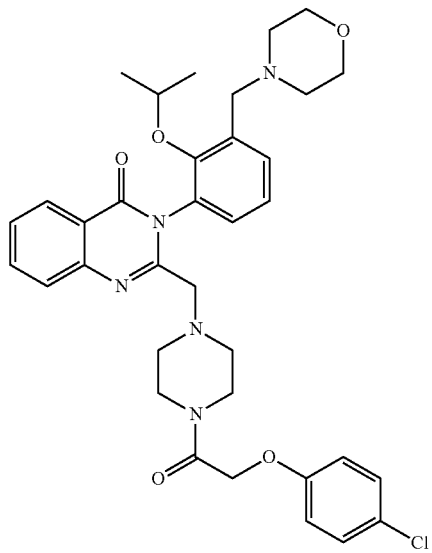
(52)
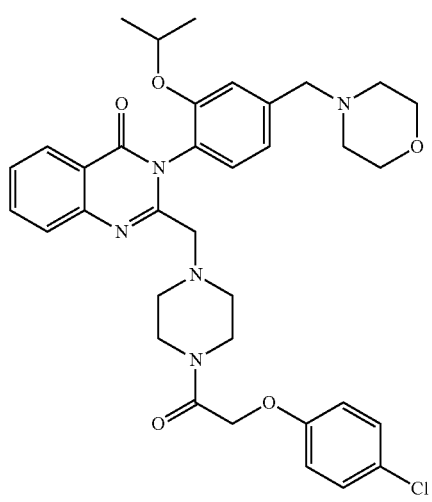
(40)
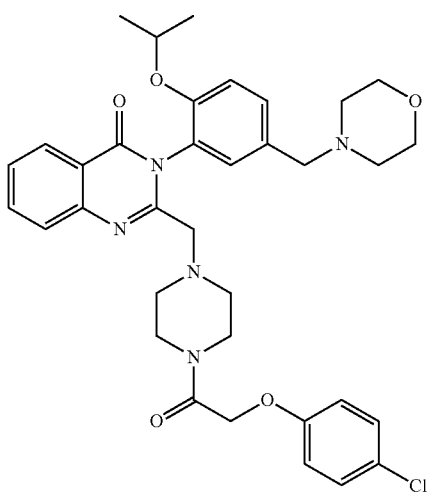
(15)
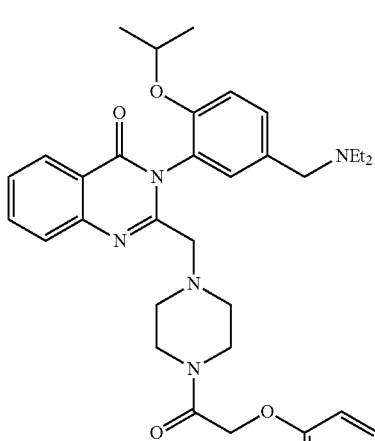
(17)
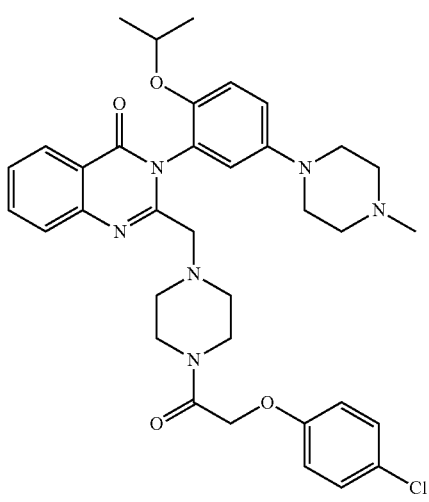

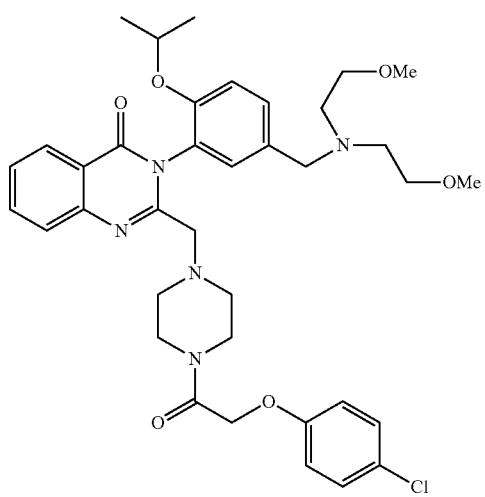
(18)
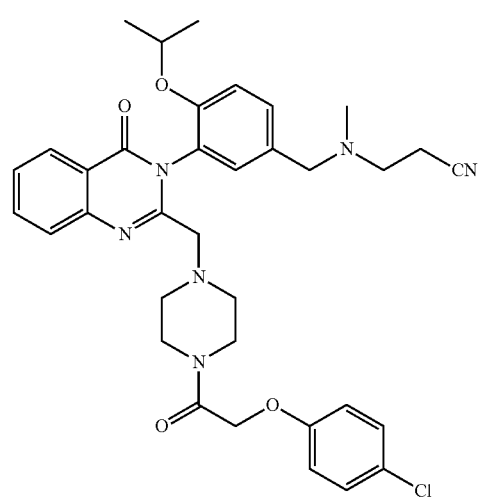
(19)
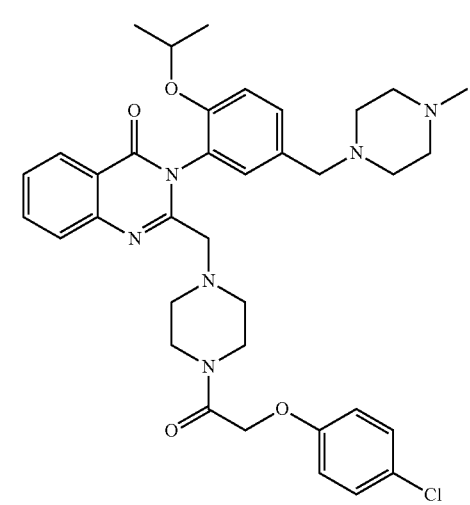
(60)
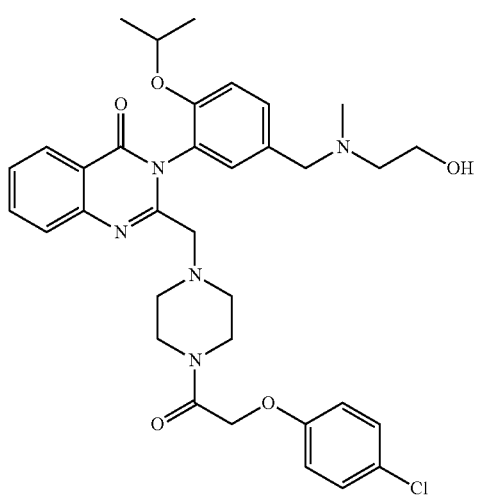
(21)
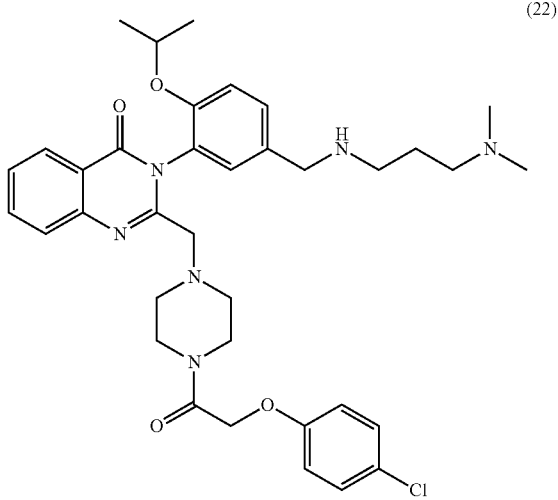
(22)
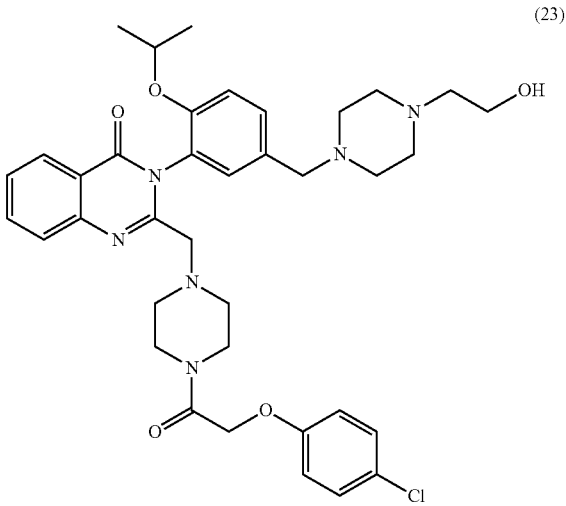
(23)

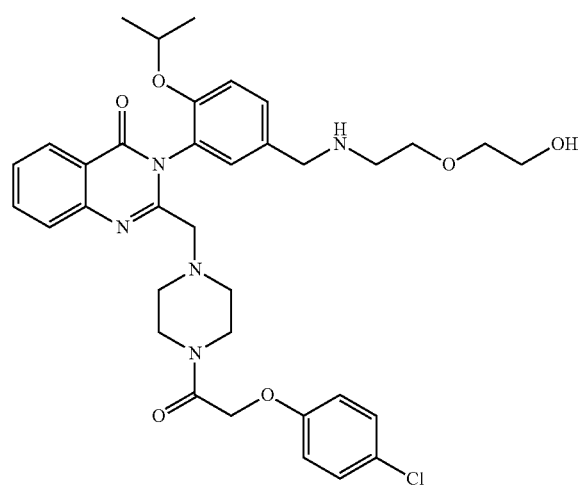
(24)
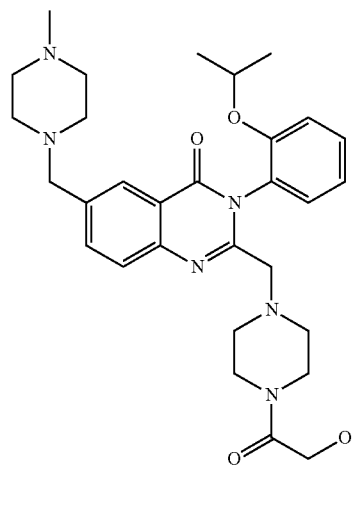
(3)
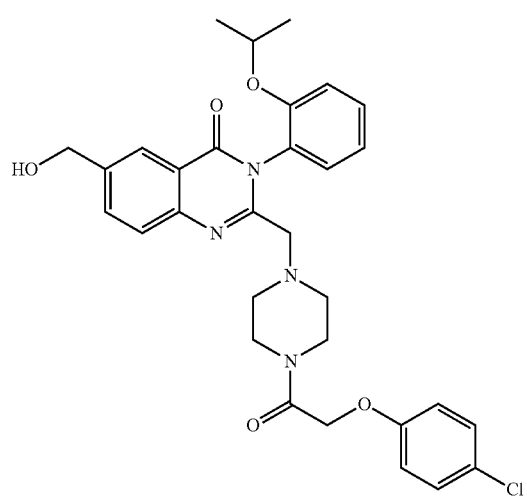
(1a)
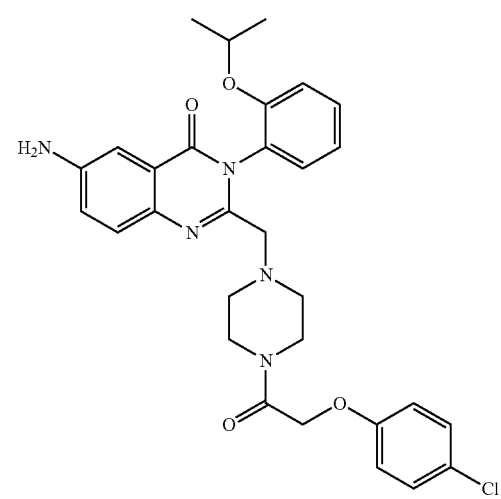
(4)
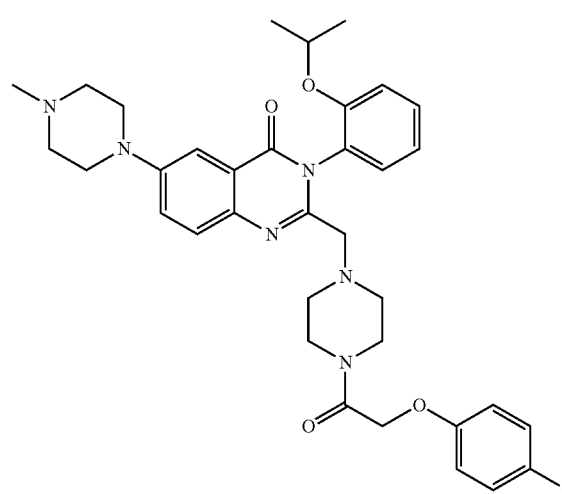
(2)
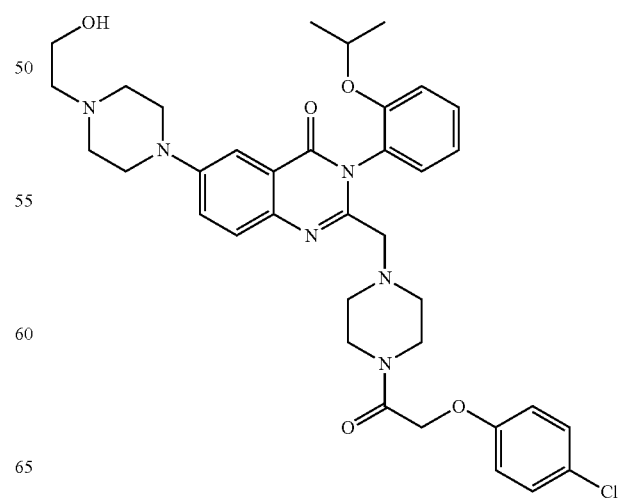
(5)

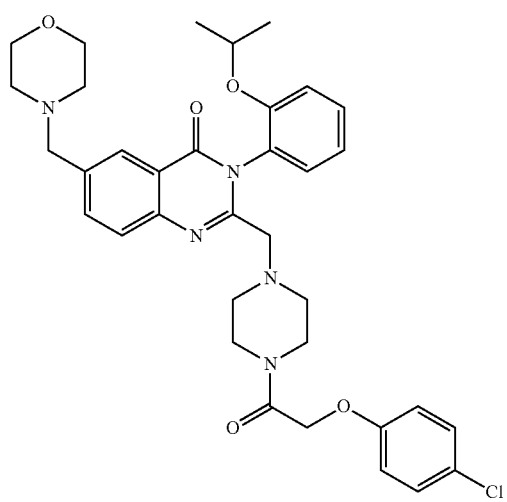
(6)
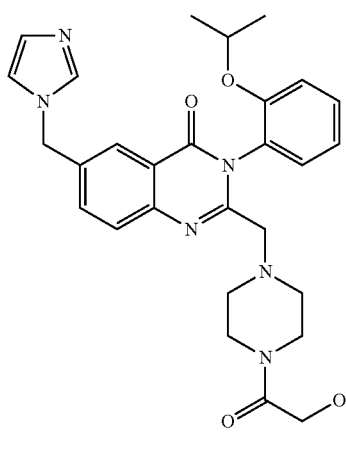
(9)
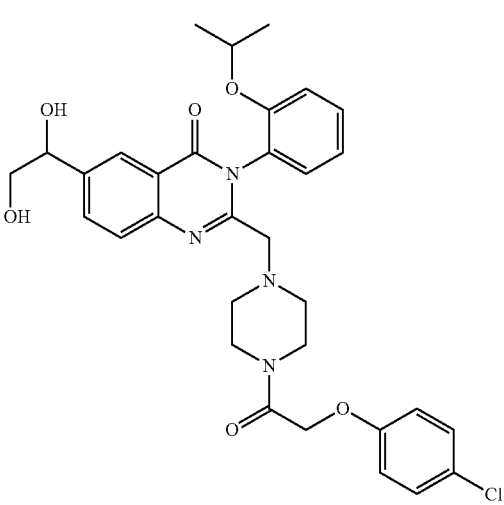
(7)
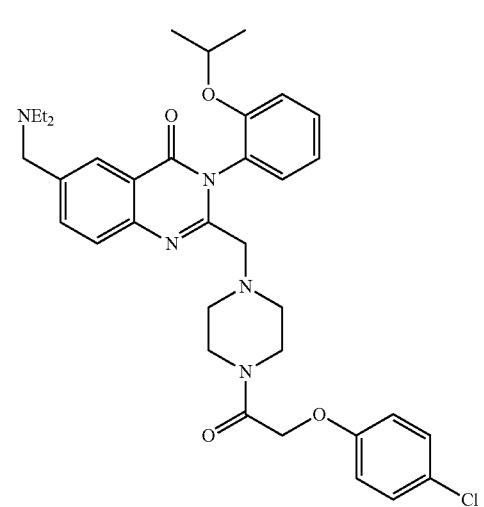
(8)
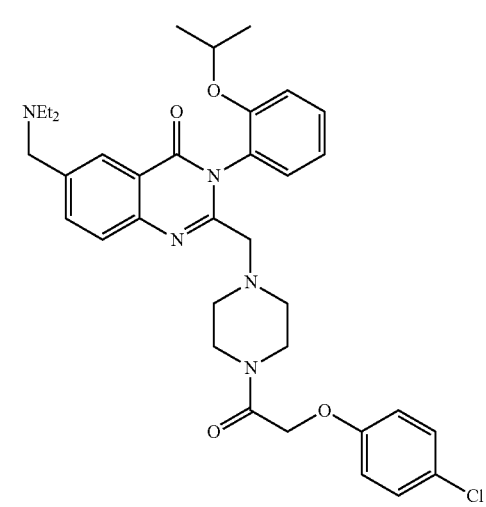
(11)
(8)

-continued

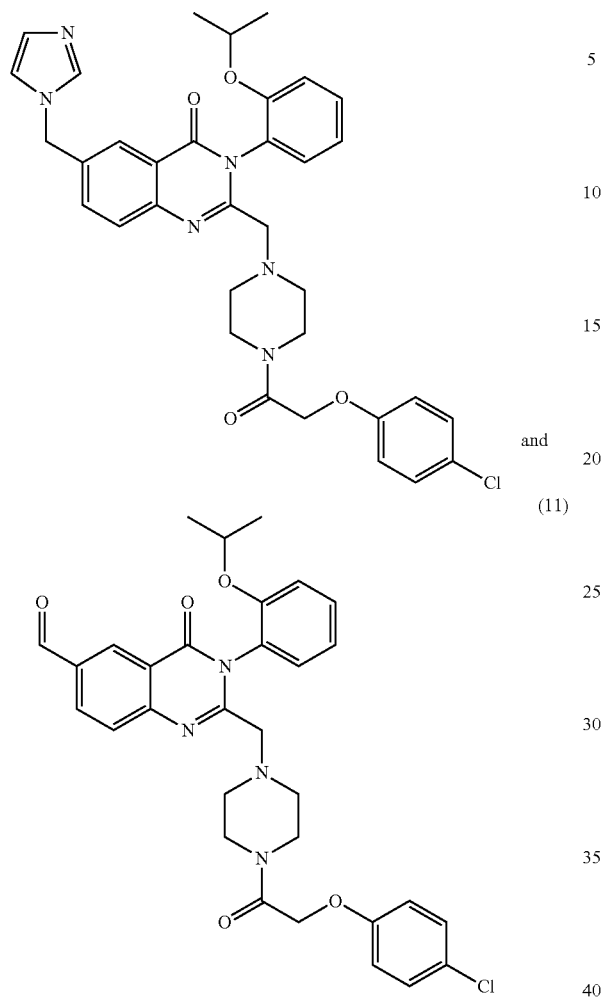

or an N-oxide, crystalline form, hydrate, or pharmaceutically acceptable salt thereof.

A further embodiment of the present invention is a method for depleting reduced glutathione (GSH) in a cell harboring an oncogenic RAS mutation. This method comprises administering to the cell an effective amount of any compound disclosed herein.

Another embodiment of the present invention is a method for depleting reduced glutathione (GSH) in a cell harboring an oncogenic RAS mutation. This method comprises administering to the cell an effective amount of a compound selected from the group consisting of:

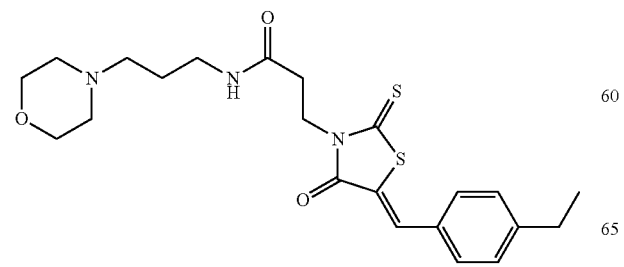

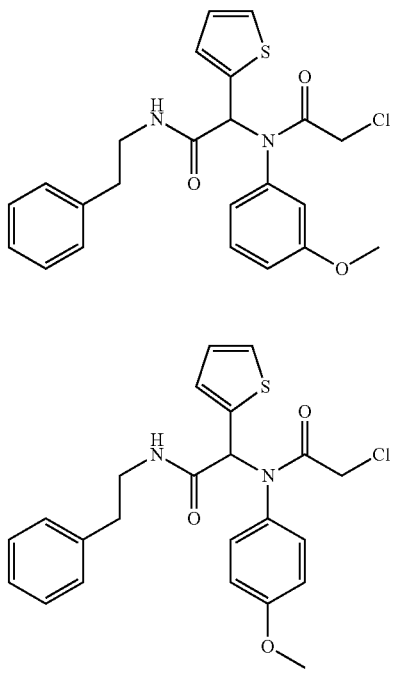

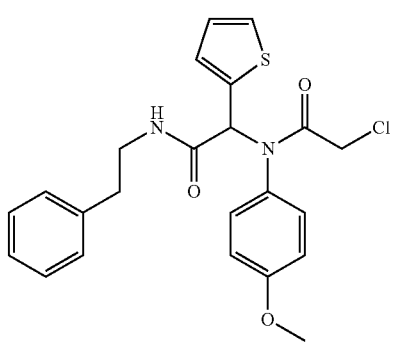

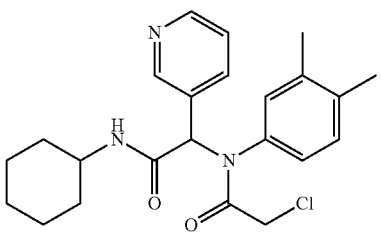

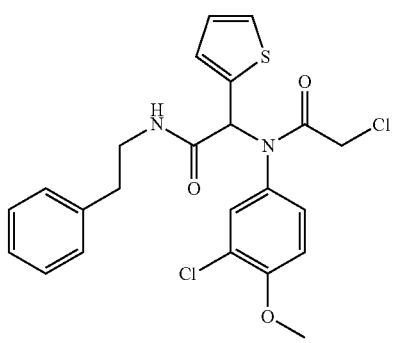

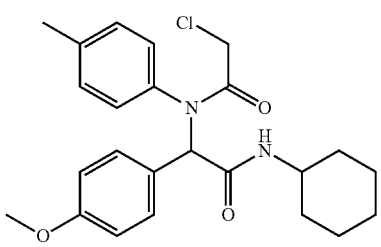

(DPI9)
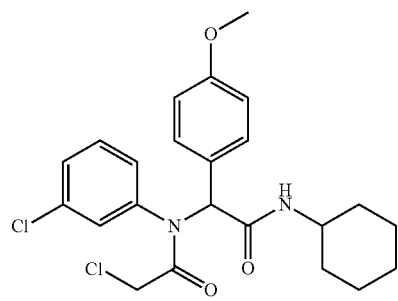
(DPI10)
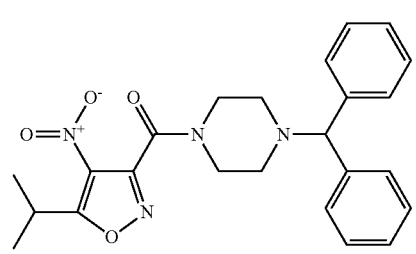
(DPI12)
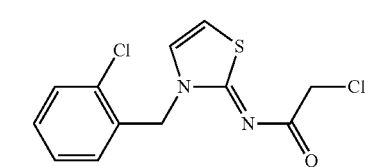
(DPI13)
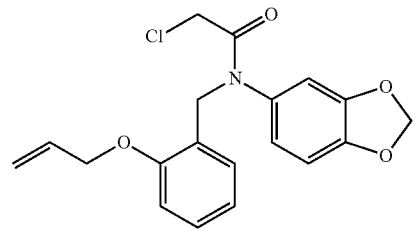
(DPI15)
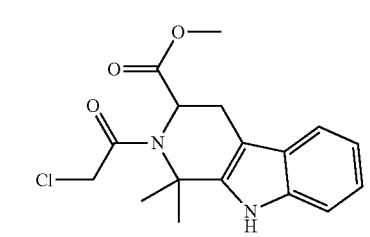
(DPI17)
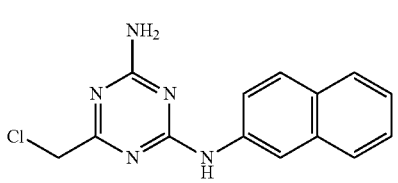
(DPI18)
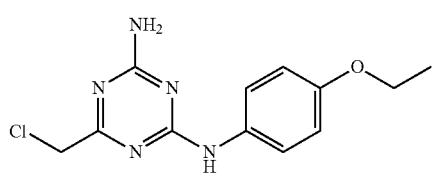
(DPI19)
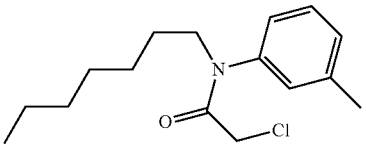
(51)
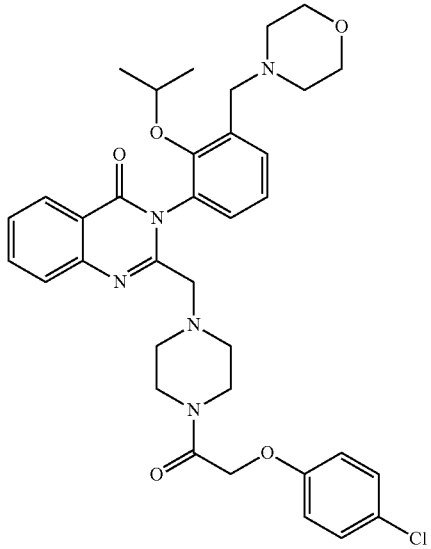
(52)
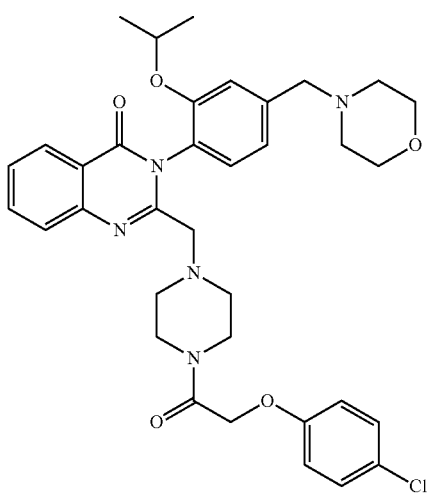

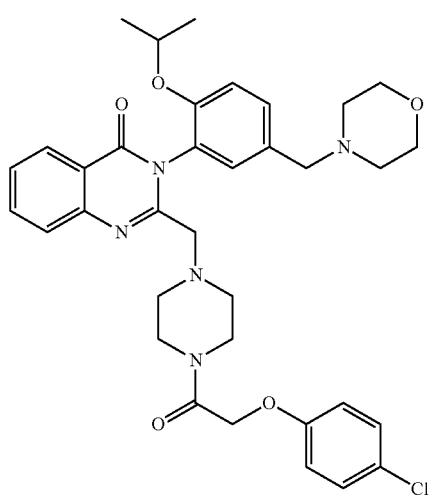
(40)
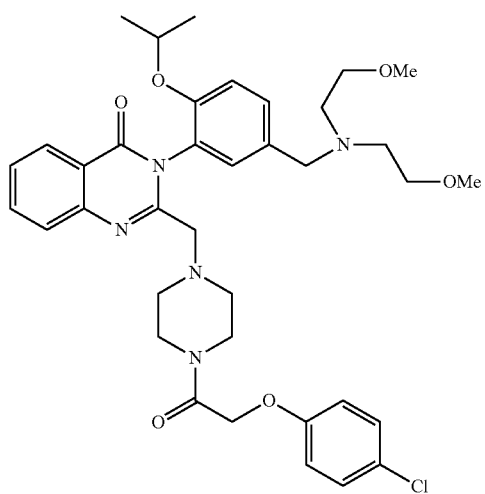
(18)
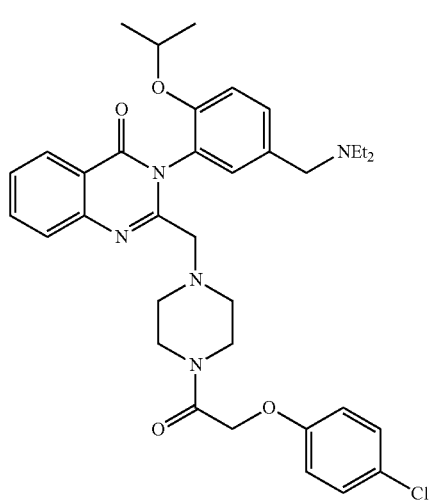
(15)
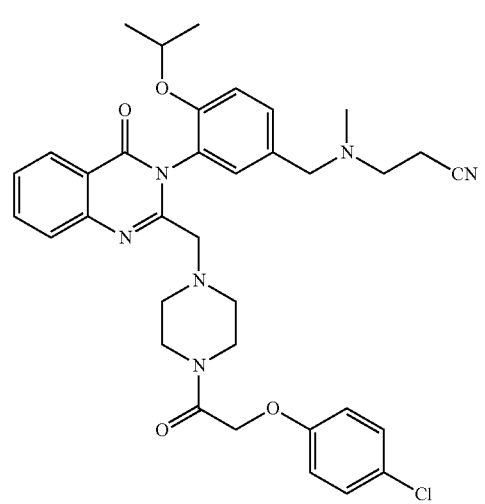
(19)
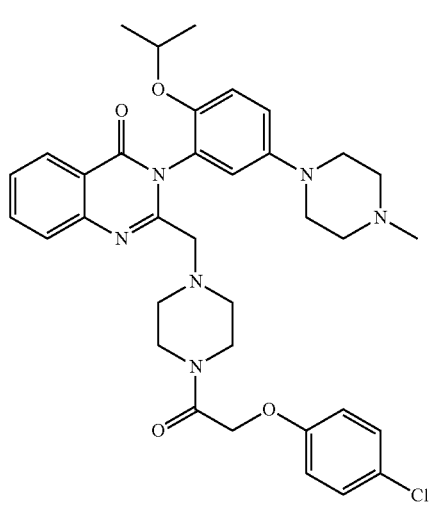
(17)
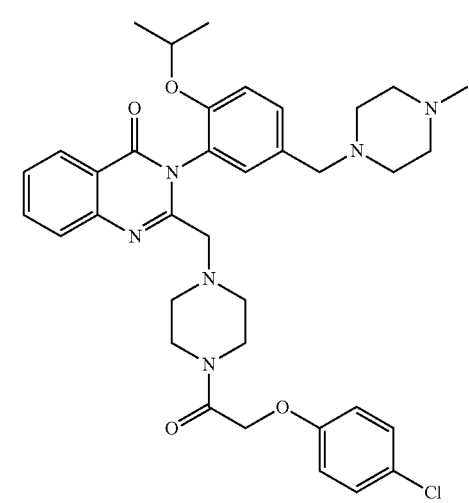
(60)

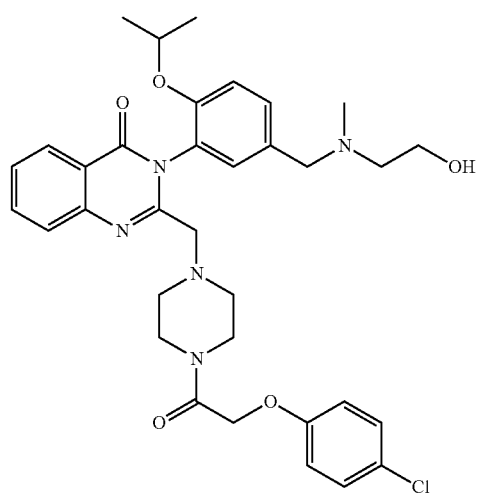
(21)
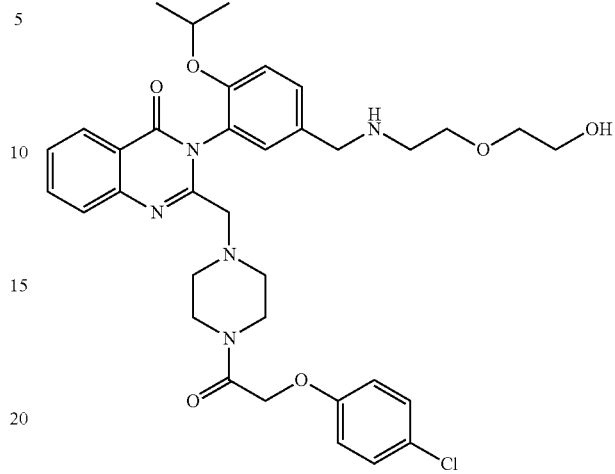
(24)
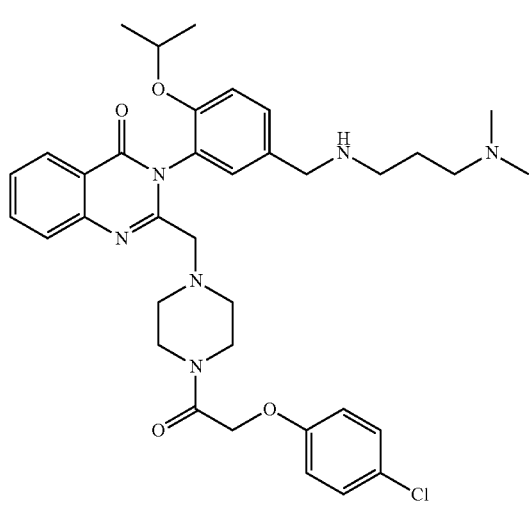
(22)
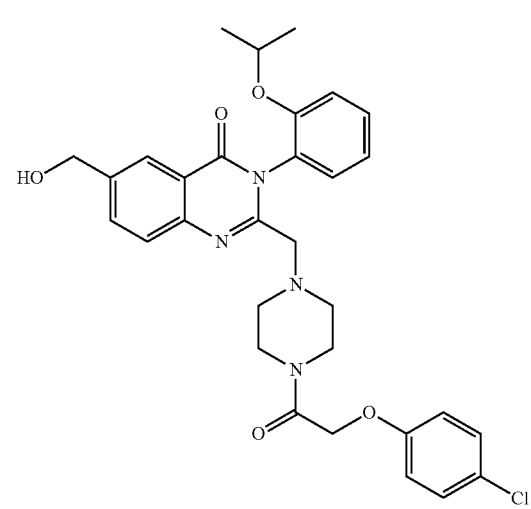
(1a)
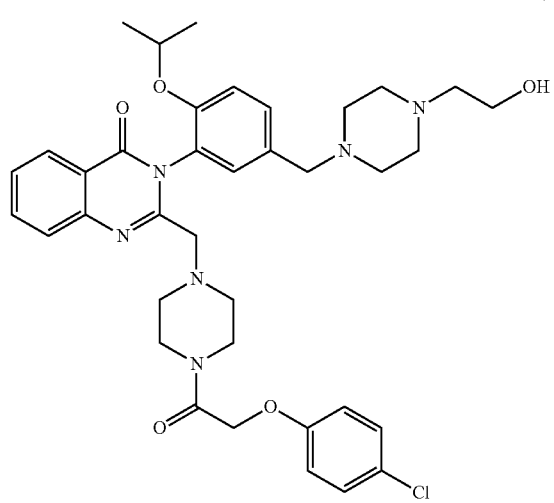
(23)
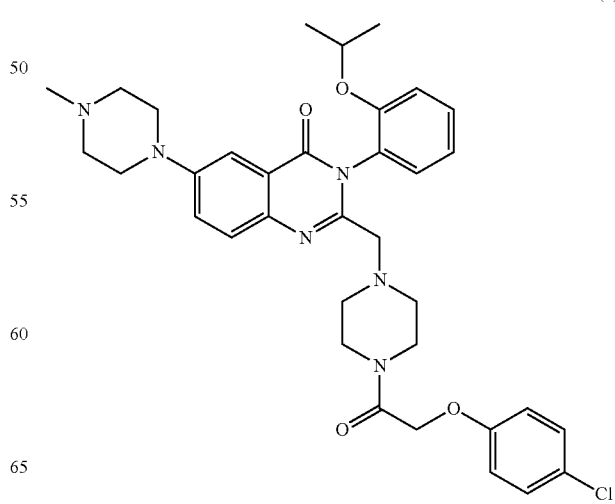
(2)

(3)
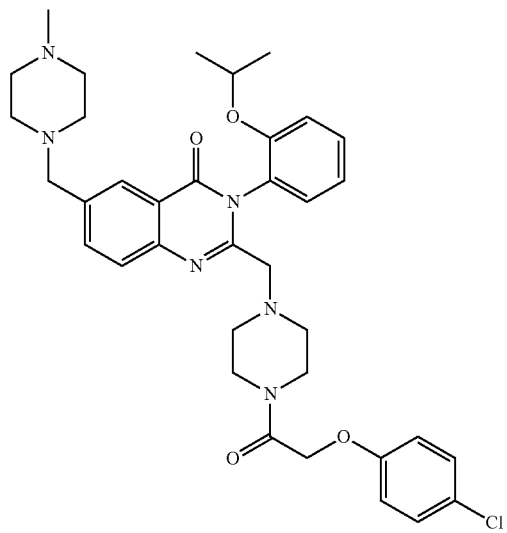
(4)
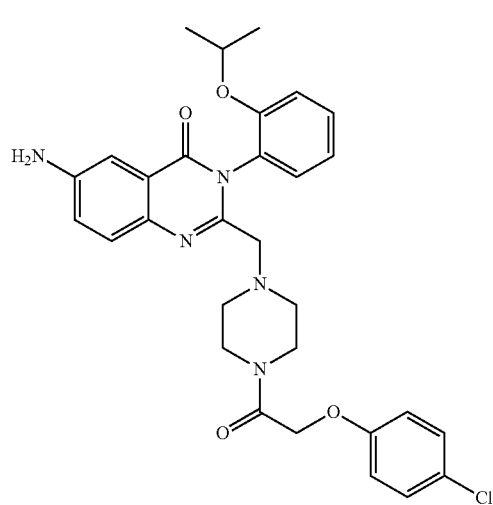
(5)
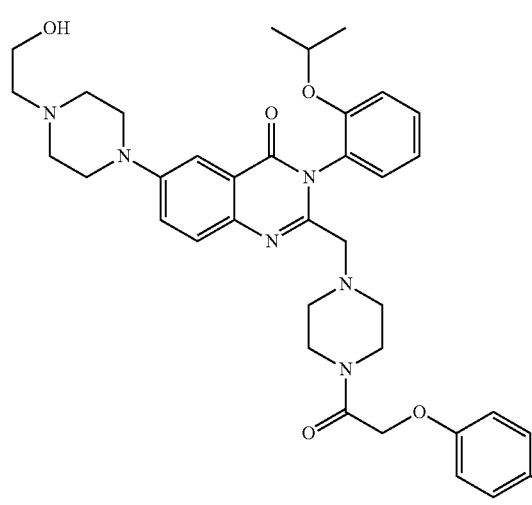
(6)
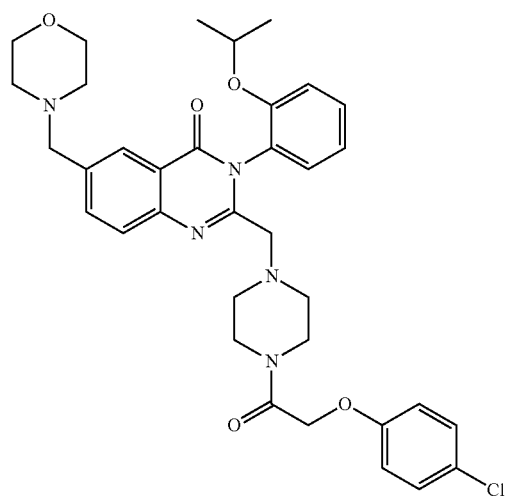
(7)
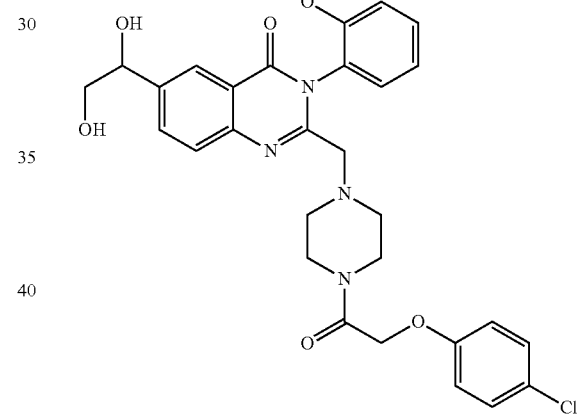
(8)
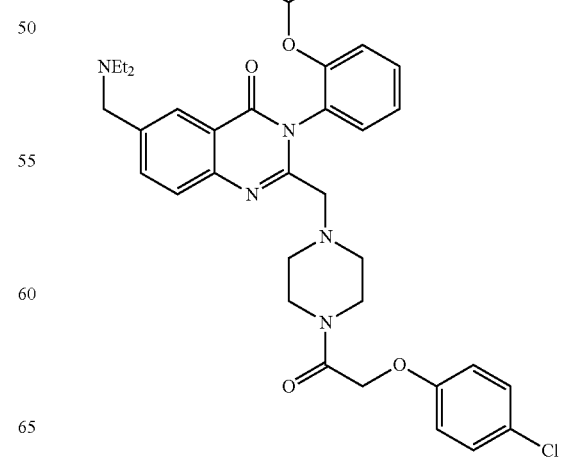

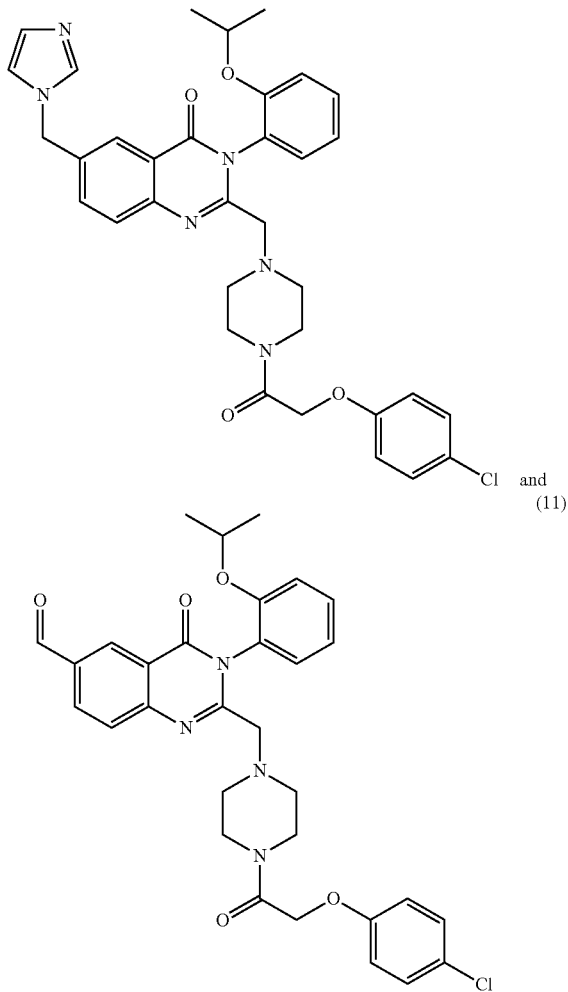

or an N-oxide, crystalline form, hydrate, or pharmaceutically acceptable salt thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1a is a graph showing the fold changes in metabolites upon erastin treatment. 264 metabolites from HT-1080 cells were analyzed.

FIG. 1b are graphs showing dose-dependent depletion of GSH by erastin in HT-1080 cells and U-2 OS cells. Data are presented as mean±standard deviation (s.d.); n=3.

FIG. 1c shows the structure of certain synthesized erastin analogs according to the present invention. Potency ($GI_{50}$) and selectivity of each analog is shown. Selectivity is the ratio of $GI_{50}$ (BJeH):$GI_{50}$ (BJeLR).

FIG. 1d is a plot showing GSH depletion by various erastin analogs. HT-1080 cells were incubated with 10 μM of erastin analogs for 5 hours or 100 μM buthioninesulfoximine (BSO) for 12 hours before measurement of GSH concentration. GSH in each sample was first normalized to the DMSO sample, then box-and-whisker plots were generated (n=3-8). Mid-line, median; box, 25th to 75th percentiles; and whiskers, minimum and maximum. , P<0.01, with respect to PYR-ERA; *, P<0.001.

FIG. 1e shows light microscopy images (top panel) and a growth inhibition plot (bottom panel) demonstrating that BSO induces the RSL phenotype. BJeLR and DRD are cells expressing $HRAS^{G12V}$, whereas BJeH and BJeHLT are isogenic counterparts lacking $HRAS^{G12V}$. Data are presented as mean±s.d.; n=3. Scale bars, 60 μm.

FIG. 1f is a plot showing that Erastin and BSO induced the RSL phenotype through a similar mechanism. The pattern of cell death inhibition was similar between erastin and BSO. The name of cell death inhibitors and the treatment condition is listed in Table 1 below.

TABLE 1

Figure 1:
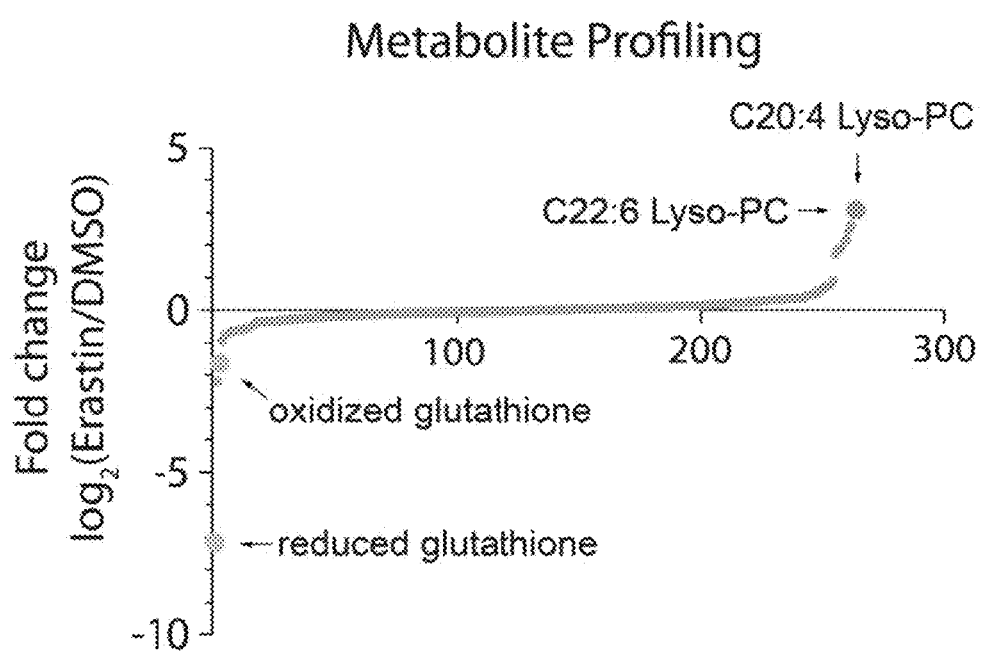
FIG. 1 shows that metabolite profiling revealed cellular glutathione (GSH) depletion as the most significant change upon erastin treatment.
Figure 1:
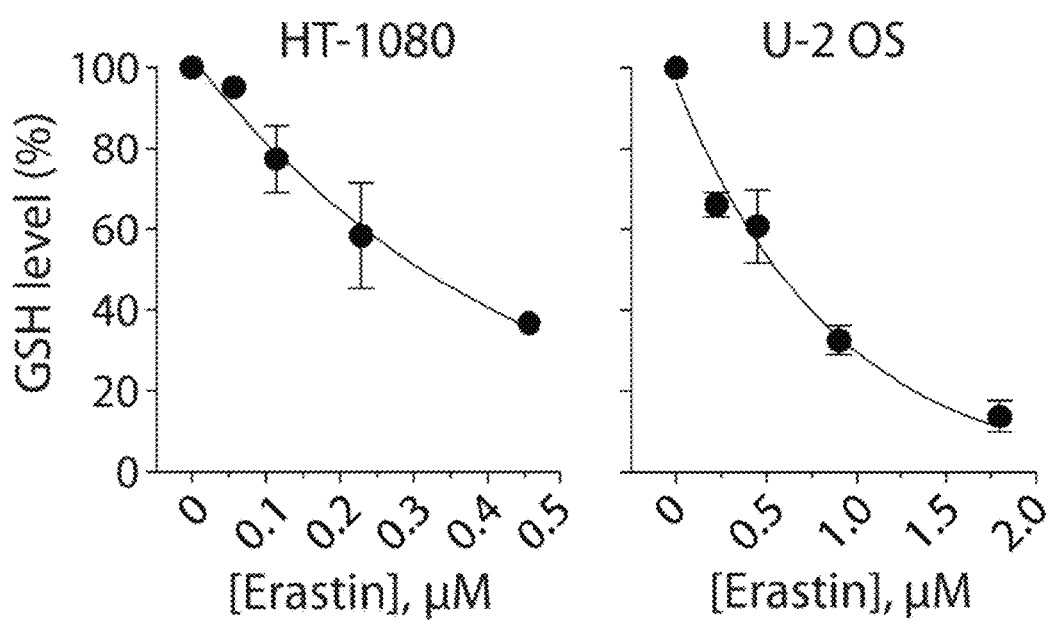
Figure 1:
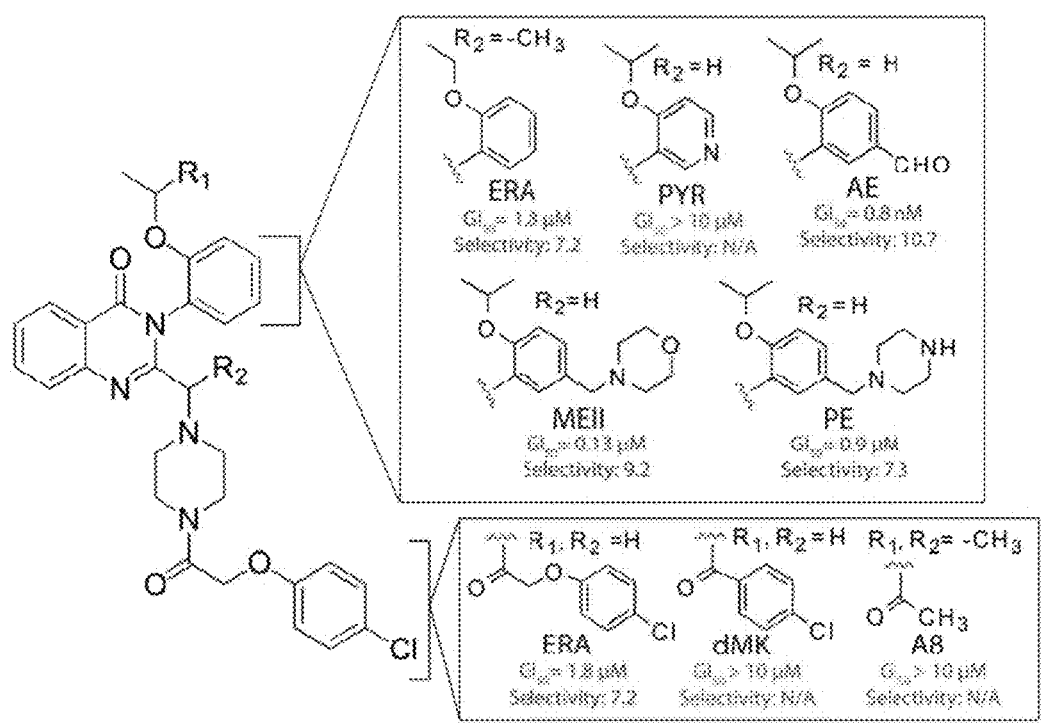
Figure 1:
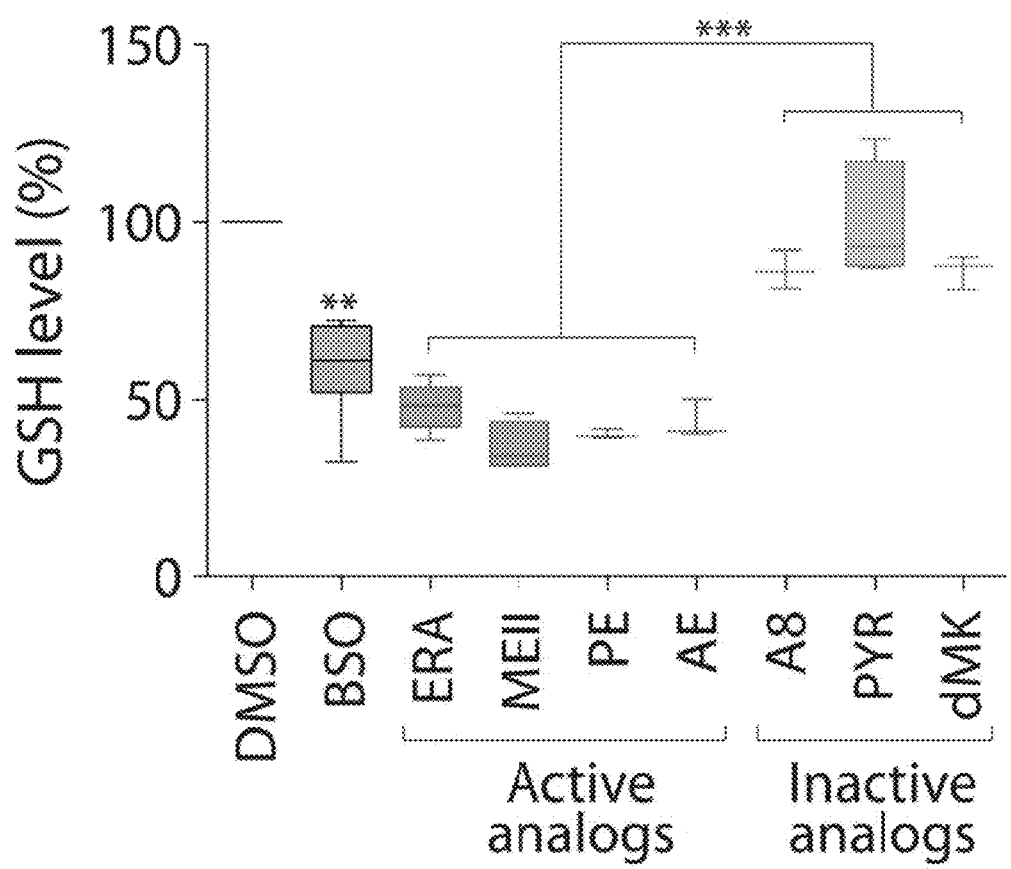
Figure 1:
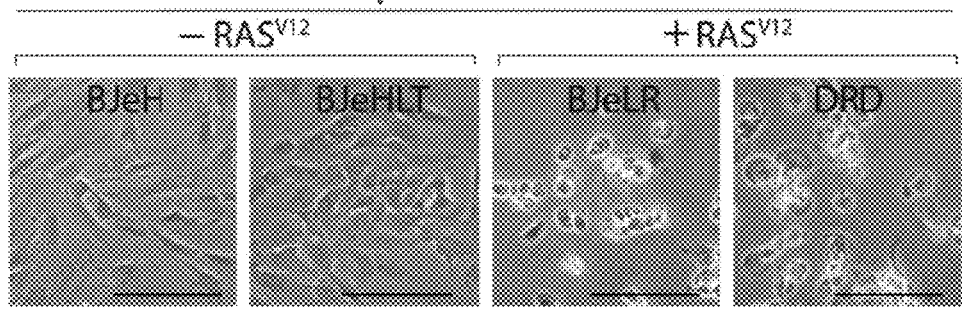
Figure 1:
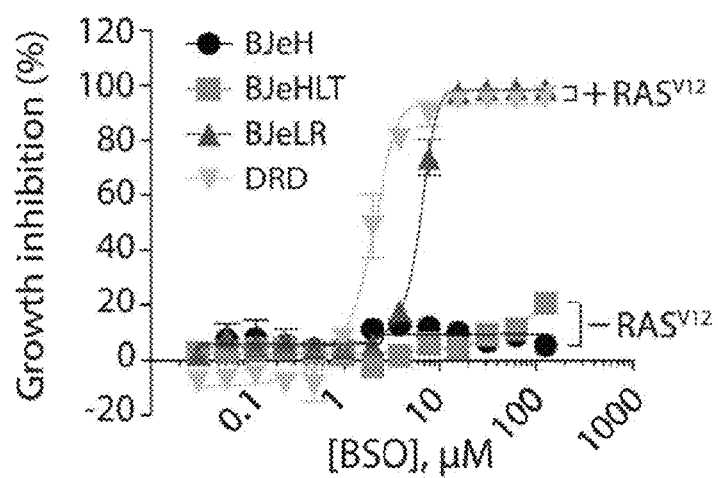
Figure 1:
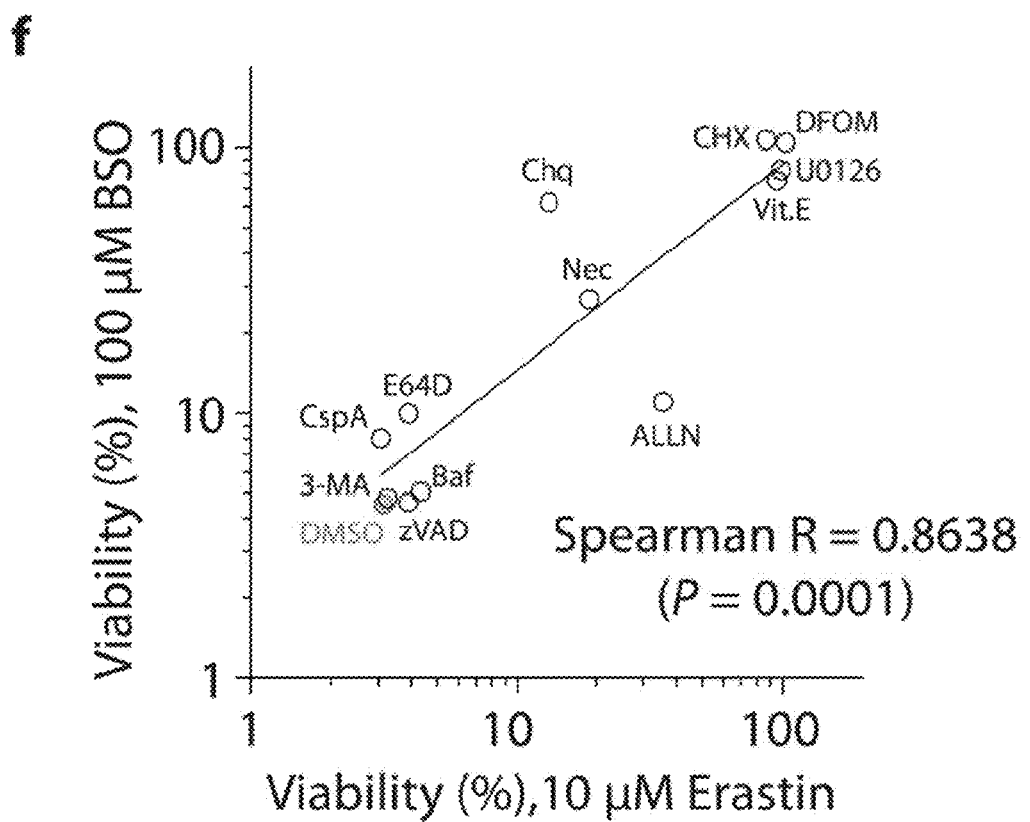

Name and treatment condition of cell death inhibitors used in FIG. 1f.

| Abbr. | Inhibitor | Target | Concentration, μM |
|---|---|---|---|
| 3-MA | 3-methyladenine | formation of preautophagosome | 1000 |
| zVAD | z-VAD-fmk | caspases | 50 |
| Baf | Bafilomycin A1 | autophagosome-lysosome fusion | 1 |
| CspA | Cyclosporin A | cyclophilin D | 5 |
| E64D | E64D | calpains/cathepsins | 100 |
| ALLN | ALLN | calpains | 2.5 |
| Nec | Necrostatin-1 | RIP1 kinase | 10 |
| Chq | Chloroquine | autophagosome-lysosome fusion | 10 |
| Vit.E | Vitamin E | lipophilic antioxidant | 100 |
| U0126 | U0126 | MEK inhibitor | 10 |
| CycH | Cycloheximide | Translation elongation | 1.5 |
| DFOM | Deferoxamine | iron chelator | 100 |

Figure 2:
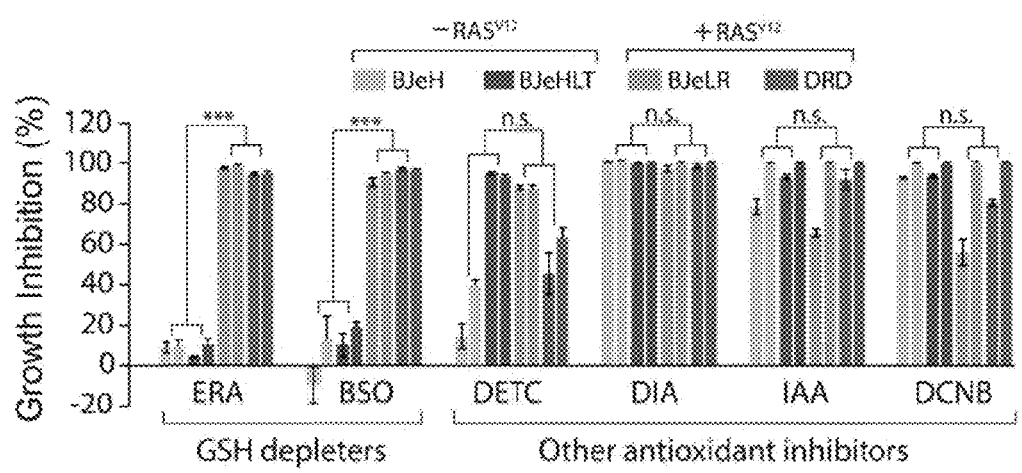
Figure 2:
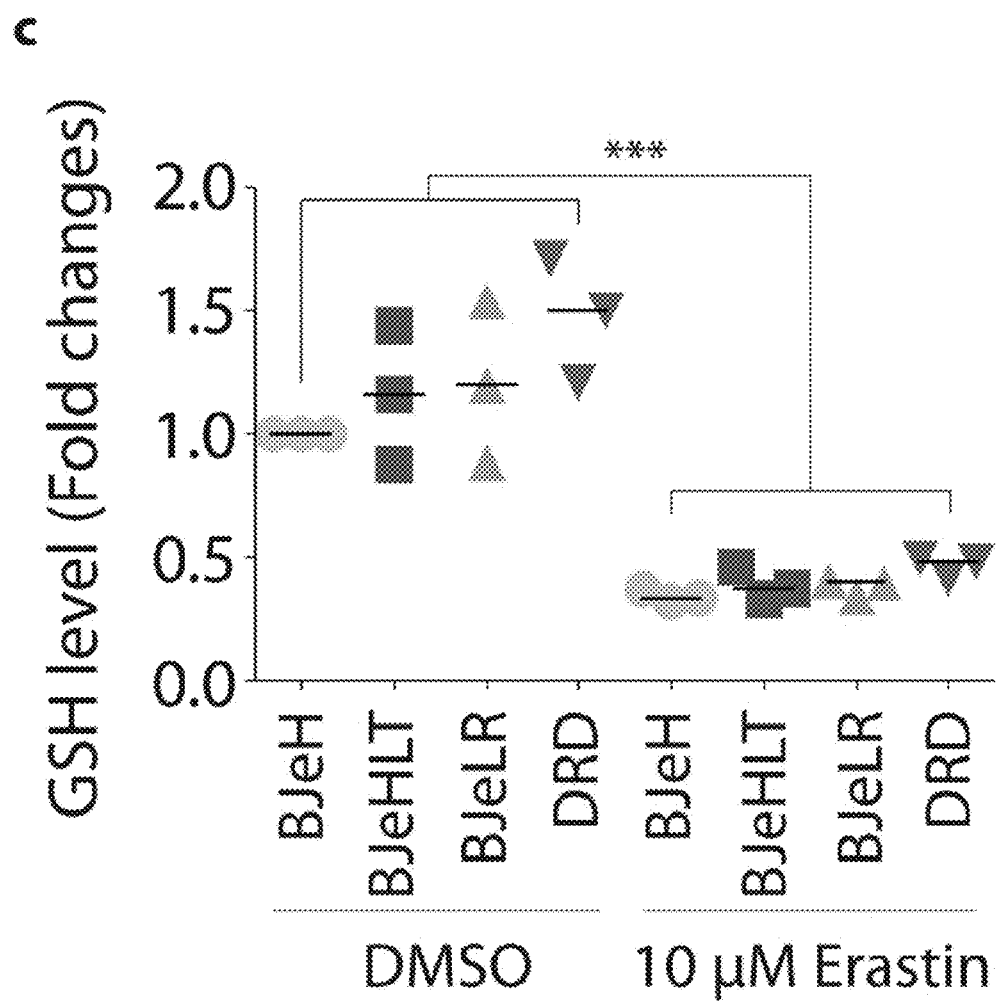
Figure 2:
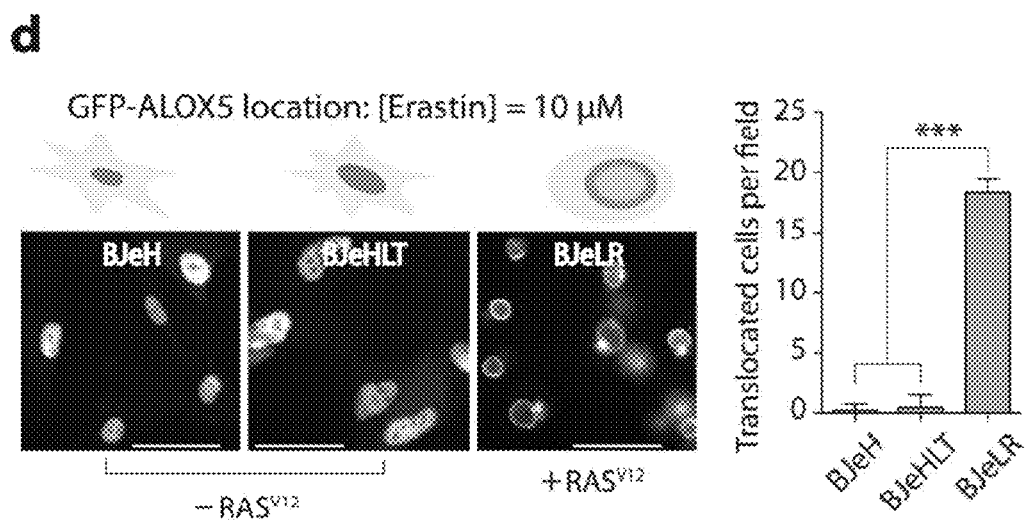
Figure 2:
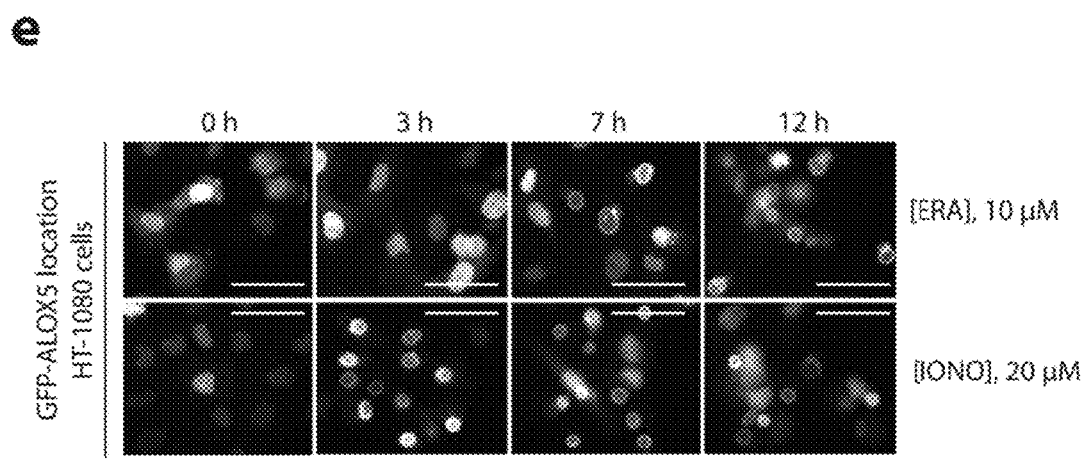
Figure 2:
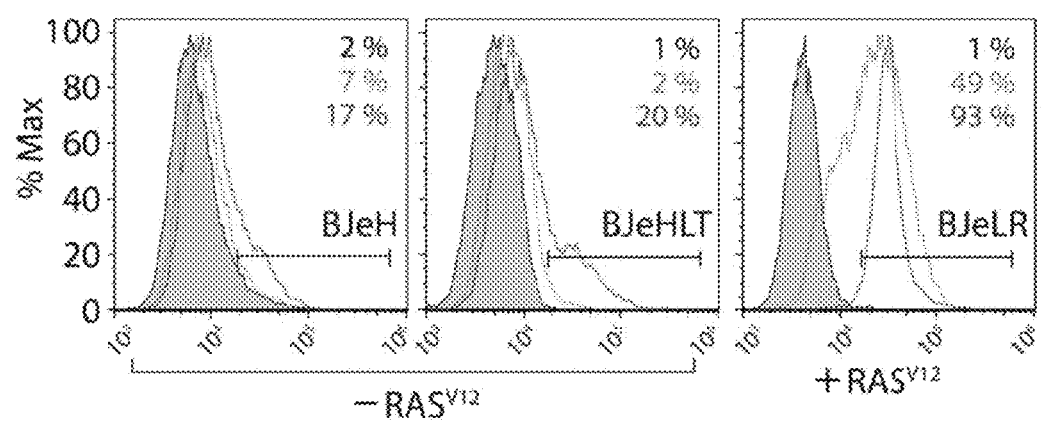
Figure 2:
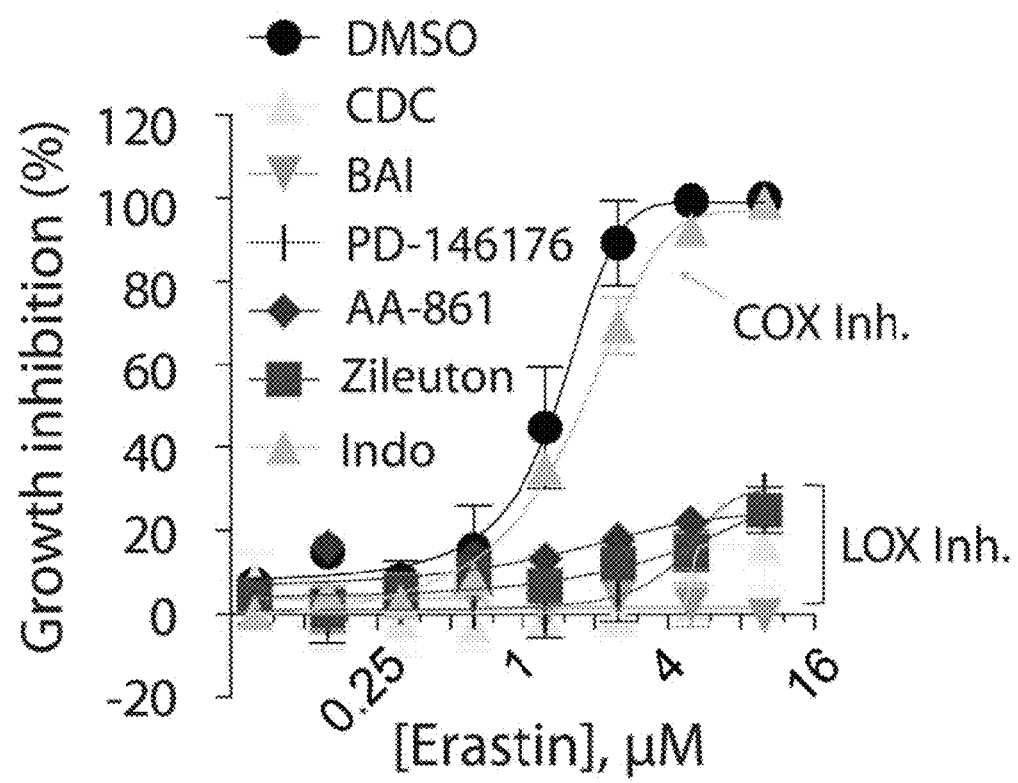

FIG. 2 shows that selective activation of lipoxygenases is responsible for the RSL phenotype of erastin.

FIG. 2a is a graph showing various basal ROS levels among BJ-derived cell lines, which were compared using $H_2DCF$, a ROS detection dye, and flow cytometric analysis. The horizontal lines indicate the mean of normalized ROS levels; n=8; *, P<0.05.

FIG. 2b is a series of bar graphs showing the results of experiments in which antioxidant-targeting compounds were tested in four BJ-derived cells to determine whether they exhibited an RSL phenotype. The graphs indicate growth inhibition in the 4 BJ-derived cell lines at two different concentrations (2× $GI_{50}$ and 4× $GI_{50}$ for each compound in BJeLR cells). Bar graph: mean±s.d.; n=3; n.s., not significant; ***, P<0.001.

FIG. 2c is a graph showing that erastin depletes cellular GSH equally in the 4 BJ-derived cell lines. Cells were treated with either DMSO or erastin for 12 hours followed by GSH quantification as described in Example 1 below. ***, P<0.001.

FIG. 2d shows a panel of microscopy images and a graph demonstrating that GFP-ALOX5 translocated to the nuclear membrane only in BJeLR cells upon 10 μM erastin treatment. Bar graph: mean+s.d.; n=3-4; ***, P<0.001. Scale bars, 60 μm.

FIG. 2e shows a series of time course microscopy images of GFP-ALOX5 translocation in HT-1080 cells upon treatment with erastin or ionomycin. Scale bars, 60 μm.

FIG. 2f is a series of graphs showing that erastin selectively generated lipid peroxides in BJeLR cells. The respective percentages in each graph indicate the percentage of the cell population that is BODIPY-C11 positive upon 0, 5, and 10 μM erastin treatment for 6 hours.

FIG. 2g is a graph showing that ALOX inhibitors, but not a COX inhibitor, strongly suppressed erastin-induced cell death. Five different ALOX inhibitors (CDC, BAI, PD-146176, AA-861, Zileuton) and one COX inhibitor (Indo) were tested for their ability to suppress erastin lethality. The detailed treatment condition is listed in Table 2 below. Data are presented as mean±s.d.; n=3.

TABLE 2

List of ALOX and COX inhibitors used in this study. The indicated concentration was used in the experiment of FIG. 2g and FIG. 3c.

| Abbr. | Full name | Concentration | Vendor | Cat# |
|---|---|---|---|---|
| CDC | cinnamyl-3,4-dihydroxy-a-cyanocinnamate | 20 μM | Santa Cruz | sc-200562 |
| BAI | Baicalein | 10 μM | Santa Cruz | sc-200494 |
| PD-146176 | PD-146176 | 5 μM | Santa Cruz | sc-200678 |
| AA-861 | AA-861 | 2 μM | Santa Cruz | sc-200570 |
| Zileuton | Zileuton | 50 μM | Santa Cruz | sc-204417 |
| Indo | Indomethacin | 200 μM | Santa Cruz | I-7378 |

Figure 3:
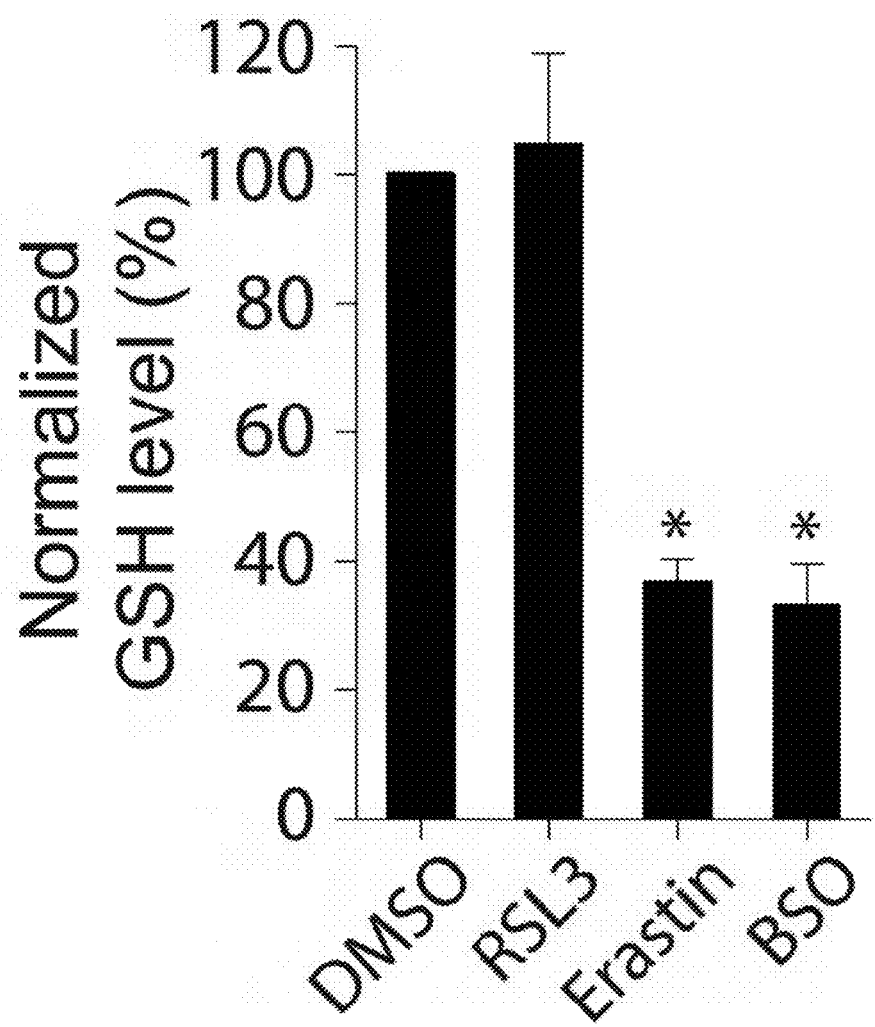
Figure 3:
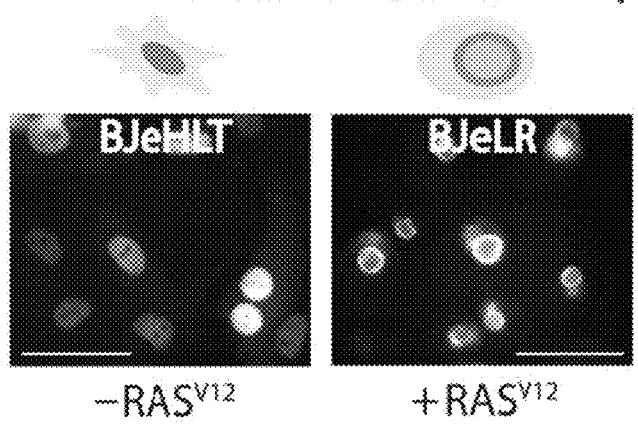
Figure 3:
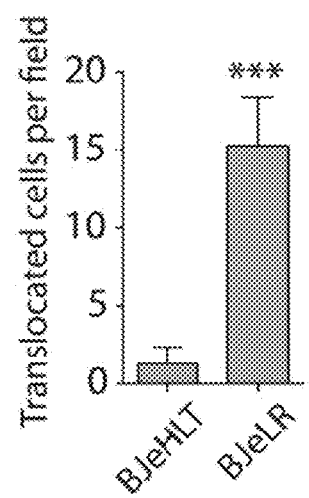
Figure 3:
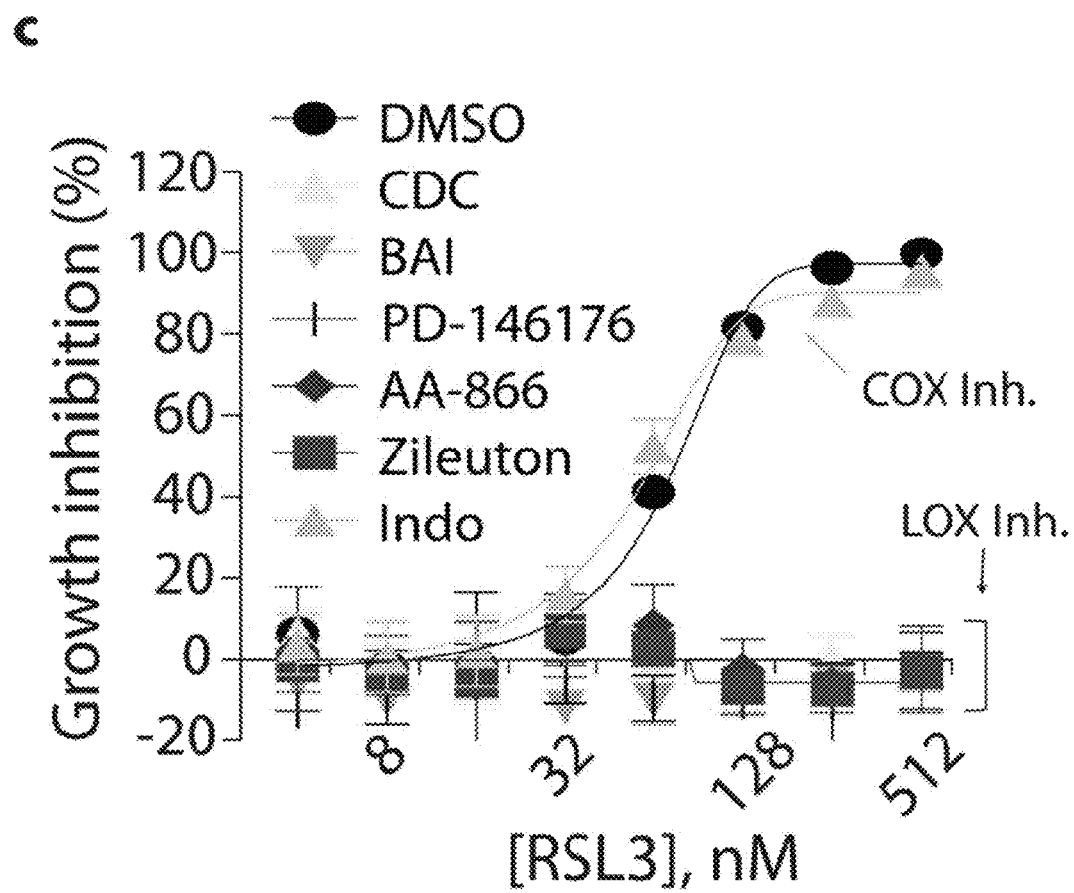
Figure 3:
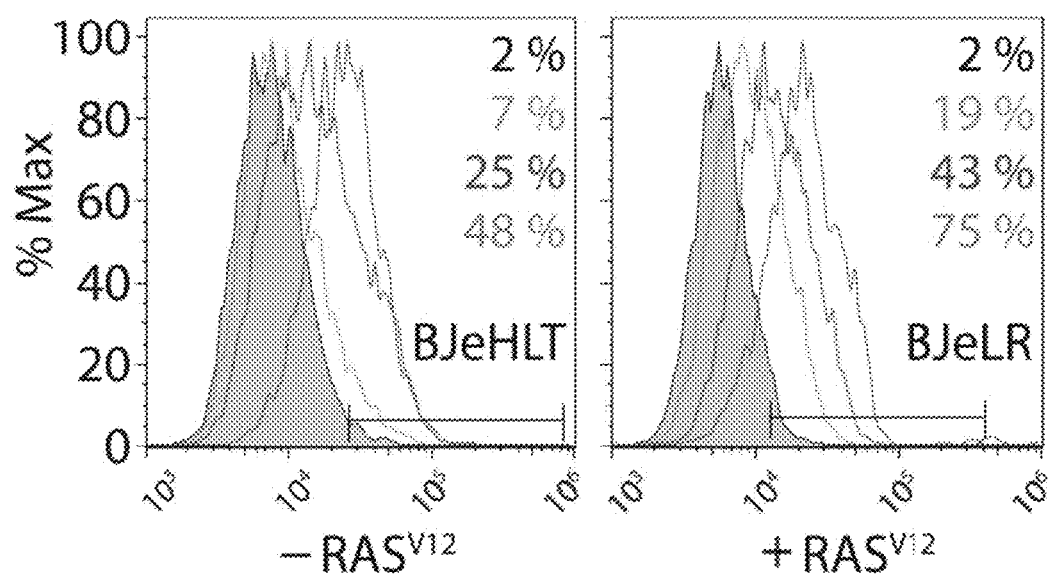
Figure 3:
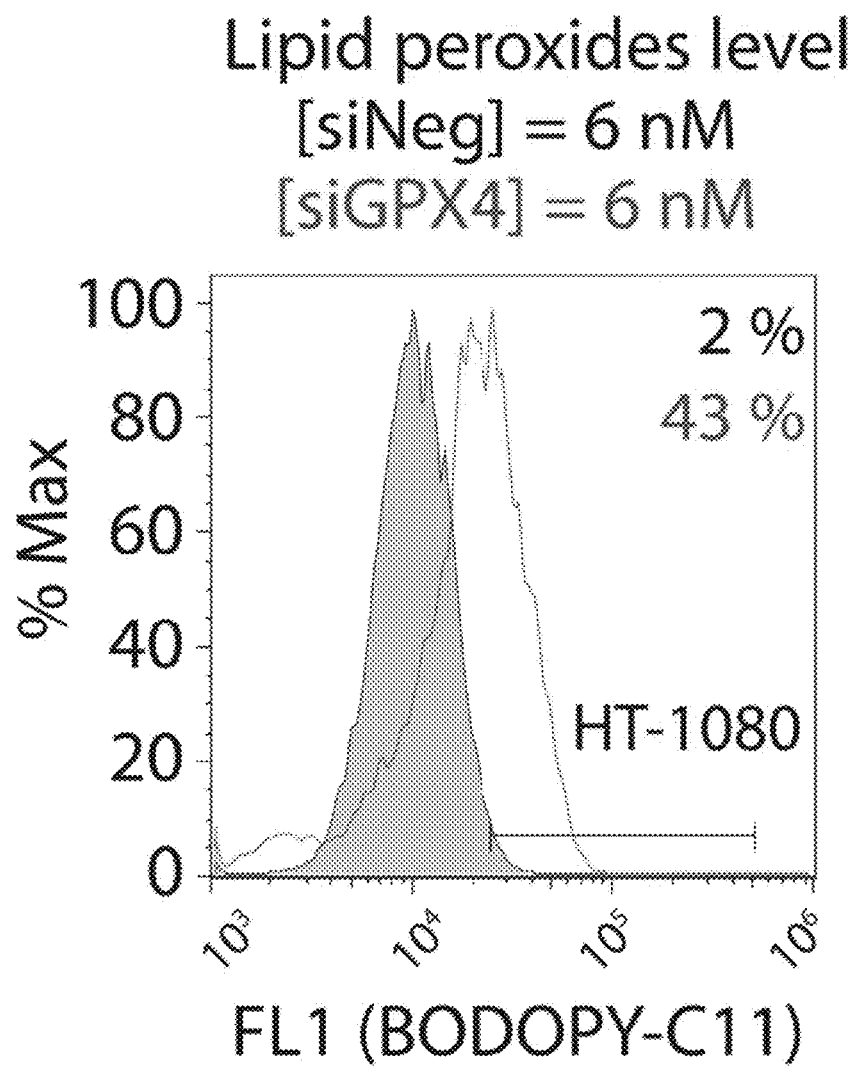
Figure 3:
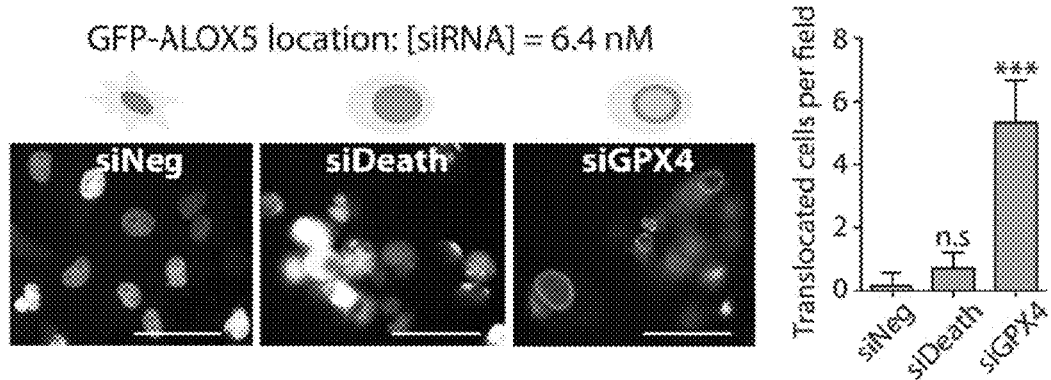
Figure 3:
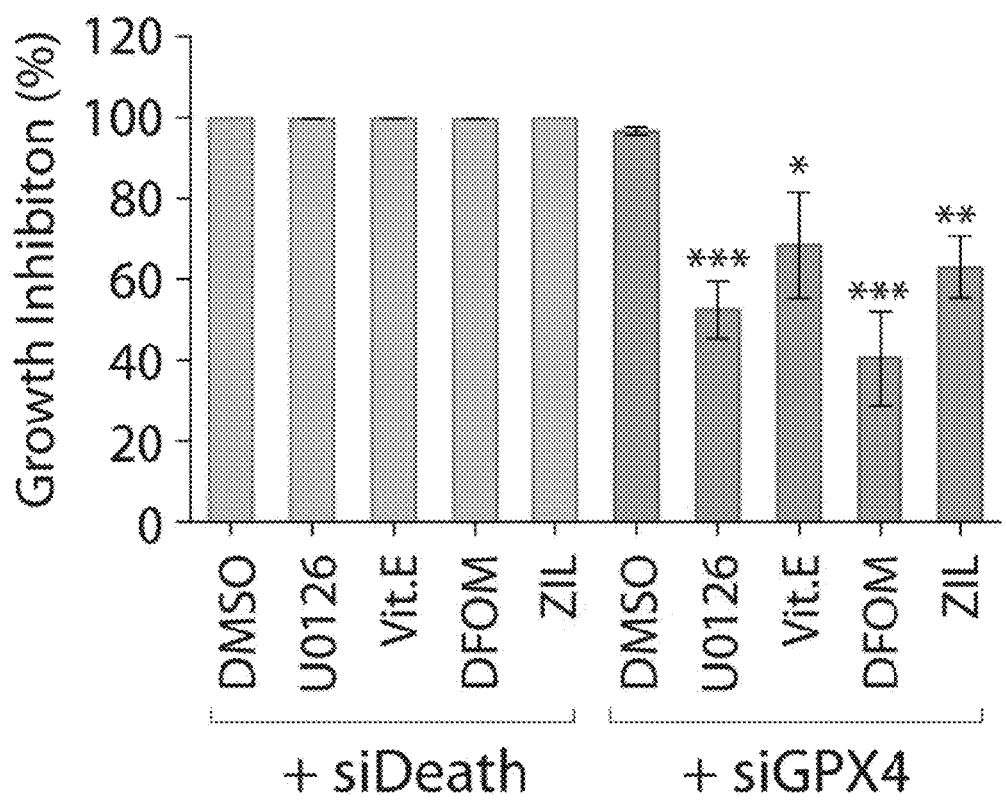
Figure 3:
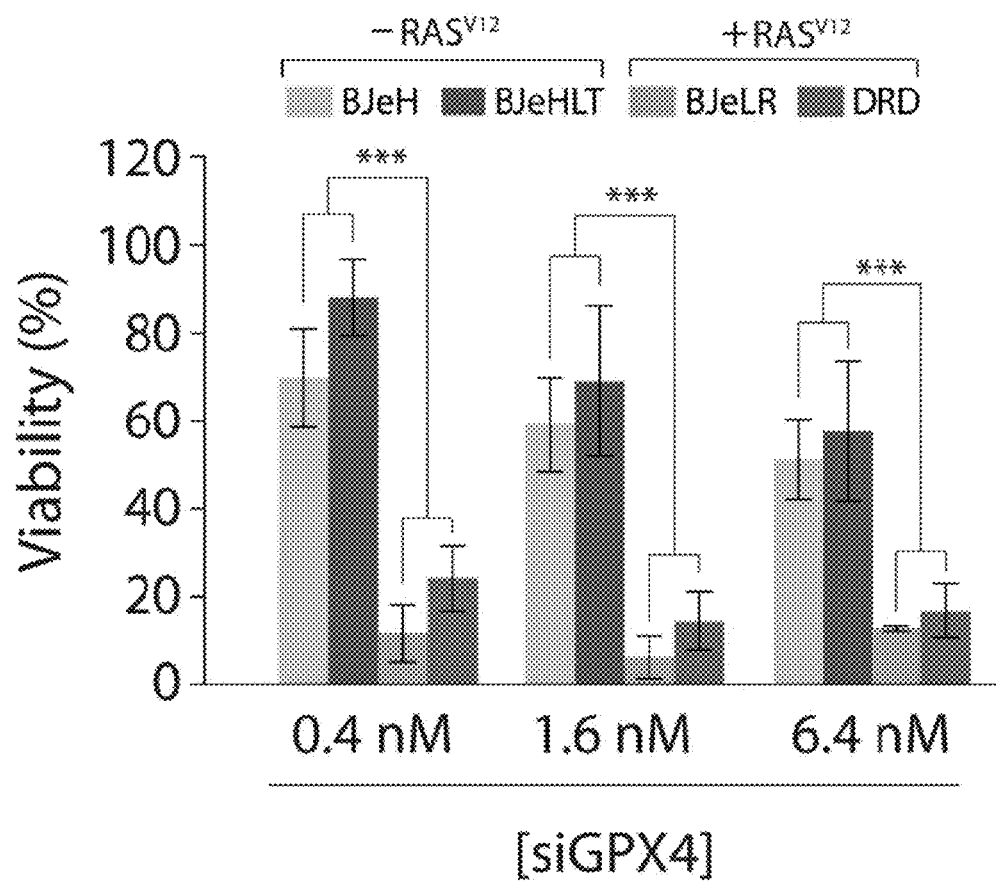

FIG. 3 shows that RSL3-induced ferroptosis activates an ALOX-dependent pathway.

FIG. 3a is a bar graph showing that RSL3 does not deplete GSH. The level of GSH was determined in BJeLR cells after treating with 2 μM RSL3, 10 μM erastin, or 1 mM BSO. Bar graph: mean+s.d.; n=3. *, $P<0.05$.

FIG. 3b shows microscopy images of GFP-ALOX5 and a bar graph demonstrating that GFP-ALOX5 translocated to the nuclear membrane upon RSL3 treatment (0.4 μM) in BJeLR cells, but not in BJeHLT cells. 0.4 μM RSL3 exhibited selective lethality in BJeLR cells. Bar graph: mean+s.d.; n=6 for BJeHLT, n=7 for BJeLR; ***, $P<0.001$. Scale bars, 60 μm FIG. 3c is a graph showing that the lethality of RSL3 was suppressed by ALOX inhibitors, but not by a COX inhibitor, in BJeLR cells. Data are presented as mean±s.d.; n=3.

FIG. 3d are graphs showing that RSL3 treatment generated lipid peroxides in the plasma membrane, as erastin did. The respective percentages in each graph indicate the percentage of BODIPY-C11 positive cell population upon 0, 0.1, 0.2, 0.4 μM RSL3 treatment.

FIG. 3e is a graph showing that HT-1080 cells transfected with a pool of siRNAs targeting GPX4 showed increased lipid peroxide level as assessed by BODIPY-C11 staining. siNeg has no homology to any known mammalian gene and was used as a negative control.

FIG. 3f shows a series of microscopy images of GFP-ALOX5 and a bar graph demonstrating that GFP-ALOX5 remained within the nucleus when siNeg was transfected; however, GFP-ALOX5 translocated to the nuclear membrane upon siGPX4 transfection. Another control siRNA, called siDeath, did not cause translocation during cell death. Bar graph: mean+s.d.; n=6, 7, 6 for siNeg, siDeath and siGPX4, respectively; n.s., not significant; ***, $P<0.001$. Scale bars, 60 μm FIG. 3g is a bar graph showing that known inhibitors of ferroptosis, 10 μM U0126, 100 μM Vit. E, 100 μM DFOM, or 50 μM ZIL, were able to suppress siGPX4-induced cell death. Cell death induced by siDeath could not be suppressed by any known ferroptosis inhibitor. Bar graph: mean±s.d.; n=3; *, $P<0.05$; , $P<0.01$; *, $P<0.001$.

FIG. 3h is a bar graph showing that knockdown of GPX4 displayed an RSL phenotype in the four BJ-derived isogenic cell lines. Bar graph: mean±s.d.; n=3; ***, $P<0.001$.

Figure 4:
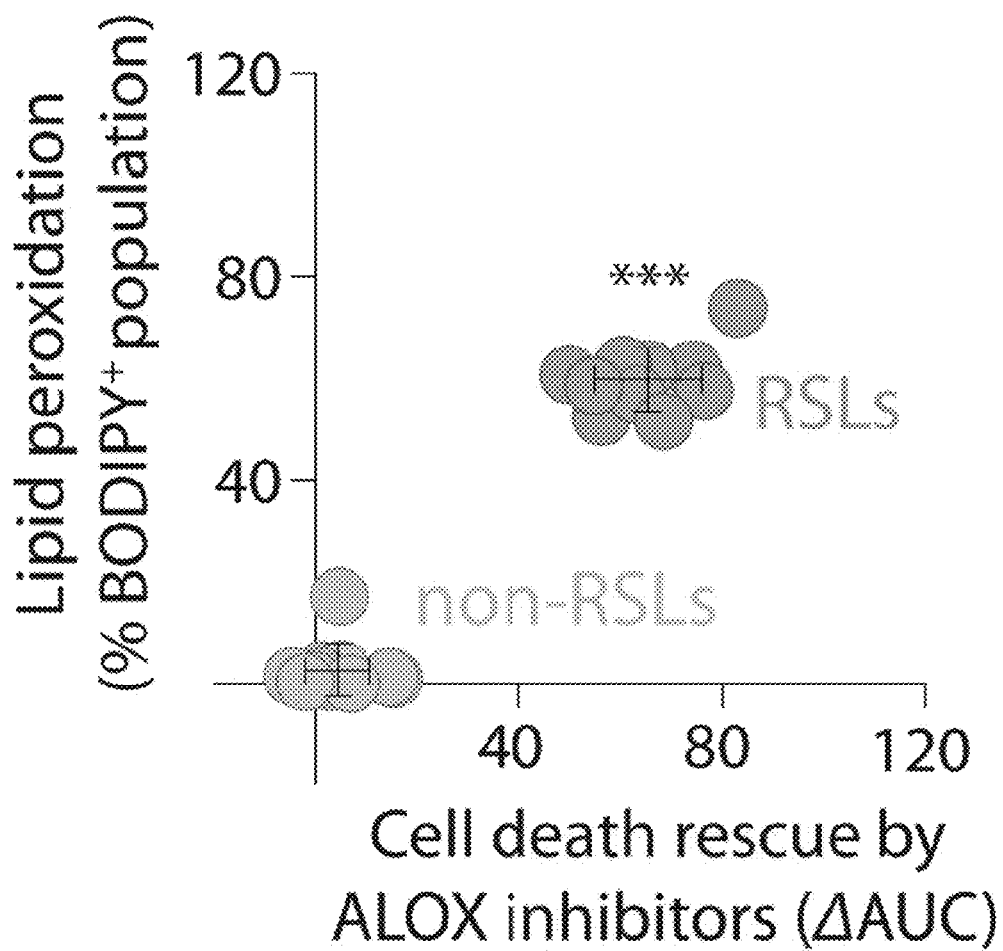
Figure 4:
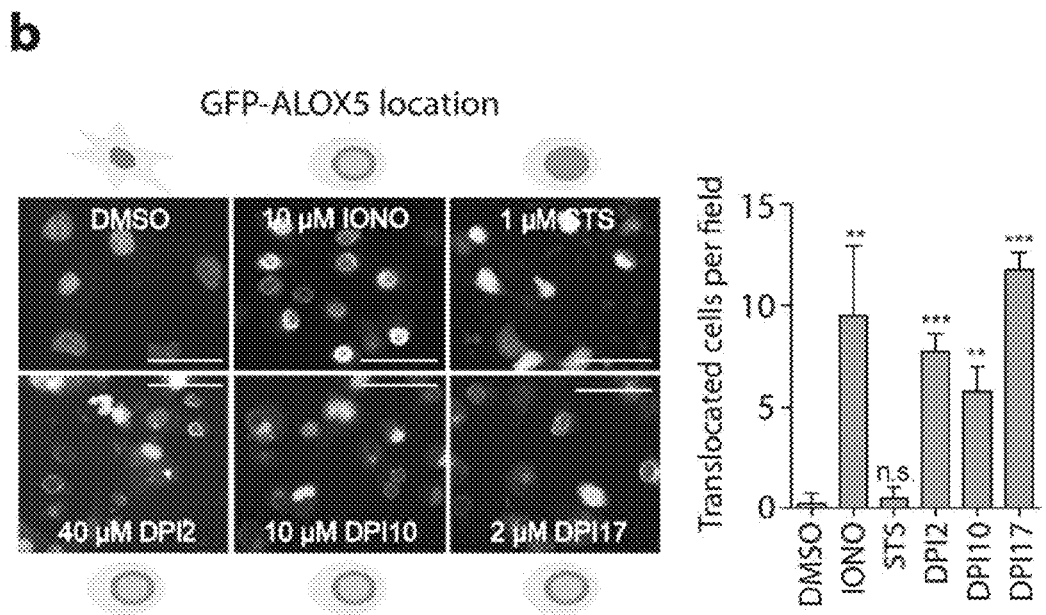
Figure 4:
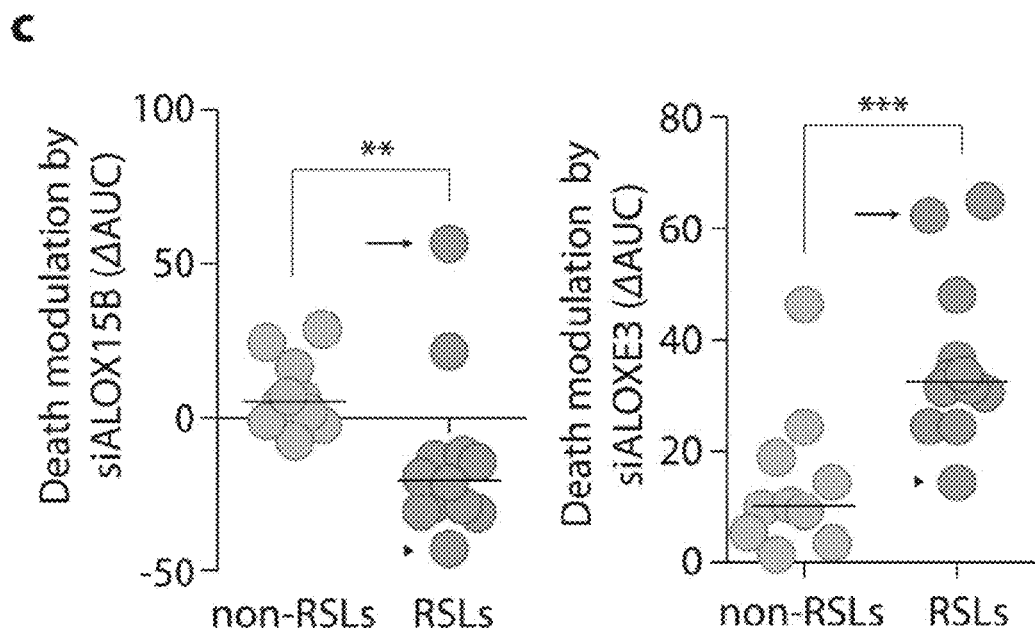
Figure 4:
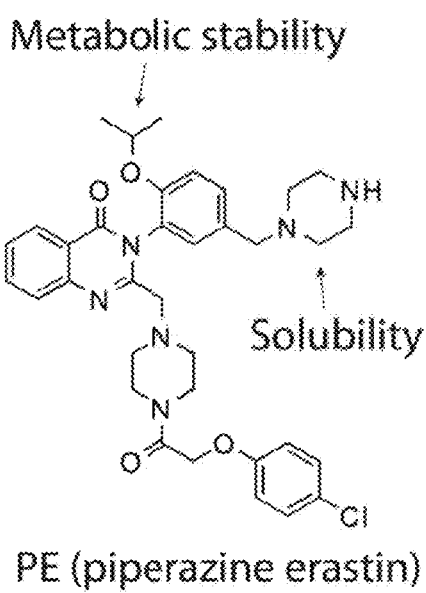
Figure 4:
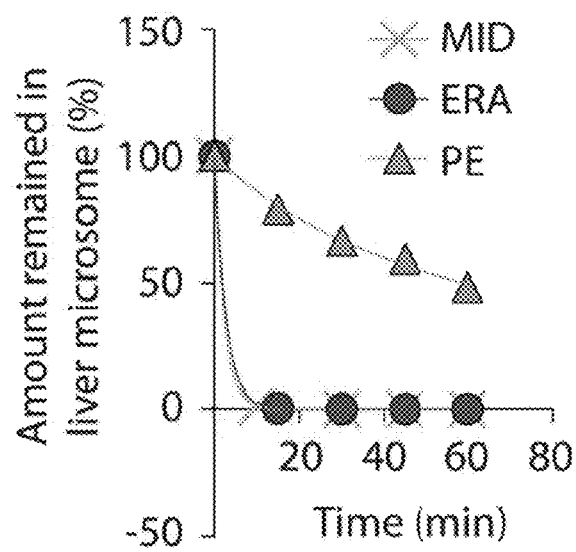
Figure 4:
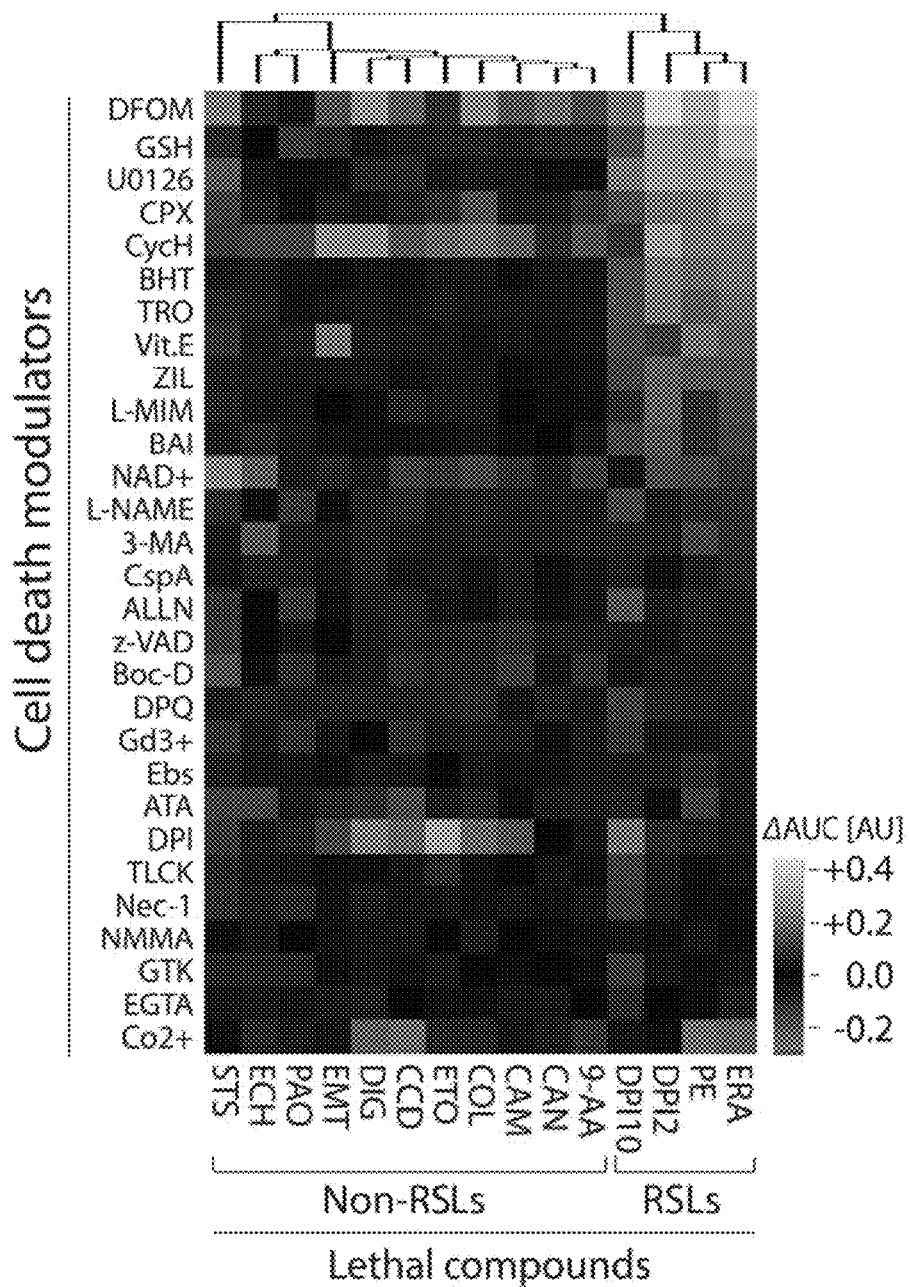
Figure 4:
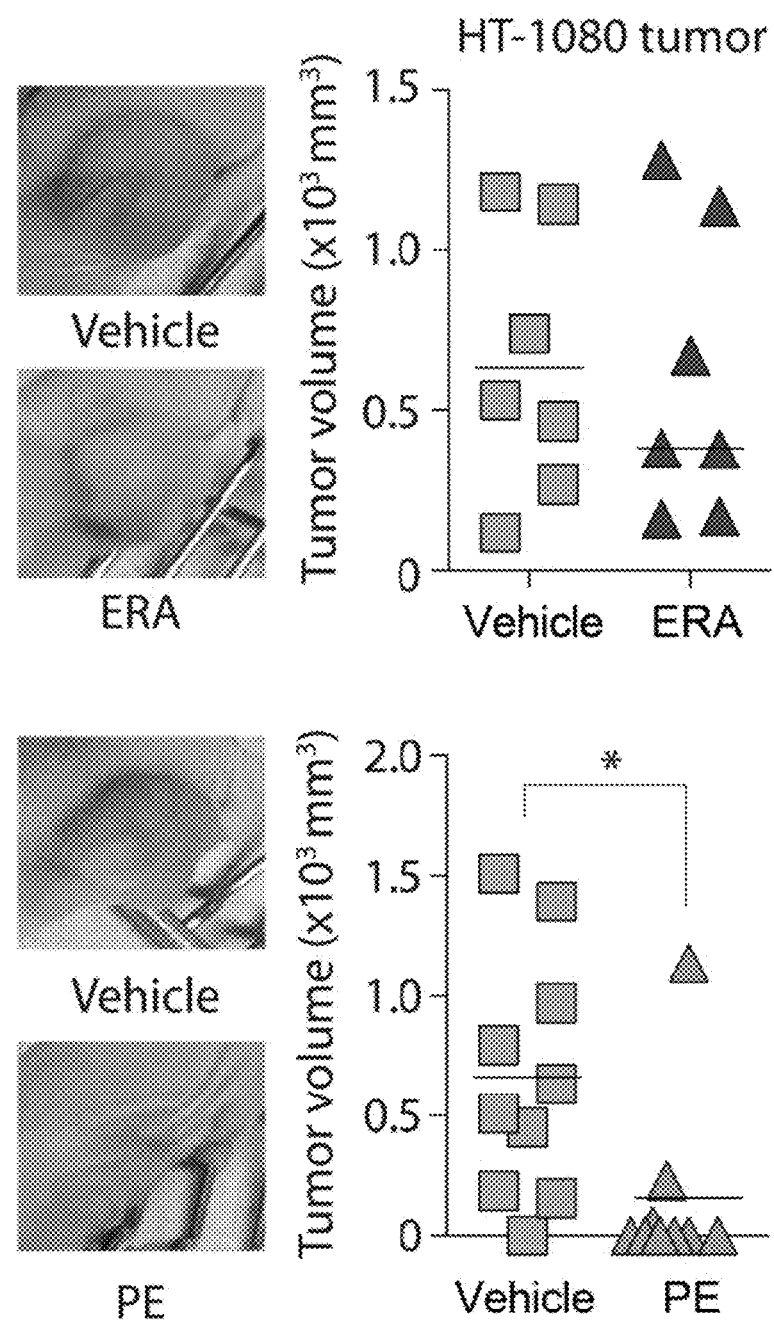
Figure 4:
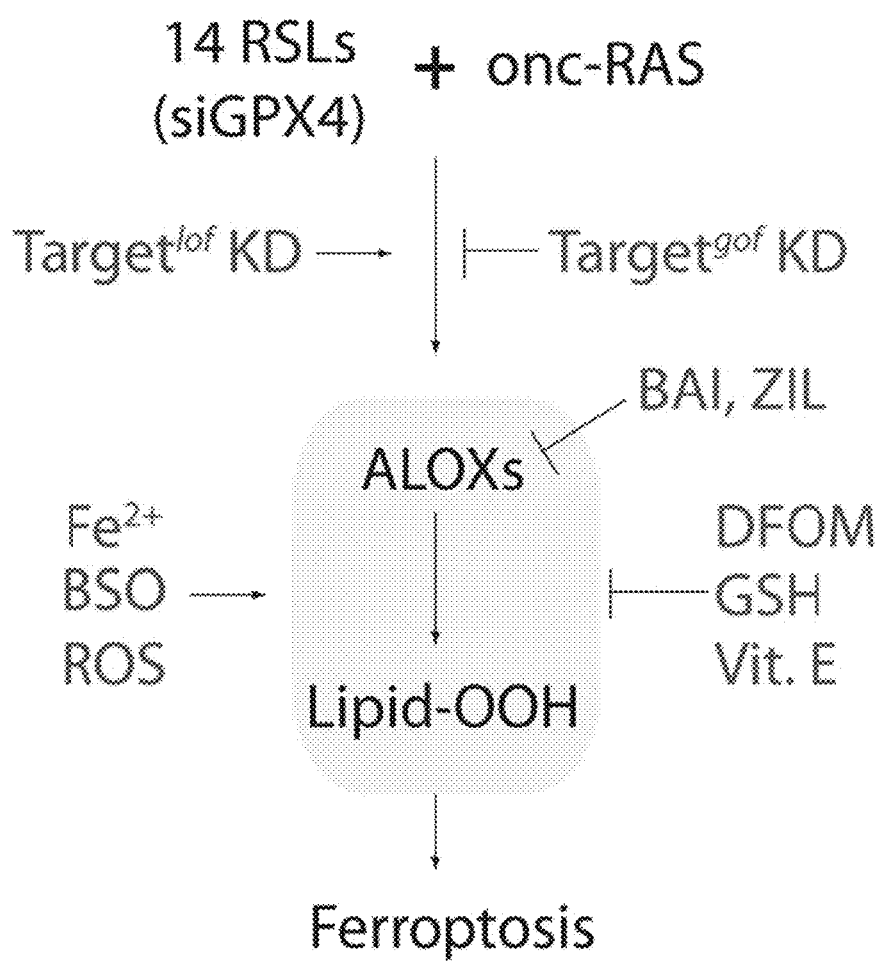

FIG. 4 shows that synthetic lethality with oncogenic-RAS occurs through a lipoxygenase-dependent pathway.

FIG. 4a is a graph showing that RSL compounds, but not non-RSL compounds, caused an increase in BODIPY-C11 fluorescence intensity, a measure of lipid peroxidation. Moreover, the lethality of RSL compounds depended on ALOX activity. The degree of cell death rescue by each ALOX inhibitor was calculated as ΔAUC. A larger ΔAUC indicates a greater rescue by the ALOX inhibitor. Capped lines indicates mean±s.d.; n=10 for RSLs, n=11 for non-RSLs; ***, $P<0.001$.

FIG. 4b shows a series of microscopy images of GFP-ALOX5 and a bar graph demonstrating that the administration of three structurally different RSL compounds, DPI2, DPI10, and DPI17 translocated GFP-ALOX5 to the nuclear membrane in HT-1080 cells, whereas the administration staurosporine (STS), a non-RSL compound, did not. Ionomycin (IONO) was used as a positive control for translocation. Bar graph presents mean+s.d.; n=4; n.s., not significant; , $P<0.01$; *, $P<0.001$. Scale bars, 60 μm.

FIG. 4c are graphs showing that knockdown of ALOXE3 rescued cells from death induced by 12 RSL compounds, whereas ALOX15B knockdown sensitized cells to RSL compounds in HT-1080 cells. Arrow and arrowhead indicate erastin and RSL3, respectively. The horizontal lines indicate median value of each group; n=10 for non-RSLs, n=12 for RSLs; , $P<0.01$; *, $P<0.001$.

FIG. 4d shows the structure of piperazine erastin (PE or Compound 30) and a graph demonstrating that PE has improved metabolic stability in comparison to erastin in a mouse liver microsome assay. Midazolam was used as a positive control for metabolic degradation. The structure of PE is shown on the left. Each data point is a mean of duplicates.

FIG. 4e is a graph showing modulatory profiling (Wolpaw et al., 2011) with PE, erastin, and other lethal molecules. This graph confirmed that PE induced a similar form of cell death as erastin in HT-1080 cells. ΔAUC with a positive sign indicates suppression of cell death, whereas a negative sign indicates sensitization by cell death modulators upon lethal compound treatment. Detailed treatment conditions are shown in Tables 3 and 4 below.

TABLE 3

The table shows the lethal compounds used in the modulatory profiling of FIG. 4e.

| Abbreviation | Full name | Mechanism | Highest conc. in 14-point, 2-fold dilution series (μM) |
|---|---|---|---|
| 9-AA | 9-Aminoacridine | DNA intercalating agent | 50 |
| CAN | Cantharidin | Protein phosphatase inhibitor | 200 |
| CAM | Camptothecin | Topoisomerase I inhibitor | 1 |
| COL | Colchicine | Microtubule depolymerizing agent | 0.6 |
| CCD | Cytochalasin D | Binds to actin and inhibits cytoskeletal function | 10 |
| DIG | Digoxin | Inhibits Na/K ATPase pump | 6.4 |
| ECH | Echinomycin | DNA intercalating agent | 0.002 |
| EMT | Emetine | Inhibits protein synthesis | 0.4 |
| ETO | Etoposide | Topoisomerase II inhibitor | 120 |
| PAO | Phenylarsine oxide | Metabolic poison, protein phosphatase inhibitor | 0.1 |

TABLE 3-continued

The table shows the lethal compounds used in the modulatory profiling of FIG. 4e.

| Abbreviation | Full name | Mechanism | Highest conc. in 14-point, 2-fold dilution series (µM) |
|---|---|---|---|
| STS | Staurosporine | Protein kinase inhibitor | 1 |
| DPI2 | — | unknown | 22.34 |
| DPI10 | — | unknown | 23 |
| ERA | Erastin | Targeting VDAC and system xc- | 18 |
| PE | Piperizine erastin | Targeting VDAC and system xc- | 8 |

TABLE 4

The table shows the cell death modulators used in the modulatory profiling of FIG. 4e.

| Abbreviation | Full name | Mechanism | Concentration (µM) |
|---|---|---|---|
| CspA | Cyclosporine A | Targets CypD | 5 |
| ALLN | ALLN | Inhibits calpains | 2.5 |
| Boc-D | Boc-D-fluoromethylketone | Inhibits caspases | 50 |
| z-VAD | z-VAD-fluoromethylketone | Inhibits caspases | 50 |
| L-NAME | L-NG-Nitroarginine methyl ester | Inhibits nitric oxide synthase | 300 |
| Gd3+ | Gadolinium | Calcium channel blocker | 656 |
| NMMA | NG-Methyl-L-arginine acetate | Inhibits nitric oxide synthase | 250 |
| NAD+ | beta-Nicotinamide adenine dinucleotide | Inhibits sirtuin | 2000 |
| ATA | aurintricarboxylic acid | Topoisomerase II inhibitor | 38 |
| ActD | Actinomycin D | Transcription inhibitor | 0.016 |
| 3-MA | 3-methyladenine | Inhibits pre-autophagosome | 1000 |
| CycH | Cycloheximide | Translation elongation inhibitor | 1.5 |
| Nec-1 | Necrostatin-1 | Inhibits RIP1 kinase | 10 |
| Vit.E | Vitamine E | Lipophilic antioxidant | 100 |
| DFOM | Deferoxamine | Iron chelator | 100 |
| U0126 | U0126 | MEK inhibitor | 10 |
| EGTA | EGTA | Calcium chelator | 2000 |
| DPQ | DPQ | PARP inhibitor | 10 |
| Co2+ | Cobalt chloride | Calcium channel blocker | 656 |
| TLCK | — | Serine protease inhibitor | 100 |
| BHT | Butylated hydroxytoluene | Antioxidant | 400 |
| TRO | Trolox | Antioxidant | 100 |
| L-MIM | L-Mimosine | Cell cycle inhibitor/iron chelator | 200 |
| GSH | reduced glutathione | Antioxidant | 2000 |
| BAI | Baicalein | Inhibits lipoxygenase | 10 |
| ZIL | Zileuton | Inhibits lipoxygenase | 50 |
| DPI | NOX inhibitor1 | NOX inhibitor | 5 |
| GTK | GTK137831 | NOX inhibitor | 20 |
| CPX | Ciclopirox olamine | Lipophilic iron chelator | 5 |
| Ebs | Ebselen | Glutathion peroxidase mimetic | 5 |

FIG. 4f are photographs and plots showing that PE (Compound 30) has improved efficacy over erastinin (ERA) in preventing HT-1080 tumor formation in a mouse xenograft model. The images show representative tumors in live mice from each treatment group. The horizontal lines in the graphs indicate the mean value of tumor size in each group; n=7 in erastin testing; n=10 in PE testing; *, P<0.05.

FIG. 4g is a scheme showing a proposed molecular pathway enabling RAS-synthetic-lethality and ferroptotic cell death by the RSL compounds; lof: loss of function, gof: gain of function.

Figure 5:
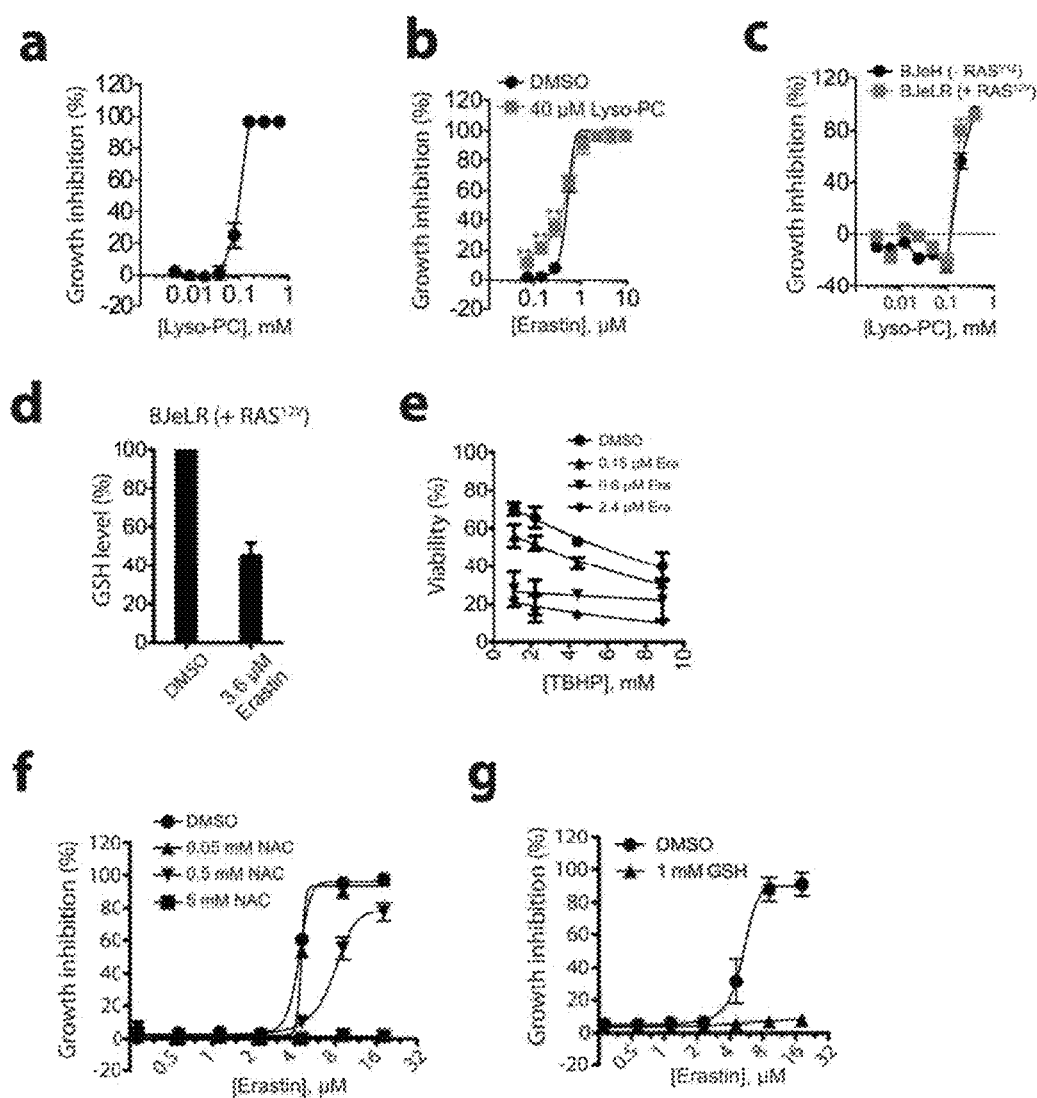

FIGS. 5a-c are graphs showing that lysophosphatidyl choline (Lyso-PC) contributes to the lethality of erastin but does not account for the selectivity toward oncogenic-RAS-expressing cells. Data are presented as mean±s.d.; n=3; **, P<0.01. Cell viability was determined using alamar blue after 24 hours of incubation with indicated compound. In FIG. 5a, HT-1080 cells were incubated with the indicated amount of Lyso-PC. In FIG. 5b, Erastin was added to HT-1080 cells in a 2-fold dilution series in the presence or absence of lyso-PC. In FIG. 5c, BJeH (wild type HRAS) or BJeLR ($HRAS_{G12V}$) cells were treated with lyso-PC.

FIGS. 5d-g are graphs showing that GSH depletion is a functionally important biochemical change in erastin-induced cell death. Data are presented as mean±s.d.; n=3; **, P<0.01. In FIGS. 5e-g, cell viability was determined using alamar blue after 24 hours of incubation with indicated compound. In FIG. 5d, Erastin was added to BJeLR cells for 24 hours. The cellular GSH level in each sample was determined as set forth in Example 1. FIG. 5e shows that GSH depletion by erastin sensitized cells to TBHP-induced oxidative stress in U-2 OS cells. FIG. 5f shows that supplementation with N-acetyl cystein (NAC), a GSH precursor, rescued U-2 OS cells from cell death by erastin. In FIG. 5g, HT-1080 cells were treated with erastin in the presence or absence of 1 mM GSH for 24 hours.

Figure 6:
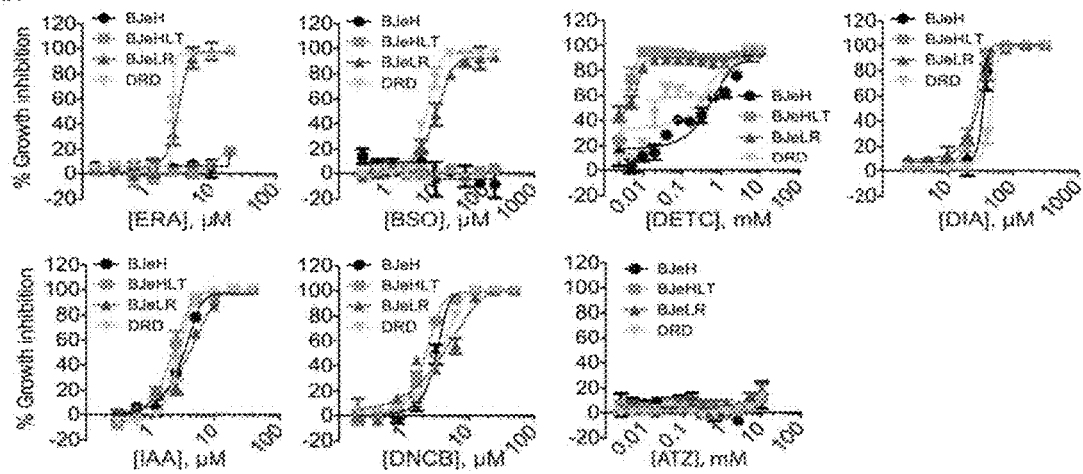

FIG. 6 shows testing of compounds targeting cellular antioxidant systems in the four BJ-derived cell lines. FIG. 6a shows a series of growth inhibition curves of antioxidant inhibitors in the 4 cell lines. FIG. 6b is a table listing the compounds used in the 4 BJ-derived cell line testing of FIG. 6a with the target information. Data are presented as mean±s.d.; n=3.

Figure 7:
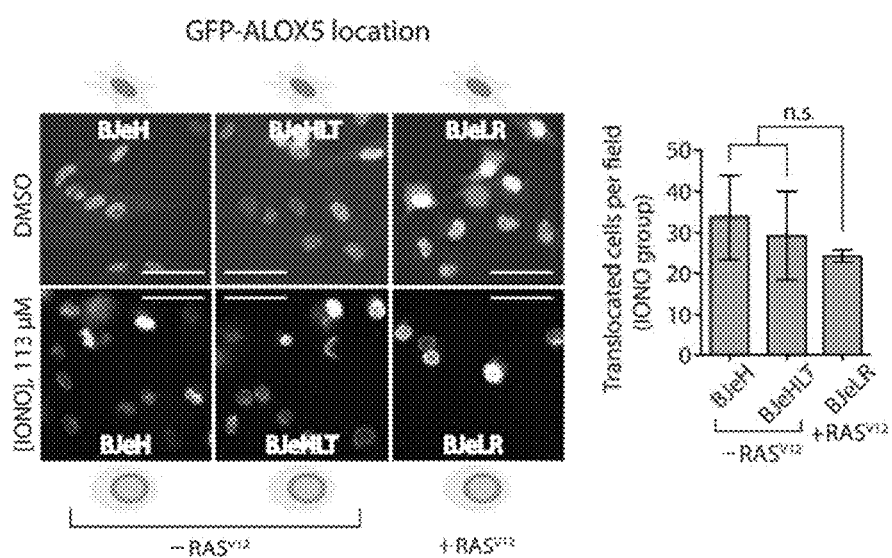

FIG. 7 shows a series of microscopy images and a graph demonstrating that GFP-ALOX5 translocated to the peri-nuclear membrane region upon ionomycin treatment. GPF-ALOX5 remained within the nucleus when expressed in BJeH, BJeHLT, and BJeLR cells (upper panel), but translocated to the perinuclear membrane region upon ionomycin treatment (lower panel). Unlike erastin-induced translocation (FIG. 2d), all three BJ cell lines responded equally to ionomycin treatment. BJ cells were treated with 113 µM ionomycin for 12 hours. Bar graph; n=3-4; n.s.=not significant. Scale bar=60 µm.

FIG. 8a shows a series of graphs demonstrating that erastin and RSL3 share a common dependency on iron, MEK, and reactive oxygen species. FIG. 8b shows a series of graphs demonstrating that erastin and RSL3 exhibited different responses to other cell death inhibitors. BJeLR cells were treated with erastin or RSL3 in the presence or absence of the indicated inhibitors for 24 hours followed by viability determination using alamar blue dye. DFOM: Deferoxamine, Vit.E: Vitamine E, $Co^{2+}$: $CoCl_2$, TLCK: serine protease inhibitor, CHX: Cycloheximide, NAC: N-acetylcystein. Data are presented as mean±s.d.; n=3.

Figure 9:
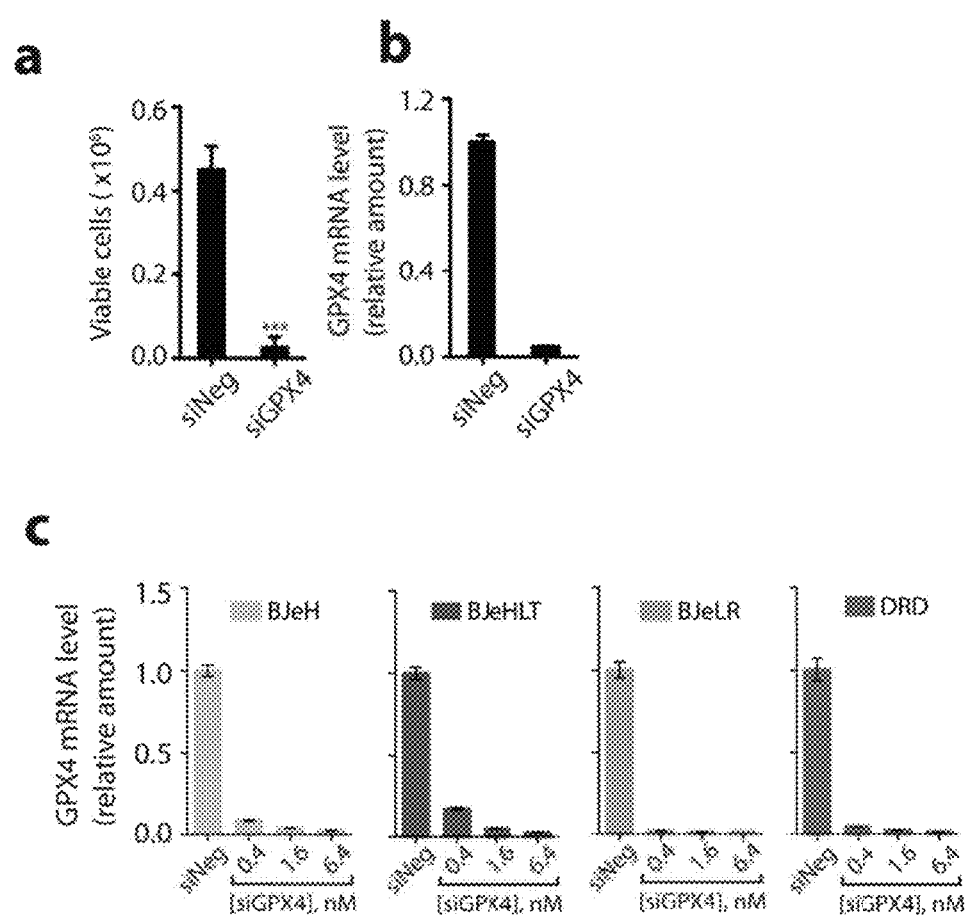

FIG. 9 shows the effect of siGPX4 on cell viability and GPX4 mRNA level. In FIG. 9a, HT-1080 cells were transfected with 6.4 nM siGPX4 for 4 days, and cell viability was determined by ViCell. FIG. 9b is a graph showing that a qPCR experiment confirmed the reduction of gPX4 expression in HT-1080 cells transfected with siGPX4. FIG. 9c is a series of graphs showing the confirmation of GPX4 knockdown by the siRNA pool using qPCR analysis in 4 BJ-derived cell lines. Comparative analysis was carried out using ACTB (human actin B) gene as an endogenous control. Data are presented as mean±s.d.; n=3.

Figure 10:
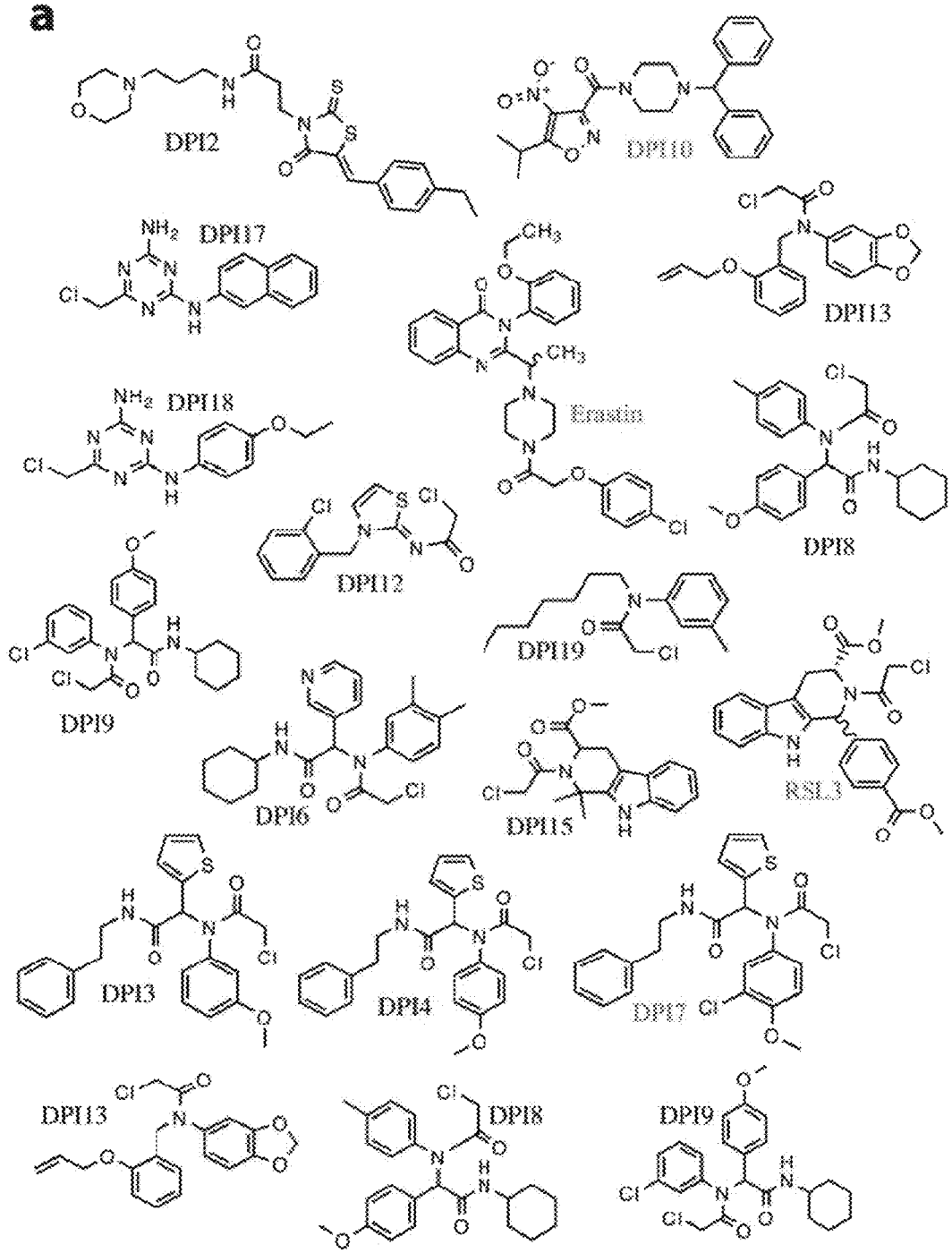

FIG. 10 shows the structure of certain RSL compounds discovered from a high throughput screening campaign of greater than 1 million compounds with the four BJ-derived cell lines. Of those compounds, 80,497 were purchased and synthesized in the inventors' laboratory, 303,282 compounds were obtained through the Molecular Libraries Probe Production Centers Network (MLPCN), and 658,301 compounds were made in collaboration with the Genomics Institute of the Novartis Research Foundation (GNF). Structure of erastin, RSL3, DPI7, and DPI10, were known previously.

Figure 10B:
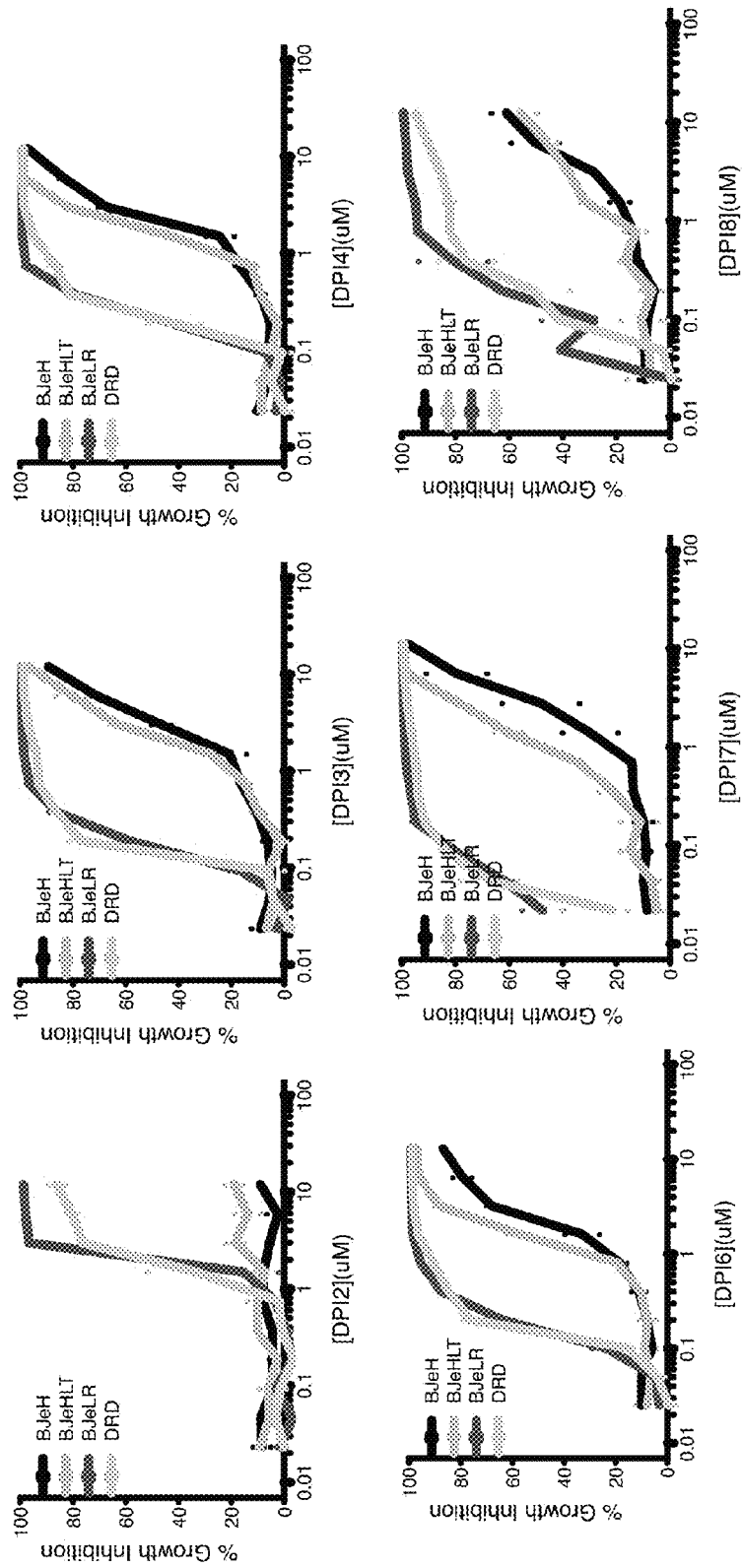
Figure 10B:
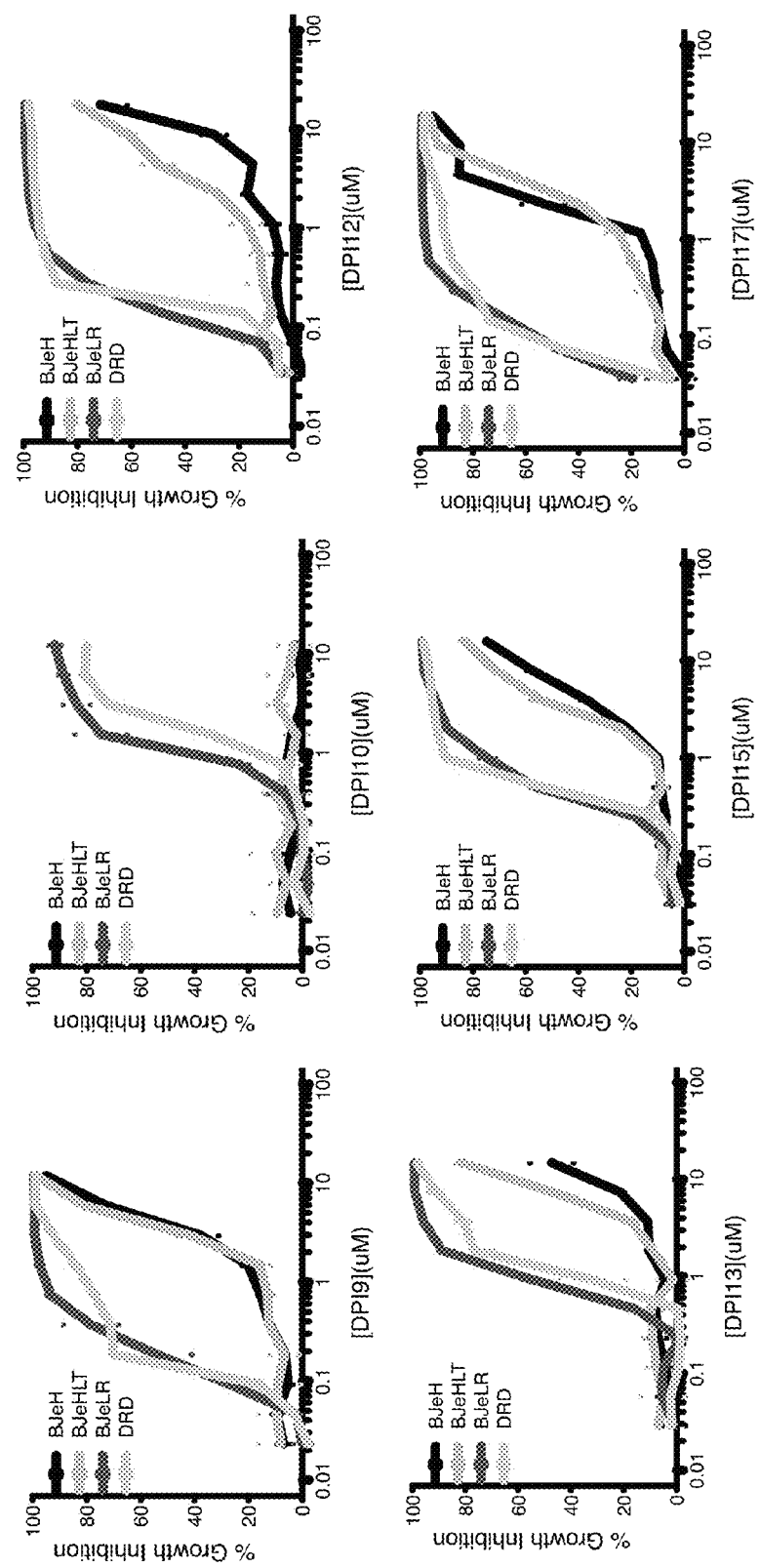
Figure 10B:
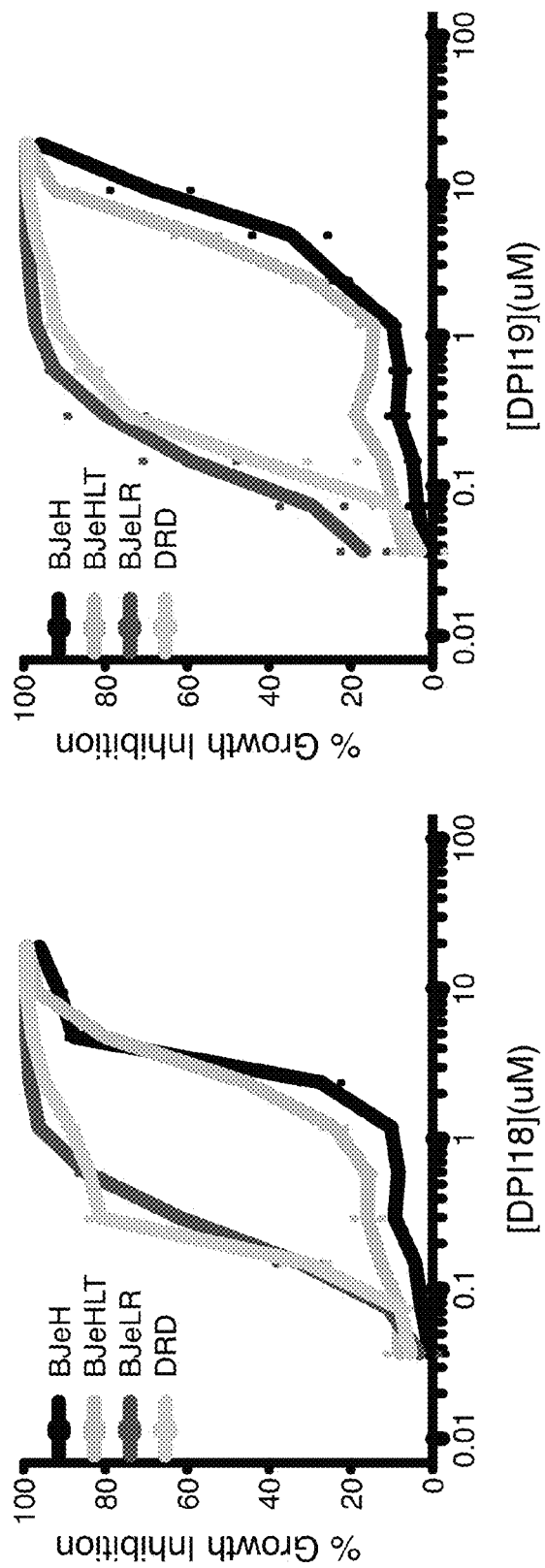
Figure 10:
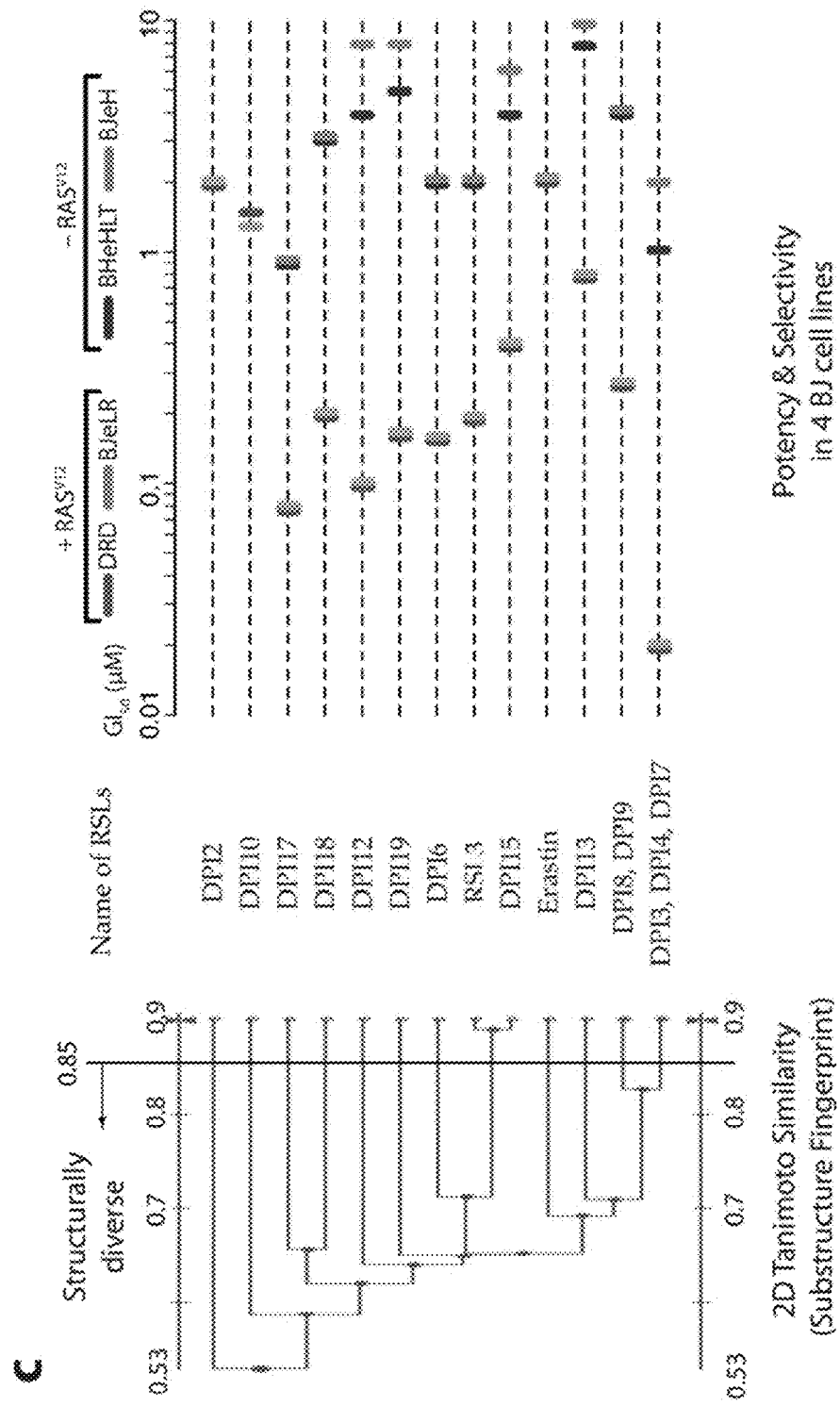

FIG. 10b shows a series of graphs demonstrating that the RSL phenotype of 14 compounds (as indicated) was confirmed in the 4-BJ cell system. The RSL compounds demonstrate increased potency in two cell lines with oncogenic-RAS (BJeLR and DRD) compared to two cell lines without oncogenic-RAS (BJeH and BJeHLT). Cells were incubated with each compound for 2 days followed by viability determination using alamar blue. The line shows mean of duplicate data points.

FIG. 10c is a graph showing the fourteen RSL compounds from FIG. 10b clustered based on 2-dimensional (2-D) structure similarity and their respective potency and selectivity. The Tanimoto equation was used to compute the degree of similarity. The Tanimoto score is a fraction between 0 and 1 where 0 means no similarity and 1 means identical. The inventors considered that compounds clustered with >0.85 Tanimoto similarity as a single group, which resulted in the characterization of 12 different groups.

FIG. 11a shows a series of graphs demonstrating that ten additional RSL compounds were tested and were found to generate lipid peroxides. The indicated RSL compounds were added to BJeLR cells at 10 μM for 6 hours (or 12 hours for DPI2) to induce cell death. FIG. 11b shows a series of graphs demonstrating that eleven diverse non-RSL compounds were tested for lipid peroxide generation in BJeLR cells. Only phenylarsine oxide (PAO) showed weak generation of lipid peroxides, whereas all the other lethal compounds did not show any lipid peroxide generation. The indicated lethal compounds were administered to BJeLR cells to induce cell death according to the conditions shown in FIG. 11c. After cell death was initiated, cells were stained with BODIPY-C11 (581/591) and subjected to flow cytometric analysis to assess the level of lipid peroxidation. The number in each graph indicates percentage of BODIPY-C11 stain positive cells out of parental cell population. FIG. 11c is a table showing treatment conditions for the non-RSL compounds used in FIG. 4a and FIG. 11a.

FIG. 12a shows a series of graphs demonstrating that ALOX inhibitors prevented cell death by all RSL compounds. Data points represent mean of duplicates, FIG. 12b show a series of graphs demonstrating that ALOX inhibitors did not rescue cell death induced by 11 diverse non-RSL compounds. HT-1080 cells were seeded in 384-well plates, treated with the indicated amount of compounds with or without 10 μM of BAI or 50 μM of ZIL for 24 hours. The percent growth inhibition was determined using alamar blue. Data are presented as mean±s.d.; n=3.

FIG. 13a shows a series of micrographs demonstrating that RSL compounds induced translocation of GFP-ALOX5 to the perinuclear membrane region, whereas non-RSL lethal compounds did not. HT-1080 cells stably expressing GFPALOX5 were treated with the indicated compounds under the conditions detailed in FIG. 13b. Under these conditions, cells were dying or dead (see the last photo of DMSO sample which shows untreated cells). Note that digioxin (DIG) did translocate GFP-ALOX5 to the perinuclear membrane region in a small portion of the cell population (arrow). Digioxin is known to increase cellular calcium concentration that can translocate GFP-ALOX5, similarly to ionomycin. Scale bars, 60 μm.

FIG. 13b is a table showing treatment conditions used in FIG. 4b and FIG. 13a.

FIG. 13c shows a series of microscopy images demonstrating that a few digoxin treated cells showed translocation but not selectively in three BJeLR cell lines (arrow). Scale bars=100 μm. Cells were treated with 10 μM digoxin for 12 hours.

Figure 14:
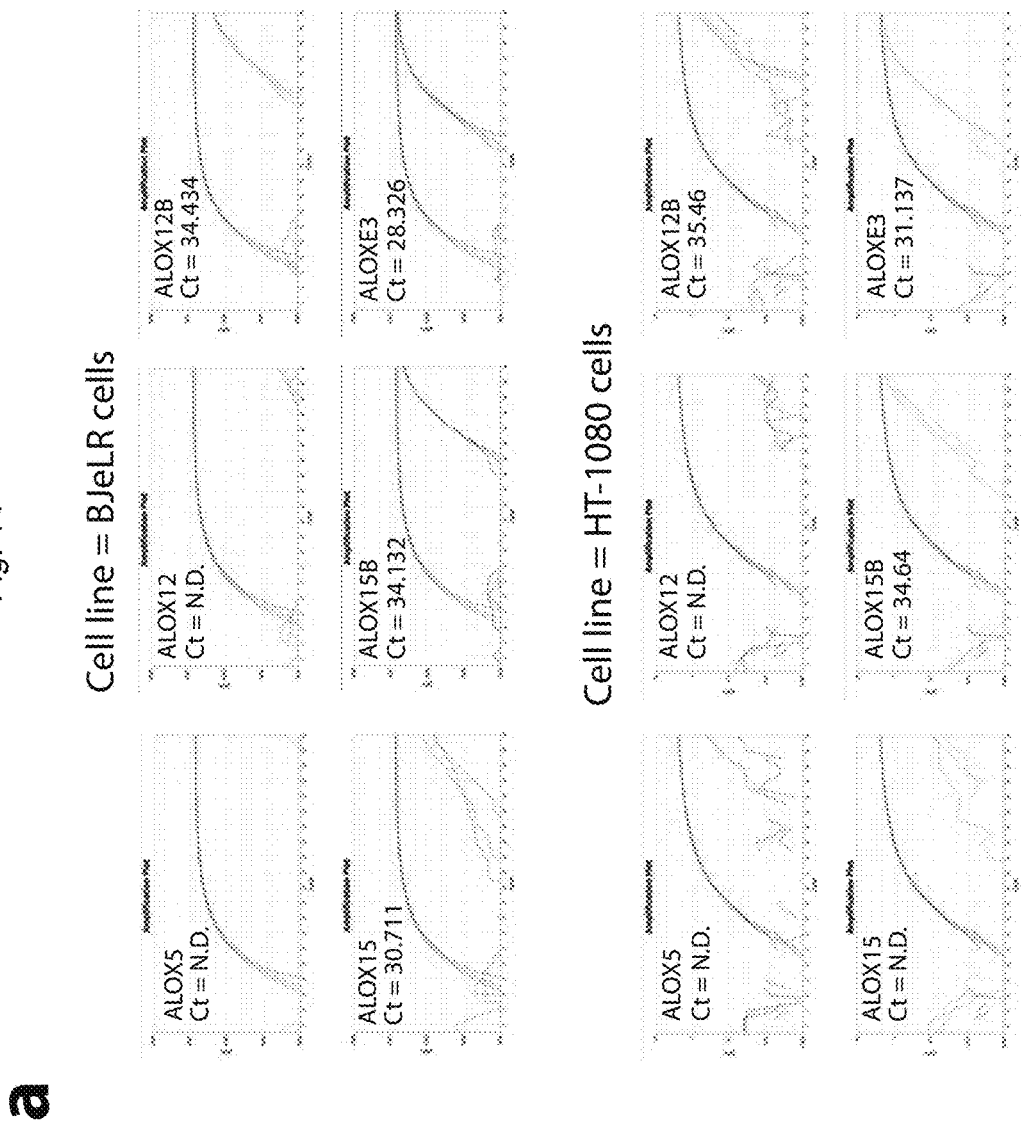
Figure 14:
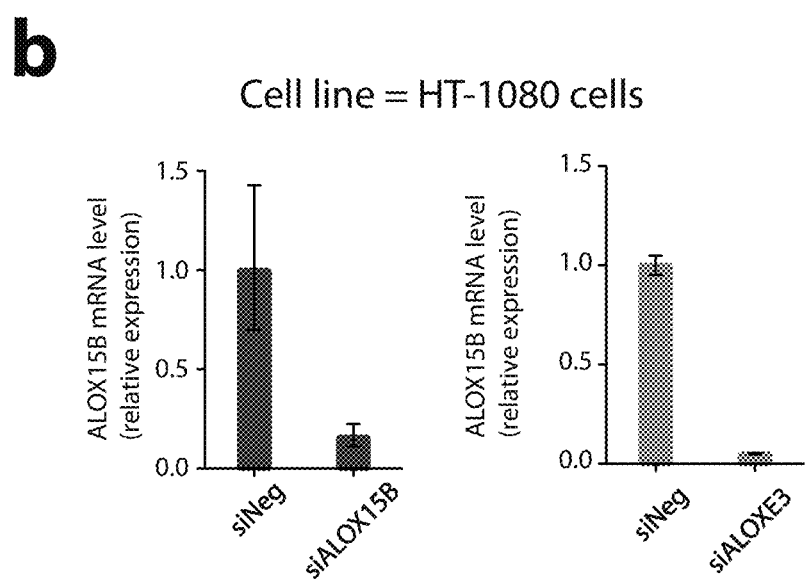

FIG. 14a shows a series of graphs demonstrating the expression analysis of ALOX genes in BJeLR and HT-1080 cells. The graphs show the amplification plot of each ALOX isoform. Triplicate samples were analyzed for each gene using mRNA from either cell line. ACTB gene amplification was served as endogenous control. The gene name and the Ct (cycle of threshold) number are presented. N.D.=not determined. Ct value of greater than 35 is considered weak expression, which suggests that ALOXE3 is the major isoform expressed in these cell lines.

FIG. 14b shows two graphs demonstrating that the knockdown of ALOX15B and ALOXE3 expression by a pool of siRNAs was confirmed using qPCR analysis. Data are presented as mean±s.d.; n=3.

Figure 15:
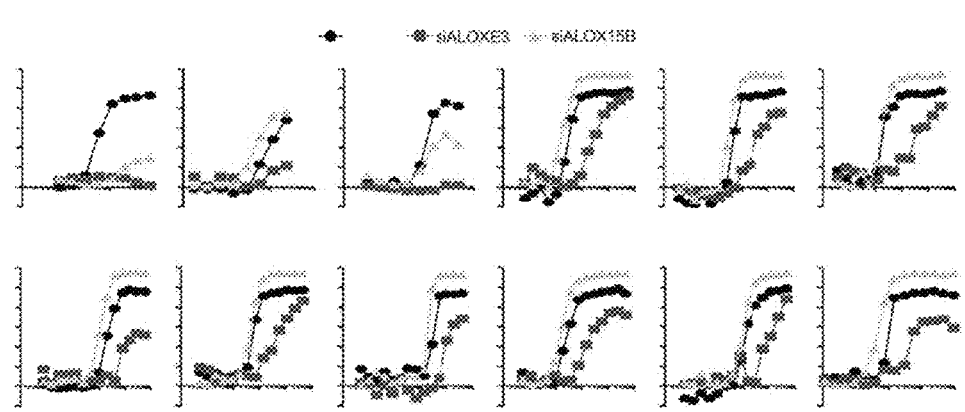
Figure 15:
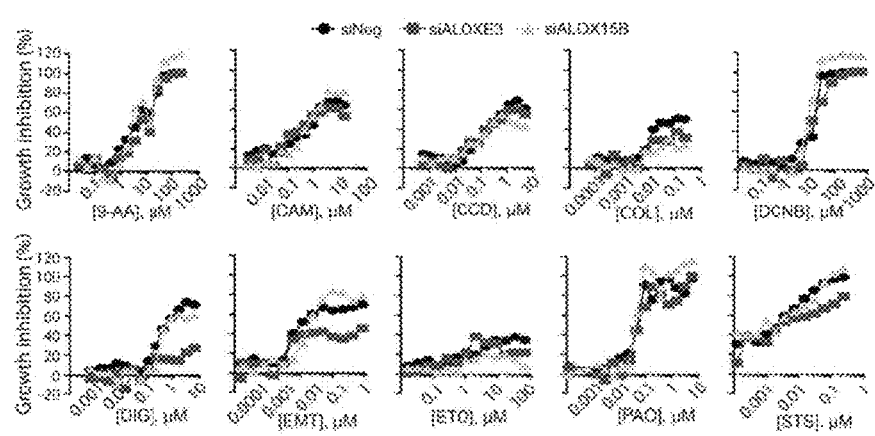

FIG. 15 shows modulation of RSL-induced cell death (FIG. 15a) or non-RSL-induced cell death (FIG. 15b) by knockdown of ALOX15B or ALOXE3. HT-1080 cells were transfected with siRNA pools targeting either ALOX15B or ALOXE3, and then, treated with the indicated RSL compounds in 2-fold dilution series. 24 hours after compound treatment, alamar blue was added to the culture at a final concentration of 10% in growth media to determine cell viability. The percent growth inhibition was calculated from the fluorescence intensity of each well in 384-well assay plates. Data points represent mean of duplicates.

Figure 16:
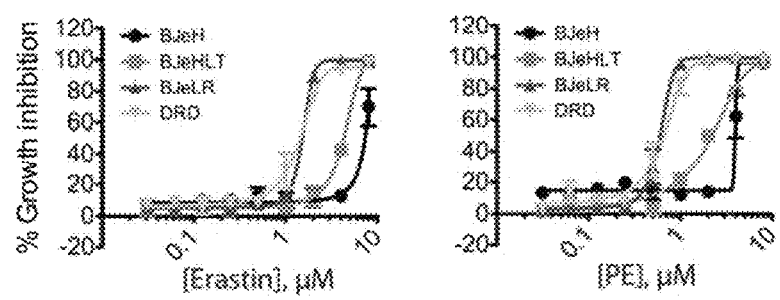
Figure 16:
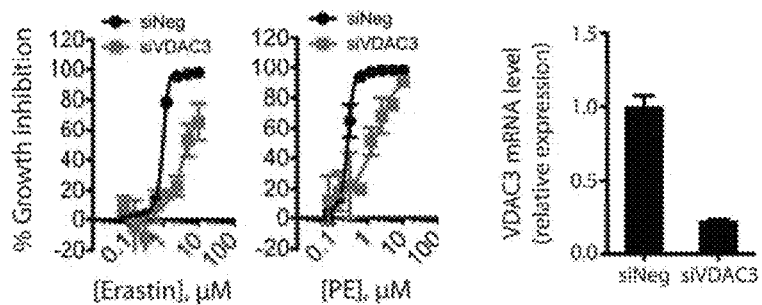

FIG. 16 shows that PE (Compound 30) is an erastin analog with improved solubility, and metabolic stability. In FIG. 16a, PE was added to the 4 BJ-derived cell lines and its potency and selectivity were compared with erastin. FIG. 16b is a table showing the summary of a comparison between PE and erastin. The water solubility was determined using a microplate nephelometer (NEPHELOstar, BMG labtech, Cary, N.C.). FIG. 16c shows a series of graphs demonstrating that knockdown of VDAC3 rescued HT-1080 cells from cell death by erastin and PE, suggesting that they act through the same mechanism. FIG. 16c also shows confirmation of VDAC3 knockdown using qPCR method.

Figure 17:
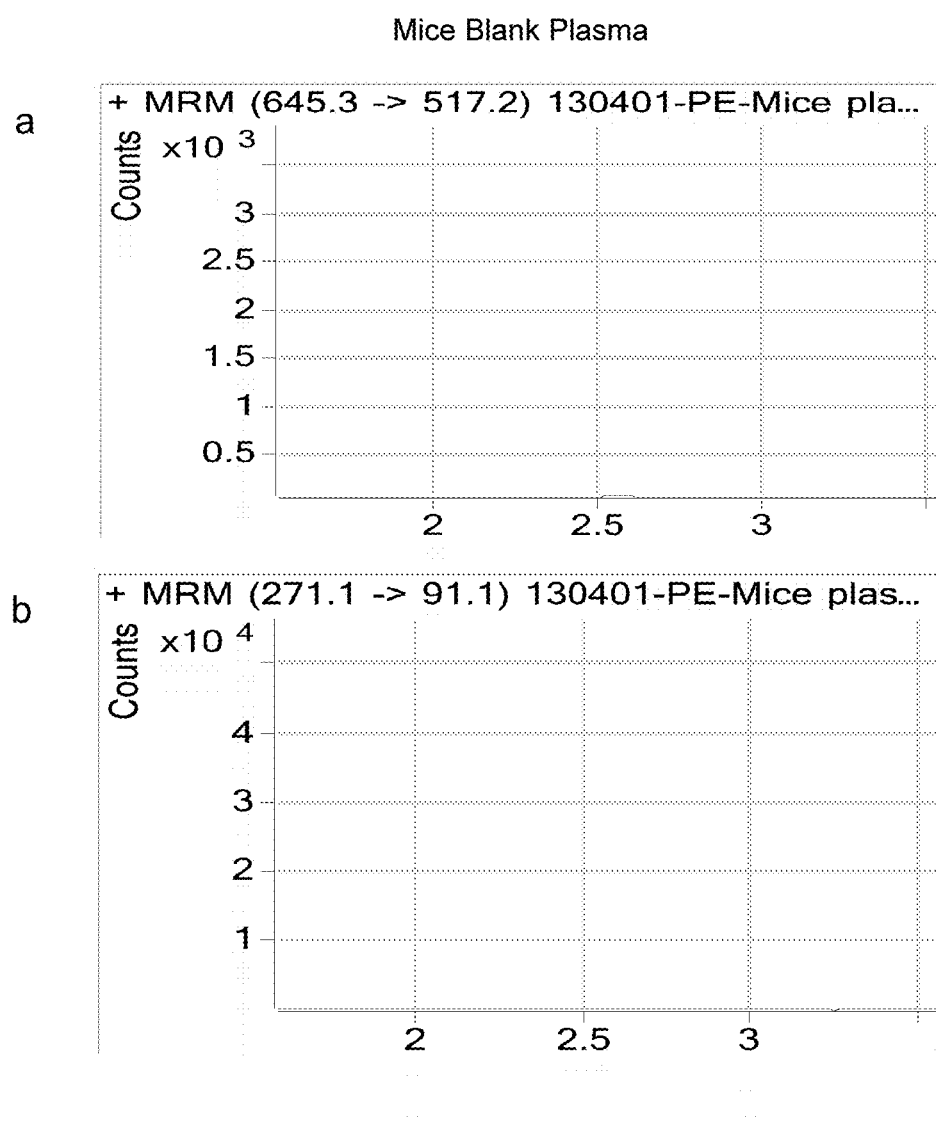
Figure 17:
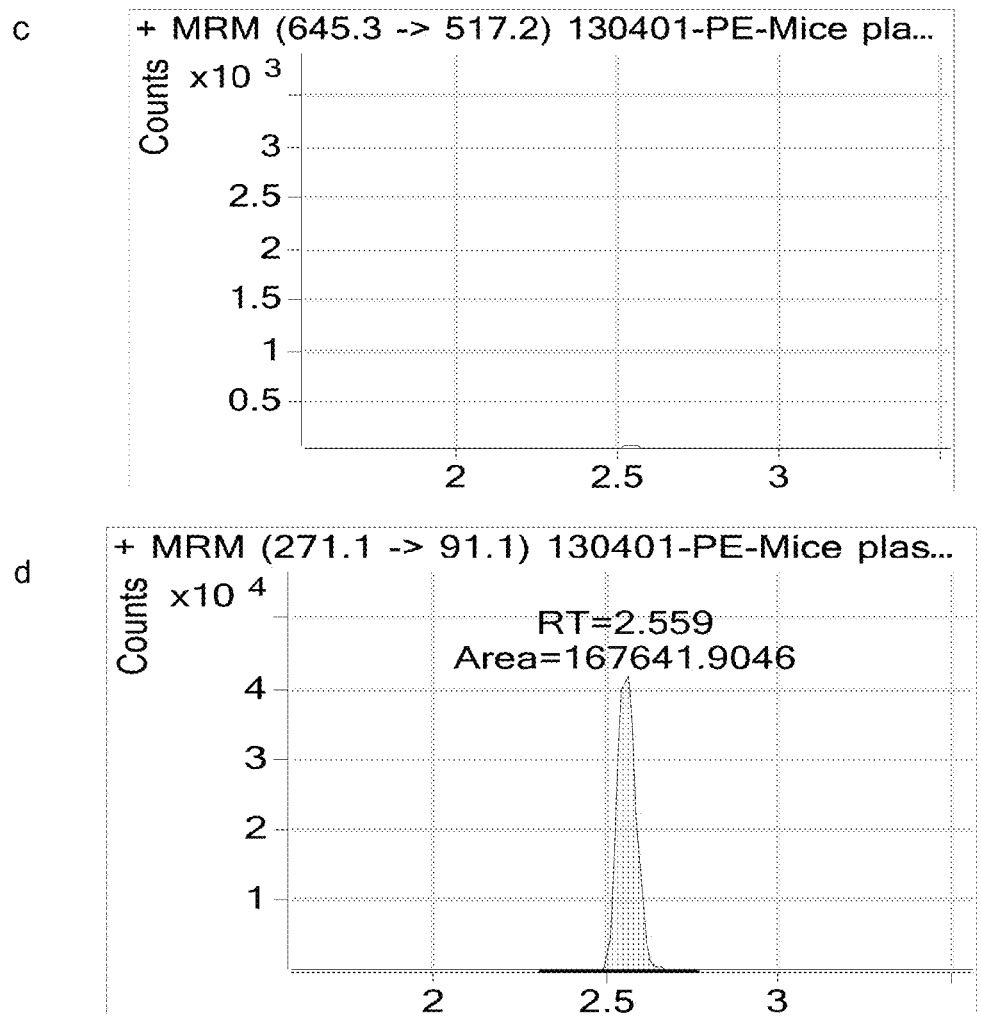
Figure 17:
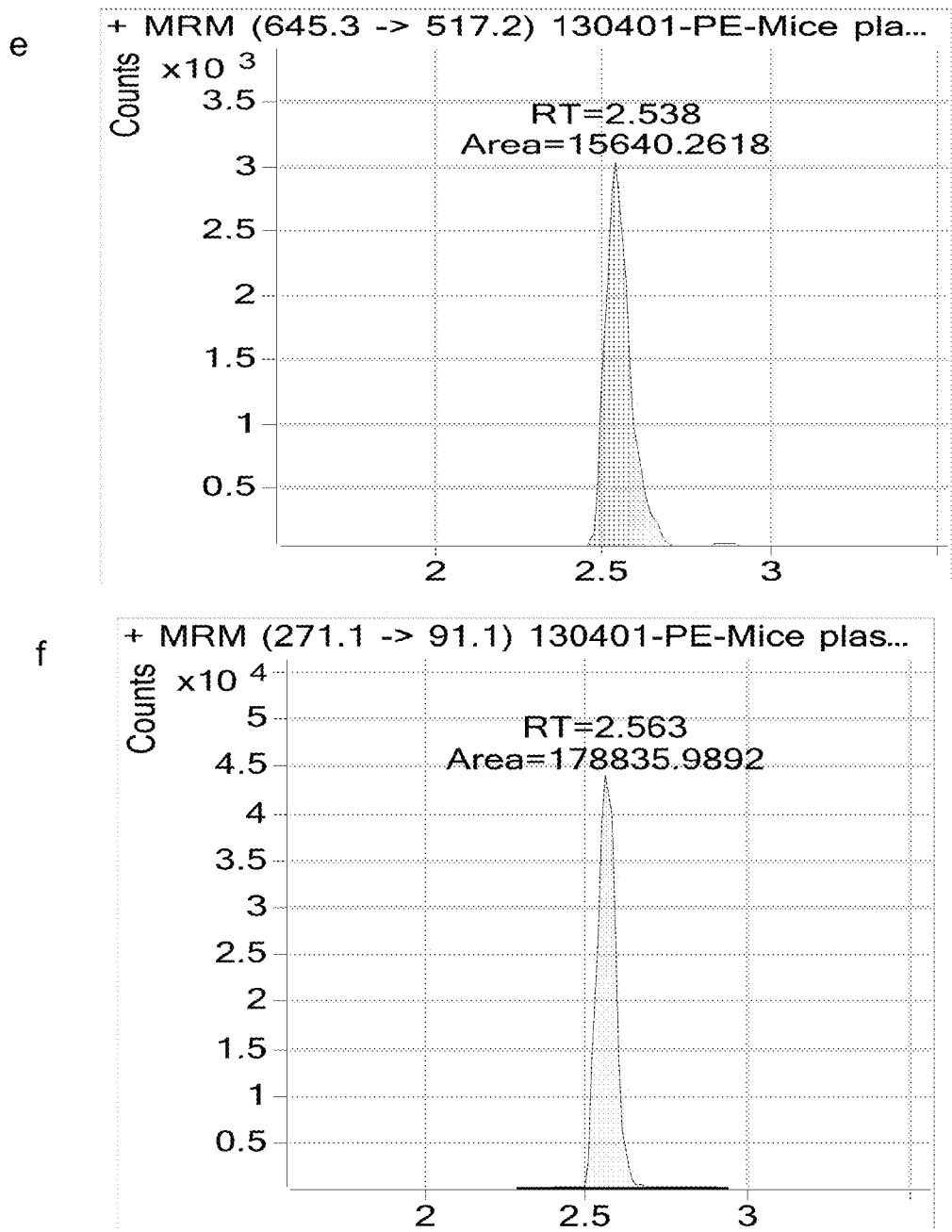
Figure 17:
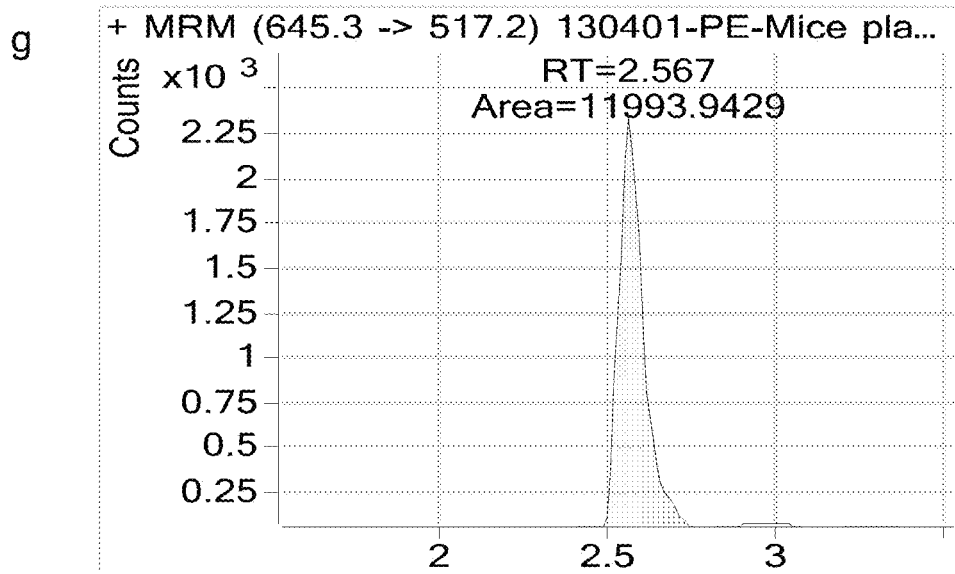
Figure 17:
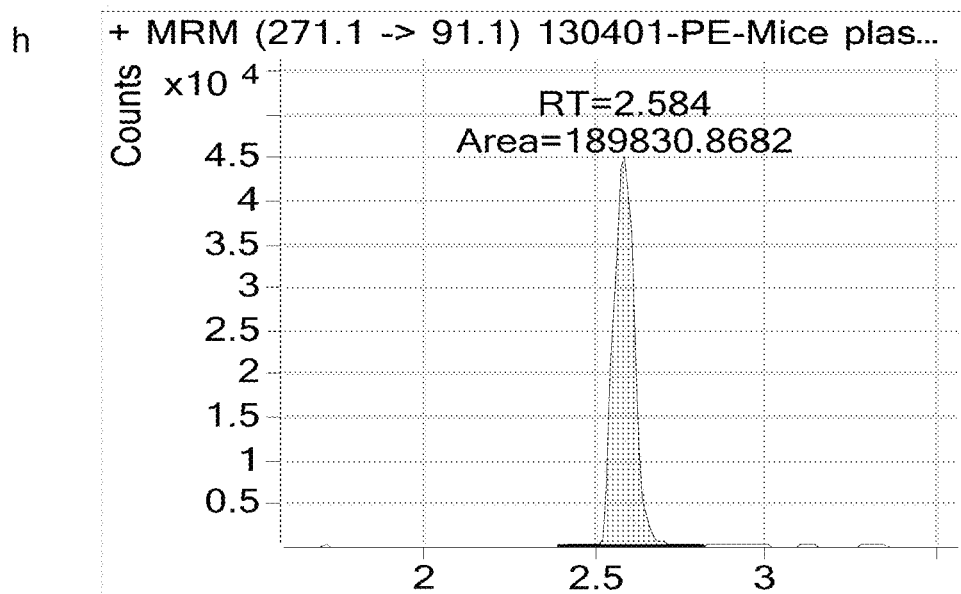

FIG. 17 shows chromatographic graphs for various plasma samples subjected to LC-MS/MS (liquid chromatography tandom mass spectrometry) analysis. IS=internal standard, PE=compound 30. FIGS. 17a and 17b shows blank samples for testing mice plasma. FIGS. 17c and 17d show blank samples (FIG. 17c) and after the addition of an internal standard, tolbutamide (FIG. 17d). FIG. 17e shows a blank sample spiked with PE (100 ng/mL), and FIG. 17f shows a blank sample spiked with the internal standard. FIGS. 17g and 17h show plasma samples from animal 108 1 hour following intravenous and oral administration.

Figure 18:
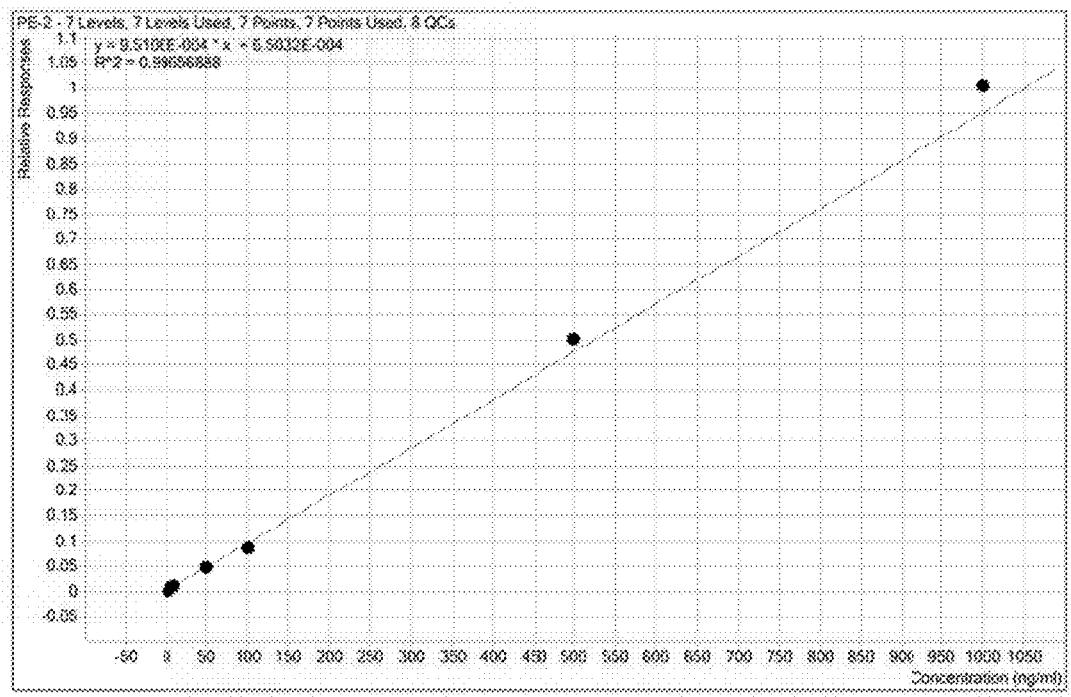

FIG. 18 shows a calibration curve for plasma samples subjected to LC-MS/MS analysis.

Figure 19:
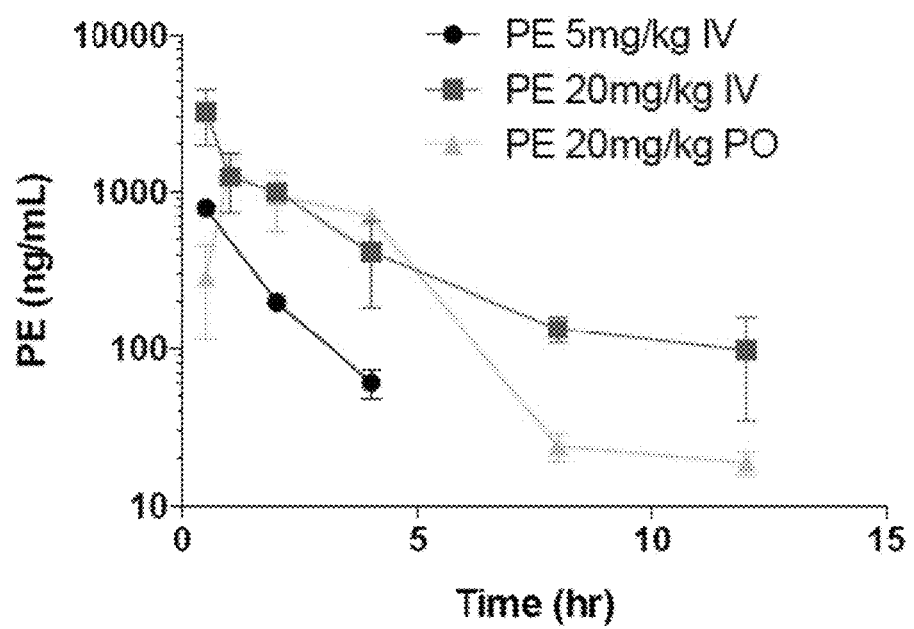

FIG. 19 shows plasma concentration-time curves of PE in male C57BL6/j mice following intravenous (IV) and oral (PO) administration of various doses of PE as labeled. Data points represent mean±s.d.

Figure 20:
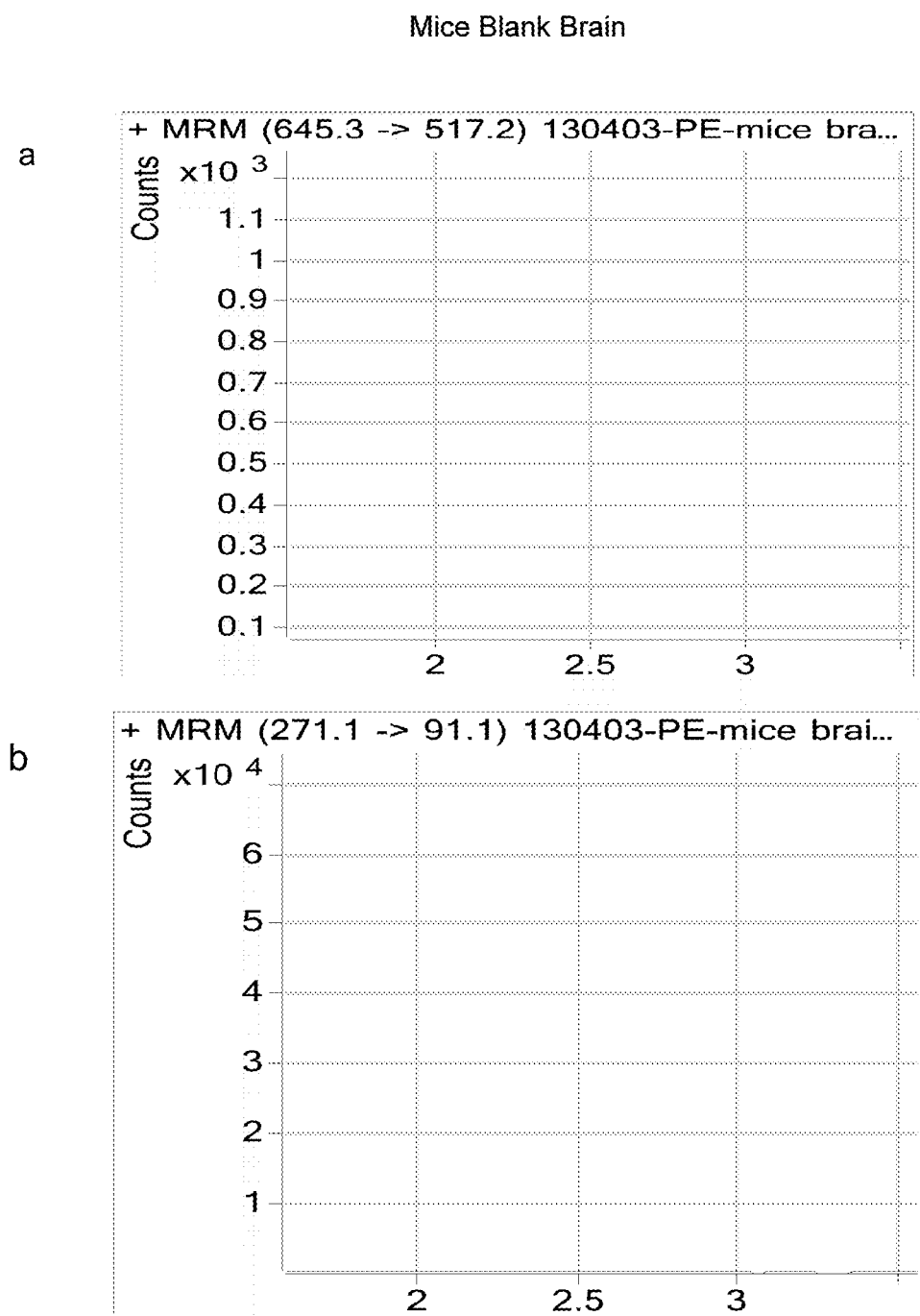
Figure 20:
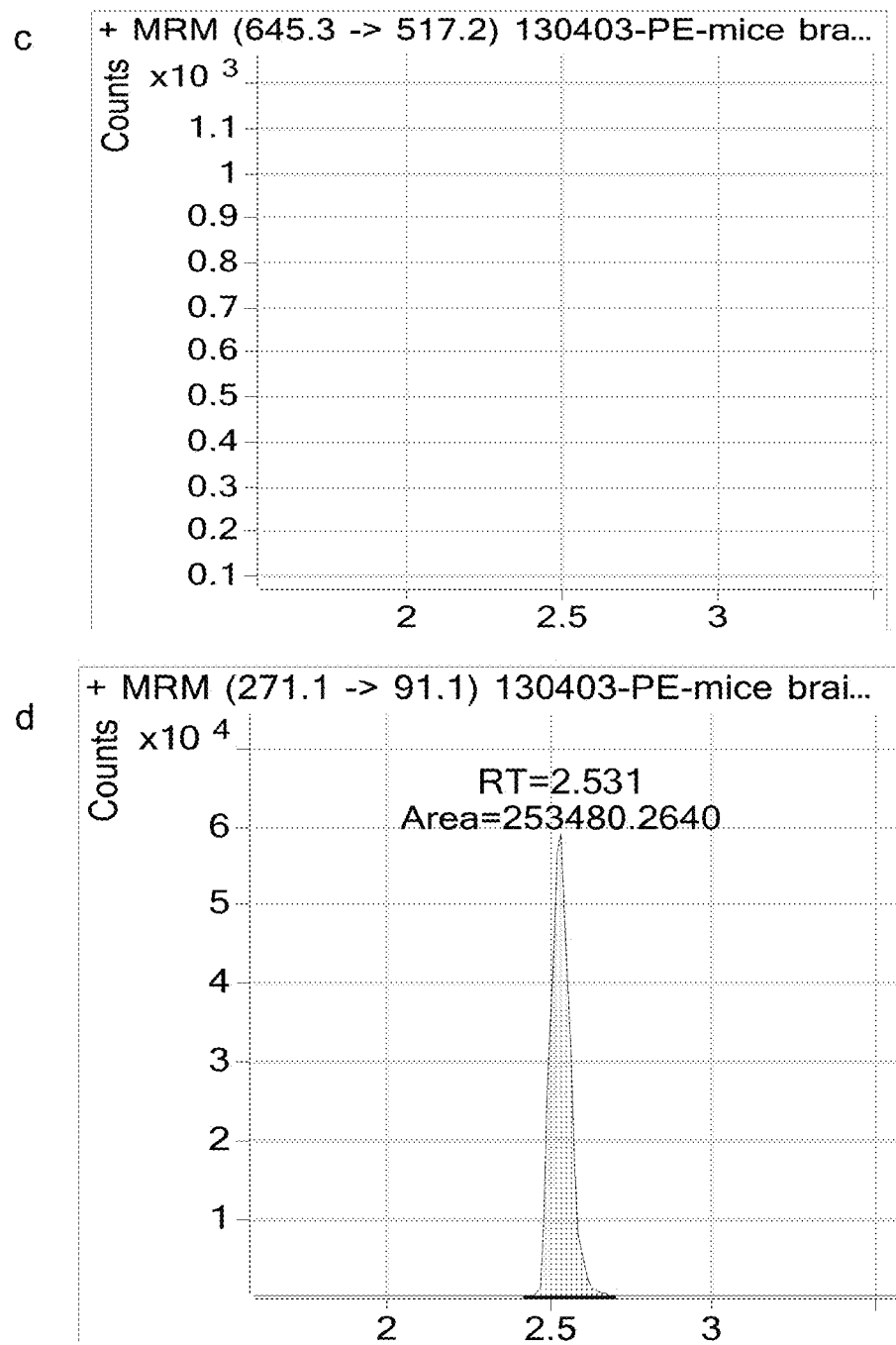
Figure 20:
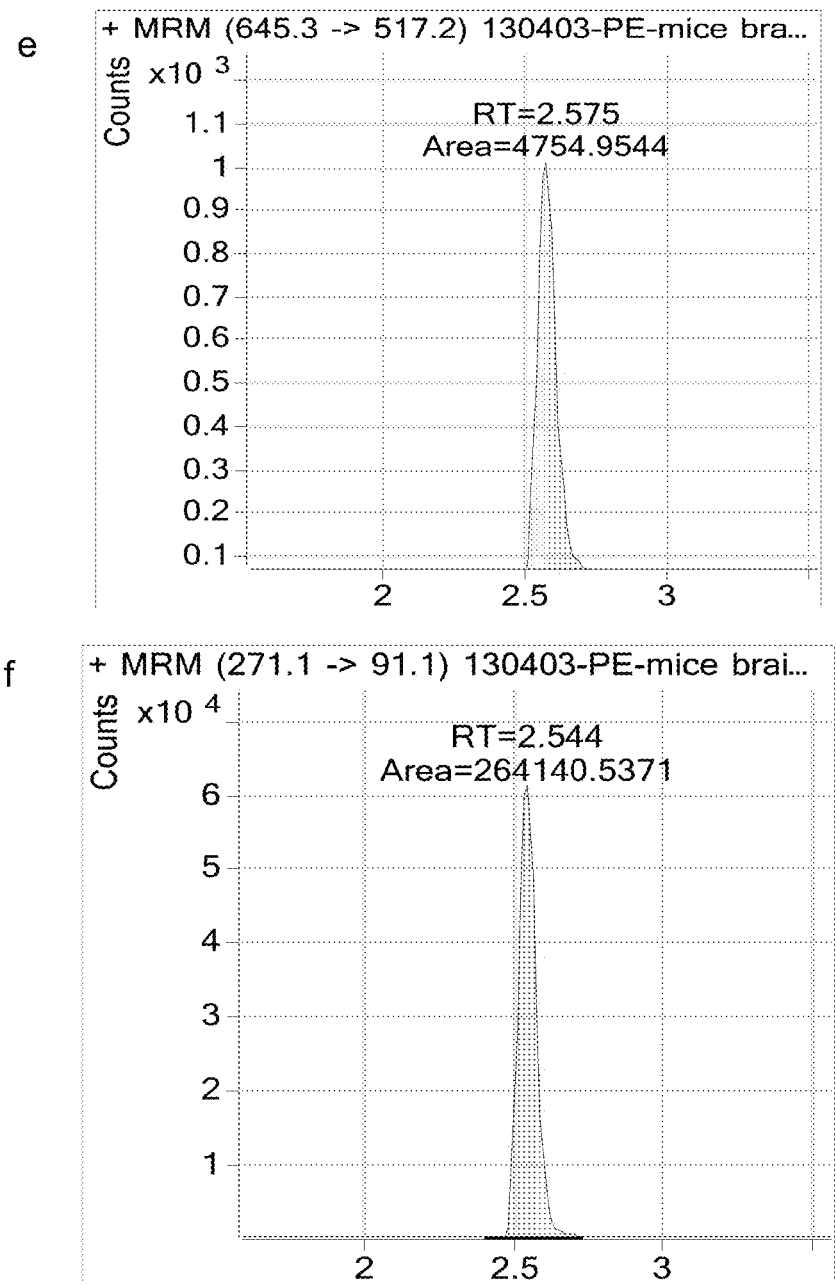
Figure 20:
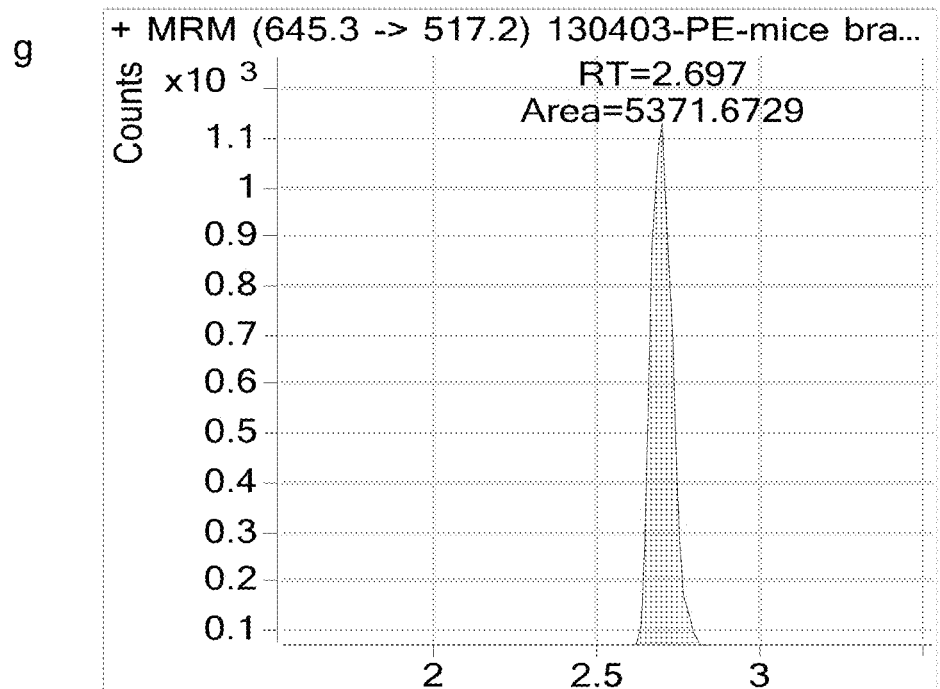
Figure 20:
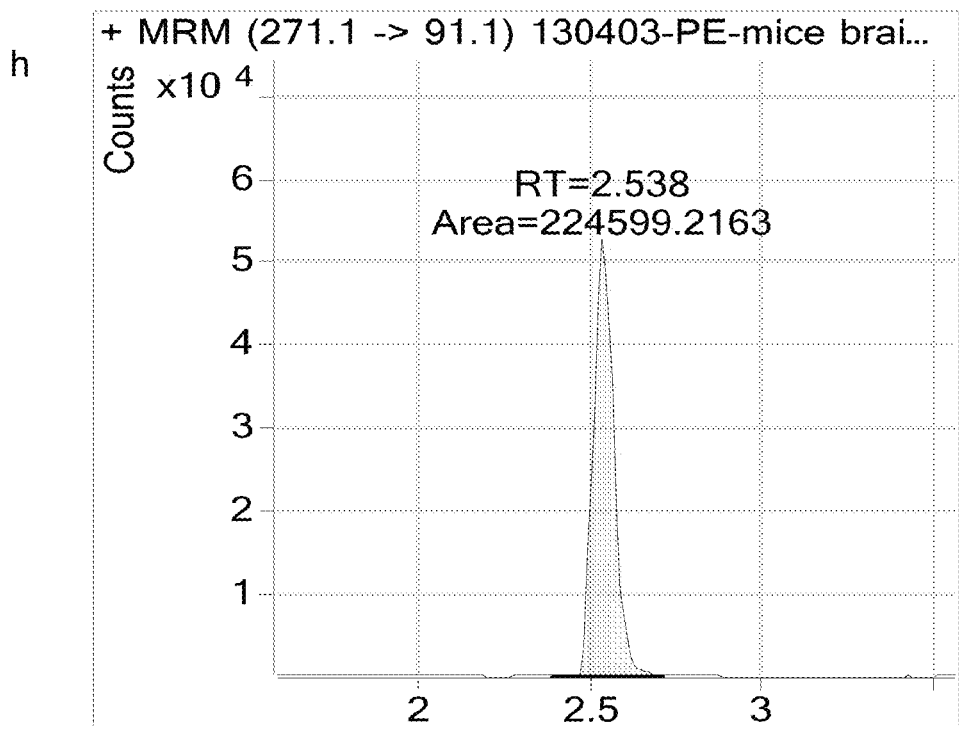

FIG. 20 shows chromatographic graphs for brain samples subjected to LC-MS/MS analysis. FIGS. 20a and 20b show blank samples for testing mice brain. FIGS. 20c and 20d show blank samples before (FIG. 20c) and after the addition of an internal standard, tolbutamide (FIG. 20d). FIG. 20e shows a blank sample spiked with PE (100 ng/mL), and FIG. 20f shows a blank sample spiked with the internal standard. FIGS. 20g and 20h show brain samples from animal 104 half an hour following intravenous and oral administration.

Figure 21:
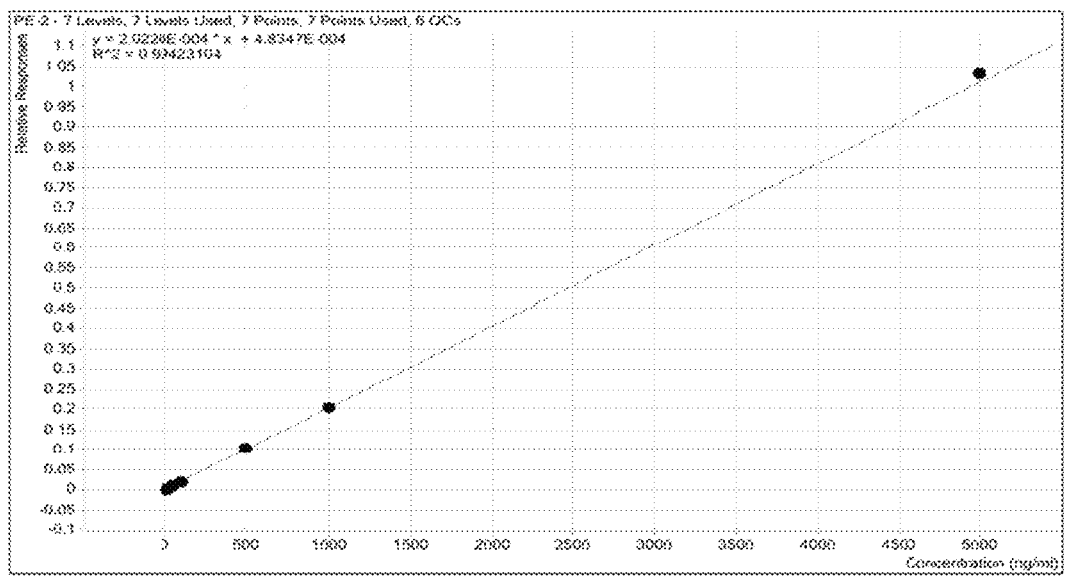

FIG. 21 shows a calibration curve for brain samples subjected to LC-MS/MS analysis.

Figure 22:
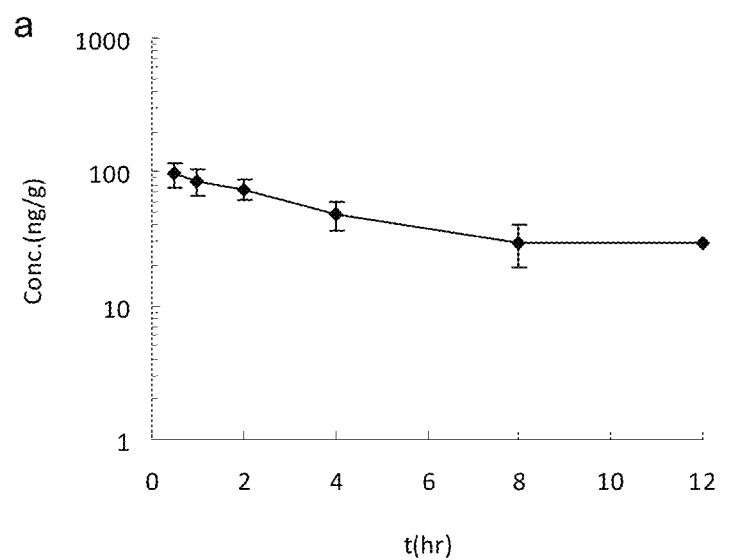
Figure 22:
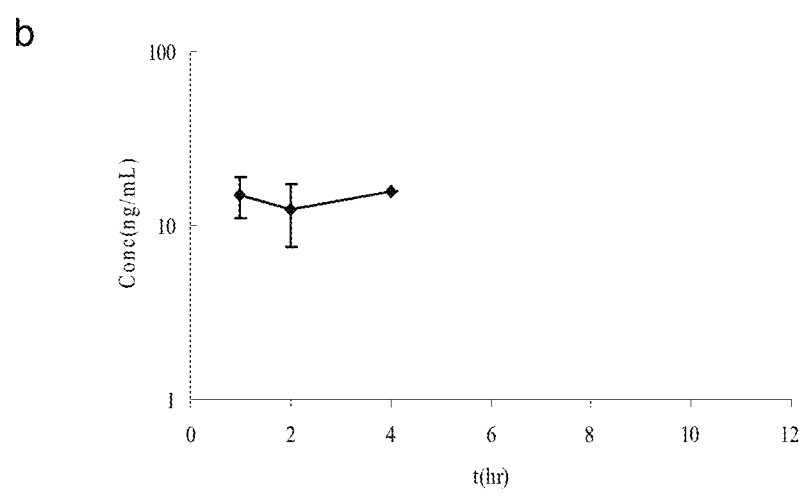

FIG. 22 shows brain concentration-time curves of PE in male C57BL6/j mice following IV (FIG. 22a) and PO (FIG. 22b) administration of PE at 20 mg/kg (n=3 for each route of administration). Data points represent mean±s.d.

Figure 23:
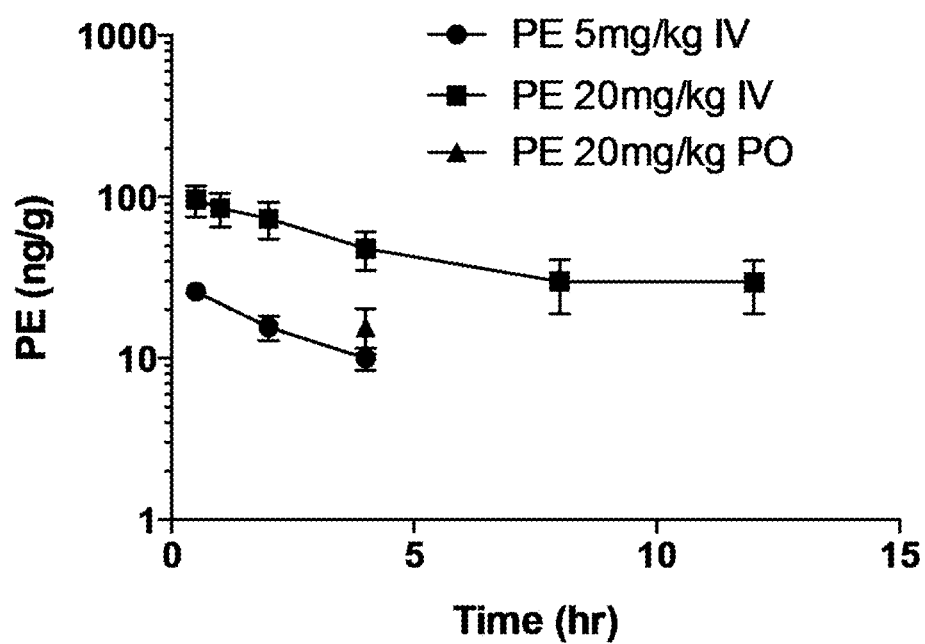

FIG. 23 shows, on the same axes, a set of brain concentration-time curves of PE in male C57BL6/j mice following IV and PO administration.

Figure 24:
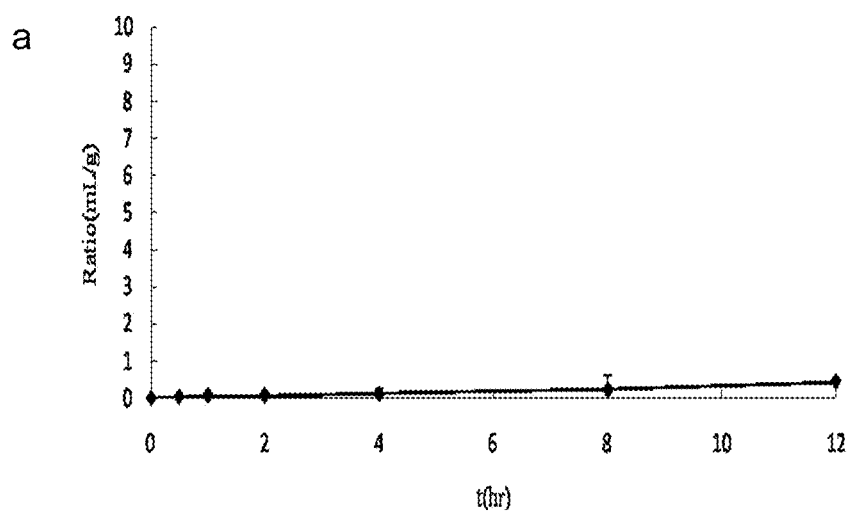
Figure 24:
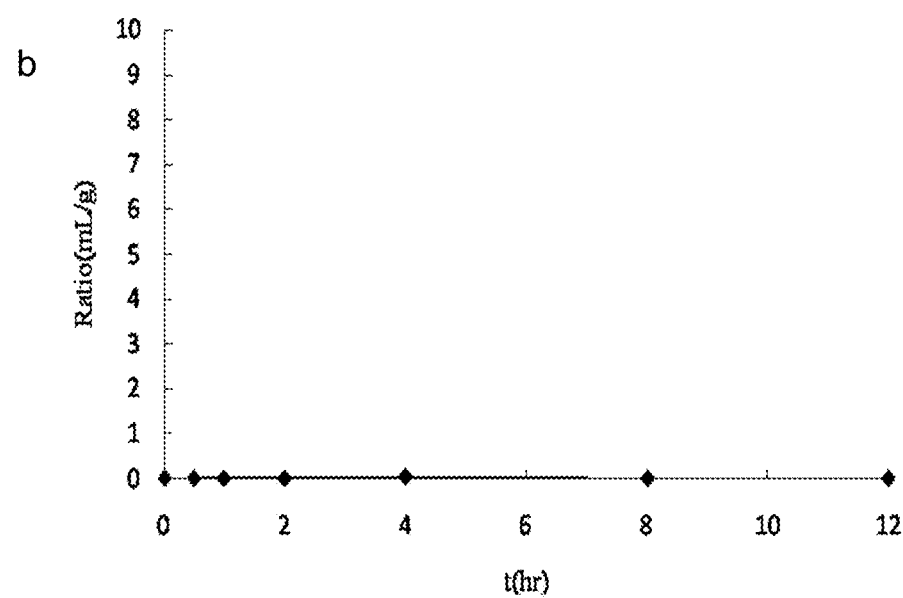

FIG. 24 shows brain-plasma concentration ratio curves of PE in male C57BL6/j mice following IV and PO administration. Data points represent mean±s.d.

DETAILED DESCRIPTION OF THE INVENTION

One embodiment of the present invention is a compound that has the structure (1):

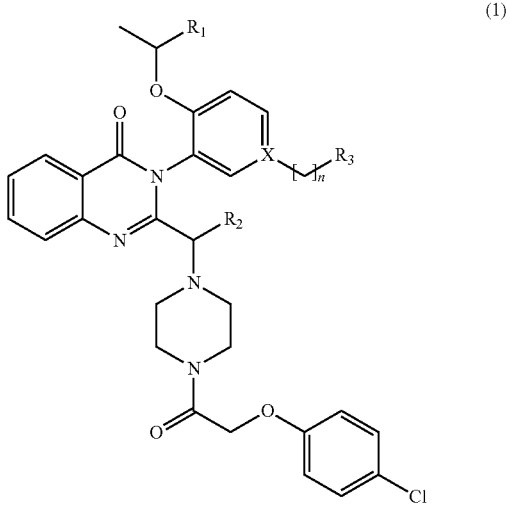

(1)

wherein $R_1$ is selected from the group consisting of H, $C_{1-4}$ alkyl, $C_{1-4}$ alkoxy, hydroxy, and halogen;

$R_2$ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;

$R_3$ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, with the proviso that when X is C, n=0, and $R_3$ is nothing, $R_1$ cannot be H when $R_2$ is $CH_3$, or an N-oxide, crystalline form, hydrate, or pharmaceutically acceptable salt thereof.

As used herein, the term "alkyl" refers to the radical of saturated aliphatic groups that does not have a ring structure, including straight-chain alkyl groups, and branched-chain alkyl groups. In certain embodiments, a straight chain or branched chain alkyl has 4 or fewer carbon atoms in its backbone (e.g., $C_1$-$C_4$ for straight chains, $C_3$-$C_4$ for branched chains).

Moreover, unless otherwise indicated, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Indeed, unless otherwise indicated, all groups recited herein are intended to include both substituted and unsubstituted options. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, an aromatic, or heteroaromatic or heteroaryl moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like.

The term "substituted" refers to moieties having substituents replacing a hydrogen on one or more carbons of the backbone. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms.

The term "$C_{x-y}$" when used in conjunction with a chemical moiety, such as, alkyl and cycloalkyl, is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc.

As used herein, "alkoxy" means an alkyl singular bonded to oxygen, or the following structure: —O-alkyl.

The term "hydroxyl" or "hydroxy," as used herein, refers to the group —OH.

The terms "halo" and "halogen" are used interchangeably herein and mean halogen and include chloro, fluoro, bromo, and iodo.

The term "cycloalkyl", as used herein, refers to the radical of saturated aliphatic groups having a ring structure, including cycloalkyl (alicyclic) groups, alkyl-substituted cycloalkyl groups, and cycloalkyl-substituted alkyl groups. Certain cycloalkyls have from 3-8 carbon atoms in their ring structure, including 5, 6, 7, 8 carbons in the ring structure. Cycloalkyls can be further substituted with alkyls, alkenyls, alkoxys, alkylthios, aminoalkyls, carbonyl-substituted alkyls, —$CF_3$, —CN, and the like.

The term "heterocycloalkyl" refers to substituted or unsubstituted non-aromatic ring structures, preferably 3- to 8-membered rings, whose ring structures include at least one heteroatom, preferably one to four heteroatoms, more preferably one or two heteroatoms. The term "heterocycloalkyl" also includes polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocycloalkyl groups include, for example, piperidine, piperazine, pyrrolidine, morpholine, lactones, lactams, and the like.

The term "heteroatom" as used herein means an atom of any element other than carbon or hydrogen. Preferred heteroatoms are nitrogen, oxygen, and sulfur; more preferably, nitrogen and oxygen.

The term "aryl" as used herein includes substituted or unsubstituted single-ring aromatic groups in which each atom of the ring is carbon. Preferably the ring is a 3- to 8-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "heteroaryl" includes substituted or unsubstituted aromatic single ring structures, preferably 3- to 8-membered rings, more preferably 5- to 7-membered rings, even more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "aralkyl", as used herein, refers to an alkyl group substituted with an aryl group.

The term "carbonyl" means a functional group composed of a carbon atom double-bonded to an oxygen atom: C=O. Carbonyls include without limitation, aldehydes, ketones, carboxylic acids, esters, and amides.

As used herein, an "N-oxide" means a compound containing an N—O bond with three additional hydrogen and/or side chains attached to N, so that there is a positive charge on the nitrogen. The N-oxides of compounds of the present invention may be synthesized by simple oxidation procedures well known to those skilled in the art. For example, the oxidation procedure described by P. Brougham et al. (Synthesis, 1015 1017, 1987), allows the two nitrogen of a piperazine ring to be differentiated, enabling both the N-oxides and N,N'-dioxide to be obtained. Other oxidation procedures are disclosed in, e.g., U.S. Patent Publication No. 20070275977; S. L. Jain, J. K. Joseph, B. Sain, Synlett, 2006, 2661-2663; A. McKillop, D. Kemp, Tetrahedron, 1989, 45, 3299-3306; R. S. Varma, K. P. Naicker, Org. Lett., 1999, 1, 189-191; and N. K. Jana, J. G. Verkade, Org. Lett., 2003, 5, 3787-3790. Thus, the present invention includes these and other well known procedures for making N-oxides, so long as the end product is sufficiently effective as set forth in more detail below.

The term "crystalline form", as used herein, refers to the crystal structure of a compound. A compound may exist in one or more crystalline forms, which may have different structural, physical, pharmacological, or chemical characteristics. Different crystalline forms may be obtained using variations in nucleation, growth kinetics, agglomeration, and breakage. Nucleation results when the phase-transition energy barrier is overcome, thereby allowing a particle to form from a supersaturated solution. Crystal growth is the enlargement of crystal particles caused by deposition of the chemical compound on an existing surface of the crystal. The relative rate of nucleation and growth determine the size distribution of the crystals that are formed. The thermodynamic driving force for both nucleation and growth is supersaturation, which is defined as the deviation from thermodynamic equilibrium. Agglomeration is the formation of larger particles through two or more particles (e.g., crystals) sticking together and forming a larger crystalline structure.

As used herein, a "hydrate" means a compound that contains water molecules in a definite ratio and in which water forms an integral part of the crystalline structure of the compound. Methods of making hydrates are known in the art. For example, some substances spontaneously absorb water from the air to form hydrates. Others may form hydrates upon contact with water. In most cases, however, hydrates are made by changes in temperature or pressure. Additionally, the compounds of the present invention as well as their salts may contain, e.g., when isolated in crystalline form, varying amounts of solvents, such as water. Included within the scope of the invention are, therefore, all hydrates of the compounds and all hydrates of salts of the compounds of the present invention, so long as such hydrates are sufficiently effective as set forth in more detail below.

In one aspect of the present embodiment, the compound has the structure (10):

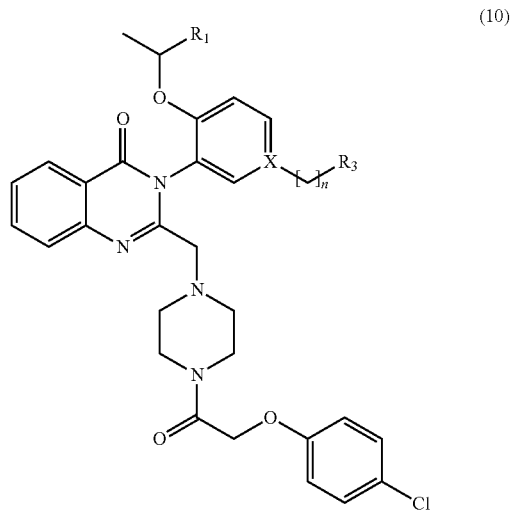

(10)

wherein $R_1$ is selected from the group consisting of H, $C_{1-4}$ alkyl, $C_{1-4}$ alkoxy, hydroxy, and halogen;

R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, or an N-oxide, crystalline form, hydrate, or pharmaceutically acceptable salt thereof.

In another aspect of this embodiment, the compound has the structure (20):

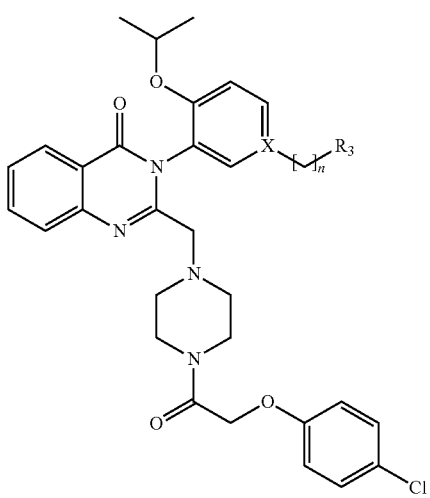

(20)

wherein

R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, or an N-oxide, crystalline form, hydrate, or pharmaceutically acceptable salt thereof.

In a further aspect of this embodiment, the compound is selected from the group consisting of:

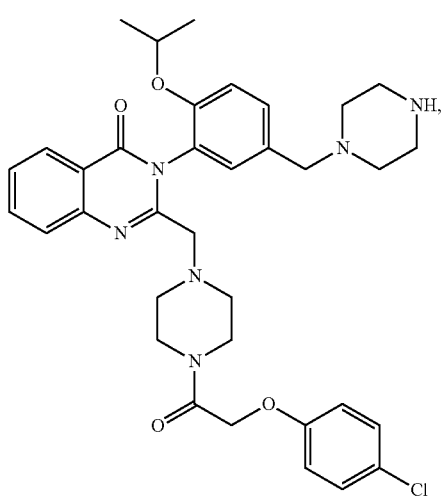

(30)

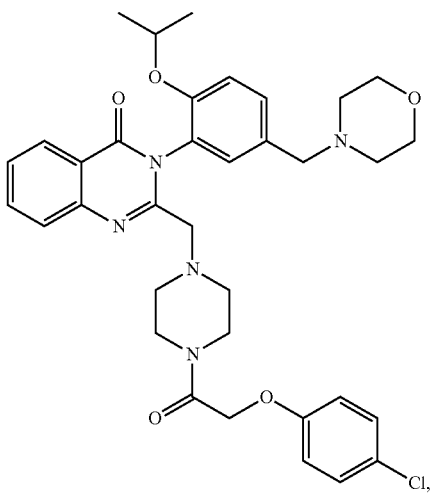

(40)

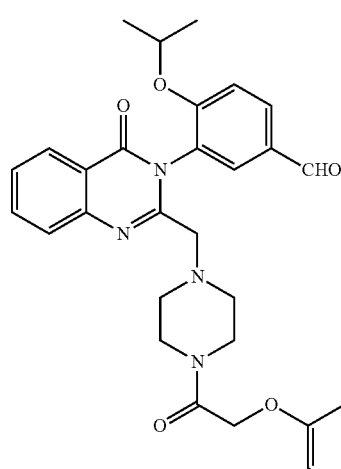

(50)

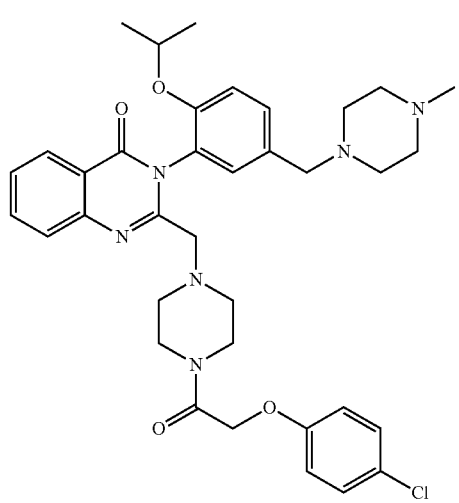

(60)

or an N-oxide, crystalline form, hydrate, or pharmaceutically acceptable salt thereof. Preferably, the compound has the structure (30):

51

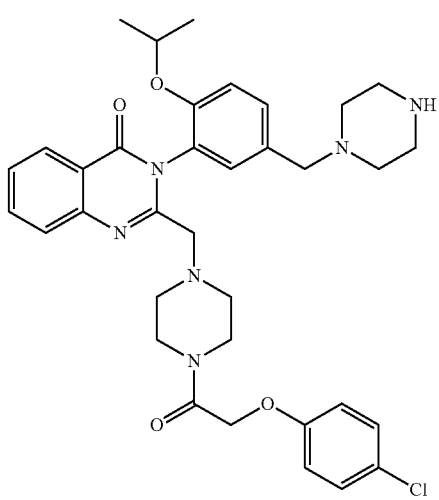

(30)

or an N-oxide, crystalline form, hydrate, or pharmaceutically acceptable salt thereof.

An additional embodiment of the present invention is a composition. This composition comprises a pharmaceutically acceptable carrier and a compound having the structure (1):

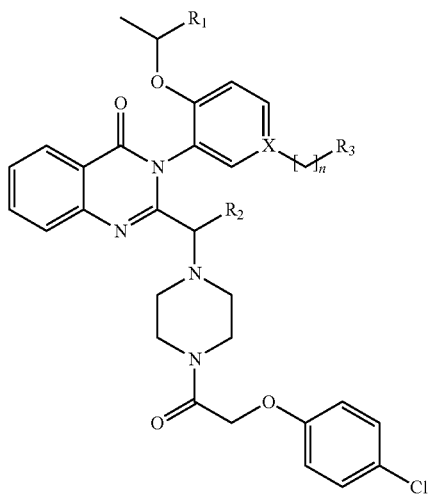

(1)

wherein $R_1$ is selected from the group consisting of H, $C_{1-4}$ alkyl, $C_{1-4}$ alkoxy, hydroxy, and halogen;

$R_2$ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;

$R_3$ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, with the proviso that when X is C, n=0, and $R_3$ is nothing, $R_1$ cannot be H when $R_2$ is $CH_3$, or an N-oxide, crystalline form, hydrate, or pharmaceutically acceptable salt thereof.

52

In one aspect of this embodiment, the compound has the structure (10):

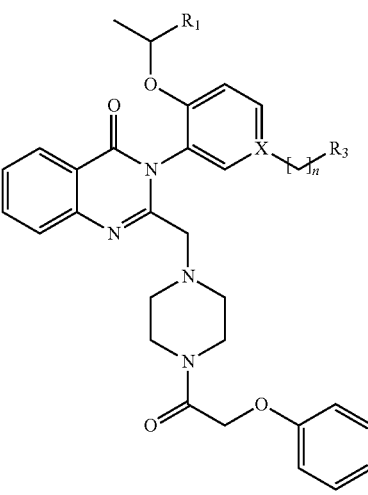

(10)

wherein $R_1$ is selected from the group consisting of H, $C_{1-4}$ alkyl, $C_{1-4}$ alkoxy, hydroxy, and halogen $R_3$ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, or an N-oxide, crystalline form, hydrate, or pharmaceutically acceptable salt thereof.

In another aspect of this embodiment, the compound has structure (20):

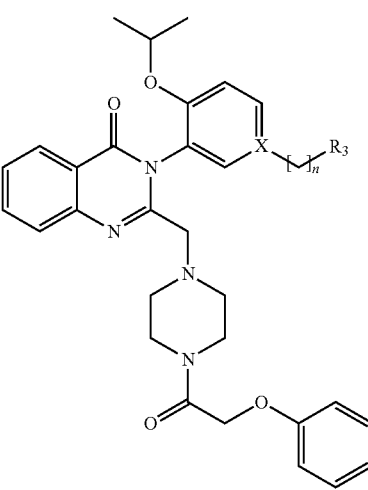

(20)

wherein $R_3$ is selected from the group consisting nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, or an N-oxide, crystalline form, hydrate, or pharmaceutically acceptable salt thereof.

In an additional aspect of this embodiment, the compound is selected from the group consisting of:

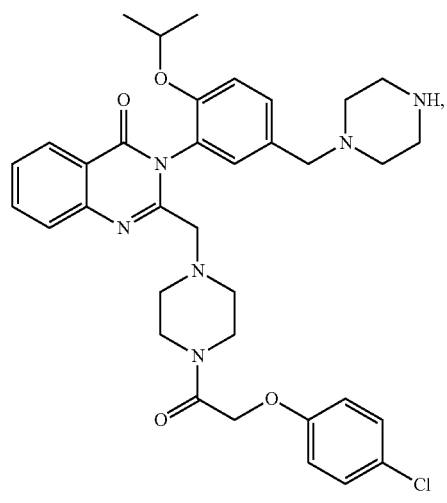
(30)

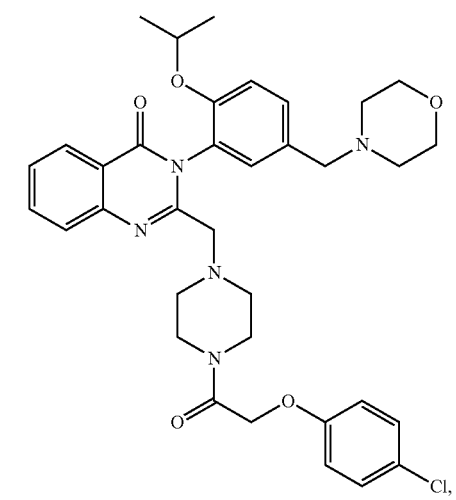
(40)

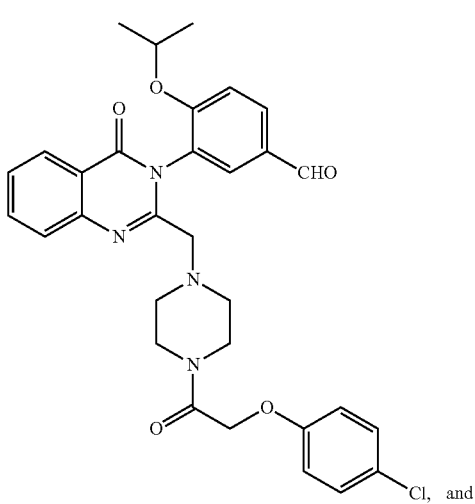
(50)

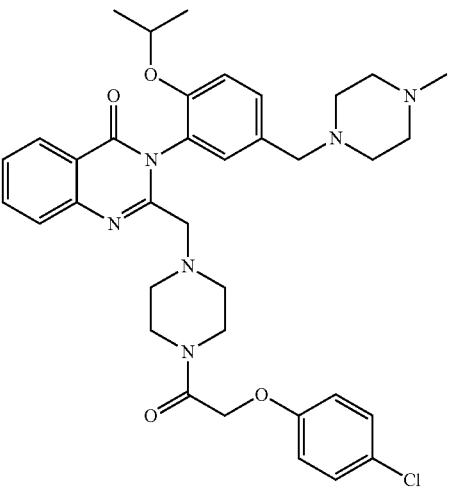
(60)

or an N-oxide, crystalline form, hydrate, or pharmaceutically acceptable salt thereof.

A further embodiment of the present invention is a composition. This composition comprises a pharmaceutically acceptable carrier and a compound having the structure (30):

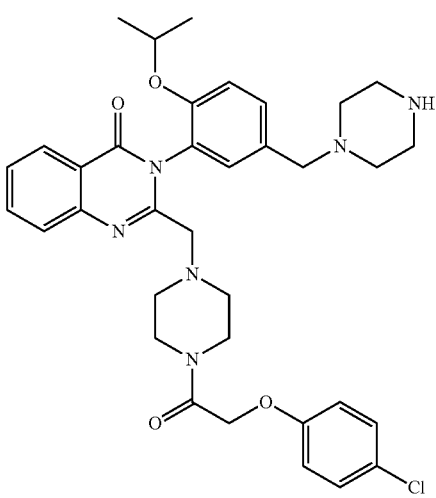
(30)

or an N-oxide, crystalline form, hydrate, or pharmaceutically acceptable salt thereof.

Another embodiment of the present invention is a method for treating or ameliorating the effects of a cancer comprising a cell that harbors an oncogenic RAS mutation. This method comprises administering to a subject in need thereof a therapeutically effective amount of any compound disclosed herein.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt or reverse the progression of disease development. However, because every treated subject may not respond to a particular treatment protocol, regimen, process or remedy, treating does not require that the desired physiologic response or outcome be achieved in each and every subject or subject, e.g., patient, population. Accordingly, a given subject or subject, e.g., patient, population may fail to respond or respond inadequately to treatment.

As used herein, the terms "ameliorate", "ameliorating" and grammatical variations thereof mean to decrease the severity of the symptoms of a disease in a subject.

As used herein, "cancer" means uncontrolled growth of abnormal cells that harbor an oncogenic RAS mutation. The present invention includes those cancers selected from the following group that have one or more cells that harbor an oncogenic RAS mutation: adrenocortical carcinoma, anal cancer, bladder cancer, bone cancer, brain tumor, breast cancer, carcinoid tumor, carcinoma, cervical cancer, colon cancer, endometrial cancer, esophageal cancer, extrahepatic bile duct cancer, Ewing family of tumors, extracranial germ cell tumor, eye cancer, gallbladder cancer, gastric cancer, germ cell tumor, gestational trophoblastic tumor, head and neck cancer, hypopharyngeal cancer, islet cell carcinoma, kidney cancer, laryngeal cancer, leukemia, lip and oral cavity cancer, liver cancer, lung cancer, lymphoma, malignant mesothelioma, Merkel cell carcinoma, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell tumor, pancreatic cancer, paranasal sinus and nasal cavity cancer, parathyroid cancer, penile cancer, pituitary cancer, plasma cell neoplasm, prostate cancer, rhabdomyosarcoma, rectal cancer, renal cell cancer, transitional cell cancer of the renal pelvis and ureter, salivary gland cancer, Sezary syndrome, skin cancer (such as cutaneous t-cell lymphoma, Kaposi's sarcoma, and melanoma), small intestine cancer, soft tissue sarcoma, stomach cancer, testicular cancer, thymoma, thyroid cancer, urethral cancer, uterine cancer, vaginal cancer, vulvar cancer, Wilms' tumor. Preferably, the cancer is a sarcoma.

As used herein, an "oncogenic RAS mutation" means a cellular change that results in the abnormal activation of any of the RAS family of genes (such as, e.g., H-RAS, K-RAS 4A, K-RAS 4B, M-RAS, N-RAS and R-RAS). RAS serves as a molecular switch in a large network of signaling pathways in cells. It cycles between the GDP-bound inactive form and the GTP-bound active form. Mutations in RAS have been found in about 30% of all human cancers. For example, various mutations, such as point mutations corresponding to amino acid numbers 12, 13, 59, 60 of H-RAS, may lead to impaired GTPase activity, resulting in inappropriate activation of RAS, such as constitutively activation of RAS.

As used herein, a "subject" is a mammal, preferably, a human. In addition to humans, categories of mammals within the scope of the present invention include, for example, agricultural animals, veterinary animals, laboratory animals, etc. Some examples of agricultural animals include cows, pigs, horses, goats, etc. Some examples of veterinary animals include dogs, cats, etc. Some examples of laboratory animals include rats, mice, rabbits, guinea pigs, etc.

A further embodiment of the present invention is a method for treating or ameliorating the effects of a cancer comprising a cell that harbors an oncogenic RAS mutation. This method comprises administering to a subject in need thereof a therapeutically effective amount of any composition disclosed herein.

Another embodiment of the present invention is a method for treating or ameliorating the effects of a cancer comprising a cell that harbors an oncogenic RAS mutation. The method comprises administering to a subject in need thereof a therapeutically effective amount of a composition comprising a pharmaceutically acceptable carrier and a compound having the structure (30):

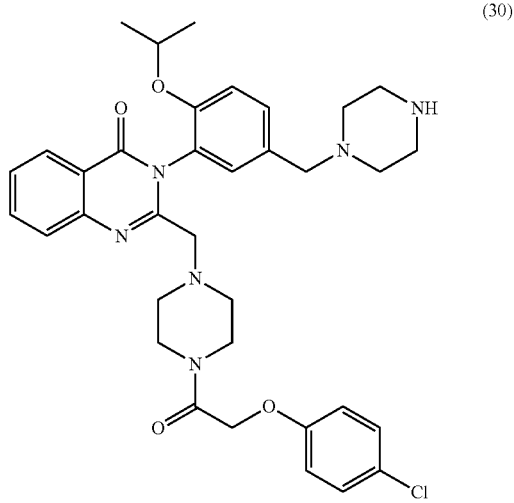

(30)

or an N-oxide, crystalline form, hydrate, or pharmaceutically acceptable salt thereof.

An additional embodiment of the present invention is a method for modulating a lipoxygenase in a ferroptosis cell death pathway. This method comprises administering to a cell an effective amount of a compound having the structure (1):

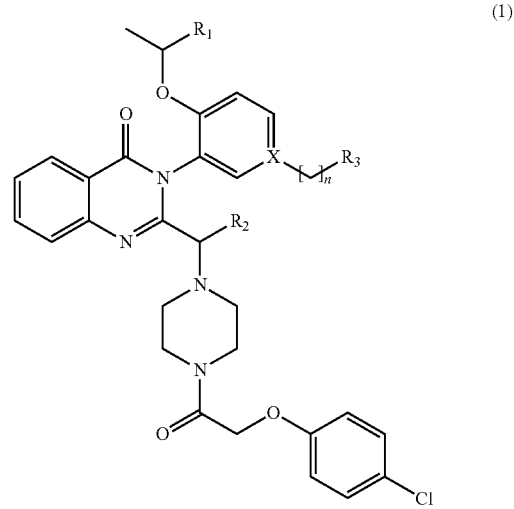

(1)

wherein

R₁ is selected from the group consisting of H, $C_{1-4}$ alkyl, $C_{1-4}$ alkoxy, hydroxy, and halogen;

R₂ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;

R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, with the proviso that when X is C, n=0, and R₃ is nothing, R₁ cannot be H when R₂ is $CH_3$, or an N-oxide, crystalline form, hydrate, or pharmaceutically acceptable salt thereof.

As used herein, the terms "modulate", "modulating" and grammatical variations thereof mean to change, such as increasing the activity or expression of lipoxygenase. A "lipoxygenase" means an enzyme that catalyzes the oxidation of unsaturated fatty acids with oxygen to form peroxides of the fatty acids. Lipoxygenases according to the present invention include those polypeptides encoded by the ALOX genes, including ALOX5, ALOX12, ALOX12B, ALOX15, ALOX15B, and ALOXE3. Preferably, the ALOX gene is the ALOXE3 gene as set forth in more detail below.

As used herein, "ferroptosis" means regulated cell death that is iron-dependent. Ferroptosis is characterized by the overwhelming, iron-dependent accumulation of lethal lipid reactive oxygen species. Ferroptosis is distinct from apoptosis, necrosis, and autophagy. Assays for ferroptosis are as disclosed, for instance, in Dixon et al., 2012.

In one aspect of this embodiment, the compound has the structure (10):

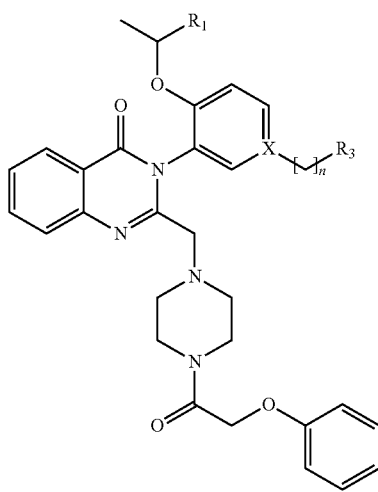

(10)

wherein

R₁ is selected from the group consisting of H, $C_{1-4}$ alkyl, $C_{1-4}$ alkoxy, hydroxy, and halogen R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, or an N-oxide, crystalline form, hydrate, or pharmaceutically acceptable salt thereof.

In another aspect of this embodiment, the compound has the structure (20):

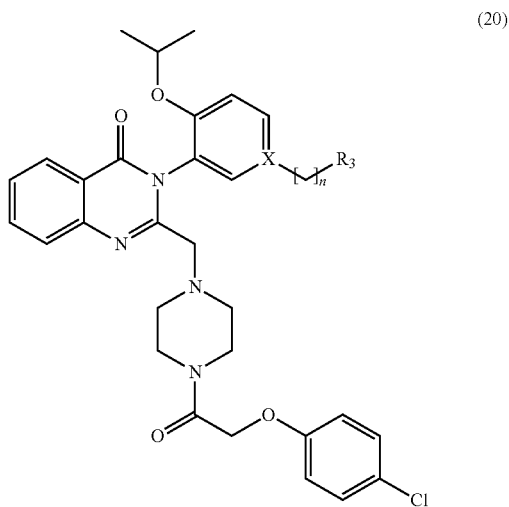

(20)

wherein

R₃ is selected from the group consisting nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, or an N-oxide, crystalline form, hydrate, or pharmaceutically acceptable salt thereof. Preferably, the compound is selected from the group consisting of:

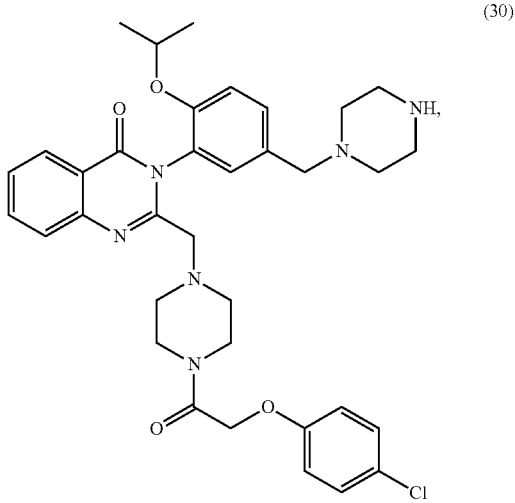 [SMILES: CC(C)Oc1ccc(CN2CCNCC2)cc1-n1c(CN2CCN(C(=O)COc3ccc(Cl)cc3)CC2)nc2ccccc2c1=O]

(30)

(40)

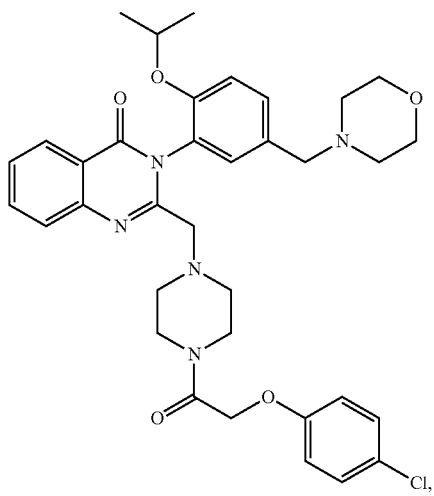

(50)

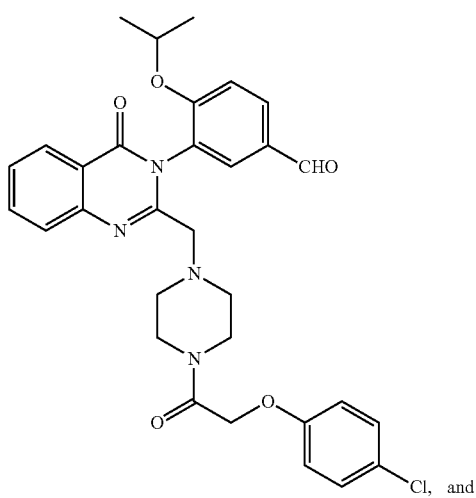
Cl, and (60)

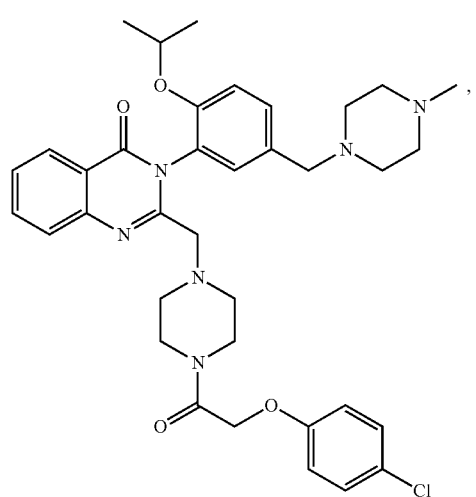

or an N-oxide, crystalline form, hydrate, or pharmaceutically acceptable salt thereof. More preferably, the compound has the structure (30):

(30)

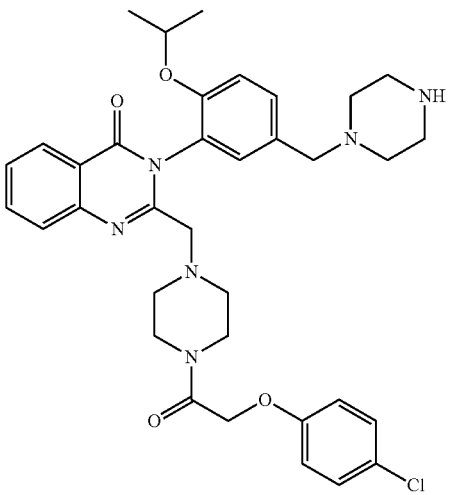

or an N-oxide, crystalline form, hydrate, or pharmaceutically acceptable salt thereof.

In another aspect of this embodiment, the modulation comprises activation of one or more polypeptides encoded by ALOX genes. As used herein, "ALOX" refers to arachidonate lipoxygenase such as, e.g., those identified above.

A further embodiment of the present invention is a method for depleting reduced glutathione (GSH) in a cell harboring an oncogenic RAS mutation comprising administering to the cell an effective amount of a compound having the structure (1):

(1)

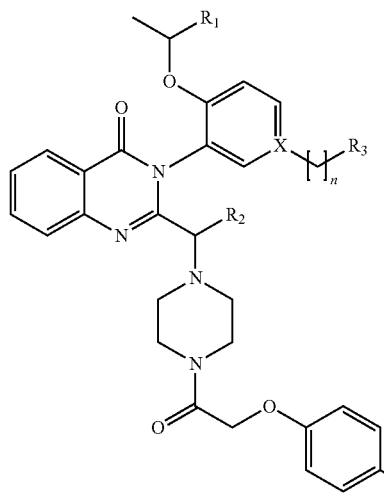

wherein $R_1$ is selected from the group consisting of H, $C_{1-4}$ alkyl, $C_{1-4}$ alkoxy, hydroxy, and halogen;

$R_2$ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;

$R_3$ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, with the proviso that when X is C, n=0, and $R_3$ is nothing, $R_1$ cannot be H when $R_2$ is $CH_3$, or an N-oxide, crystalline form, hydrate, or pharmaceutically acceptable salt thereof. In this embodiment, "depleting" means reducing or decreasing.

In one aspect of this embodiment, the compound has the structure (10):

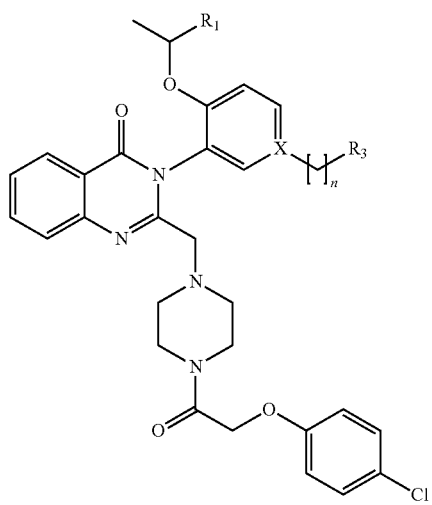
(10)

wherein $R_1$ is selected from the group consisting of H, $C_{1-4}$ alkyl, $C_{1-4}$ alkoxy, hydroxy, and halogen $R_3$ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6,
or an N-oxide, crystalline form, hydrate, or pharmaceutically acceptable salt thereof.

In another aspect of this embodiment, the compound has the structure (20):

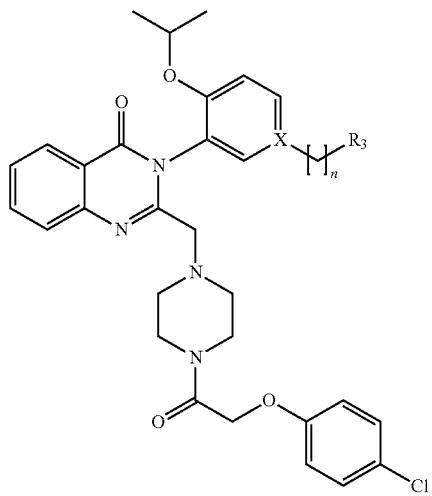
(20)

wherein $R_3$ is selected from the group consisting nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, or an N-oxide, crystalline form, hydrate, or pharmaceutically acceptable salt thereof. Preferably, the compound is selected from the group consisting of:

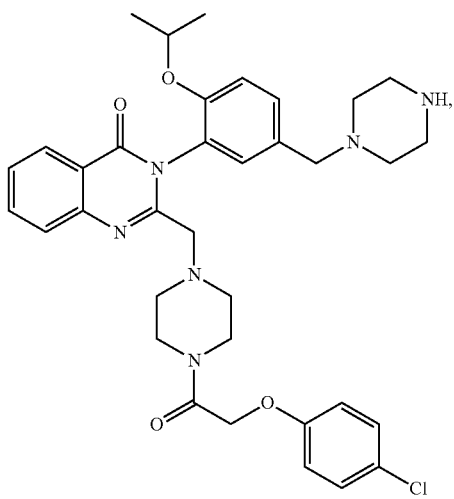
(30)

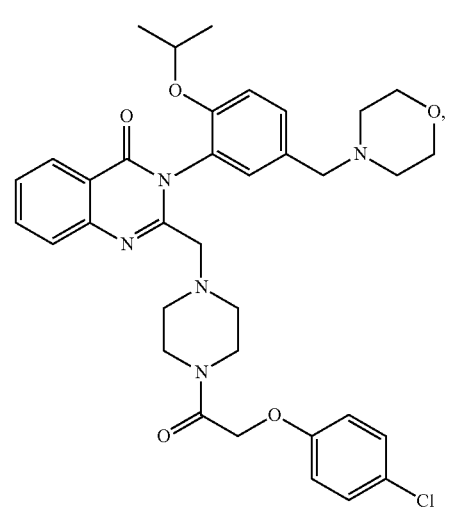
(40)

63

-continued

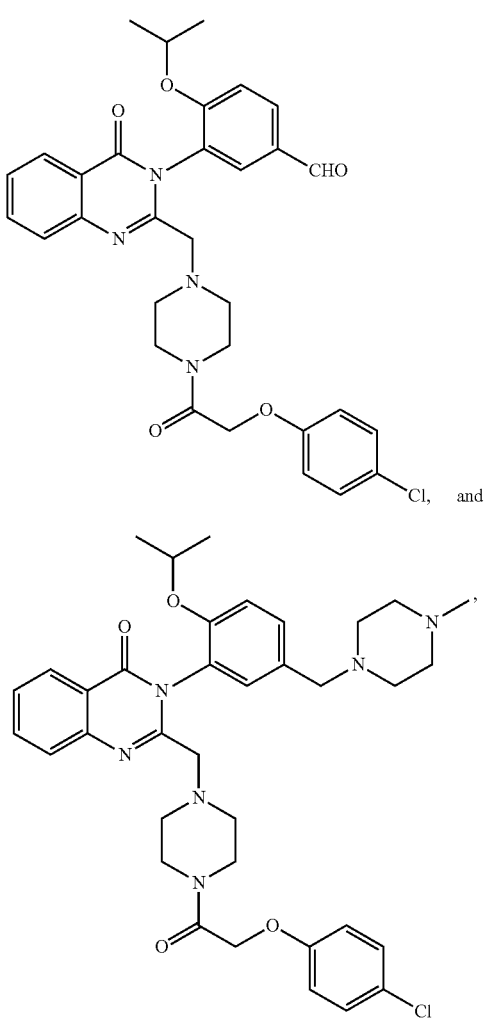

(50)

(60)

or an N-oxide, crystalline form, hydrate, or pharmaceutically acceptable salt thereof. More preferably, the compound has the structure (30):

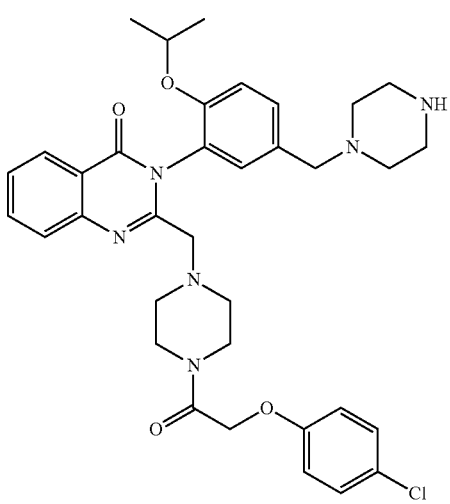

(30)

64 or an N-oxide, crystalline form, hydrate, or pharmaceutically acceptable salt thereof.

Another embodiment of the present invention is a compound having the structure (100):

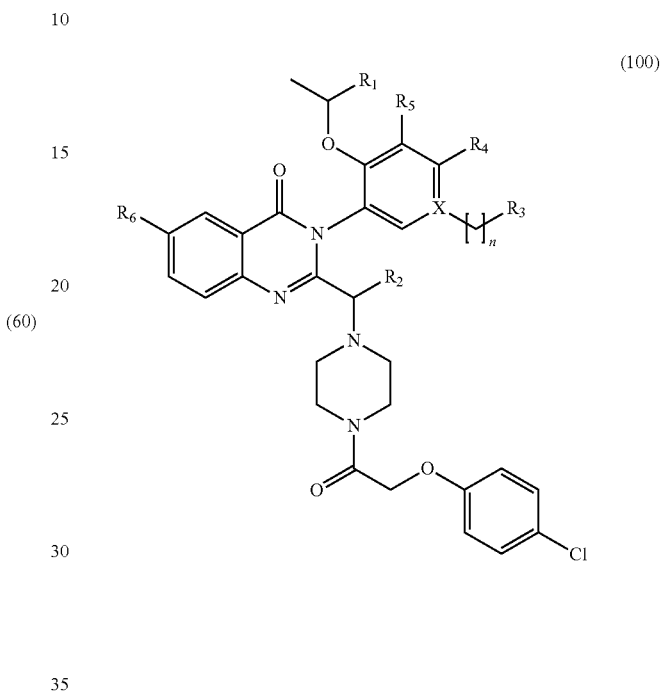

(100)

wherein $R_1$ is selected from the group consisting of H, $C_{1-4}$ alkyl, $C_{1-4}$ alkoxy, hydroxy, and halogen;

$R_2$ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;

$R_3$ is selected from the group consisting of nothing, H, $C_{1-4}$ alkyl, $C_{1-4}$ alkoxy, carbonyl, $C_{3-8}$ cycloalkyl, and $C_{3-8}$ heterocycloalkyl;

$R_4$ and $R_5$ are independently selected from the group consisting of H, $C_{3-8}$ cycloalkyl, and $C_{3-8}$ heterocycloalkyl;

$R_6$ is selected from the group consisting of H, —$NH_2$, $C_{1-4}$ alkyl, $C_{1-4}$ alkoxy, carbonyl, aryl, heteraryl, $C_{3-8}$ cycloalkyl, and $C_{3-8}$ heterocycloalkyl;

X is selected from the group consisting of C, N, and O; and n is an integer from 0-6, with the proviso that when X is C, n=0, and $R_3$ is nothing, $R_1$ cannot be H when $R_2$ is $CH_3$, or an N-oxide, crystalline form, hydrate, or pharmaceutically acceptable salt thereof.

In one aspect of this embodiment, the compound has the structure (200):

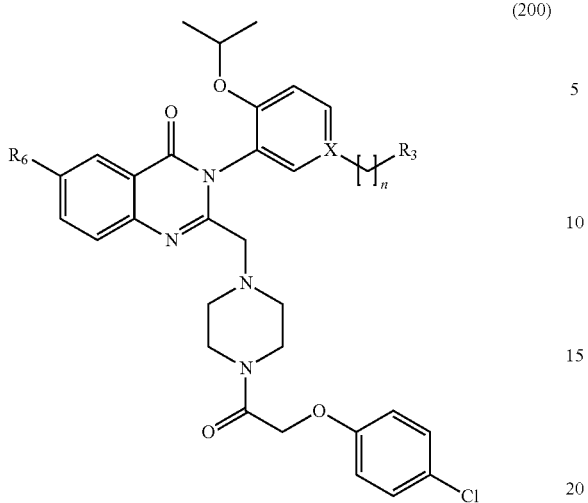

(200)

wherein

R$_3$ is selected from the group consisting of nothing, C$_{1-4}$ alkyl, C$_{1-4}$ alkoxy, carbonyl, C$_{3-8}$ cycloalkyl, and C$_{3-8}$ heterocycloalkyl;

R$_6$ is selected from the group consisting of H, —NH$_2$, C$_{1-4}$ alkyl, C$_{1-4}$ alkoxy, carbonyl, aryl, heteraryl, C$_{3-8}$ cycloalkyl, and C$_{3-8}$ heterocycloalkyl;

X is selected from the group consisting of C, N, and O; and n is an integer from 0-6, or an N-oxide, crystalline form, hydrate, or pharmaceutically acceptable salt thereof.

In another aspect of this embodiment, the compound has the structure (300):

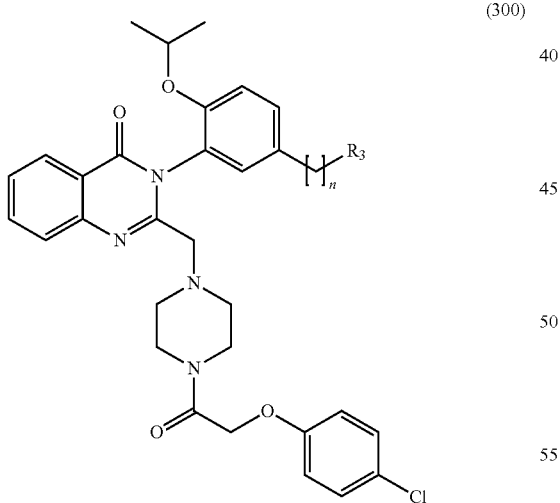

(300)

wherein

R$_3$ is selected from the group consisting of nothing, C$_{1-4}$ alkyl, C$_{1-4}$ alkoxy, carbonyl, C$_{3-8}$ cycloalkyl, and C$_{3-8}$ heterocycloalkyl;

n is an integer from 0-6, or an N-oxide, crystalline form, hydrate, or pharmaceutically acceptable salt thereof.

In a further aspect of this embodiment, the compound is selected from the group consisting of:

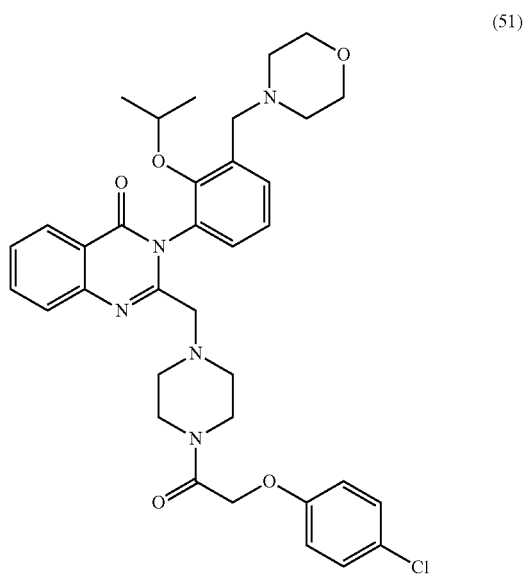

(51)

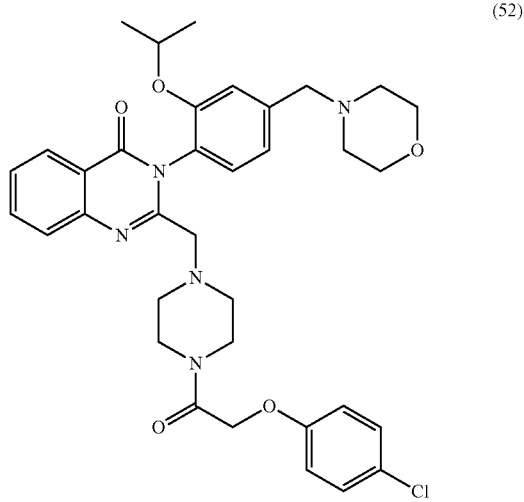

(52)

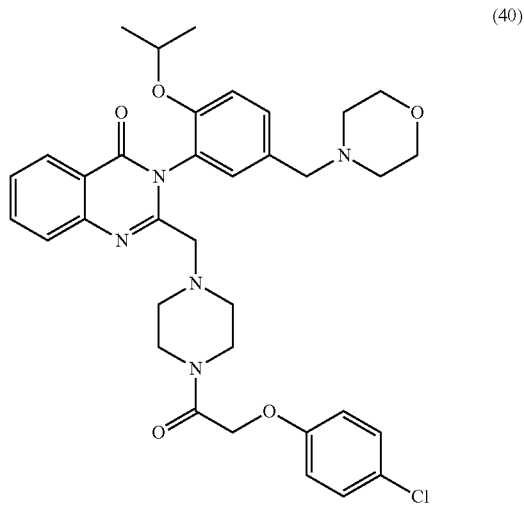

(40)

(15)
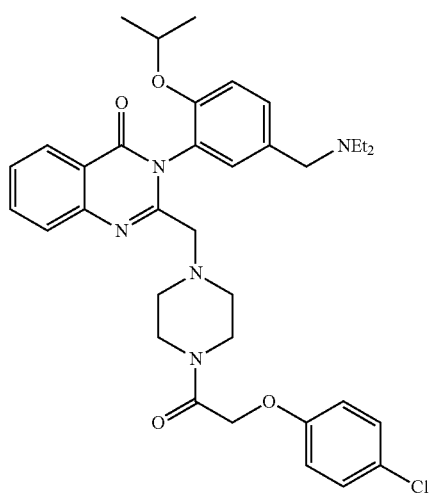
(17)
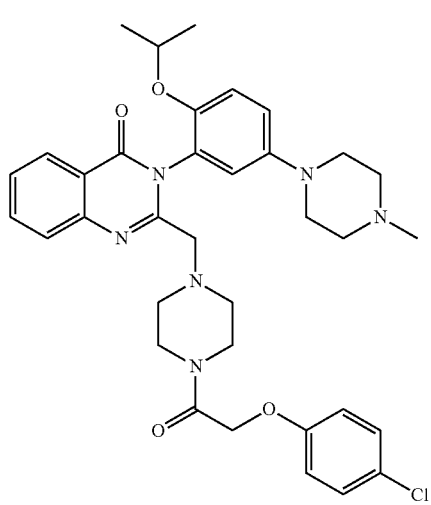
(18)
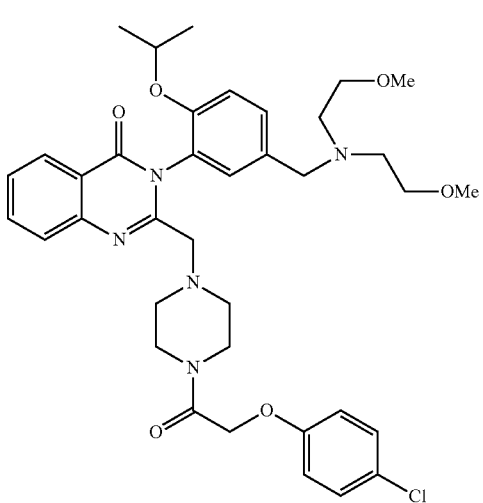
(19)
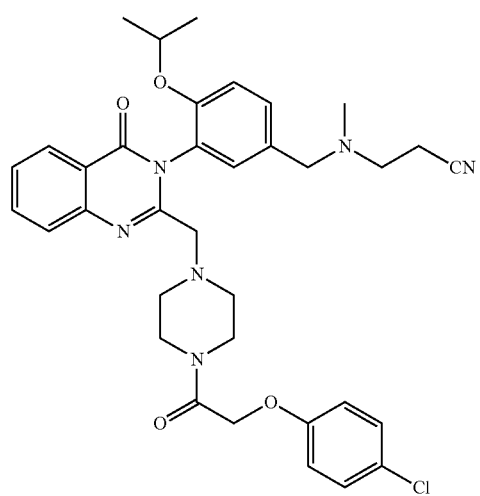
(60)
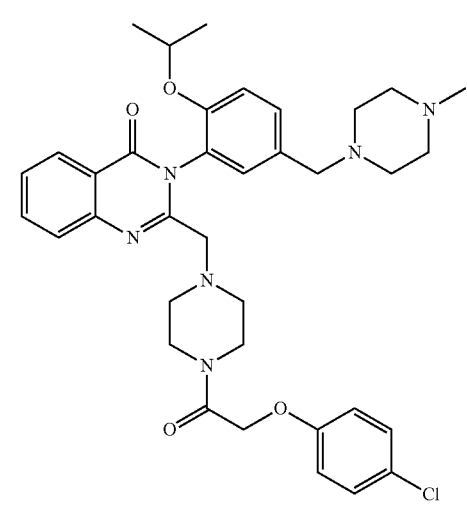
(21)
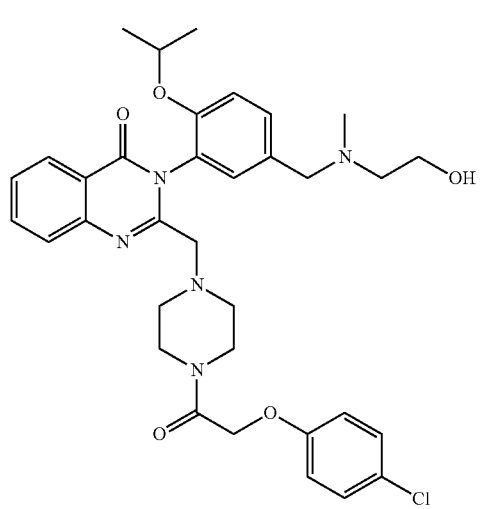

(22)
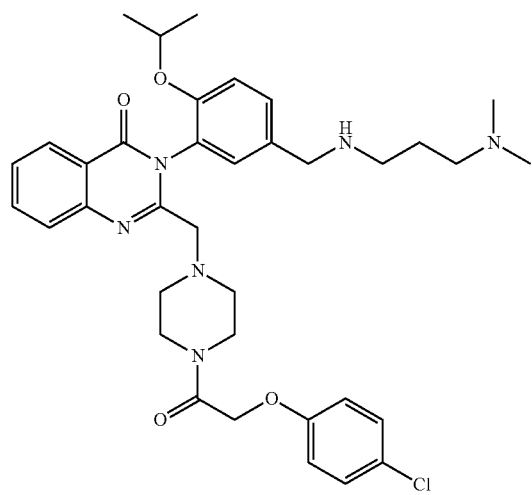
(1a)
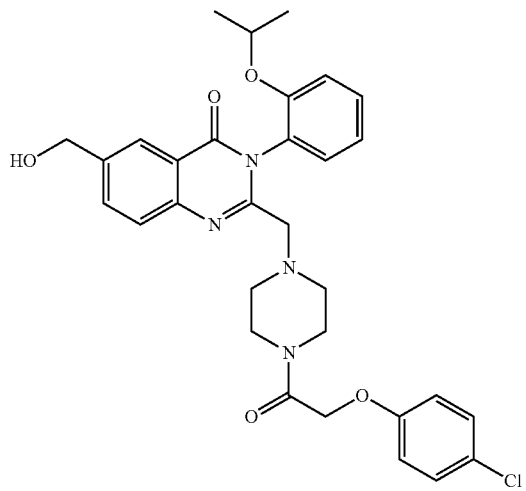
(23)
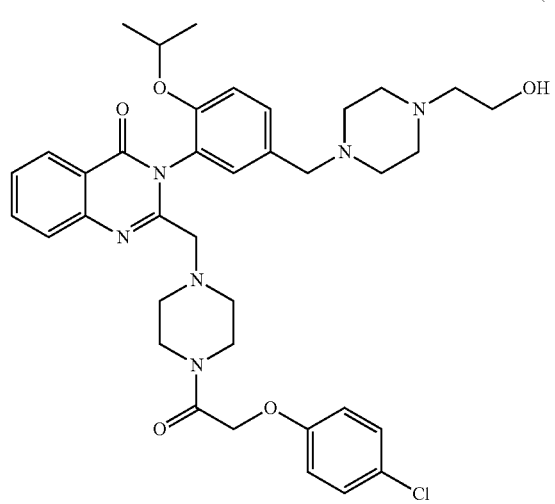
(2)
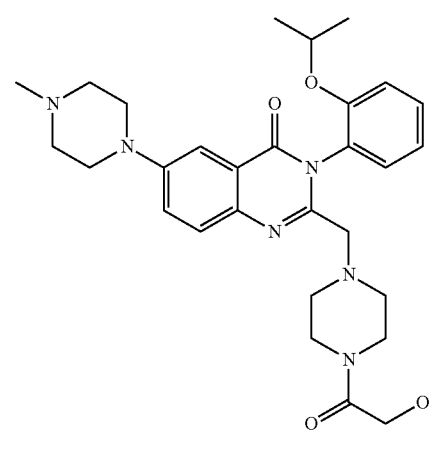
(24)
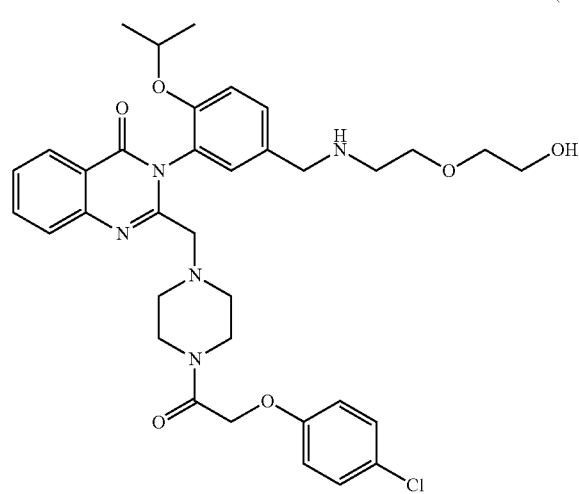
(3)
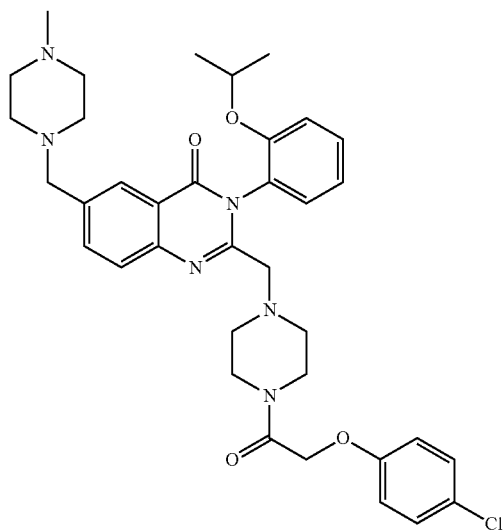

(4)
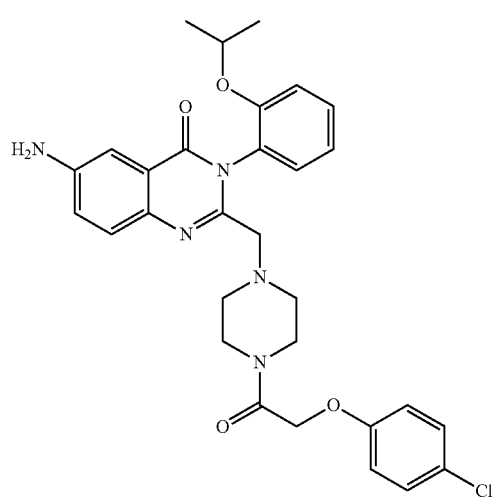
(5)
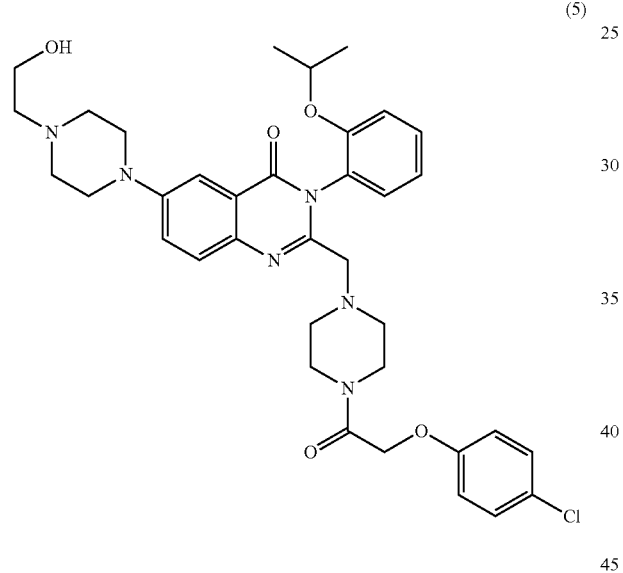
(6)
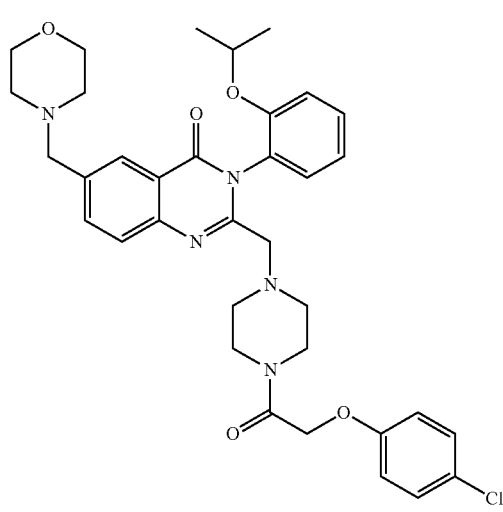
(7)
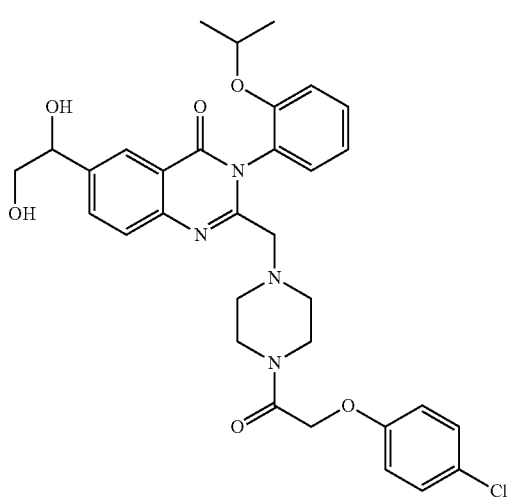
(8)
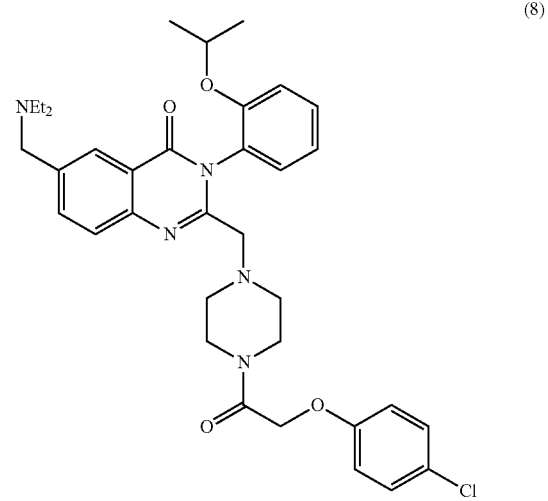
(9)
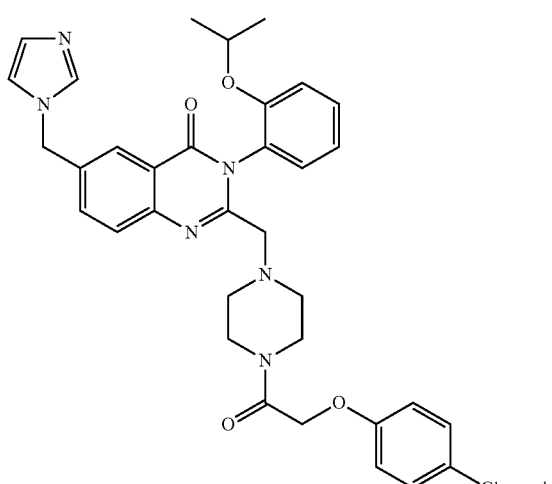
and (11)

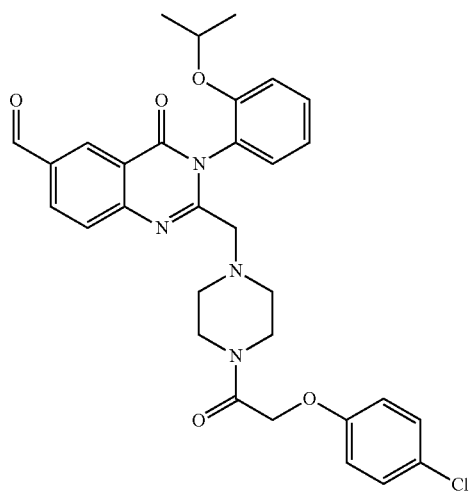

or an N-oxide, crystalline form, hydrate, or pharmaceutically acceptable salt thereof.

An additional embodiment of the present invention is a composition. This composition comprises a pharmaceutically acceptable carrier and any compound disclosed herein.

Another embodiment of the present invention is a method for treating or ameliorating the effects of a cancer comprising a cell that harbors an oncogenic RAS mutation. This method comprises administering to a subject in need thereof a therapeutically effective amount of a compound selected from the group consisting of:

(DPI2)

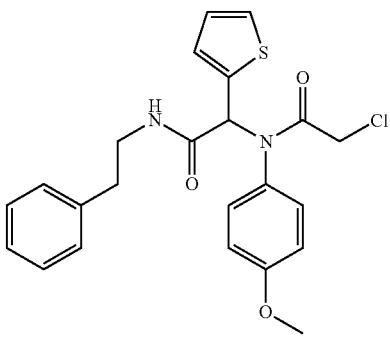

(DPI3)

(DPI4)

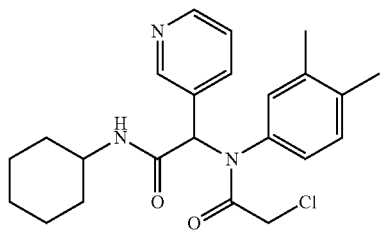

(DPI6)

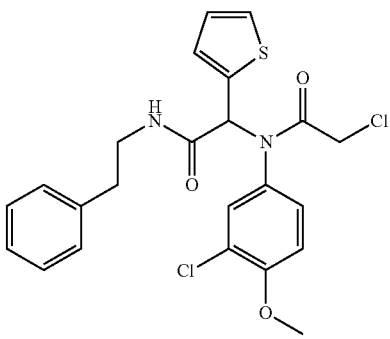

(DPI7)

(DPI8)

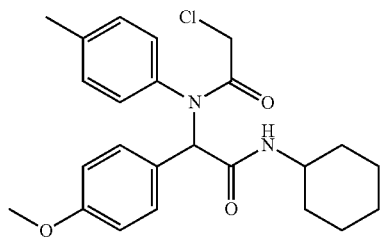

(DPI9)

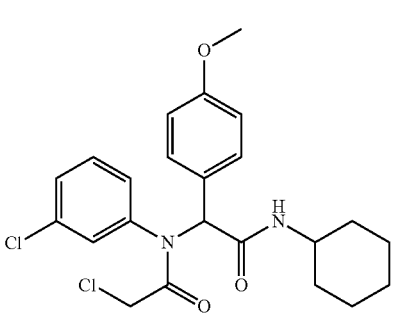

75
-continued
(DPI10)
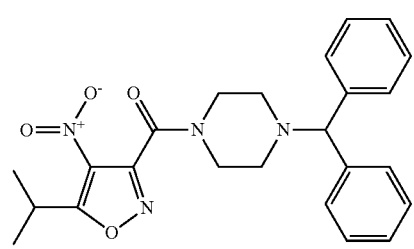
(DPI12)
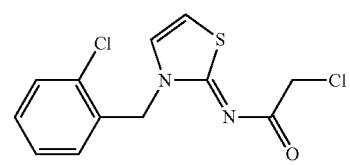
(DPI13)
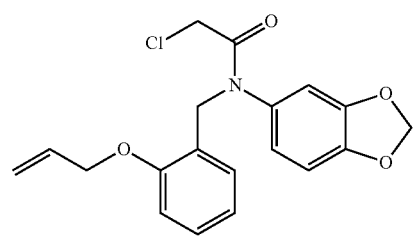
(DPI15)
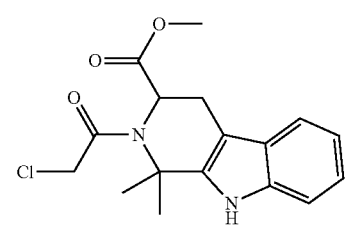
(DPI17)
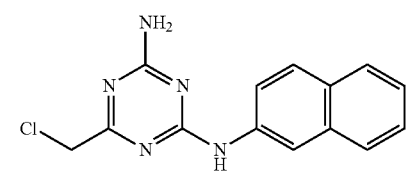
(DPI18)
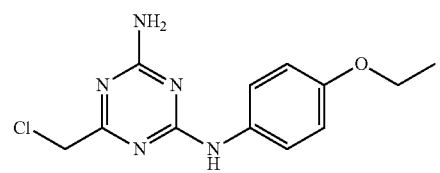
(DPI19)
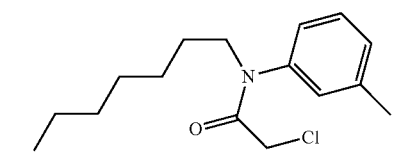
76
-continued
(51)
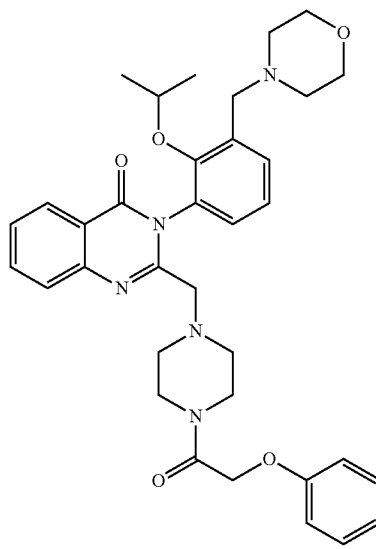
(52)
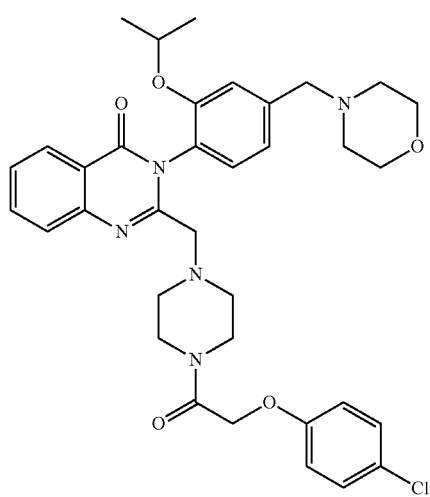
(40)
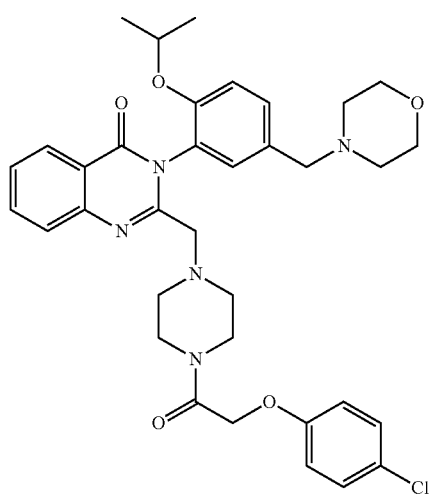

77
-continued
(15)
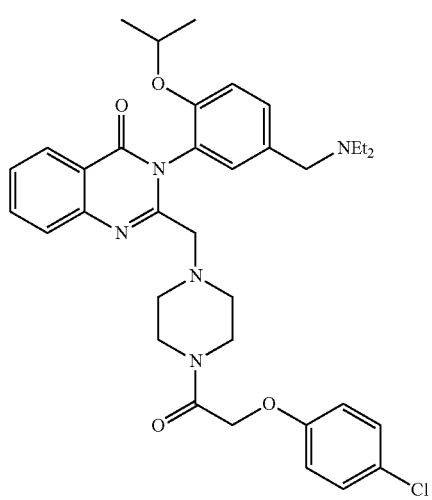
(17)
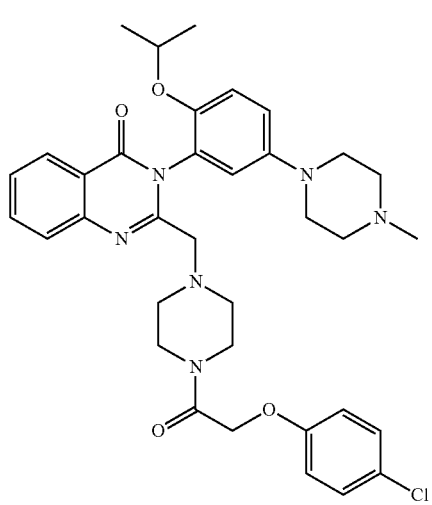
(18)
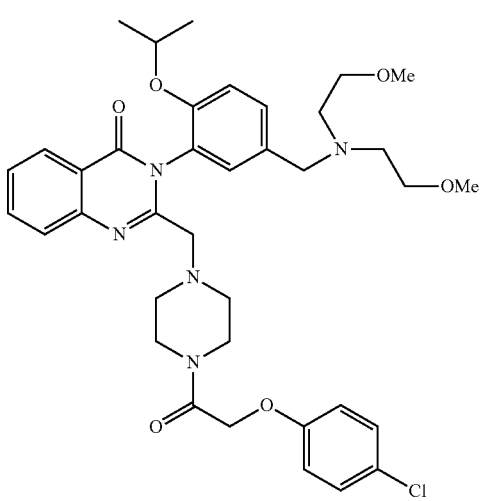
78
-continued
(19)
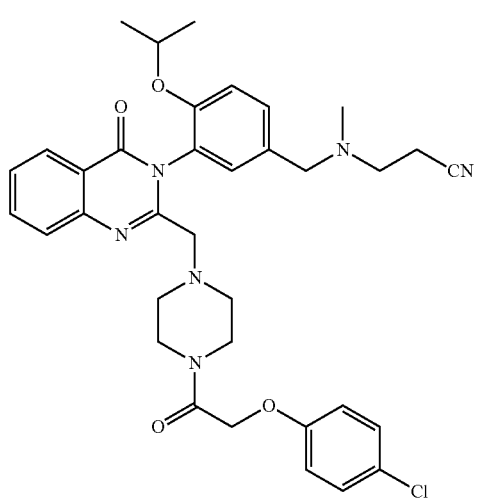
(60)
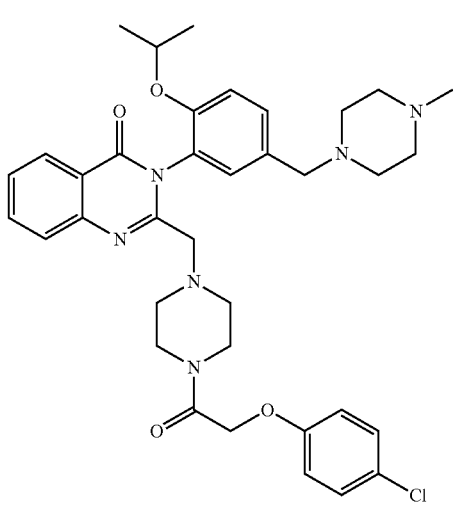
(21)
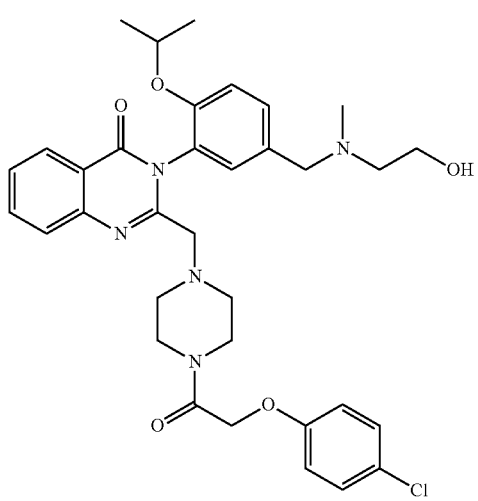

(22)
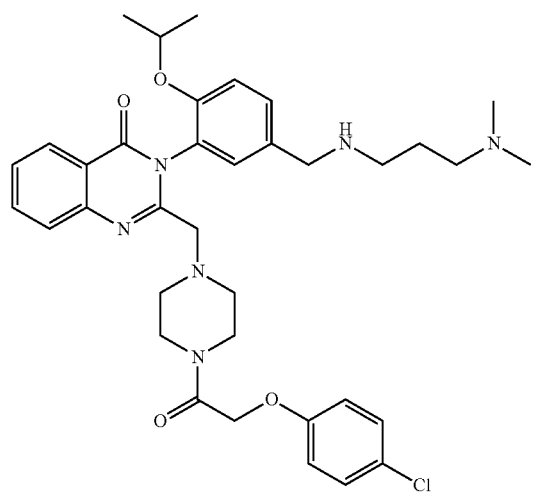
(23)
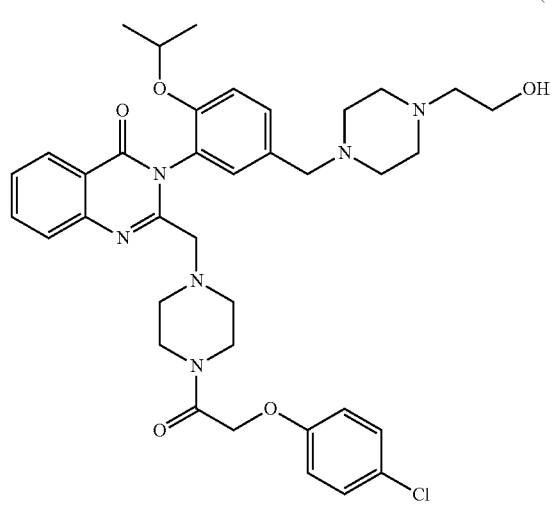
(24)
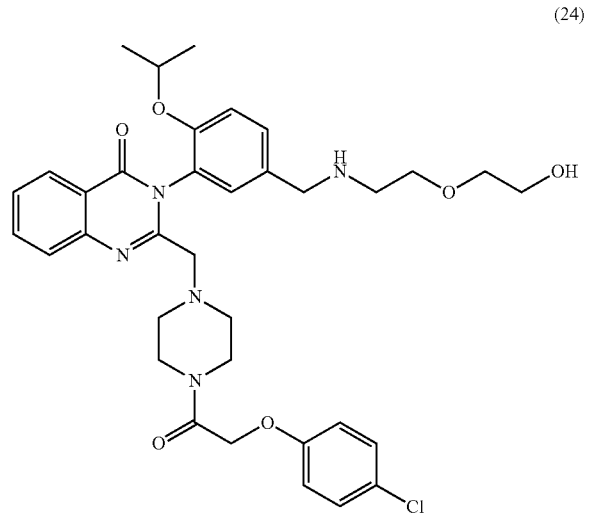
(1a)
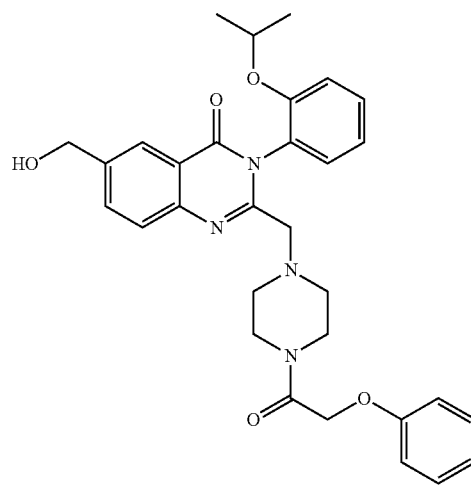
(2)
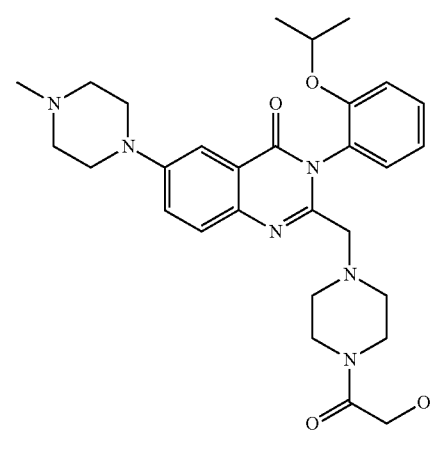
(3)
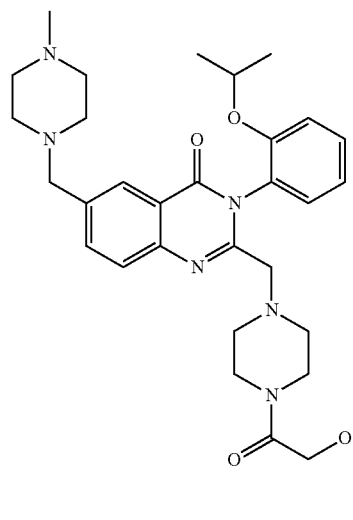

(4)
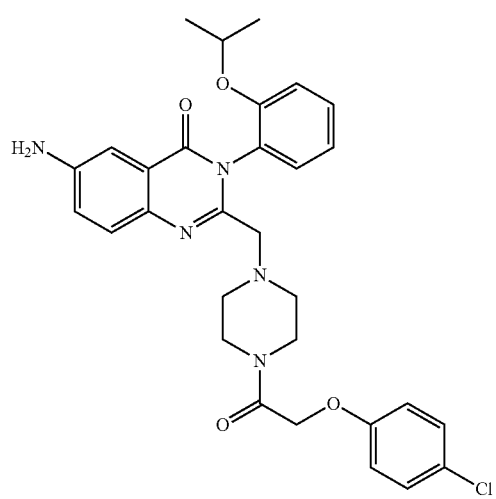
(5)
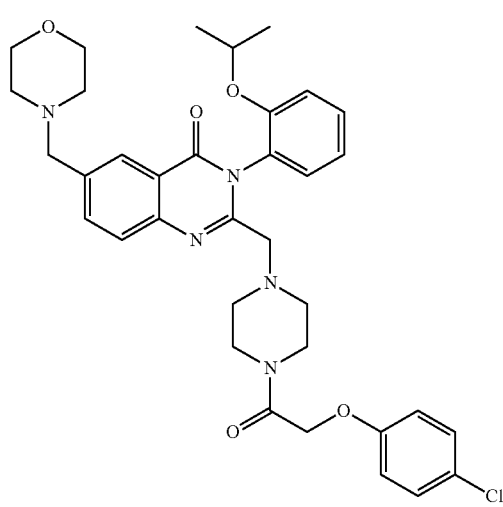
(6)
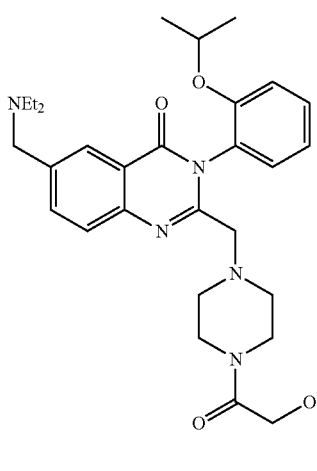
(7)
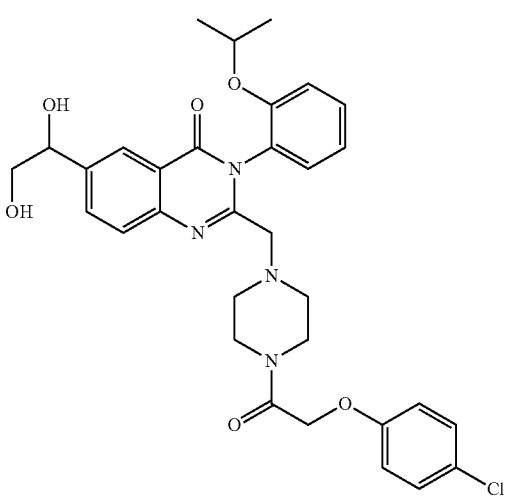
(8)
(9)
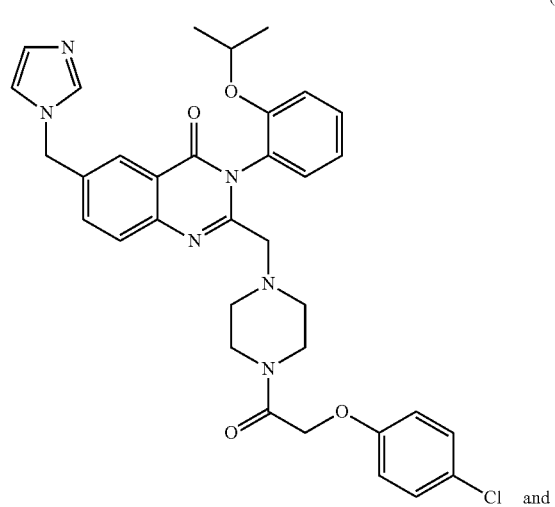
and

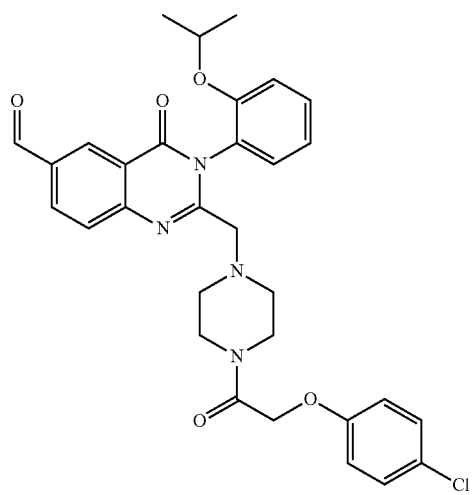
(11)
or an N-oxide, crystalline form, hydrate, or pharmaceutically acceptable salt thereof.
In one aspect of this embodiment, the compound is selected from the group consisting of:
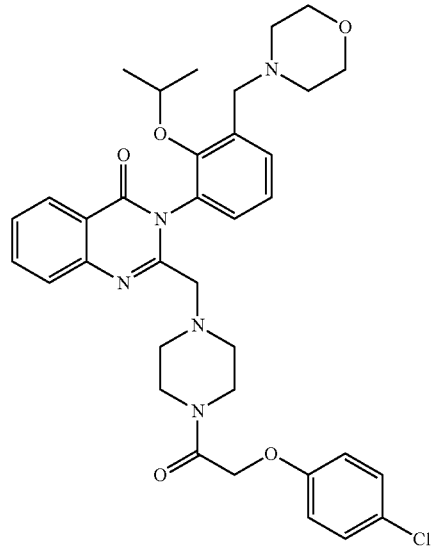
(51)
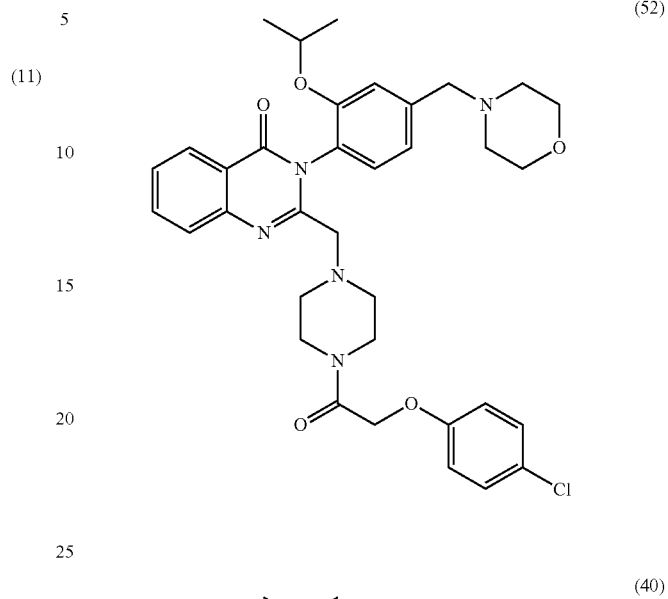
(52)
(40)
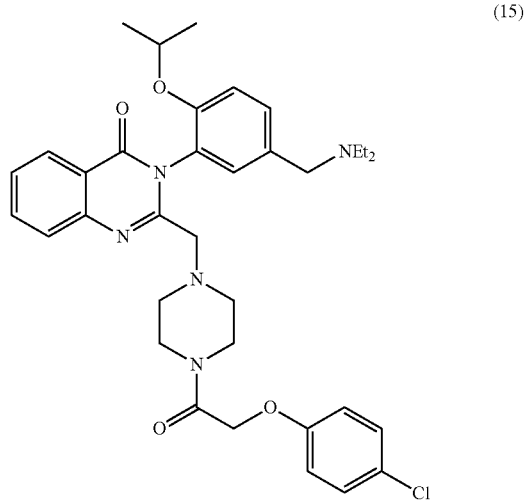
(15)

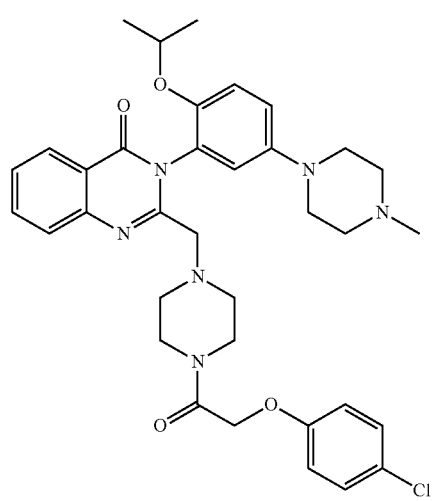
(17)
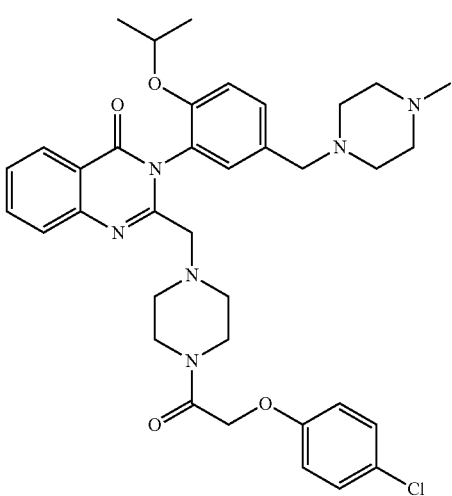
(60)
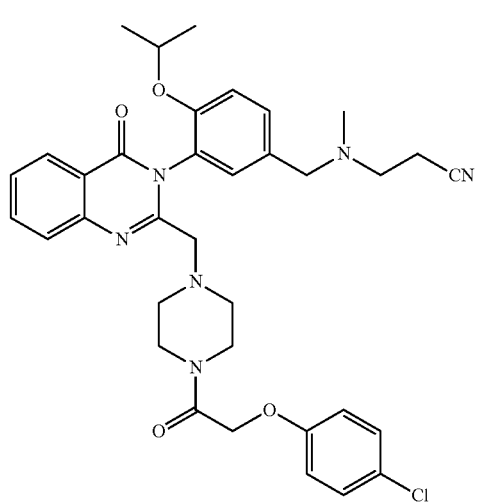
(18)
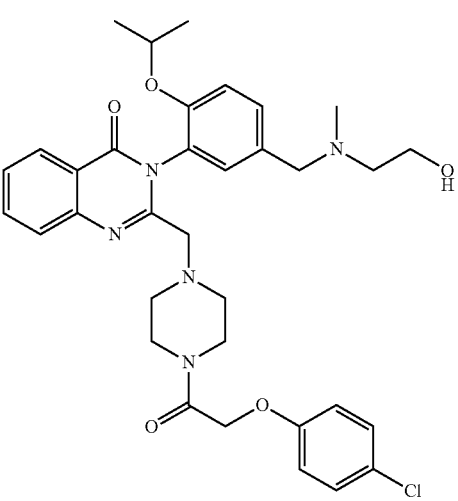
(21)
(19)
(22)

87
-continued
(23)
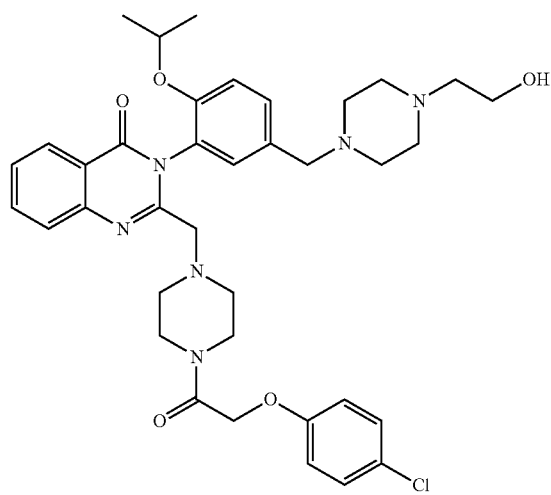
(24)
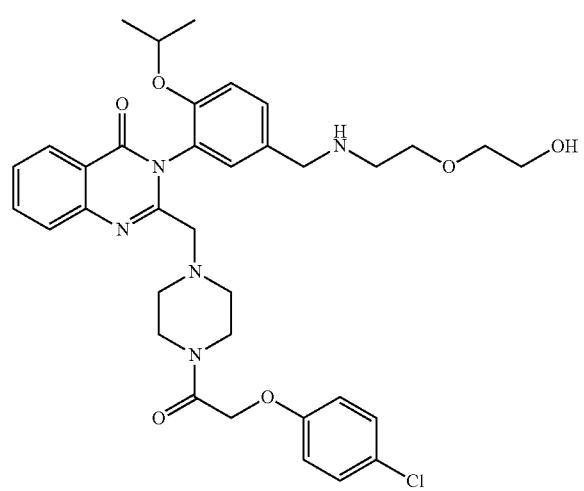
(1a)
88
-continued
(4)
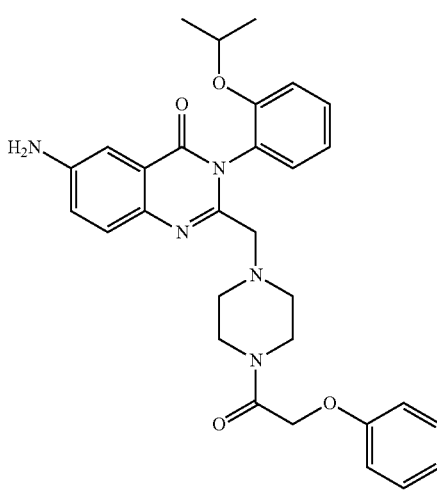
(6)
(7)
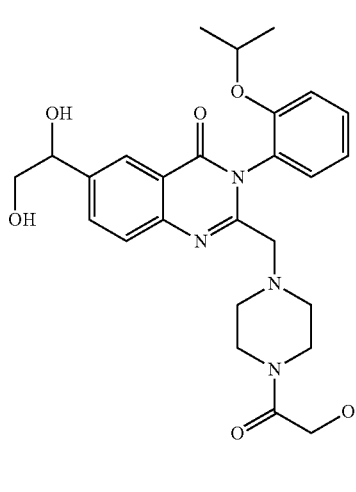

-continued
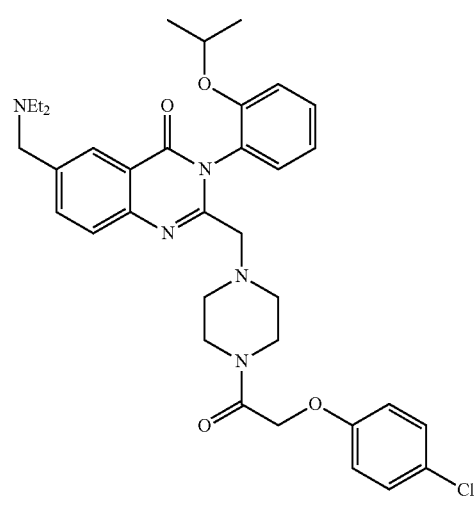
(8)
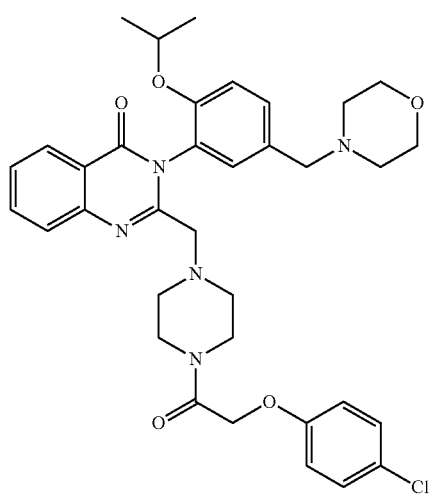
(40)
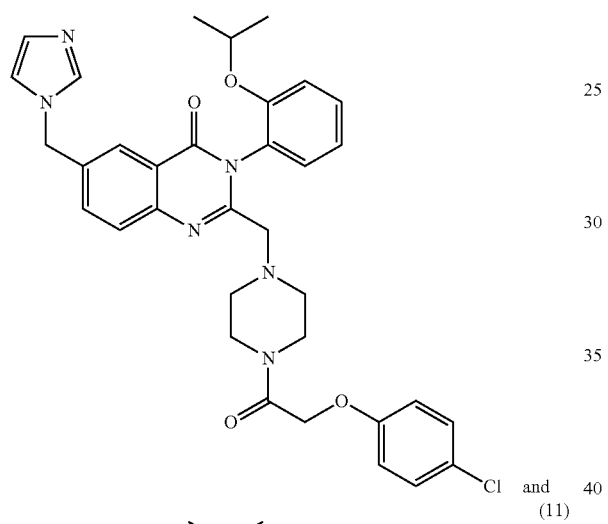
(9)
and
(11)
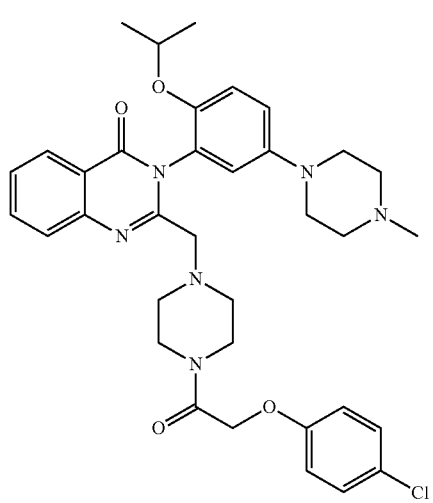
(17)
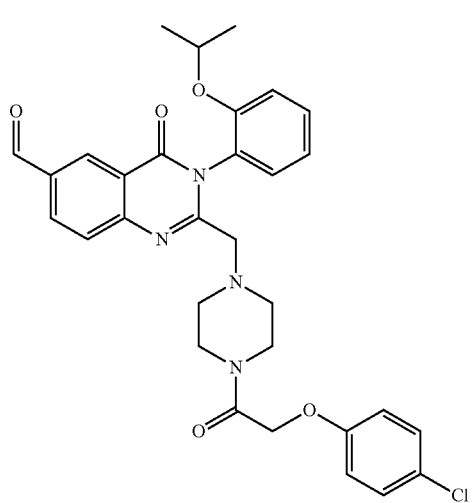
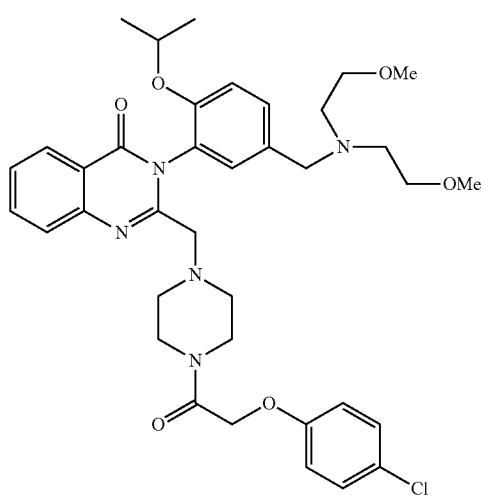
(18)
or an N-oxide, crystalline form, hydrate, or pharmaceutically acceptable salt thereof.
In another aspect of this embodiment, wherein the compound is selected from the group consisting of:

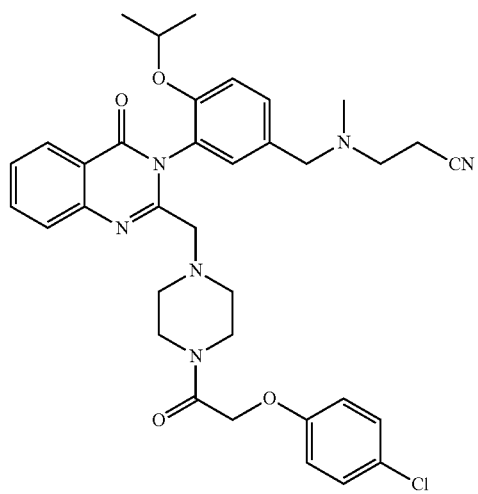

(19)

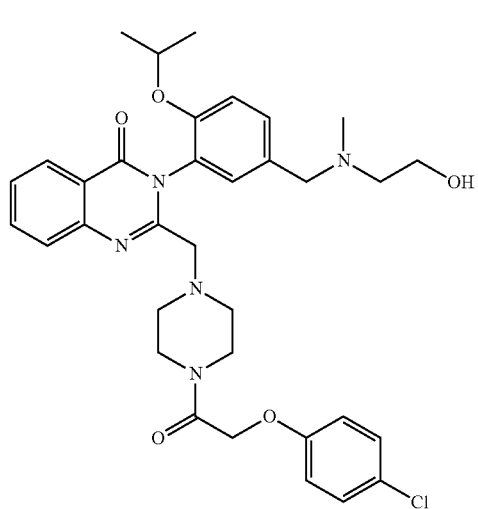

(60)

(21)

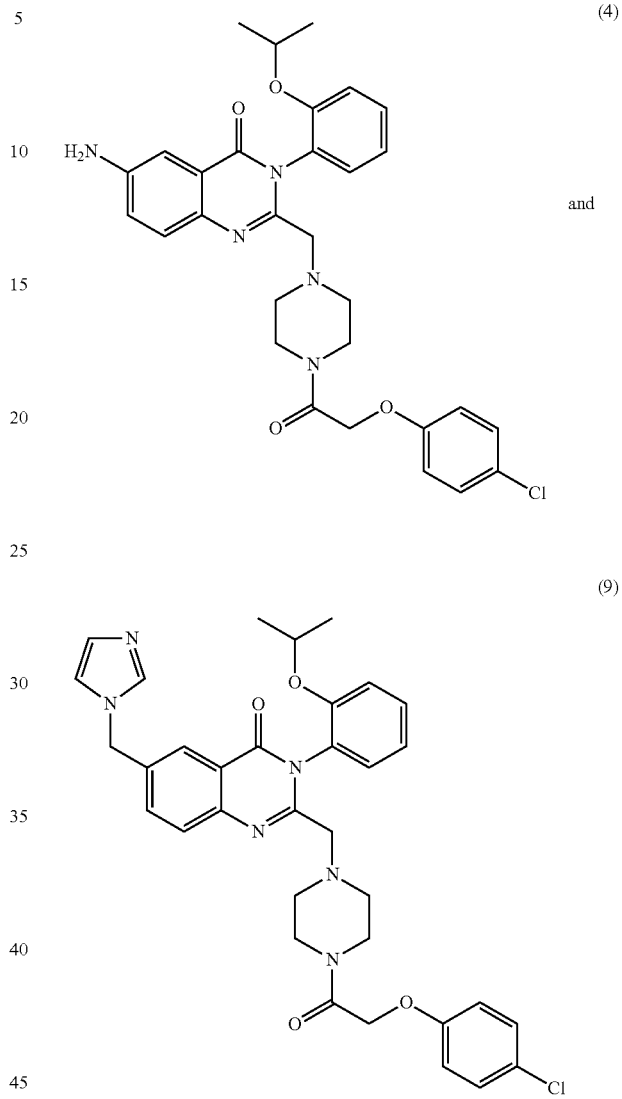

or an N-oxide, crystalline form, hydrate, or pharmaceutically acceptable salt thereof.

Another embodiment of the present invention is a method for modulating a lipoxygenase in a ferroptosis cell death pathway. This method comprises administering to a cell an effective amount of any compound or composition disclosed herein.

In one aspect of this embodiment, the modulation comprises activation of one or more polypeptides encoded by ALOX genes. Suitable and preferred ALOX genes are disclosed herein.

An additional embodiment of the present invention is a method for modulating a lipoxygenase in a ferroptosis cell death pathway. This method comprises administering to a cell an effective amount of a compound selected from the group consisting of:

(DPI2) 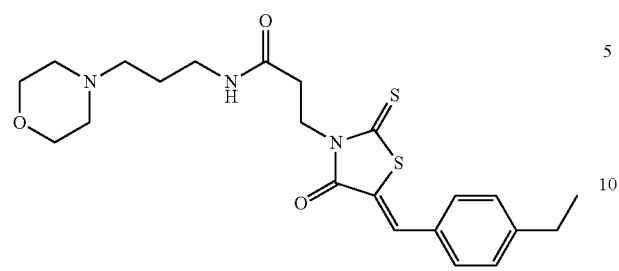
(DPI3) 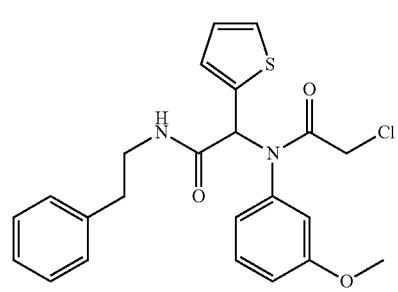
(DPI4) 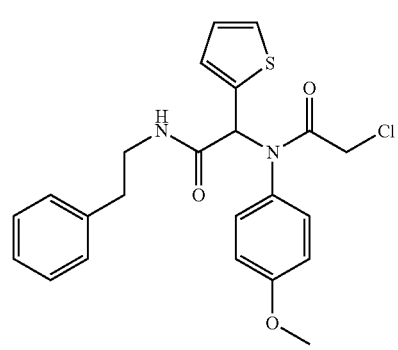
(DPI6) 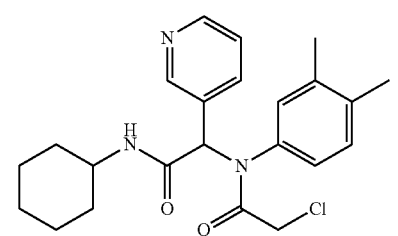
(DPI7) 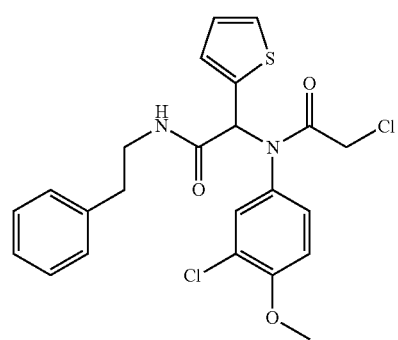
(DPI8) 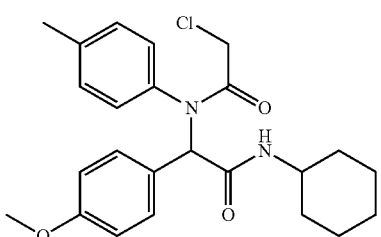
(DPI9) 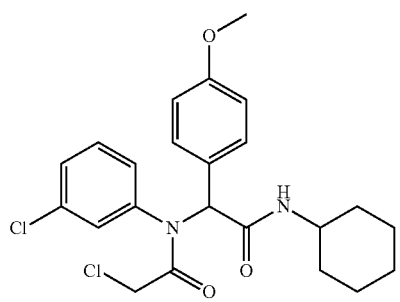
(DPI10) 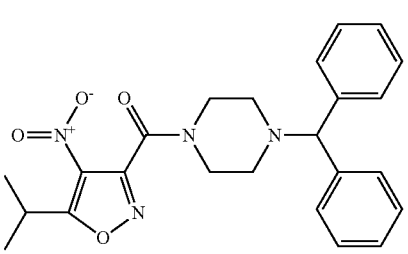
(DPI12) 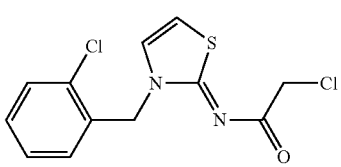
(DPI13) 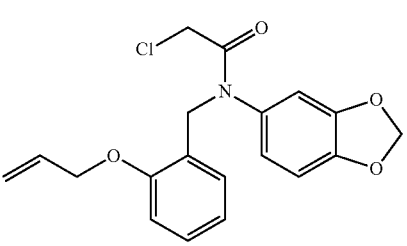
(DPI15) 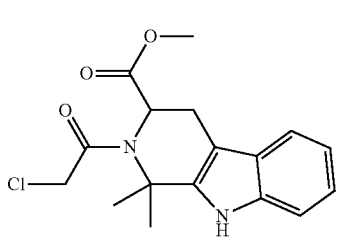
(DPI17) 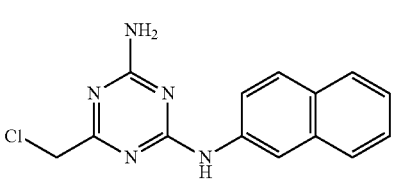

-continued
(DPI18)
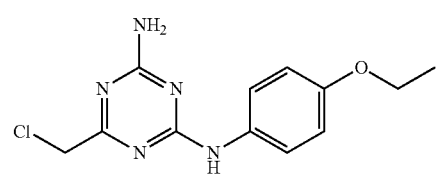
(DPI19)
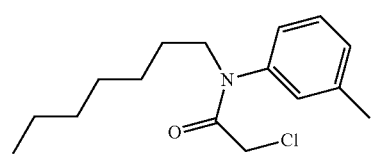
(51)
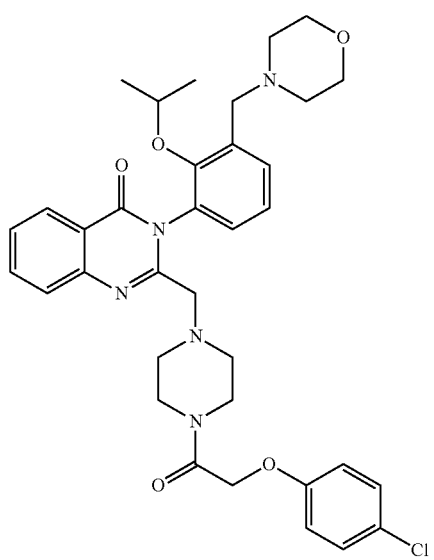
-continued
(40)
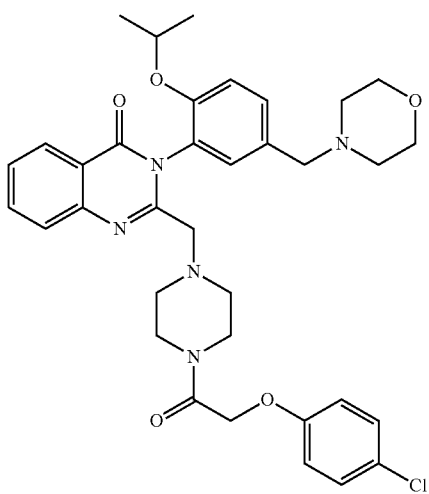
(15)
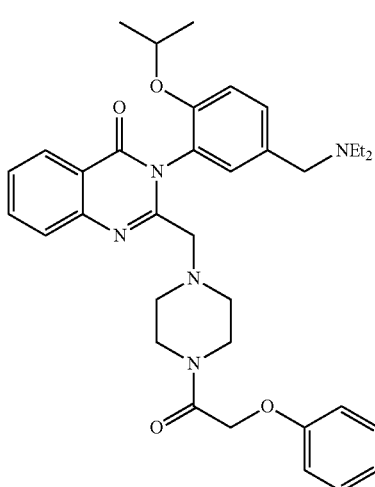
(17)
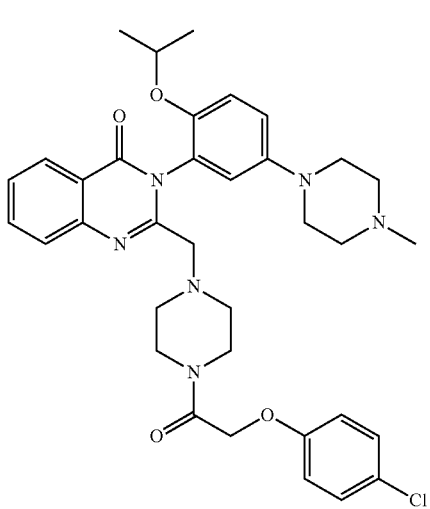

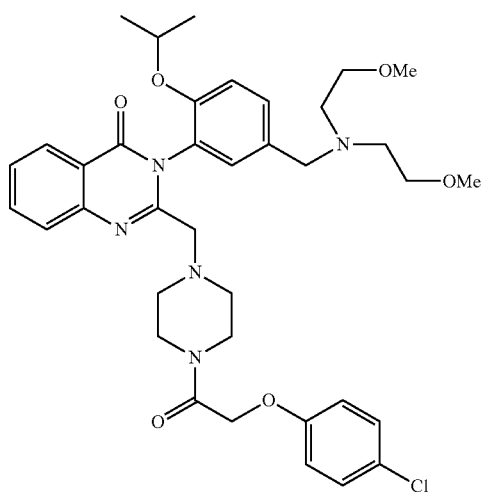
(18)
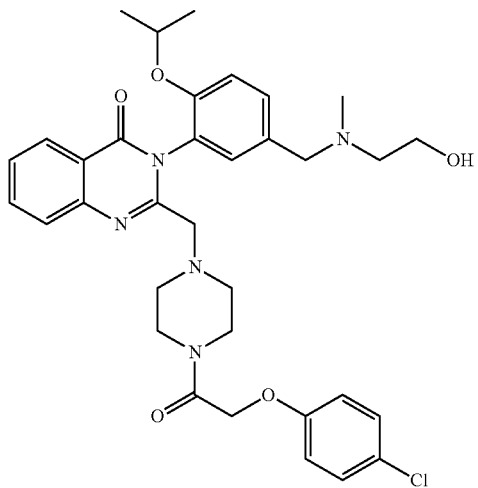
(21)
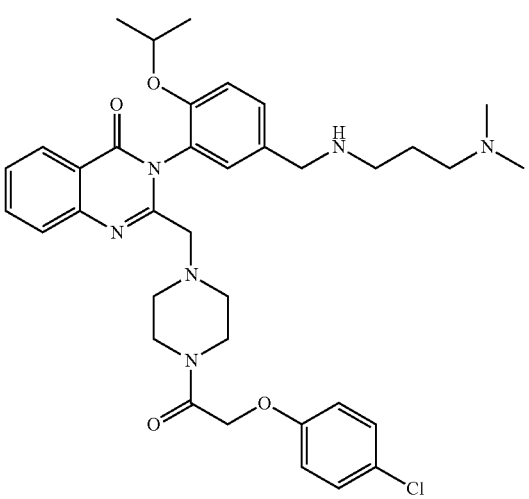
(19)
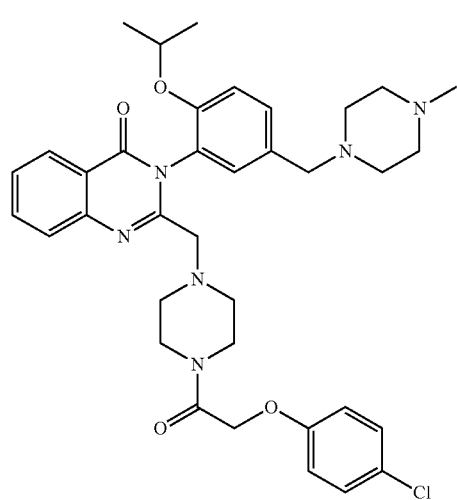
(22)
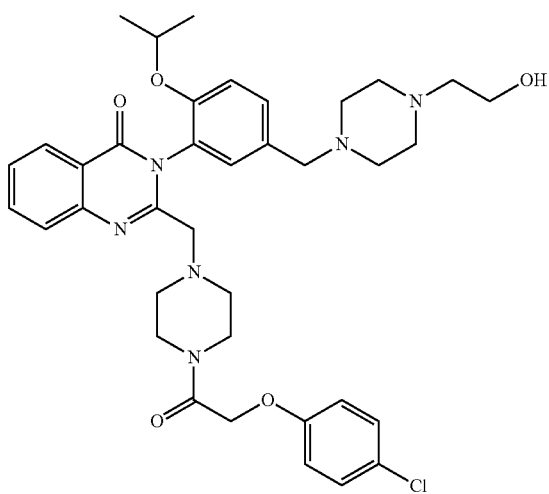
(60)
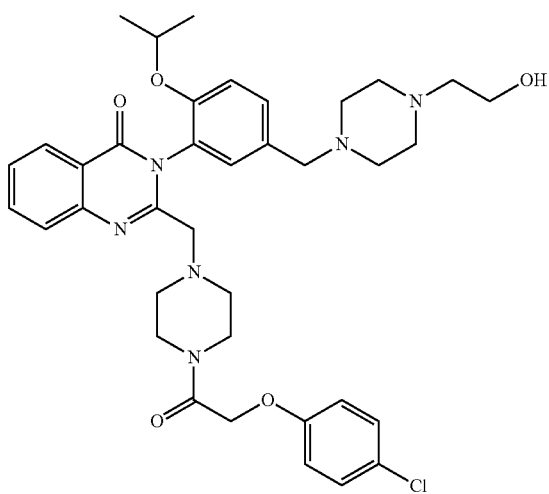
(23)

99
-continued
(24)
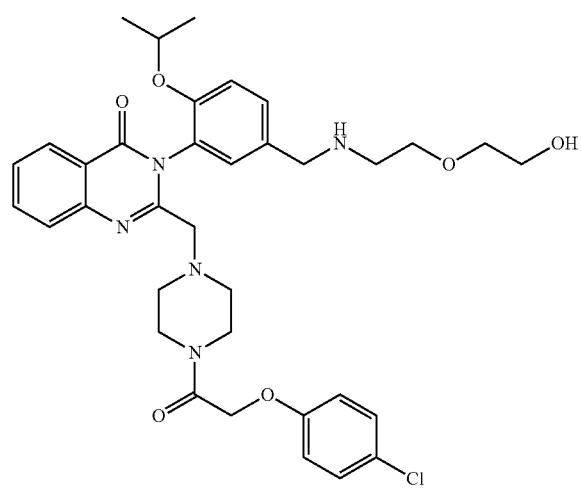
(1a)
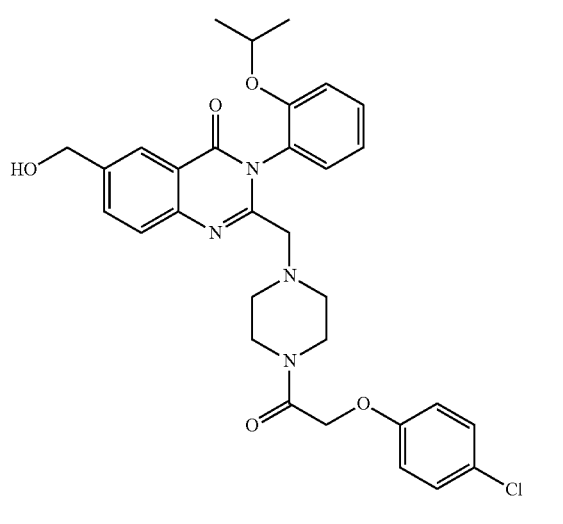
(2)
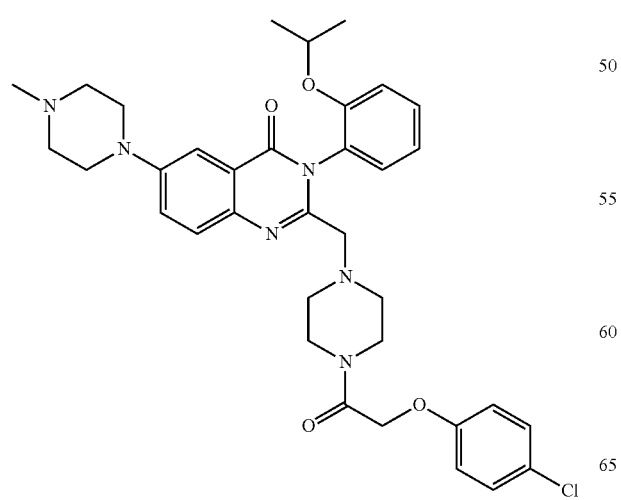
100
-continued
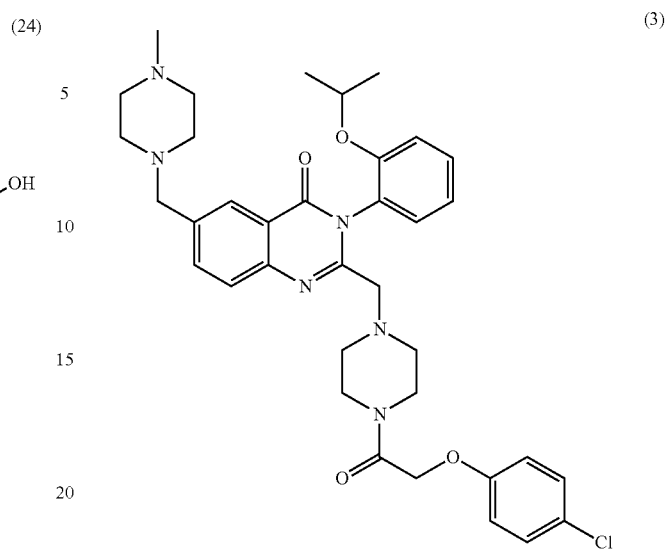
(3)
(4)
(5)

-continued
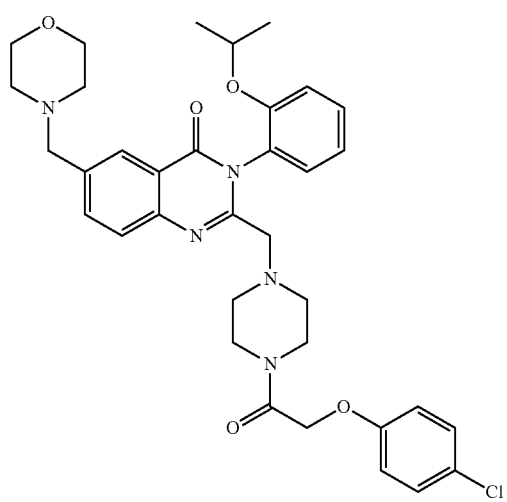
(6)
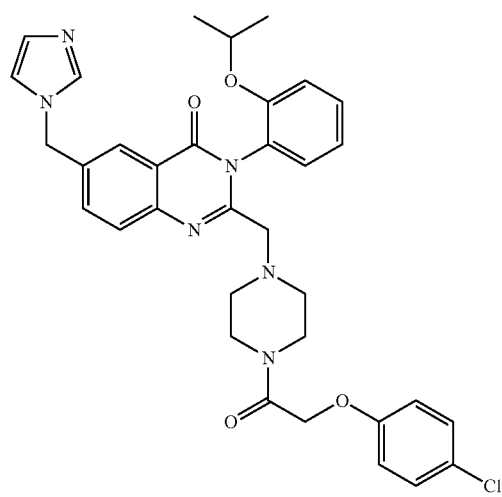
(9)
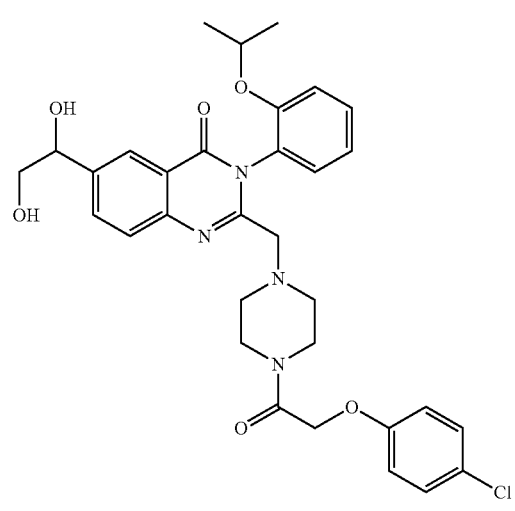
(7)
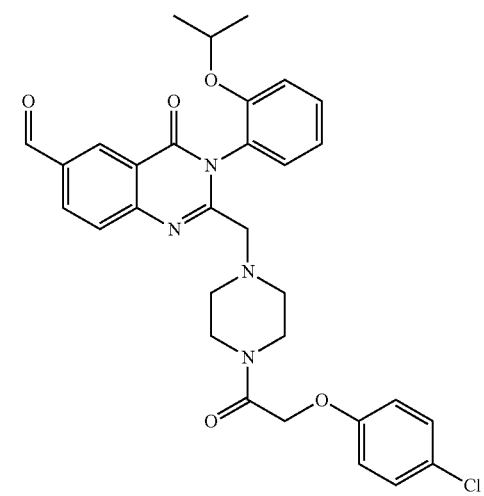
(11)
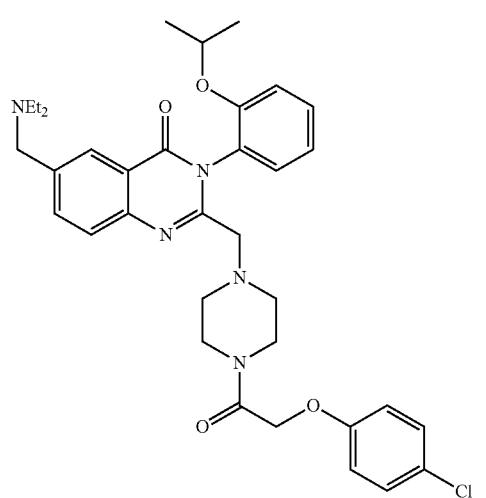
(8)

(9)

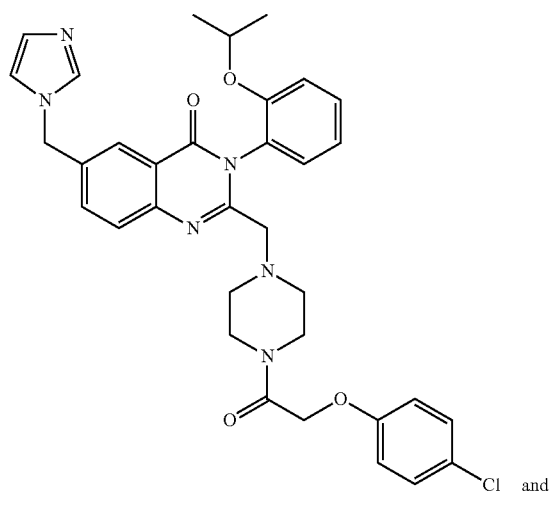

and (11)

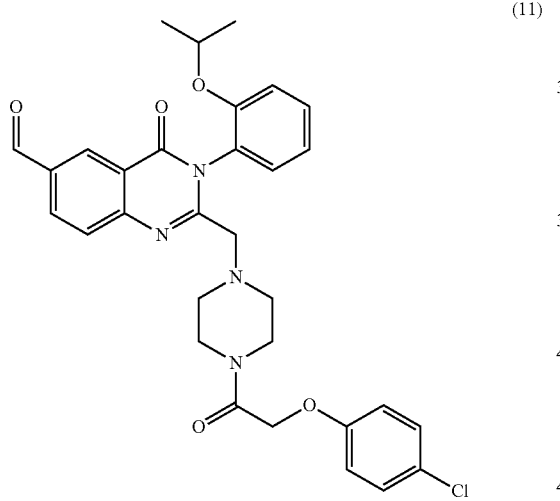

or an N-oxide, crystalline form, hydrate, or pharmaceutically acceptable salt thereof.

In one aspect of this embodiment, the modulation comprises activation of one or more polypeptides encoded by ALOX genes. Suitable and preferred ALOX genes are disclosed herein.

A further embodiment of the present invention is a method for depleting reduced glutathione (GSH) in a cell harboring an oncogenic RAS mutation. This method comprises administering to the cell an effective amount of any compound or composition disclosed herein.

Another embodiment of the present invention is a method for depleting reduced glutathione (GSH) in a cell harboring an oncogenic RAS mutation. This method comprises administering to the cell an effective amount of a compound selected from the group consisting of:

(DPI2)

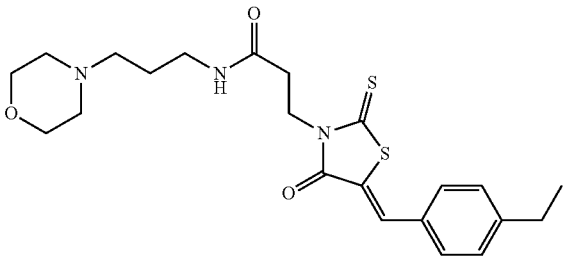

(DPI3)

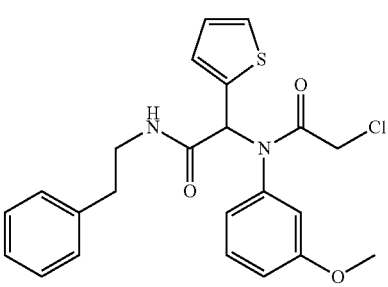

(DPI4)

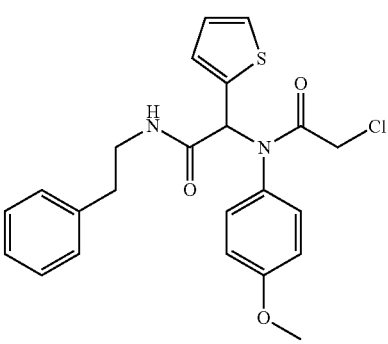

(DPI6)

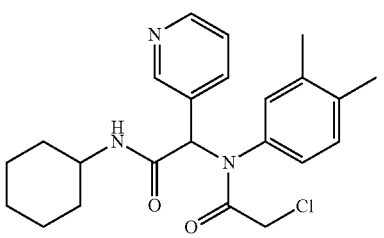

(DPI7)

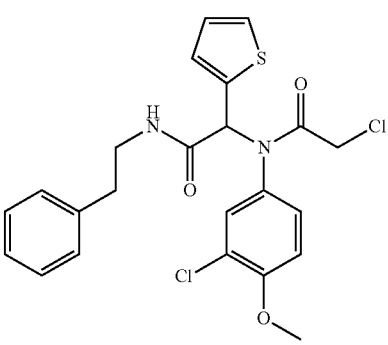

(DPI8)
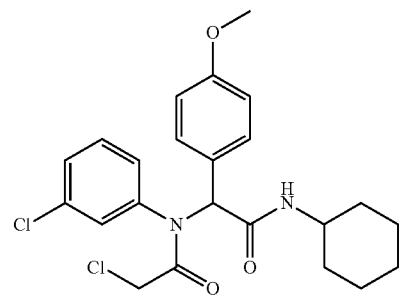
(DPI9)
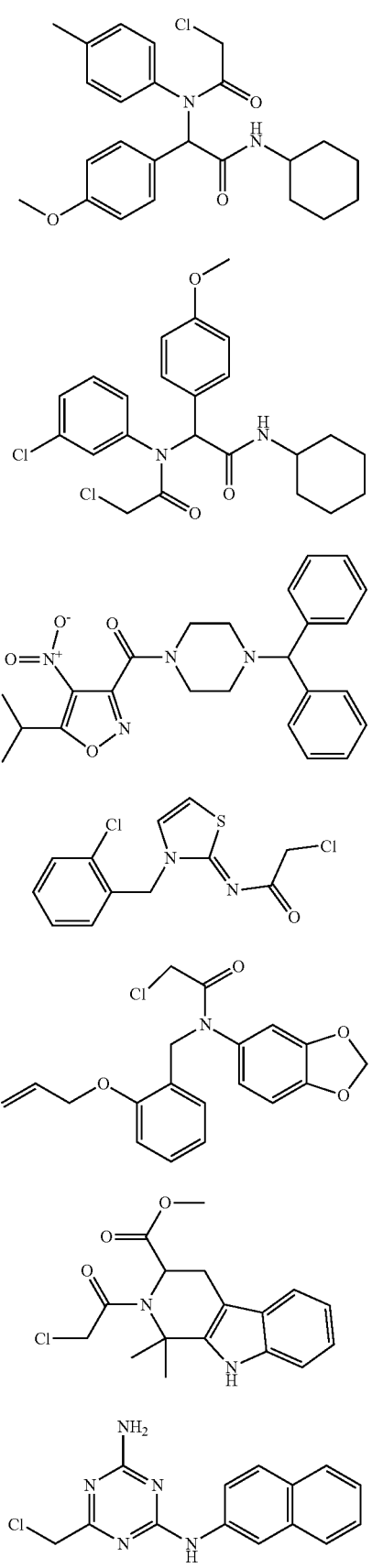
(DPI10)
(DPI12)
(DPI13)
(DPI15)
(DPI17)
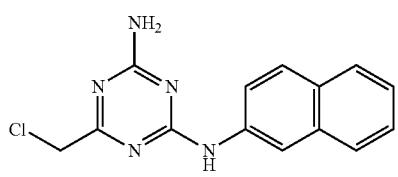
(DPI18)
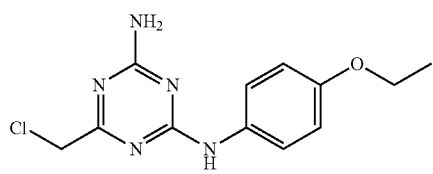
(DPI19)
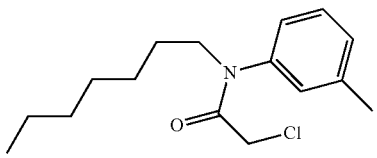
(51)
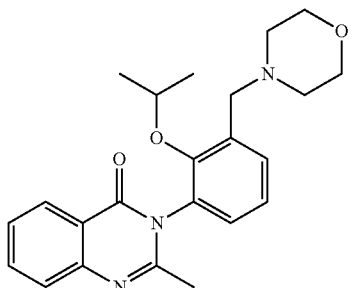
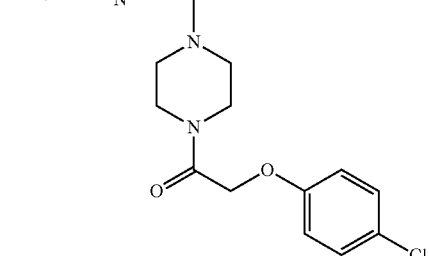
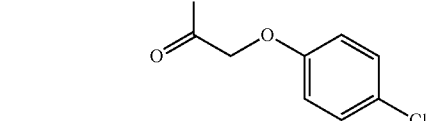
(52)
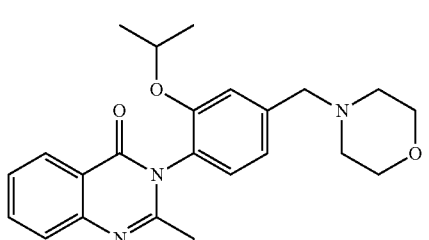
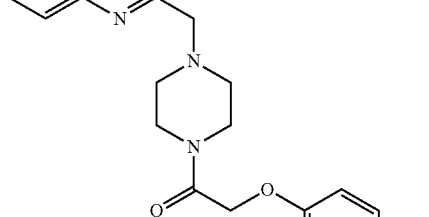

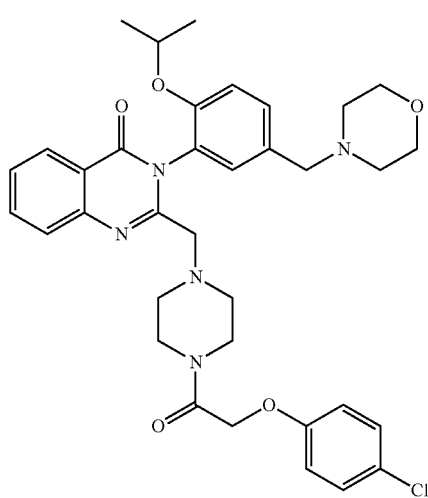
(40)
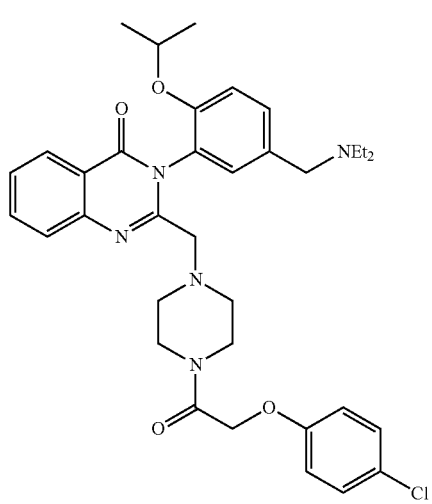
(15)
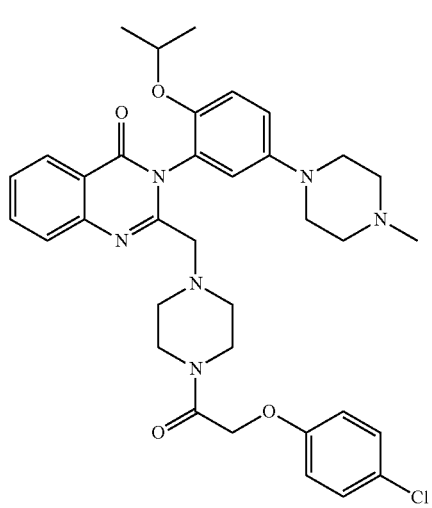
(17)
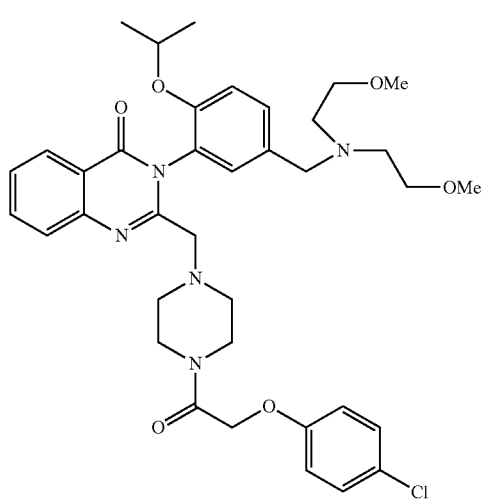
(18)
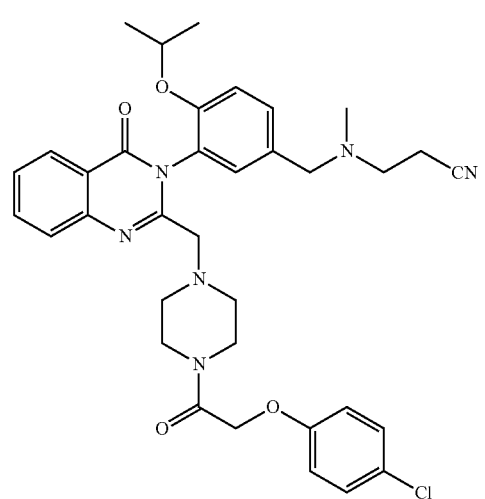
(19)
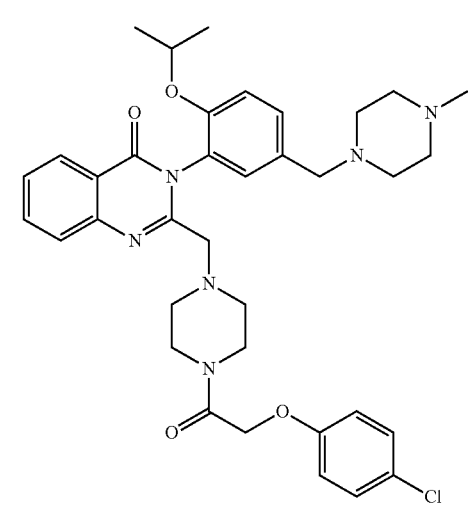
(60)

-continued
(21)
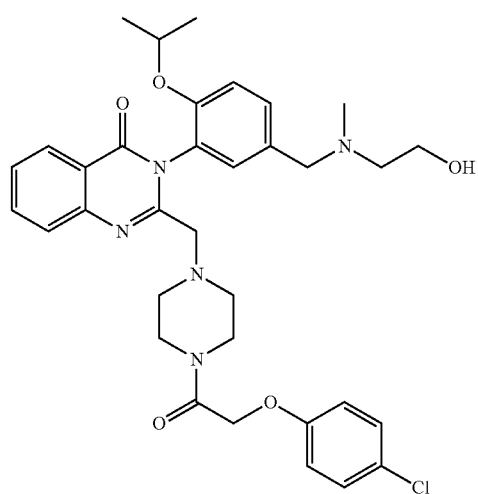
(22)
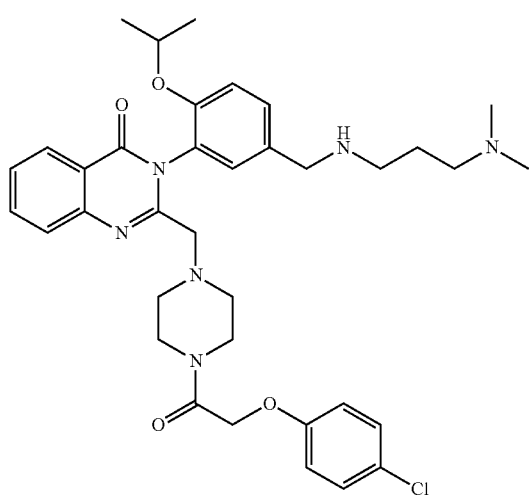
(23)
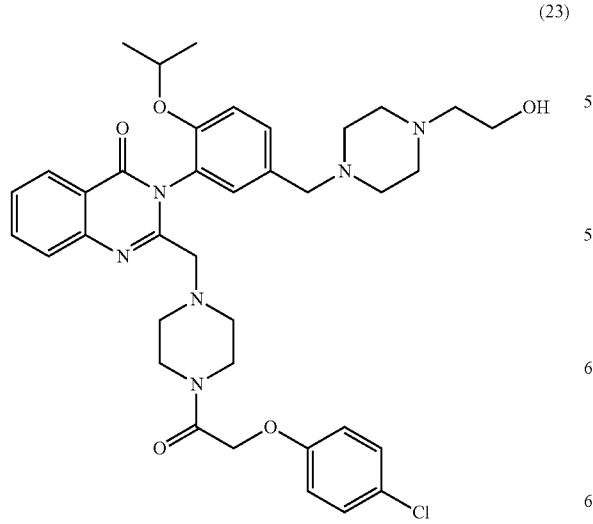
-continued
(24)
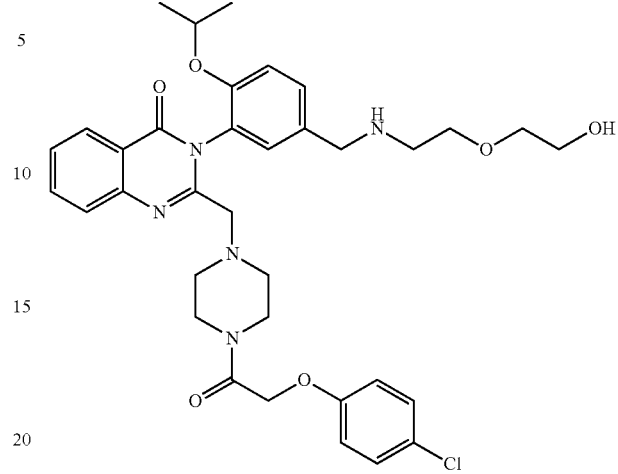
(1a)
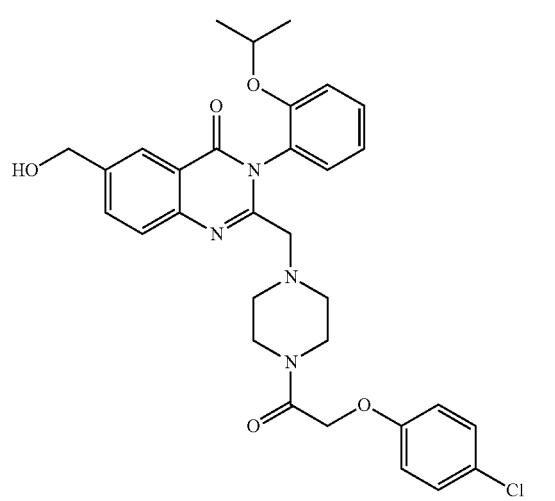
(2)
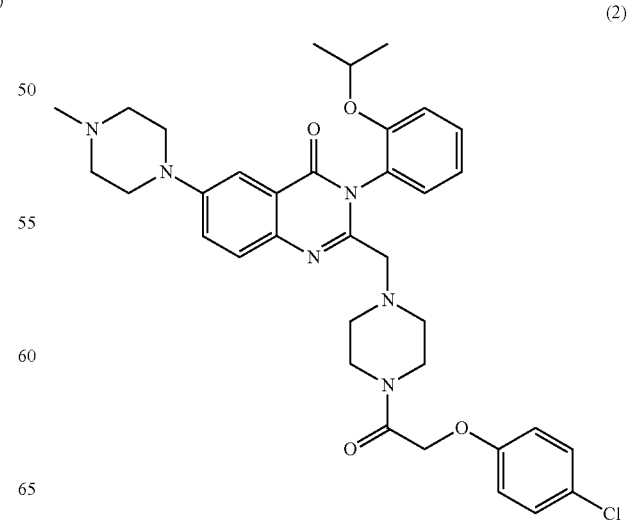

111
-continued
(3)
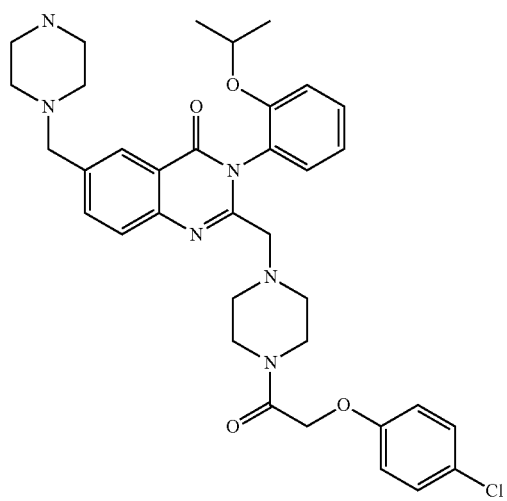
112
-continued
(6)
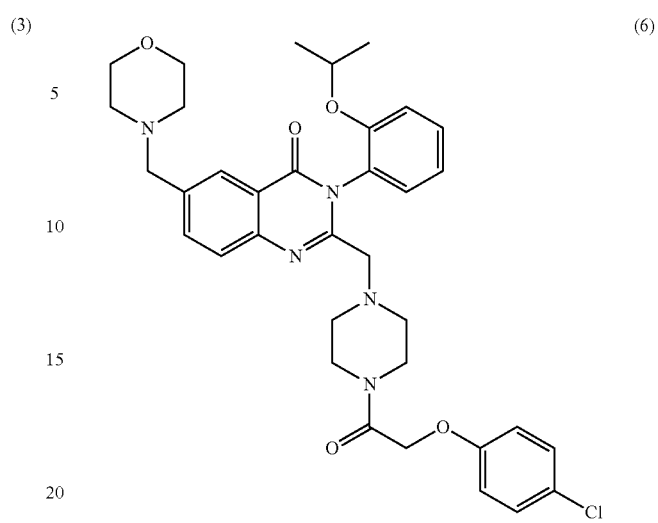
(4)
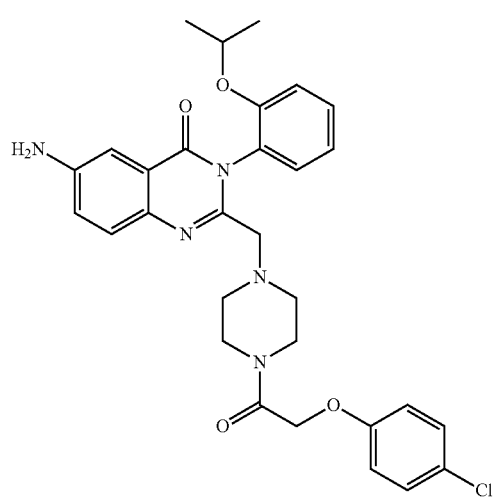
(7)
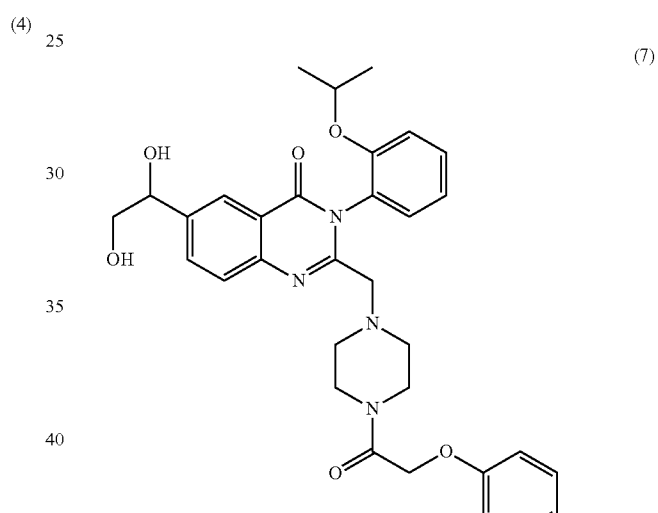
(5)
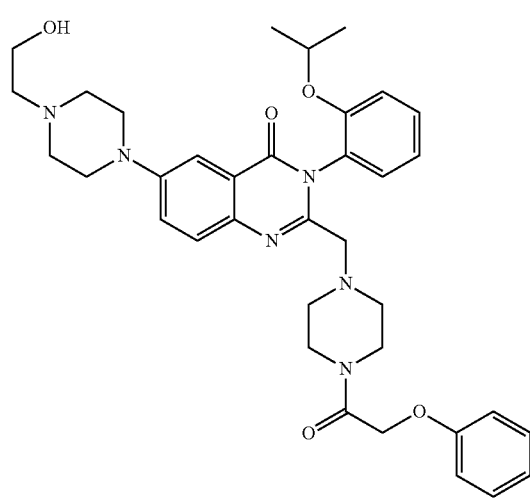
(8)
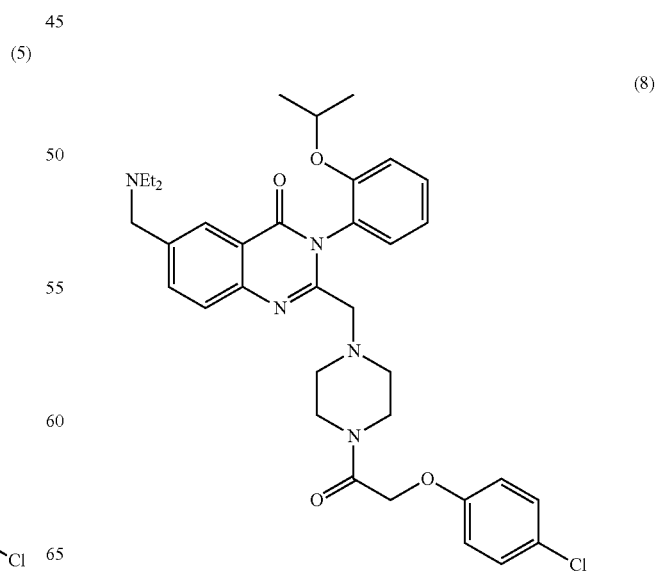

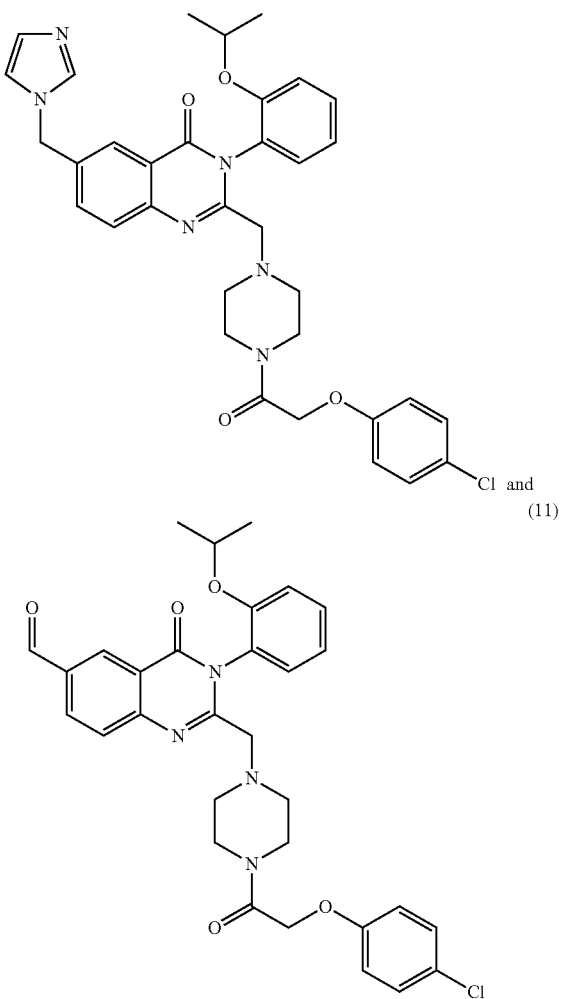

or an N-oxide, crystalline form, hydrate, or pharmaceutically acceptable salt thereof.

In the present invention, an "effective amount" or "therapeutically effective amount" of a compound or composition, is an amount of such a compound or composition that is sufficient to effect beneficial or desired results as described herein when administered to a subject or a cell. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of the subject, and like factors well known in the arts of, e.g., medicine and veterinary medicine. In general, a suitable dose of a compound or composition according to the invention will be that amount of the compound or composition, which is the lowest dose effective to produce the desired effect with no or minimal side effects. The effective dose of a compound or composition according to the present invention may be administered as two, three, four, five, six or more sub-doses, administered separately at appropriate intervals throughout the day.

A suitable, non-limiting example of a dosage of a compound according to the present invention or a composition comprising such a compound, is from about 1 ng/kg to about 1000 mg/kg, such as from about 1 mg/kg to about 100 mg/kg, including from about 5 mg/kg to about 50 mg/kg. Other representative dosages of a compound or a composition of the present invention include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg.

As used herein, a "pharmaceutically acceptable salt" means a salt of the compounds of the present invention which are pharmaceutically acceptable, as defined herein, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

A compound or composition of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a compound or composition of the present invention may be administered in conjunction with other treatments. A compound or composition of the present invention maybe encapsulated or otherwise protected against gastric or other secretions, if desired.

The compositions of the invention are preferably pharmaceutically acceptable and may comprise one or more active ingredients in admixture with one or more pharmaceutically-acceptable carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21$^{st}$ Edition, Lippincott Williams and Wilkins, Philadelphia, Pa.). More generally, "pharmaceutically acceptable" means that which is useful in preparing a composition that is generally safe, non-toxic, and neither biologically nor otherwise undesirable and includes that which is acceptable for veterinary use as well as human pharmaceutical use.

Pharmaceutically acceptable carriers are well known in the art (see, e.g., Remington, The Science and Practice of Pharmacy (21$^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The compositions of the invention may, optionally, contain additional ingredients and/or materials commonly used in such compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions for rectal or vaginal administration may be presented as a suppository, which maybe prepared by mixing one or more active ingredient(s) with one or more suitable nonirritating carriers which are solid at room temperature, but liquid at body temperature and, therefore, will melt in the rectum or vaginal cavity and release the active compound. Compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

Compositions suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The following examples are provided to further illustrate the methods of the present invention. These examples are illustrative only and are not intended to limit the scope of the invention in any way.

EXAMPLES

Example 1

Materials And Methods

Synthesis of Erastin Analogs

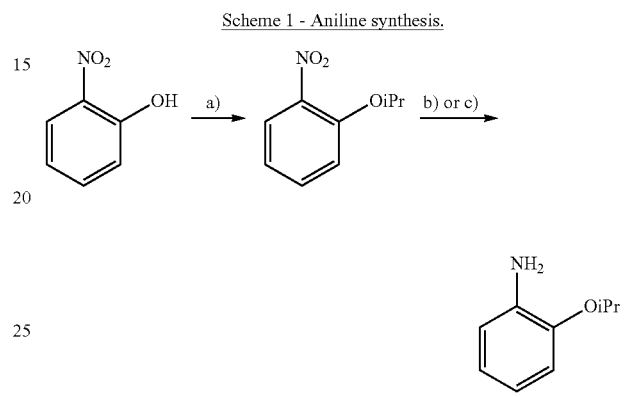

Scheme 1 - Aniline synthesis.

(a) 2-iodopropane (2.0 eq), K$_2$CO$_3$ (1.2 eq), DMF, 50° C., 12 hours; (b) SnCl$_2$ (4.0 eq), HCl (1M, 3.0 eq), THF, 50° C., 24 hours; (c) H$_2$ (1 atm) Pd/C (10%), MeOH, 12-72 hours.

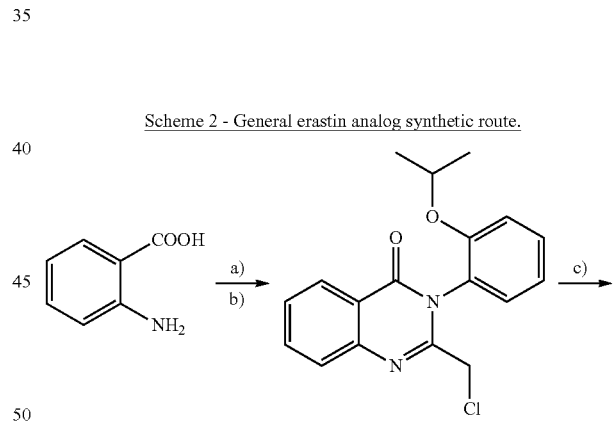

Scheme 2 - General erastin analog synthetic route.

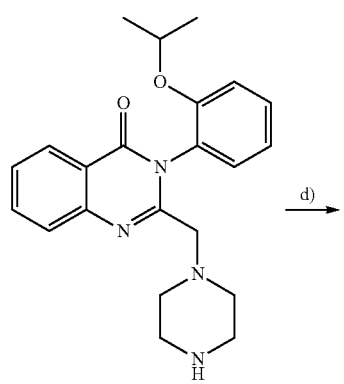

119
-continued

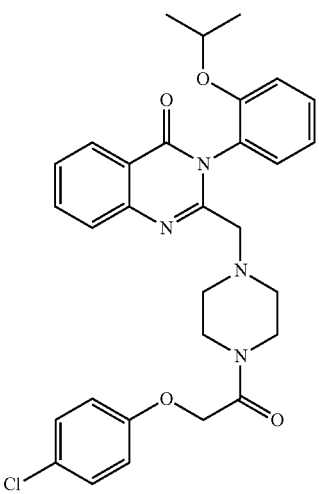

(a) TEA (1.1 eq), chloroacetyl chloride (1.1 eq), THF, 0° C. to 25° C., 6 hour; (b) PCl₃ (1.2 eq), EDIPA (1.0 eq), then 2-isoproxyaniline (1.1 eq), dioxane, 25° C. to 70° C., 6 hours; (c) piperazine (3.0 eq), THF, 25° C., 14 hours; (d) EDIPA, 4-DMAP, 4-chlorophenoxy acetylchloride, CH₂Cl₂ 0° C. to 25° C., 3 hours.

Scheme 3 - AE (Compound 50) and PE (Compound 30) synthesis.

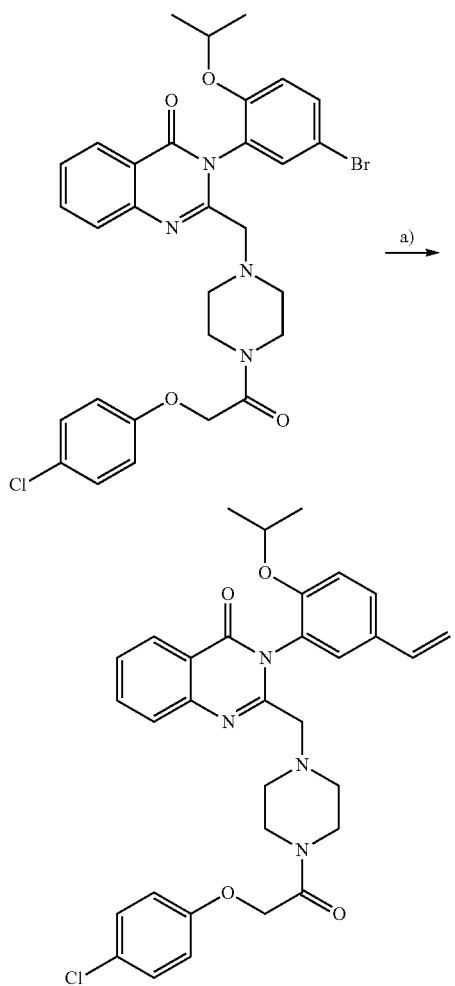

120
-continued

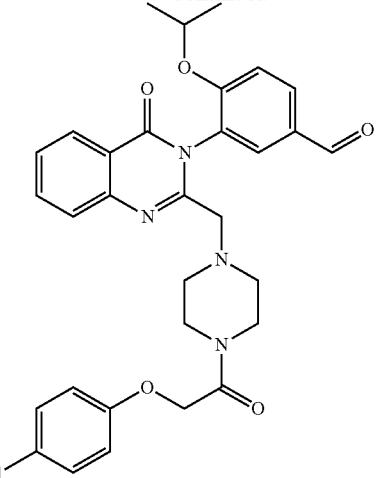

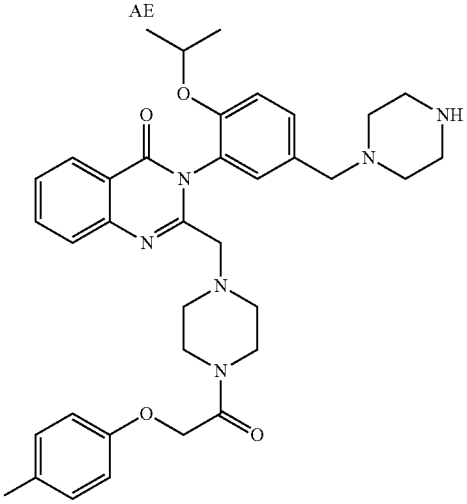

(a) tributylvinyl tin (1.5 eq), PdCl₂(PPh₃)₂ (5%); (b) OsO₄ (3%), dioxane:water (3:1), 10 minutes, then NaIO₄ (2.0 eq), 25° C., 24 hours; (c) piperazine (6.0 eq), ZnCl₂ (0.1 eq), 1,2-dichloroethane, 25° C., 3 hours, then NaBH₃CN in MeOH, 40° C., 4 hours.

1-isopropoxy-2-nitrobenzene (general procedure 1)

2-Iodopropane (14.4 mL, 143.8 mmol, 2.0 eq) was added to a stirred solution of 2-nitrophenol (10 g, 71.9 mmol) and potassium carbonate (14.9 g, 108 mmol, 1.5 eq) in dimethylformamide (DMF) (160 mL) and the mixture was subsequently heated to 50° C. for 12 hours. Upon completion, the reaction contents were added to water and extracted twice with ethyl acetate. The combined organic layers were dried (Na₂SO₄), concentrated, and purified by combiflash 0-20% EtOAc to afford 1-isopropoxy-2-nitrobenzene (11.7 g, 90% yield). ¹H NMR (400 MHz, CDCl3): δ 7.71 p.p.m. (d app, J=8.4 Hz, 1H), 7.46 (t app, J=8 Hz, 1H), 7.07 (d app, J=8.4 Hz, 1H), 6.97-6.93 (m, 1H), 4.66 (h, J=1.5 Hz, 1H), 1.35-1.33 (m, 6H); ¹³C NMR (125 MHz): δ 141.0, 133.7, 125.2, 120.0, 116.1, 72.5, HRMS (m/z): [M+] calculated for C₉H₁₁NO₃ 181.19. found 182.08.

2-isopropoxyaniline (general procedure 2)

To a solution of 1-isopropoxy-2-nitrobenzene (11.7 g, 64.6 mmol) in methanol (300 mL) Pd/C (10%) (5% wt, 0.585 g) was added and stirred under hydrogen (1 atm) for 72 hour. Upon completion, the reaction was filtered over celite, concentrated, and purified by combiflash 0 to 30% EtOAc to afford 2-isopropoxyaniline (7.88 g, 81% yield). $^1$H NMR (400 MHz, CDCl$_3$): δ 6.80-6.79 p.p.m. (m, 2H), 6.78-6.75 (m, 2H), 4.59 (h, 1.5 Hz, 1H), 3.85 (s, 1H), 1.42 (d, J=6 Hz, 2H); $^{13}$C NMR (125 MHz): δ 145.4, 137.4, 121.1, 118.4, 115.4, 113.7, 70.6 HRMS (m/z): [M+] calculated for C$_9$H$_{13}$NO 151.21. found 151.47.

Bromo-isopropoxy amine (general procedure 3)

To a solution of 4-bromo-1-isopropoxy-2-nitrobenzene (prepared using general procedure 1, 84%, 17.54 g, 67.4 mmol) in THF (270 mL), HCl (1 M aq, 270 mL, 270 mmol, 4.0 eq) and stannous chloride (38 g, 282 mmol, 3.0 eq) were added and heated to 50° C. for 24 hours. Upon completion, the mixture was quenched with saturated aqueous sodium bicarbonate, filtered over celite, and the crude product was extracted twice with ethyl acetate. The combined organic layers were dried (Na$_2$SO$_4$), concentrated, and purified by combiflash 0 to 30% EtOAc to yield bromo-isopropoxy amine (9.93 g, 64% yield) $^1$H NMR (400 MHz, CDCl3): δ 6.82 p.p.m. (d, J=2.4 Hz, 1H), 6.77 (dd, J1=8.5 Hz, J2=2.4 Hz, 1H), 6.63 (d, J=8.6 Hz, 1H), 4.46 (hept, J=1.5 Hz, 1H), 1.33 (d, J=6.0, 6H), $^{13}$C NMR (125 MHz): δ 114.4, 138.9, 120.6, 117.6, 114.8, 113.2, 71.0 HRMS (m/z): [M+] calculated for C9H13NOBr 230.1. found 229.01.

2-(2-chloroethanamido)benzoic acid (general procedure 4)

A solution of chloroacetyl chloride (2.09 mL, 26.25 mmol, 1.2 eq) in THF (40 mL) was added dropwise, over about 1 hour, to a solution of triethyl amine (3.05 mL, 21.9 mmol, 1.0 eq) and anthranillic acid (3.00 g, 21.9 mmol) in THF (120 mL) at 0° C. The mixture was slowly warmed to 25° C. and stirred for an additional 4 hours. Upon completion, the reaction contents were diluted with EtOAc and washed with 1 M HCl and water. The organic layer was dried (Na$_2$SO$_4$), the solvent was removed, and the crude solid was triturated with dichloromethane to afford 2-(2-chloroethanamido)benzoic acid (3.20 g, 68% yield). $^1$H NMR (400 MHz, C6D6OS): δ 11.81 p.p.m. (s, 1H), 8.53 (d, J=8.4 Hz, 1H), 8.02 (dd, J1=7.9, J2=1.5), 7.63 (m, 1H), 7.21 (m, 1H), 4.45 (s, 2H). $^{13}$C NMR (125 MHz): δ 169.8, 165.7, 140.4, 134.6, 131.6, 123.9, 120.3, 117.3, 43.9; HRMS (m/z): [M+] calculated for C$_9$H$_8$ClNO$_3$ 213.62. found 213.02.

2-(chloromethyl)-3-(2-isopropoxyphenyl)quinazolin-4(3H)-one (general procedure 5)

Ethyldiisopropylamine (EDIPA) (0.326 mL, 1.87 mmol, 1.0 eq) was added to a solution of 2-(2-chloroethanamido) benzoic acid (0.400 g, 1.87 mmol) at 25° C. in dioxane (10 mL) and stirred for 2 minutes before the dropwise addition of phosphorous trichloride (0.309 mL, 2.25 mmol, 1.2 eq). After 5 minutes of stirring, 0-isopropoxyaniline (0.311 g, 2.06 mmol, 1.1 eq) was added, and the resulting mixture was heated to 70° C. and stirred for an additional 6 hours. Upon completion, the reaction was carefully quenched with saturated aqueous NaHCO$_3$, diluted with water, and extracted 3 times with EtOAc. The combined organic layers were dried (Na$_2$SO$_4$), concentrated, and the crude material was purified by combi flash 0 to 50% EtOAc in hexanes to provide 2-(chloromethyl)-3-(2-isopropoxyphenyl)quinazolin-4(3H)-one (333 mg, 54% yield). $^1$H NMR (400 MHz, CDCl3): δ 8.32 p.p.m. (m, 1H), 7.89 (m, 1H), 7.54 (m, 1H), 7.38 (dd, J1=7.7, J2=1.6, 1H), 7.11 (m, 1H), 4.58 (hept, J=1.5 Hz, 1H), 4.38 (d, J=12 Hz, 1H), 4.19 (d, J=12 Hz, 1H), 1.26 (d, J=6.1, 3H), 1.17 (d, J=6.1, 1H), $^{13}$C NMR (125 MHz): δ 161.6, 153.0, 152.4, 147.2, 134.5, 131.1, 130.8, 127.6, 127.5, 127.3, 125.3, 121.4, 121.0, 114.3, 71.2, 43.7, 22.2, 21.8; HRMS (m/z): [M+] calculated for C$_{18}$H$_{17}$ClN$_2$O$_2$ 328.79. found 329.1.

3-(2-isopropoxyphenyl)-2-(piperazin-1-ylmethyl) quinazolin-4(3H)-one (general procedure 6)

Piperazine (263 mg, 3.06 mmol, 3.0 eq) was added to a solution of 2-(chloromethyl)-3-(2-isopropoxyphenyl)quinazolin-4(3H)-one (0.335 g, 1.01 mmol) in THF (5 mL) and the resulting mixture was stirred at 25° C. for an additional 14 hours. The reaction mixture was then concentrated and purified directly by combiflash 0 to 20% MeOH in DCM to provide 3-(2-isopropoxyphenyl)-2-(piperazin-1-ylmethyl) quinazolin-4(3H)-one (0.301 g, 77% yield). $^1$H NMR (400 MHz, CDCl3): δ 8.30 p.p.m. (m, 1H), 7.78 (m, 2H), 7.49 (m, 1H), 7.42 (m, 1H), 7.30 (m, 1H), 7.07 (m, 2H), 4.56 (h, J=1.5 Hz, 1H), 3.26 (s, 1H), 2.85 (m, 3H), 2.65 (s, 3H), 2.52 (m, 2H), 2.37 (m, 1H), 2.23 (m, 2H). $^{13}$C NMR (125 MHz): δ 162.1, 153.7, 153.0, 147.2, 134.2, 132.1, 131.1, 130.9, 130.4, 127.4, 127.1, 126.8, 126.4, 121.3, 120.5, 120.4, 114.3, 71.1, 71.0, 61.5, 53.3, 51.3, 45.3, 22.2, 21.8; HRMS (m/z): [M+] calculated for C$_{22}$H$_{26}$N$_4$O$_2$ 378.47. found, 379.21.

2-((4-(2-(4-chlorophenoxy)ethanoyl)piperazin-1-yl) methyl)-3-(2-isopropoxyphenyl)quinazolin-4(3H)-one (general procedure 7)

EDIPA (0.166 mL, 0.954 mmol, 1.2 eq) was added to a solution of 3-(2-isopropoxyphenyl)-2-(piperazin-1-ylmethyl)quinazolin-4(3H)-one, which was then cooled to 0° C., before the sequential addition of 4-chlorophenoxyacetyl chloride (0.196 g, 0.954 mmol, 1.2 eq) and 4-DMAP (49 mg, 0.390 mmol, 0.5 eq). The mixture was slowly warmed to 25° C. and stirred for an additional 3 hours. Upon completion, the reaction was quenched with saturated aqueous NaHCO$_3$ and extracted 3 times with dichloromethane. The combined organic layers were dried (Na$_2$SO$_4$), concentrated, and the crude material was purified by combi flash 0 to 5% MeOH in DCM to provide 2-((4-(2-(4 chlorophenoxy)ethanoyl) piperazin-1-yl)methyl)-3-(2-isopropoxyphenyl)quinazolin-4(3H)-one (270 mg, 62% yield). $^1$H NMR (400 MHz, CDCl3): δ 8.32 p.p.m. (dd, J1=8.0 Hz, J2=0.8 Hz, 1H), 7.83-7.75 (m, 2H), 7.54-7.47 (m, 1H), 7.45-7.42 (m, 1H), 7.30-7.23 (m, 3.5H), 7.10-7.06 (m2H), 6.89-6.86 (m, 2H), 4.64 (s, 1H), 4.57 (h, J=1.5, 1H), 3.51-3.44 (m, 4H), 3.28 (s, 2H), 2.54-2.42 (m, 2H), 2.30-2.26 (m, 2H), 1.21 (d, J=6 Hz, 3H), 1.13 (d, J=6 Hz, 3H); $^{13}$C NMR (125 MHz): δ 166.1, 162.1, 156.6, 134.5, 130.9, 130.7, 129.7, 127.6, 127.3, 126.8, 126.5, 121.5, 120.7, 116.1, 114.6, 71.4, 68.0, 61.0, 53.1, 52.8, 45.3, 42.1, 22.4, 22.0; HRMS (m/z): [M+] calculated for C$_{30}$H$_{31}$N$_4$O$_4$Cl 547.4. found 547.21.

2-((4-(2-(4-chlorophenoxy)ethanoyl)piperazin-1-yl) methyl)-3-(4-isopropoxypyridin-3-yl)quinazolin-4 (3H)-one (Pyr erastin)

Prepared according to the general procedures described in scheme 1 (using general procedure 2 for the reduction of 4-isopropoxy-3-nitropyridine) and scheme 2, starting from 4-hydroxy-3-nitropyridine, 5% overall. $^1$H NMR (400 MHz, CDCl3): δ 8.25 (dd, J1=8.0 Hz, J2=1.3 Hz, 1H), 7.79-7.76 (m, 1H), 7.71-7.69 (m, 1H), 7.62 (d, J=2.4 Hz, 1H), 7.5-7.46 (m, 3H), 7.24-7.21 (m, 4H), 6.87-6.84 (m, 3H), 6.63 (d, J=7.8 Hz, 1H), 4.63 (s, 3H), 4.41-4.1 (m, 1H), 3.52-3.42 (m, 9H), 2.60 (m, 1H), 2.39 (m, 4H), 1.54 (d, J=6.8 Hz), 10H) $^{13}$C NMR (125 MHz): δ 173.4, 166.12, 162.0, 156.4, 138.3, 137.0, 134.6, 129.5, 127.1, 121.1, 120.2, 115.9, 67.8, 61.5, 58.9, 52.9, 45.5, 45.1, 42.0, 29.7, 23.1, 23.0, HRMS (m/z): [M+] calculated for 548.03. found, 548.21.

2-((4-(4-chlorophenylcarbonyl)piperazin-1-yl) methyl)-3-(2-isopropoxyphenyl)quinazolin-4(3H)-one (DmK erastin)

Synthesized from 3-(2-isopropoxyphenyl)-2-(piperazin-1-ylmethyl)quinazolin-4(3H)-one and 4-chlorobenzyoyl chloride using general procedure 7 (82% yield). $^1$H NMR (400 MHz, CDCl3): δ 8.30 p.p.m. (d, J=8.4 Hz, 1H), 7.76 (m, 2H), 7.49 (m, 1H), 7.41 (m, 1H), 7.37 (m, 2H) 7.34 (m, 3H), 7.07 (m, 1H), 4.55 (h, J=1.5 Hz, 1H), 3.65 (s, 2H), 3.30 (s, 3H), 2.48 (s, 2H), 2.25 (s, 2H), 1.23 (d, J=6 Hz, 3H), 1.15 (d, J=6 Hz, 3H). $^{13}$C NMR (125 MHz): δ 169.2, 162.0, 153.5, 153.1, 147.1, 135.7, 134.3, 134.1, 130.8, 130.5, 129.0, 128.7, 128.6, 127.4, 127.1, 126.9, 126.4, 121.3, 120.5, 114.4, 71.2, 61.0, 53.5, 22.3, 21.8; HRMS (m/z): [M+] calculated for $C_{29}H_{29}ClN_4O_3$ 517.02. found, 517.21.

2-((4-(2-(4-chlorophenoxy)ethanoyl)piperazin-1-yl) methyl)-3-(2-isopropoxy-5-vinylphenyl)quinazolin-4(3H)-one To a degassed solution of 3-(5-bromo-2-isopropoxyphenyl)-2-((4-(2-(4-chlorophenoxy)ethanoyl)piperazin-1-yl)methyl)quinazolin-4(3H)-one (synthesized using the procedures described in scheme 2 using bromo-isopropoxy amine) (6.67 g, 10.8 mmol) in dioxane (100 mmol), PdCl$_2$(PPh$_3$)$_2$ (5%, 0.378 g, 0.539 mmol) was added and the resulting mixture was stirred for 10 minutes before the addition of tributylvinyl tin (4.73 mL, 16.2 mmol, 1.5 eq). The reaction was heated to 70° C. and stirred for 24 hours, cooled to room temperature, and a solution of KF (2 M, 16.2 mmol, 8.1 mL, 1.5 eq) was added and then stirred for an additional 12 hours. Upon completion, the reaction was filtered, and the filtrate was diluted with saturated aqueous NaHCO$_3$ and extracted 3 times with EtOAc. The combined organic layers were dried (Na$_2$SO$_4$), concentrated, and the crude material was purified by combi flash 0 to 5% DCM in methanol to provide 2-((4-(2-(4-chlorophenoxy)ethanoyl)piperazin-1-yl)methyl)-3-(2-isopropoxy-5-vinyl-phenyl)quinazolin-4(3H)-one (4.47 g, 72% yield). $^1$H NMR (400 MHz, CDCl3): δ 8.25 p.p.m. (d, J=2.0 Hz, 1H), 7.86 (dd, J1=8.5 Hz, J2=3.0 Hz, 1H), 7.68 (d, J=8.5, 1 H), 7.38 (dd, J1=8.4 Hz, J2=2 Hz, 1H), 7.22 (m, 3H), 7.00 (d, J=8.6 Hz, 1H), 6.85 (d, J=4.8 Hz, 2H), 6.81 (d, J=11 Hz, 1H), 5.88 (d, 17.5 Hz, 1H), 5.36 (d, 11 Hz, 1H) 4.62 (s, 2H), 4.52 (m, 1H), 3.70 (m, 4.5H), 3.49 (m, 7H), 2.46 (m, 7H) 2.32 (m, 1H), 2.22 (m, 1H), 1.21 (d, J=6 Hz, 3H), 1.13 (d, J=6 Hz, 3H). $^{13}$C NMR (125 MHz): δ 166.0, 161.9, 156.4, 153.1, 152.2, 146.7, 136.4, 135.7, 131.8, 131.0, 130.9, 130.3, 129.5, 127.7, 126.7, 126.2, 124.7, 121.3, 115.9, 115.5, 114.3, 112.4, 71.4, 67.9, 67.0, 62.4, 60.8, 53.6, 52.9, 52.7, 45.2, 42.0, 22.3, 21.8; HRMS (m/z): [M+] calculated for $C_{32}H_{33}ClN_4O_4$ 573.08. found, 573.27.

3-(2-((4-(2-(4-chlorophenoxy)ethanoyl)piperazin-1-yl)methyl)-4-oxoquinazolin-3(4H)-yl)-4-isopropoxy-benzaldehyde (AE) (Compound 50)

To a solution of 2-((4-(2-(4-chlorophenoxy)ethanoyl)piperazin-1-yl)methyl)-3-(2-isopropoxy-5-vinylphenyl)quinazolin-4(3H)-one (0.625 g, 1.09 mmol) in dioxane:water (3:1, 20 mL), OsO$_4$ (3%, 0.0327 mmol) was added dropwise and the mixture was stirred for 10 minutes before the addition of NaIO$_4$ (0.332 g, 2.18 mmol, 2.0 eq) in several portions over 30 minutes. The reaction was stirred for 24 hours and then diluted with saturated aqueous NaHCO$_3$ and extracted 3 times with EtOAc. The combined organic layers were dried (Na$_2$SO$_4$), concentrated, and the crude material was purified by combi flash 0 to 5% DCM in methanol to provide 3-(2-((4-(2-(4-chlorophenoxy)ethanoyl)piperazin-1-yl)methyl)-4-oxoquinazolin-3(4H)-yl)-4-isopropoxybenz-aldehyde (0.4 g, 64% yield). $^1$H NMR (400 MHz, CDCl3): δ 9.92 p.p.m. (s, 1H), 8.28 (dd, J1=7.9, J2=1.0 Hz, 1H), 7.96 (dd, J1=8.6, J2=2.0 Hz, 2H), 7.89 (m, 1H), 7.80 (m, 1H), 7.78 (m, 1H), 7.51 (m, 1H) 7.22 (m, 3H), 7.16 (d, J=8.4, 1H), 6.84 (d, J=8.4, 2H), 4.69 (m, 1H), 4.60 (s, 2H), 3.69 (s, 4H), 3.58 (s, 1H), 3.42 (s, 4H), 2.22 (m, 2H), 2.42 (m, 2H), 2.145 (m, 2H), 1.26 (d, J=6, 3H), 1.22 (d, J=6, 3H), $^{13}$C NMR (125 MHz): δ 189.6, 165.9, 161.7, 158.4, 156.4, 152.6, 146.9, 134.6, 133.3, 133.2, 131.9, 129.7, 129.5, 129.4, 127.5, 127.3, 127.1, 127, 126.7, 121.1, 115.9, 121.0, 115.9, 113.5, 72.8, 72.2, 67.8, 67.1, 61.1, 52.9, 52.5, 45.11, 41.9 HRMS (m/z): [M+] calculated for $C_{31}H_{31}ClN_4O_5$. found, 575.20.

2-((4-(2-(4-chlorophenoxy)ethanoyl)piperazin-1-yl) methyl)-3-(2-isopropoxy-5-(piperazin-1-ylmethyl) phenyl)quinazolin-4(3H)-one (PE) (Compound 30)

To a solution of 3-(2-((4-(2-(4-chlorophenoxy)ethanoyl) piperazin-1-yl)methyl)-4-oxoquinazolin-3(4H)-yl)-4-isopropoxybenzaldehyde (70 mg, 0.122 mmol) in 1,2-dichloroethane (1 mL) and molecular sieves (50 mg), zinc chloride (0.1 eq, 1.7 mg 0.0122 mmol) and piperazine (63 mg, 0.732 mmol 6.0 eq) were added sequentially. The resulting mixture was stirred at room temperature for 3 hours before the addition of a solution of sodium cyanoborohydride (16 mg, 0.244 mmol, 2.0 eq) in methanol (0.5 mL) which was stirred for an additional 1 hour at 25° C. before being heated to 40° C. for 3 hours. Upon completion, the reaction was filtered, concentrated, and purified directly by combiflash 0→20% MeOH in DCM to provide 2-((4-(2-(4-chlorophenoxy)ethanoyl)piperazin-1-yl)methyl)-3-(2-isopropoxy-5-(piperazin-1-ylmethyl)phenyl)quinazolin-4(3H)-one (36 mg, 46% yield). $^1$H NMR (400 MHz, CDCl3): δ 8.25 p.p.m. (d, J=8.0 Hz, 1H), 7.76 (m, 2H), 7.49 (m 1H), 7.35 (m, 1H), 7.22 (m, 3H), 7.03 (d, J=8.4 Hz, 2H), 4.68 (s, 2H), 4.54 (m, 1H), 3.59 (m, 3H), 3.44 (m, 3H), 3.27 (s, 2H), 3.12 (m, 5H), 2.62 (m, 6H) 2.36 (s, 3H), 2.25 (s, 1H), 1.21 (d, J=6 Hz, 3H), 1.13 (d, J=6 Hz, 3H), $^{13}$C NMR (125 MHz): δ 162.2, 156.4, 153.1, 152.3, 147.1, 134.5, 131.2, 131.1, 129.6, 128.9, 127.5, 127.1, 127.0, 126.0, 121.1, 116.3, 114.4, 77.2, 71.3, 67.4, 61.3, 60.8, 52.7, 49.5, 44.9, 44.2, 42.1, 22.2, 21.8; HRMS (m/z): [M+] calculated for $C_{35}H_{41}ClN_6O_4$ 645.19. found, 645.29.

2-((4-(2-(4-chlorophenoxy)ethanoyl)piperazin-1-yl) methyl)-3-(2-isopropoxy-5-(morpholinomethyl)phenyl)quinazolin-4(3H)-one (MEII) (Compound 40)

Prepared from AE according to the procedure described for PE, 50% yield. $^1$H NMR (400 MHz, CDCl3): δ 8.28 p.p.m. (dd, J1=8 Hz, J2=1 Hz, 1H), 7.77 (m, 2H) 7.49 (m, 1H), 7.38 (dd, J1=8.4 Hz, J2=2 Hz, 1H), 7.22 (m, 3H), 7.00 (d, J=8.6 Hz, 1H), 6.85 (d, J=4.8 Hz, 2H), 4.60 (s, 2H), 4.51 (m, 1H), 3.69 (m, 4H), 3.52 (m, 6.5H), 3.27 (s, 2H), 2.52 (s, 1H), 2.50 (s, 4H), 2.38 (s, 1H), 2.34 (s, 1H), 2.30 (s, 1H), 1.21 (d, J=6.1 Hz, 3H), 1.13 (d, J=6.1, 3H), $^{13}$C NMR (125 MHz): δ 166.0, 156.4, 153.3, 152.3, 147.1, 134.3, 130.9, 130.3, 129.5, 127.4, 127.1, 126.9, 126.7, 126.2, 121.26, 121.2, 115.9, 114.2, 7.3, 67.9, 67.0, 62.4, 60.8, 53.6, 52.9, 52.7, 45.2, 42.0, 22.3, 21.8; HRMS (m/z): [M+] calculated for $C_{35}H_{50}ClN_5O_5$ 646.18. found, 646.28.

Synthesis and Characterization of Chemical Materials-A8

A8 was synthesized and characterized as reported previously (Barbie et al., 2009).

Metabolite Profiling 2 million HT-1080 cells were seeded in 10 cm culture dishes. The next day, cells were treated with 5 µg/mL erastin and incubated for 5 hours before metabolite extraction. 4 mL of cold 80% methanol was added to the cell monolayer to extract polar metabolites using a cell scraper. The cell lysate/methanol mixture was transferred to a 15 mL tube and centrifuged at 2,000×g at 4° C. for 10 minutes to pellet debris and proteins. The supernatant was transferred to a new tube and stored at −80° C. for liquid chromatography-mass spectrometry/mass spectrometry (LC-MS/MS) analysis. For lipid extract preparation, 3 mL of cold 100% isopropanol was added to the cell monolayer to scrape out cells. The resulting cell lysate/isopropanol mixture was transferred to a new 15 mL tube and centrifuged at 2,000×g at 4° C. for 10 minutes. The cleared supernatant was transferred to a new tube and stored at −20° C. for LC-MS/MS analysis.

RNAi Experiments

Small interfering RNA (siRNA) pools targeting ALOX15B and ALOXE3 were obtained from Dharmacon Technologies (Lafayette, Colo.). On the day of reverse-transfection, a cocktail of 1 mL of Opti-MEM (Invitrogen Corp., Carlsbad, Calif.), 6 µL of Lipofectamine RNAiMAX (Invitrogen), and 5 µL of 10 µM siRNA were prepared and transferred to each well of a 6-well plate. The 6-well plate was put in the tissue culture incubator for 20 minutes to allow the formation of transfection mixture. While the complex was forming, HT-1080 cells were trypsinized and the cell number was determined using ViCell (Trypan Blue). 200,000 cells were prepared in 1 mL of growth media with 2× serum, and then, the cell suspension was transferred to each well containing 1 mL of the transfection mix. The 6-well plate was returned to the incubator and the culture grown for 2 days. Then, cells were trypsinized and reverse-transfected again for two additional days to ensure knockdown. After a second round of reverse transfection, cells were trypsinized and treated with lethal compounds to examine the effect of the knockdown on drug sensitivity. RNA was harvested from a population of cells for RT-qPCR analysis.

GSH Depletion Assay 2 million cells were seeded on 10 cm dishes. The next day, cells were treated with compounds to induce GSH depletion followed by harvesting to determine cell number. Two million live cells from each sample were transferred to new tubes, and centrifuged at 1,000 rpm at 4° C. for 5 minutes. The cell pellet was resuspended in 1 mL of PB buffer (10 mM sodium phosphate buffer, 1 mM EDTA, pH 7) and sonicated using 60 Joule energy. The lysate was centrifuged at 13,200 rpm at 4° C. for 10 minutes, and then the cleared lysate was used to determine the amount of GSH in the sample. The QuantiChrome glutathione assay kit (BioAssay Systems, cat # DIGT-250) was used and the product instructions were followed to determine GSH level.

Cell Lines

The 4 BJ-derived cell lines, HT-1080 cells, and U-2-OS cells were maintained as described previously (Yang et al., 2008b).

RSL Testing

In order to test whether BSO and other antioxidant targeting agents exhibit the RSL phenotype, 4 BJ-derived cell lines, BJeH, BJeHLT, BJeLR, and DRD, were cultured and treated with compounds in a 2-fold dilution series as described previously (Yang et al., 2008a). Cell viability was determined using alamar blue and percent growth inhibition computed as described previously (Id.).

Cell Images

Bright field and fluorescence images were obtained using an EVOS$_{fl}$ fluorescence microscope.

Cellular ROS Assay Using Flow Cytometer 0.2 million cells were seeded in 6-well plates. The next day, culture media was replaced with 2 mL media containing 5 µM of CM-H$_2$DCF dye (Invitrogen, cat # C6827) and the culture was returned to the tissue culture incubator for 20 minutes. Cells were harvested in 15 mL tubes and washed twice with PBS followed by resuspending in 500 µL of PBS. The cell suspension was filtered through 0.4 µm nylon mesh and subjected to the flow cytometer analysis to examine the amount of ROS within cells. A C6 flow cytometry system (BD Accuri cytometers, BD Biosciences, San Jose, Calif.) was used for the flow cytometer analysis. When cells were prepared for flow cytometric analysis, different fluorescence intensities in the unstained samples were observed each time, indicating that cells had different autofluorescence upon passage. In order to compensate for changes in autofluorescence, the difference between the median fluorescence values of CM-H$_2$DCF stained samples and unstained samples were taken, and then the difference was divided by the median autofluorescence. The normalized ROS level was determined in this way for BJeH, BJeHLT, and BJeLR cells on the same day. The experiment was repeated 8 times on 8 different days.

Generating Stable Cell Lines Expressing GFP-ALOX5

A cDNA of ALOX5 (GeneBank ID: BC130332.1) was cloned into a pBabe-puro vector to express GFP fused ALOX5 (N-terminal GFP fusion) in cells. The plasmid was transfected into PLAT-GP cells (Cell Biolabs Inc., cat # RV-103, San Diego, Calif.) along with a pVSV-G helper plasmid to produce retrovirus harboring the expression plasmid. 0.2 million target cells (BJeH, BJeHLT, BJeLR or HT-1080 cells) were seeded in 10 cm tissue culture dishes and incubated in the tissue culture incubator for 1 day. A frozen stock of retrovirus solution was thawed at 37° C. for 2 minutes, and polybrene (Sigma, cat # H9268) was added at a final concentration of 8 µg/mL. Culture medium was replaced with virus/polybrene mix and the culture dish was incubated for two hours with rocking every 30 minutes. After 2 hours, 10 mL of growth media was added to culture dish, and the culture was incubated further for 2 days. Cell lines stably expressing GFP-ALOX5 protein were selected using 1.5 µg/mL puromycin and used for the GFP-ALOX5 translocation assay.

Lipid Peroxide Detection Using BODIPY-C11

Cells were treated with compounds, stained with 1 µM BODIPY-C11 (Invitrogen, cat. # D3861), and subjected to flow cytometric analysis to determine the level of plasma membrane oxidation as described in the cellular ROS assay.

Cell Death Rescue by ALOX Inhibitors and COX Inhibitor

Lethal compounds were added to HT-1080 cells in the presence or absence of ALOX or COX inhibitors in a 2-fold dilution series. The concentrations of the inhibitors are listed along with vendor information in Table 2. Cell viability was determined using alamar blue and percent growth inhibition calculated as described above.

RT-qPCR

Total RNA from cells was prepared using an RNeasy kit (Qiagen, Germantown, Md.), and was reverse-transcribed using a High Capacity cDNA Reverse Transcription kit (Life Technologies, Inc., Grand Island, N.Y.). The resulting cDNA samples were mixed with TaqMan® probes for ALOX5, ALOX12, ALOX12B, ALOX15, ALOX15B and ALOXE3 and arrayed on a 96-well plate in triplicate. Each plate was loaded onto ViiA7 Real-Time PCR system (Life Technologies) for qPCR. Comparative analysis (delta delta Ct analysis) was performed using ACTB (human actin B) Ct value as a control.

Metabolic Stability Test

The mouse liver microsome assay on erastin and PE was performed at Shanghai Medicilon Inc. (Shanghai, China).

Mice Study

Athymic nude mice (8 weeks, Charles River) were injected with 4 million HT-1080 cells subcutaneously (SC). The next day, 400 μL of vehicle (0.625% DMSO/99.375% HBSS, pH 2) or 40 mg/kg PE were delivered to the SC site where HT-1080 cells were injected. Two days later, the SC injection was repeated. Three days later, 300 μL of vehicle or 30 mg/kg PE were administered to the mice through tail vein. The tail vein injection was repeated three times more, once every other day before the final tumor size was measured in both groups.

Due to its poor solubility, erastin was prepared in 100% PEG-400 and delivered to nude mice with the same protocol as PE before the tail vein injection. 100% PEG-400 was toxic to nude mice, which prevented injection of erastin through the tail vein. Instead, erastin was injected through the SC route using the same schedule as PE until the tumor size was measured.

Statistics

To determine the significance between two groups, indicated in the figures by asterisks, comparisons were made using a Student's t-test, performed by Prism 5 software.

Example 2

Metabolite Profiling Reveals GSH Depletion as a Key Event Upon Erastin Treatment HT-1080 fibrosarcoma cells were treated with vehicle only or vehicle plus erastin, and polar metabolites and lipid samples extracted. The metabolite extract was subjected to LC-MS/MS analysis to determine the quantity of each metabolite in each sample. A total of 149 polar metabolites and 115 lipids were detected under these conditions (Table 5), and the fold change in each metabolite between vehicle-treated and erastin-treated sample was calculated (FIG. 1a).

TABLE 5

Changes in cellular metabolites upon erastin treatment.

| Metabolites | Erastin/DMSO | log2 (Erastin/DMSO) |
|---|---|---|
| glutathione reduced | 0.007019166 | −7.154484568 |
| alpha-glycerophosphocholine | 0.219393245 | −2.188408988 |
| glutathione oxidized | 0.323487361 | −1.628218751 |
| phosphocholine | 0.525200601 | −0.929059527 |
| isomer_of_erythrose-4-phosphate | 0.588678149 | −0.764449018 |
| glucuronate | 0.609972908 | −0.713182928 |
| C36:1 PC | 0.628637882 | −0.669698883 |
| C36:0 PC | 0.650147385 | −0.621161287 |
| phosphotyrosine | 0.65325359 | −0.614284946 |
| 2′-deoxyadenosine | 0.654860207 | −0.610741128 |
| C38:3 PC | 0.65972078 | −0.600072546 |
| 2-aminodipate | 0.664362669 | −0.589957085 |
| dUMP | 0.678665746 | −0.559226895 |
| C38:4 PC | 0.681438891 | −0.553343807 |
| dTMP | 0.698450125 | −0.517770996 |
| 5-HIAA | 0.728521128 | −0.457432634 |
| alpha-glycerophosphate | 0.755601314 | −0.404302884 |
| C22:6 CE | 0.784710293 | −0.349767971 |
| C20:3 CE | 0.786386118 | −0.346690241 |
| C14:0 CE | 0.78965845 | −0.340699315 |
| indoxylsulfate | 0.79128023 | −0.337739383 |
| serotonin | 0.792396909 | −0.335704842 |
| C32:0 PC | 0.794762338 | −0.331404587 |
| N-carbomoyl-beta-alanine | 0.795767915 | −0.329580363 |
| C34:0 PC | 0.797548892 | −0.326355132 |

TABLE 5-continued

Changes in cellular metabolites upon erastin treatment.

| Metabolites | Erastin/DMSO | log2 (Erastin/DMSO) |
|---|---|---|
| carnitine | 0.801997316 | −0.318330687 |
| NADH | 0.805068432 | −0.312816675 |
| triiodothyronine | 0.80664102 | −0.310001323 |
| C56:3 TAG | 0.810310731 | −0.303452849 |
| choline | 0.813880917 | −0.297110374 |
| taurine | 0.825870795 | −0.276012 |
| acetylcholine | 0.830711332 | −0.26758086 |
| kynurenic acid | 0.832177154 | −0.265037413 |
| C22:1 SM | 0.837383793 | −0.256039099 |
| C38:2 PC | 0.840512319 | −0.25065913 |
| C20:5 CE | 0.840682397 | −0.250367231 |
| OH-phenylpyruvate | 0.844239212 | −0.244276257 |
| GDP | 0.849679699 | −0.235008999 |
| ADMA | 0.858524915 | −0.220068092 |
| XMP | 0.859888851 | −0.217777906 |
| C54:1 TAG | 0.862815121 | −0.212876634 |
| creatine | 0.867524293 | −0.205023937 |
| C54:2 TAG | 0.869557029 | −0.201647447 |
| 5-hydroxytryptophan | 0.872515609 | −0.196747154 |
| C36:2 PC | 0.872862715 | −0.196173331 |
| C34:1 DAG | 0.882253588 | −0.180734703 |
| C38:5 PC | 0.883571889 | −0.178580575 |
| lactate | 0.883979768 | −0.177914745 |
| C54:10 TAG | 0.885067787 | −0.17614014 |
| thyroxine | 0.885869026 | −0.17483468 |
| cytosine | 0.886296508 | −0.174138665 |
| C24:1 SM | 0.893338826 | −0.16272063 |
| C30:0 PC | 0.895377526 | −0.159431988 |
| C52:1 TAG | 0.897011796 | −0.156801137 |
| ADMA/SDMA | 0.898537382 | −0.154349569 |
| C34:1 PC | 0.899331136 | −0.153075677 |
| UDP-galactose/UDP-glucose | 0.900255041 | −0.151594322 |
| C36:4 PC | 0.902687749 | −0.147701067 |
| cotinine | 0.903721441 | −0.146049944 |
| C54:8 TAG | 0.906711066 | −0.141285202 |
| C56:10 TAG | 0.912891825 | −0.13148418 |
| C20:4 CE | 0.91405051 | −0.129654204 |
| NAD | 0.915714934 | −0.127029543 |
| C36:2 DAG | 0.916299532 | −0.126108813 |
| dCMP | 0.918389857 | −0.122821386 |
| C18:1 CE | 0.919786047 | −0.120629782 |
| C18:1 SM | 0.924983033 | −0.112501192 |
| C36:3 PC | 0.925067537 | −0.112369398 |
| C18:3 CE | 0.927653854 | −0.108341519 |
| niacinamide | 0.928866408 | −0.106456976 |
| C16:1 CE | 0.932056894 | −0.101510073 |
| C36:1 DAG | 0.933434013 | −0.099380057 |
| dimethylglycine | 0.933774768 | −0.09885349 |
| UDP-glucuronate | 0.933907721 | −0.09864809 |
| C36:2 PE | 0.93515925 | −0.09671603 |
| CMP | 0.937603038 | −0.092950851 |
| thiamine | 0.938498287 | −0.091573984 |
| sebacate | 0.941865852 | −0.086406501 |
| C46:0 TAG | 0.942410966 | −0.085571768 |
| C30:2 PC | 0.946705557 | −0.079012305 |
| ornithine | 0.948182209 | −0.076763771 |
| C18:2 CE | 0.948348099 | −0.076511386 |
| maleate/3-methyl-2-oxobutanoate | 0.94837736 | −0.076466872 |
| leucine | 0.949707988 | −0.074444106 |
| SDMA | 0.950466635 | −0.073292111 |
| C56:4 TAG | 0.950487716 | −0.073260113 |
| allantoin | 0.951233865 | −0.072128018 |
| histamine | 0.952625653 | −0.070018696 |
| isoleucine | 0.952635304 | −0.070004079 |
| betaine | 0.952796343 | −0.069760219 |
| C34:0 PE | 0.953254544 | −0.069066592 |
| C36:0 PE | 0.95381856 | −0.068213239 |
| C22:0 SM | 0.959998728 | −0.058895601 |
| ADP | 0.961640039 | −0.05643113 |
| C24:0 SM | 0.962145378 | −0.055673196 |
| C50:0 TAG | 0.962510978 | −0.0551251 |
| salicylurate | 0.963666252 | −0.053394512 |
| C16:0 CE | 0.964279781 | −0.052476297 |
| F1P | 0.96524394 | −0.051034503 |
| lysine | 0.9653934 | −0.050811131 |

TABLE 5-continued

Changes in cellular metabolites upon erastin treatment.

| Metabolites | Erastin/DMSO | log2 (Erastin/DMSO) |
|---|---|---|
| carnosine | 0.965734713 | −0.050301159 |
| C44:0 TAG | 0.968298141 | −0.04647677 |
| C54:3 TAG | 0.969176301 | −0.045168967 |
| methionine | 0.970222491 | −0.043612471 |
| C56:2 TAG | 0.970268868 | −0.043543512 |
| C38:6 PC | 0.970772017 | −0.042795573 |
| sorbitol | 0.970919029 | −0.042577109 |
| glucose | 0.971664149 | −0.041470356 |
| creatinine | 0.972042775 | −0.040908293 |
| glycine | 0.972285702 | −0.040547789 |
| citrate | 0.9739683 | −0.038053277 |
| histidine | 0.977875379 | −0.032277475 |
| xanthosine | 0.98003751 | −0.029091127 |
| C16:1 SM | 0.980789892 | −0.027983984 |
| 4-hydroxybenzoate | 0.981508946 | −0.026926678 |
| hypoxanthine | 0.981943367 | −0.026288275 |
| C34:2 PE | 0.982012323 | −0.026186967 |
| C32:0 PE | 0.982068705 | −0.026104136 |
| tyrosine | 0.982090761 | −0.026071736 |
| fumarate | 0.9821554 | −0.025976783 |
| valine | 0.982181785 | −0.025938027 |
| C38:4 PI | 0.982255832 | −0.025829266 |
| phosphoglycerate | 0.984827133 | −0.022057585 |
| C56:9 TAG | 0.986500661 | −0.019608077 |
| arginine | 0.98662075 | −0.019432465 |
| alpha-ketoglutarate | 0.98674206 | −0.019255089 |
| NMMA | 0.988556175 | −0.016605146 |
| tryptophan | 0.991129404 | −0.012854663 |
| threonine | 0.99243953 | −0.010948895 |
| C36:1 PE | 0.995288791 | −0.006812899 |
| C52:2 TAG | 0.996404827 | −0.005196084 |
| glycocholate | 0.997470442 | −0.003654004 |
| C32:1 PC | 0.999765803 | −0.000337915 |
| 4-pyridoxate | 1.000128453 | 0.000185307 |
| UDP | 1.002008092 | 0.00289416 |
| suberate | 1.003221833 | 0.004640651 |
| phenylalanine | 1.004872604 | 0.00701261 |
| hippurate | 1.005321858 | 0.007657461 |
| C36:0 PI | 1.006349047 | 0.009130783 |
| succinate/methylmalonate | 1.008198544 | 0.011779776 |
| C18:0 CE | 1.009518499 | 0.013667348 |
| glucose/fructose/galactose | 1.010633942 | 0.015260538 |
| C50:1 TAG | 1.011393801 | 0.016344841 |
| C30:1 PC | 1.013872124 | 0.019875703 |
| glutamine | 1.014636611 | 0.020963123 |
| quinolinate | 1.015210174 | 0.021778432 |
| aspartate | 1.017140543 | 0.024519037 |
| C32:2 PE | 1.017862786 | 0.025543091 |
| C18:0 SM | 1.017897199 | 0.025591866 |
| urate | 1.017972662 | 0.025698818 |
| oxalate | 1.018599015 | 0.026586227 |
| glutamate | 1.019332193 | 0.027624292 |
| C36:2 PI | 1.020645543 | 0.029481923 |
| pimelate/3-methyladipate | 1.021056242 | 0.030062336 |
| C32:1 PE | 1.023921785 | 0.034105516 |
| hydroxyphenylacetate | 1.024067694 | 0.034311085 |
| malonate | 1.025230038 | 0.035947654 |
| xanthine | 1.026812674 | 0.038173008 |
| C16:0 SM | 1.03011789 | 0.042809454 |
| folate | 1.032057885 | 0.045523889 |
| citrulline | 1.035673991 | 0.050569944 |
| aconitate | 1.036400242 | 0.051581258 |
| C34:1 PE | 1.040149897 | 0.056791452 |
| kynurenine | 1.040294446 | 0.056991928 |
| C52:0 TAG | 1.040694863 | 0.057547126 |
| C58:6 TAG | 1.047110675 | 0.066413937 |
| C56:6 TAG | 1.047483699 | 0.066927793 |
| C34:2 PC | 1.04850576 | 0.068334787 |
| UMP | 1.048921414 | 0.068906594 |
| ribulose-5-P | 1.050528526 | 0.071115337 |
| isocitrate | 1.051095653 | 0.071893965 |
| dGMP | 1.051722504 | 0.072754102 |
| serine | 1.053459932 | 0.075135443 |
| glycodeoxycholate | 1.053739818 | 0.075518692 |
| C32:1 DAG | 1.054515427 | 0.076580201 |
| glycerol | 1.058311744 | 0.081764661 |
| C48:1 TAG | 1.058553333 | 0.082093958 |
| alanine | 1.061199956 | 0.08569652 |
| C14:0 SM | 1.06154999 | 0.086172311 |
| C56:7 TAG | 1.061814078 | 0.086531175 |
| C54:7 TAG | 1.062074534 | 0.086885014 |
| IMP | 1.064629663 | 0.090351669 |
| GMP | 1.065877096 | 0.092041093 |
| glycochenodeoxycholate | 1.066841635 | 0.093346034 |
| asparagine | 1.069265793 | 0.096620515 |
| AMP | 1.071274609 | 0.099328346 |
| C58:7 TAG | 1.071364555 | 0.099449473 |
| C50:2 TAG | 1.073465707 | 0.102276104 |
| nicotinate | 1.085143298 | 0.11788557 |
| C34:4 PC | 1.085975817 | 0.118991978 |
| proline | 1.086372681 | 0.119519106 |
| C34:2 DAG | 1.088758408 | 0.122683861 |
| cystamine | 1.090375283 | 0.124824764 |
| adipate | 1.090949568 | 0.125584411 |
| C36:3 DAG | 1.091715359 | 0.126596754 |
| proprionate | 1.091955783 | 0.126914438 |
| taurolithocholate | 1.09332259 | 0.128719138 |
| C48:0 TAG | 1.098431827 | 0.135445333 |
| cis/trans hydroxyproline | 1.09933747 | 0.136634327 |
| taurocholate | 1.108372993 | 0.148443463 |
| ribose-5-P | 1.113413382 | 0.154989328 |
| C58:8 TAG | 1.117508568 | 0.160285893 |
| C48:2 TAG | 1.12096538 | 0.164741723 |
| C52:3 TAG | 1.123502729 | 0.168003629 |
| G6P | 1.133663732 | 0.180992771 |
| C56:5 TAG | 1.133971203 | 0.181384003 |
| C34:3 PC | 1.133988835 | 0.181406437 |
| phenylacetylglycine | 1.135117956 | 0.182842224 |
| orotate | 1.137904549 | 0.186379544 |
| malate | 1.143460137 | 0.193406072 |
| PEP | 1.146683618 | 0.197467392 |
| taurodeoxycholate | 1.167748017 | 0.223728996 |
| C46:1 TAG | 1.170876947 | 0.227589464 |
| GABA | 1.172608132 | 0.229720966 |
| phosphocreatine | 1.172975218 | 0.230172534 |
| C34:1 PI | 1.17332592 | 0.230603812 |
| C58:9 TAG | 1.175775533 | 0.233612662 |
| C54:4 TAG | 1.177998885 | 0.236338174 |
| C56:8 TAG | 1.178339088 | 0.23675476 |
| taurochenodeoxycholate | 1.180889408 | 0.23987386 |
| glyceraldehyde-3-phosphate | 1.191624534 | 0.252929733 |
| pantothenate | 1.19447216 | 0.256373229 |
| ascorbate | 1.196279953 | 0.258555047 |
| C32:2 PC | 1.218164138 | 0.284708538 |
| trimethylamine-N-oxide | 1.222211727 | 0.289494228 |
| DHAP | 1.227273271 | 0.295456523 |
| 5-HIAA | 1.230853823 | 0.299659437 |
| C50:3 TAG | 1.241015719 | 0.31152139 |
| Anthranilic acid | 1.242119129 | 0.312803546 |
| adenine | 1.25362125 | 0.326101541 |
| thymine | 1.257201762 | 0.330216199 |
| C32:1 PI | 1.261000876 | 0.334569278 |
| cystathionine | 1.262988673 | 0.336841701 |
| cAMP | 1.266090474 | 0.340380502 |
| C54:6 TAG | 1.266720903 | 0.341098691 |
| C50:5 TAG | 1.277049931 | 0.352814934 |
| C52:5 TAG | 1.27898172 | 0.354995644 |
| pyruvate | 1.2826948 | 0.359177941 |
| C34:2 PI | 1.286345341 | 0.36327801 |
| F16DP/F26DP/G16DP | 1.302764118 | 0.38157589 |
| C52:4 TAG | 1.305344833 | 0.384430974 |
| C54:5 TAG | 1.315083914 | 0.395154859 |
| C54:9 TAG | 1.331382859 | 0.412925499 |
| adenosine | 1.375972395 | 0.460451527 |
| C36:4 PI | 1.394818145 | 0.480077037 |
| thymidine | 1.402373491 | 0.48787063 |
| sucrose | 1.408292599 | 0.493947112 |
| C48:3 TAG | 1.520115971 | 0.604181392 |
| C46:2 TAG | 1.541893629 | 0.624703241 |
| C52:6 TAG | 1.601679465 | 0.679585459 |

TABLE 5-continued

Changes in cellular metabolites upon erastin treatment.

| Metabolites | Erastin/DMSO | log2 (Erastin/DMSO) |
|---|---|---|
| C44:1 TAG | 1.638829022 | 0.712665346 |
| C50:4 TAG | 1.681973845 | 0.750155272 |
| 2'-deoxycytidine | 1.737193761 | 0.796758677 |
| inosine | 1.866736341 | 0.900518175 |
| C18:0 LPC | 3.335435273 | 1.737875045 |
| C14:0 LPC | 3.625332845 | 1.858113456 |
| C18:1 LPC | 3.743522467 | 1.904396413 |
| C16:0 LPC | 3.818006928 | 1.932819721 |
| uridine | 4.368573078 | 2.127162124 |
| guanosine | 4.509507284 | 2.172969811 |
| C16:1 LPC | 5.385771704 | 2.429153077 |
| cytidine | 6.078961728 | 2.603824936 |
| C22:6 LPC | 8.455937356 | 3.079964689 |
| C20:4 LPC | 8.518404873 | 3.090583302 |

The name and fold change of the metabolites examined in FIG. 1a are listed here. The mean value of the abundance of each metabolite was calculated from four independent samples in each drug treatment condition and used to determine the fold change between erastin treatment and DMSO (the vehicle) treatment.

It was found that both reduced glutathione (GSH) and oxidized glutathione (GSSG) were depleted significantly upon erastin treatment, whereas the level of lysophosphatidyl choline (lyso-PC) was increased. This was intriguing, because lyso-PC has been reported to increase the permeability of cell membranes and to induce cell death involving oxidative species, which is rescued by antioxidants in fibroblasts (Colles et al., 2000). The effects of purified lyso-PC on erastin-induced cell death were tested in HT-1080 cells. The results show that lyso-PC modestly sensitized cells to erastin-induced cell death (FIGS. 5a and b), suggesting that lyso-PC contributes to erastin's lethality. However, lyso-PC did not show differential cytotoxicity between BJeH (BJ-TERT) and BJeLR (BJ-TERT/LT/ST/HRAS$^{V12}$) engineered cells (Yang et al., 2008a), suggesting that generation of lyso-PC is not sufficient to cause RAS synthetic lethality (FIG. 5c).

The significant depletion of GSH/GSSG, on the other hand, was intriguing, because erastin treatment induces the generation of reactive oxygen species (ROS), resulting in an oxidative form of cell death (Yagoda et al., 2007). GSH/GSSG constitutes a major cellular antioxidant system and provides reducing power to remove oxidative species. Three cell lines were treated with erastin, their GSH levels were determined using Ellman's reagent, and a dose-dependent, GSH-depleting effect of erastin was confirmed (FIG. 1b and FIG. 5d). Because GSH is a major antioxidant produced by cells, its depletion should make cells more sensitive to oxidative stress. Thus, U-2 OS cells were treated with tert-butylhydroperoxide (TBHP) in the presence of erastin, and observed that erastin made cells more sensitive to TBHP-induced cell death (FIG. 5e). Indeed, GSH depletion by erastin is necessary for erastin's lethality, because supplementing the culture medium with GSH itself or N-acetyl-cysteine (NAC), a precursor of GSH, rescued cells from erastin lethality (FIGS. 5f and 5g).

Whether the GSH-depleting activity of erastin was essential for its lethality was further tested. A synthetic route to access multiple erastin analogs was established, and these analogs were tested for potency and selectivity in BJ-derived tumorigenic cells (FIG. 1c). Three compounds (MEII, PE, AE) retained the RSL phenotype, whereas the other three (A8, PYR, dMK) did not display lethality (FIG. 1c). In addition, the following analogs were also made and tested for potency and selectivity.

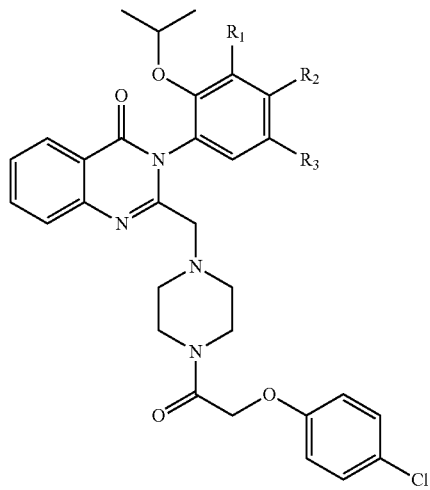

| Compound No. | R$_1$ = | R$_2$ = | R$_3$ = | EC$_{50}$ | Selectivitey score |
|---|---|---|---|---|---|
| 51 | (morpholinomethyl) | H | H | 1.17 μM | 4 |

-continued
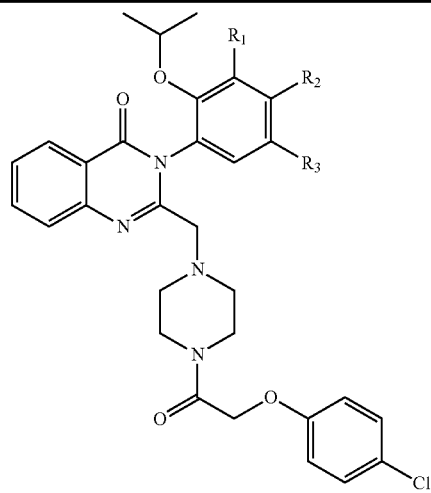
| Compound No. | R₁ = | R₂ = | R₃ = | EC₅₀ | Selectivitey score |
|---|---|---|---|---|---|
| 52 | H | ⸺N(morpholine) | H | 4.7 μM | 3.3 |
| 40 | H | H | ⸺N(morpholine) | 0.13 μM | 9.2 |
*selectivity score = $EC_{50}$ (BJeH)/$EC_{50}$ (BJeLR)
Because changes at position $R_3$ of structure (100) above improved potency and selectivity, additional analogs were created and tested.
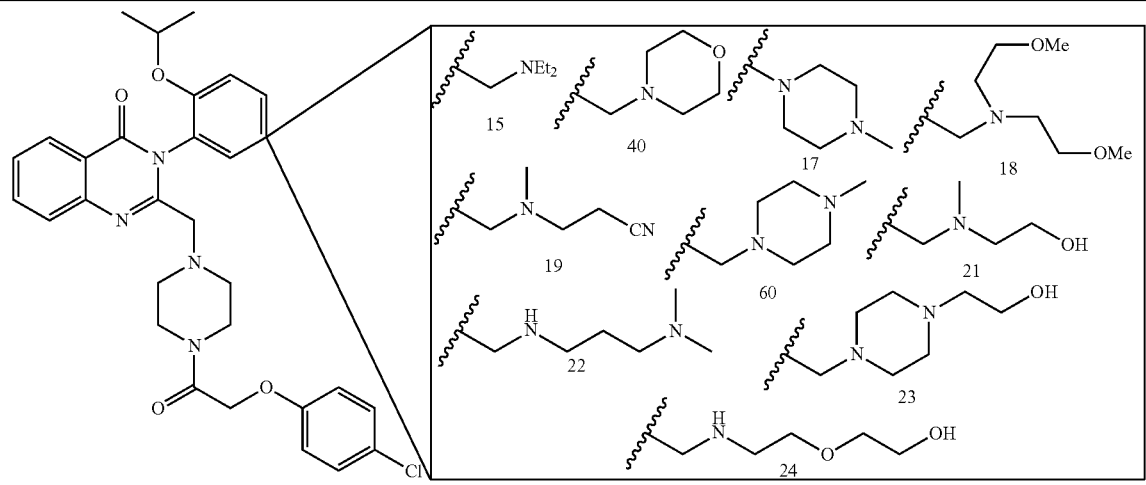
| Compound | EC₅₀ (BJeLR) | Selectivity score |
|---|---|---|
| erastin | 1.78 μM | 4.7 |
| 15 | 1.68 μM | 4.1 |
| 40 | 0.13 μM | 9.2 |
| 17 | 0.90 μM | 7.3 |
| 18 | 0.14 μM | 5.9 |
| 19 | 0.26 μM | 5.1 |

| | | |
|---|---|---|
| 60 | 0.60 μM | 3.8 |
| 21 | 0.36 μM | 3.7 |
| 22 | 2.30 μM | 3.3 |
| 23 | 1.20 μM | 2.8 |
| 24 | 2.10 μM | 2.5 |

Changes at other positions other than R₃ of structure (100) above generally lowered the selectivity and potency, as demonstrated by the testing of the following analogs.

The inventors reasoned that if GSH depletion was sufficient for erastin lethality, then GSH depletion by other reagents should phenocopy erastin's selective lethality in the

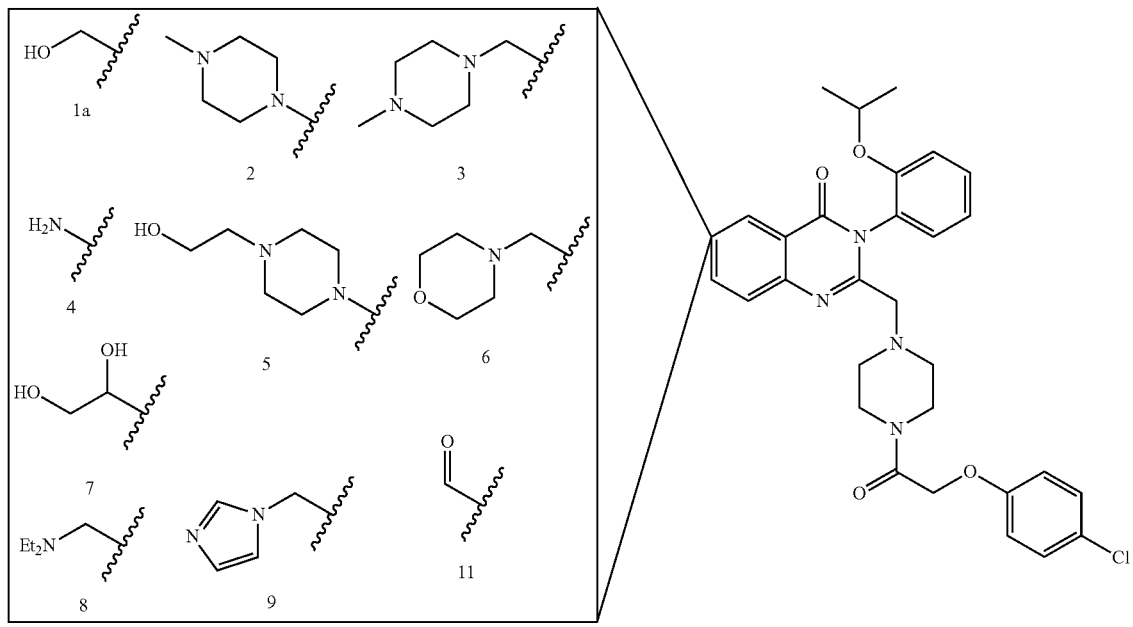

| Compound | EC$_{50}$ (BJELR) | Selectivity Score |
|---|---|---|
| erastin | 1.8 μM | 4.7 |
| 1a | 4.8 μM | 3.5 |
| 2 | >10 μM | N/A |
| 3 | >10 μM | N/A |
| 4 | 0.9 μM | >25.0 |
| 5 | >10 μM | N/A |
| 6 | 2.7 μM | 3.8 |
| 7 | 3.7 μM | 4.5 |
| 8 | 4.4 μM | 2.4 |
| 9 | 0.47 μM | 6.3 |
| 11 | 2.0 μM | 6.8 |

Of these analogs, six analogs (MEII (Compound 40), PE (Compound 30), AE (Compound 50), A8, PYR, and dMK) were tested along with erastin in HT-1080 cells, and the relationship between the GSH-depleting activity and the lethality of each analog was examined (FIG. 1d). As set forth above, three compounds (MEII, PE, AE) retained the RSL phenotype, whereas the other three (A8, PYR, dMK) did not display lethality (FIG. 1c). Buthioninesulfoximine (BSO) was used as a positive control for GSH depletion. BSO is an irreversible inhibitor of γ-glutamyl cysteine synthetase, which catalyzes the first step in glutathione synthesis, and has been widely used for depleting GSH in a variety of experimental conditions. Active analogs of erastin depleted cellular GSH more effectively than inactive analogs of erastin (FIG. 1d), which further suggested that the GSH-depleting activity of erastin is necessary for erastin-induced cell death.

four BJ-cell line system, which consists of isogenic cell lines (two with and two without oncogenic-HRAS), through which RSLs such as erastin were discovered (Dolma et al., 2003). When the four BJ-derived cells were treated with BSO, an RSL phenotype was observed (FIG. 1e), suggesting that GSH depletion by erastin is sufficient for its oncogenic-RAS-selective lethality.

The cell death pathways activated by erastin and BSO appeared to be similar, as assessed by profiling a panel of cell death inhibitors against each compound in an adaptation of the recently reported modulatory profiling strategy (FIG. 10 (Wolpaw et al., 2011). These results indicated that erastin likely acts through a dual targeting mechanism to induce synthetic lethality. First, it binds and perturbs mitochondrial VDACs as reported (Kumar et al., 2012), and second, it depletes GSH through preventing cystine uptake via inhibition of system xc- (Dixon et al., 2012). Both knockdown of VDAC2/3 (Kumar et al., 2012) and supplementation of GSH (FIG. 5g) were effective in rescuing cells from erastin's lethality.

Example 3

Targeting Antioxidants is not Sufficient to Induce Ferroptosis

Because GSH depletion appeared to be critical for erastin lethality, how GSH depletion by erastin induces synthetic lethality with RAS was investigated. It has been hypothesized that most cancer cells, including RAS-transformed cells (Irani et al., 1997), are under high levels of oxidative stress (Szatrowski et al., 1991), which needs to be balanced by increasing the ROS-scavenging capacity to prevent oxidative damage (Hussain et al., 2003). In this model, targeting ROS-scavenging systems, including GSH, could cause an imbalance in this equilibrium, leading to oxidative cell death (Chuang et al., 2003; Trachootham et al., 2006). In order to test whether this simple hypothesis could explain erastin's selective lethality, basal ROS levels in the four BJ-derived engineered cell lines was examined using $H_2DCF$, a ROS sensor. It was confirmed that BJeLR cells have elevated ROS compared to BJeH and BJeHLT (BJ-TERT/LT/ST) cells. However, the level of increase varied among passages (FIG. 2a). Initially, the inventors speculated that this finding could explain why GSH-depleting reagents such as erastin and BSO induce selective cell death in oncogenic-RAS expressing cells. If true, other anti-oxidant targeting reagents should also induce the RSL phenotype in these four BJ cell lines. To test this possibility, the four BJ cell lines were treated with a SOD inhibitor (DETC), a thiol-reactive reagent (DIA), a glutaredoxin inhibitor (IAA), a thiredoxinreductase inhibitor (DCNB), or a catalase inhibitor (ATZ) (FIG. 2b and FIG. 6). Erastin and BSO consistently showed an RSL phenotype in these four BJ cells; however, none of the other anti-oxidant targeting compounds displayed an RSL phenotype, which indicates that it is not possible to induce oncogenic-RAS-selective lethality by simply targeting the antioxidant system. Instead, these results suggested that unique biochemical changes downstream of GSH depletion were responsible for the synthetic lethality with oncogenic RAS.

One possibility for those results was that erastin selectively depletes GSH in tumor cells harboring oncogenic RAS. Thus, the degree of GSH depletion upon erastin treatment in the 4 BJ cell lines was examined (FIG. 2c). It was found that these four BJ-derived cell lines contained varying amounts of basal GSH in the absence of any treatment, as reported previously (Kang et al., 1992), but were depleted of GSH to a similar low level upon erastin treatment. The concentration of erastin used in this experiment was lethal to BJeLR and DRD cells (containing oncogenic HRAS), but was not lethal to BJeH and BJeHLT cells (with wild-type RAS proteins) even upon prolonged incubation (FIG. 2b). Therefore, the selective lethality among these cells was not caused by differential depletion of GSH or by differences in the basal level of GSH. Rather, downstream events occurring after GSH depletion were selectively activated in the sensitive cell lines.

Example 4

Selective Activation of ALOXs is Responsible for RSL Phenotype of Erastin

One consequence of GSH depletion could be activation of lipoxygenases (products of ALOX genes) (Li et al., 1997; Shornick et al., 1993). Lipoxygenases generate lipid peroxides from unsaturated lipids such as arachidonic acid, and use free iron as a cofactor. Oxidation of the catalytic iron is known to be an essential step in the enzyme reaction, making this a point of enzyme regulation. Depletion of GSH accelerates iron oxidation, leading to activation of lipoxygenases (Haeggstrom et al., 2011).

ALOX5 is one of the six human ALOX genes and plays a critical role in leukotriene synthesis. In the basal state, the ALOX5 protein remains in the nucleus; however, upon activation, it translocates to the nuclear membrane (Chen et al., 2001). In order to examine whether ALOX proteins are activated upon erastin treatment, GFP-tagged ALOX5 was expressed in the BJ-derived cell lines and whether erastin treatment had any effect on the location of GFP-ALOX5 was examined (FIG. 2d). A positive control for GFP-ALOX5 translocation, treatment with ionomycin, induced localization of GFP-ALOX5 to the nuclear membrane in all BJ-derived cell lines (FIG. 7). In contrast, only in BJeLR cells (harboring $HRAS^{G12V}$) was GFP-ALOX5 translocated to the nuclear membrane upon erastin treatment (FIG. 2d). These results suggested that activation of ALOX proteins after GSH depletion occurs selectively in oncogenic-RAS-expressing cells, leading to lipid peroxidation and oxidative cell death. GFP-ALOX5 was expressed in HT-1080 cells with oncogenic, mutant NRAS and the same translocation event upon erastin treatment was observed (FIG. 2e). It is unlikely that erastin activates lipoxygenases through calcium upregulation, as ionomycin does, for multiple reasons. First, the kinetics of GFP-ALOX5 translocation in response to erastin differed from that seen upon ionomycin treatment (FIG. 2e). Second, calcium chelators were not effective in suppressing erastin-induced cell death (Wolpaw et al., 2011). Third, flow cytometer analysis with Fluo-4, an intracellular calcium reporter, did not show any increase in calcium after erastin treatment (data not shown).

The three BJ-derived cell lines were stained with BODIPY-C11, a membrane targeted lipid ROS sensor, and fluorescence was monitored using flow cytometry to detect lipid peroxidation caused by the activation of ALOX proteins (FIG. 2f). BJeLR cells (with oncogenic $HRAS^{V12}$) exhibited a stronger BODIPY-C11 fluorescence than BJeH and BJeHLT cells (with wild-type RAS proteins), which further supported the hypothesis that activation of ALOXs occurs selectively in cells expressing oncogenic RAS (FIG. 2f). The activation of ALOX proteins was required for lethality, as five different ALOX inhibitors were able to prevent erastin-induced cell death (FIG. 2g). Indomethacin, a cyclooxygenase inhibitor, was only minimally effective in suppressing erastin lethality, highlighting the importance of lipoxygenases, but not cyclooxygenases, in erastin-mediated cell death.

Example 5

RSL3 Also Activates ALOX-Dependent Ferroptosis

Figure 8:
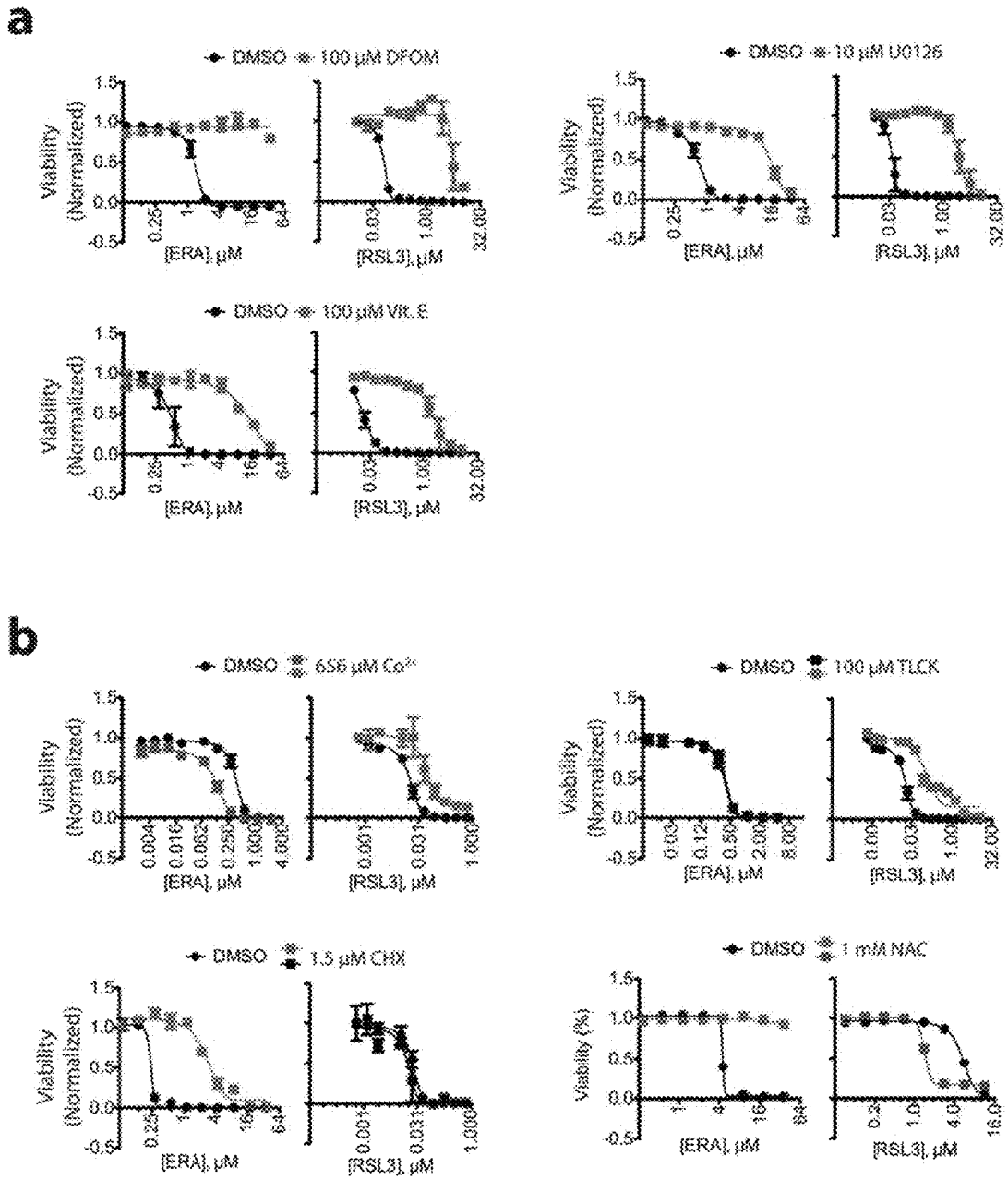

The inventors examined whether GSH depletion and activation of lipoxygenases was applicable to RSL3, another oncogenic-RAS-selective lethal compound (Yang et al., 2008a), or whether this mechanism was unique to erastin. The cell death induced by erastin and RSL3 share common features, such as iron-, MEK-, and ROS-dependence; however, tumor cells had different responses to erastin and RSL3 in the presence of cobalt, TLCK, cycloheximide, and, N-acetyl-cysteine (FIG. 8). Importantly, RSL3 is not dependent on VDAC2/3 (Yang et al., 2008) or system xc- (Dixon et al., 2012), implying that a different initiating mechanism can converge on a similar form of ferroptotic cell death.

When cellular GSH levels during RSL3-induced cell death were examined, it was found that GSH remained unaffected by a lethal RSL3 dose in BJeLR cells, which was in sharp contrast to erastin's effect (FIG. 3a). However, RSL3 caused GFP-ALOX5 translocation to the nuclear membrane in BJeLR cells, suggesting that activation of ALOX proteins could be a common lethal event between erastin and RSL3 (FIG. 3b). As with erastin, five different ALOX inhibitors, but not a COX inhibitor, suppressed cell death induced by RSL3, reinforcing the importance of ALOX proteins in the lethal mechanism of both of these two compounds (FIG. 3c). Furthermore, BODIPY-C11 staining demonstrated the generation of lipid peroxides in RSL3-treated cells (FIG. 3d).

Example 6

Synthetic Lethality with RAS Occurs Through an ALOX-Dependent Pathway

In order to validate the critical role of ALOX proteins in inducing selective lethality, cellular lipoxygenase was activated by knocking down GPX4, which is a phospholipid hydroperoxidase (Imai et al., 2003) and known to counter the effects of lipoxygenases by reducing lipid hydroperoxides, but also to negatively regulate lipoxygenases through a feedback mechanism; i.e. lipid peroxides cause further activation of ALOXs (Innai et al., 2003). Deletion of Gpx4 in mice is embryonic lethal. However, mouse embryo fibroblasts (MEFs) from Gpx4$^{+/-}$ mice have increased lipid peroxide levels compared to wild-type MEFs (Ran et al., 2003).

Knockdown of GPX4 caused an increase in the level of lipid peroxides, and induced cell death in HT-1080 cells (FIG. 3e and FIG. 9a). Cell death induced by siGPX4 accompanied translocation of GFP-ALOX5 to the nuclear membrane, as was seen with erastin and RSL3 (FIG. 3f). This translocation was specific to siGPX4, because cell death induced by a pool of siRNAs targeting multiple essential genes (siDeath) did not translocate GFP-ALOX5. Moreover, the cell death induced by siGPX4 was rescued by an iron chelator (DFOM), a MEK inhibitor (U0126), an antioxidant (Vit. E), and an ALOX inhibitor (ZIL), which suggested that GPX4 knockdown induced ferroptotic cell death (FIG. 3g). Finally, siGPX4 induced selective cell death in BJeLR and DRD cells (with oncogenic HRAS), but not BJeH and BJeHLT cells (lacking oncogenic HRAS) (FIG. 3h and FIG. 9b). In a separate study, cellular binding proteins for RSL3 were characterized using chemoproteomic approaches (data not shown). The unbiased search for RSL3-binding proteins identified GPX4 as the highest priority target. Taken together, these results indicate that GSH-depletion by erastin and GPX4 inhibition by RSL3 or siGPX4 are two mechanisms for activating lipoxygenases, leading to cell death involving oxidative lipid damage.

To determine the generality of these findings, lipid peroxidation levels and the degree of cell death suppression by ALOX inhibitors upon treatment of BJeLR cells or HT-1080 cells with other RSL compounds were examined. In a larger screening campaign to find additional RSL compounds, 14 RSLs were identified out of more than a million compounds tested (FIG. 10a) (Weiwer et al., 2012; Yang et al., 2012). The RSL activity of these 14 compounds was confirmed in the four BJ-derived cell lines (FIG. 10b). This four-BJ-cell-line testing has been productive in discovering genuine RSL compounds. For example, natural cancer cell lines with NRAS or KRAS mutations were sensitive to the RSL compounds, and knockdown of mutant RAS genes rescued cells from RSL-induced cell death (Yang et al., 2008a; Yagoda et al., 2007). Furthermore, there was a correlation between the sensitivity of erastin and phospho-ERK levels, a surrogate marker for RAS activation, in 12 natural cancer cell lines (Yagoda et al., 2007), highlighting the oncogenic RAS selectivity of RSL compounds in genuine tumor cell lines, despite the fact that they were identified from the four engineered BJ-derived cell lines.

The degree of structural similarity among these 14 RSL compounds, erastin and RSL3 was determined using the Tanimoto coefficient, in order to quantitatively define which of these 14 RSL compounds are simple analogs of each other. Most were structurally diverse, which led to the definition of 12 independent RSL groups, including erastin and RSL3 (FIG. 10c). Ten structurally diverse and representative RSLs were chosen to use in subsequent experiments.

Figure 11:
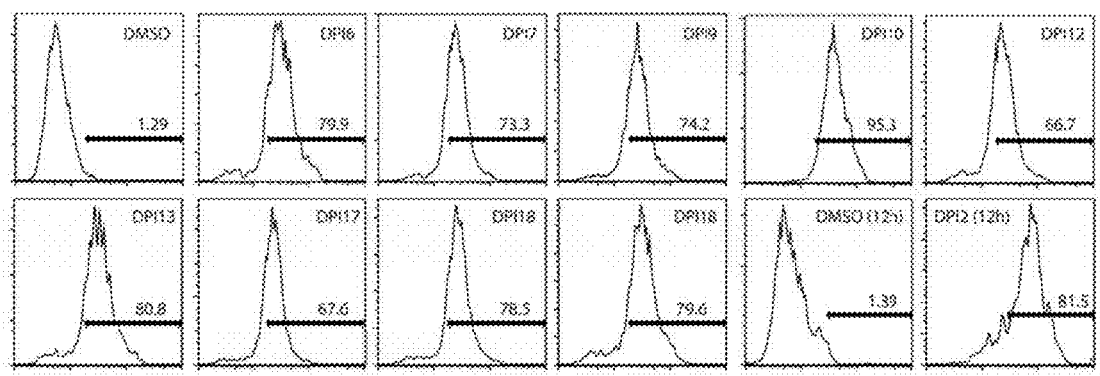
Figure 11:
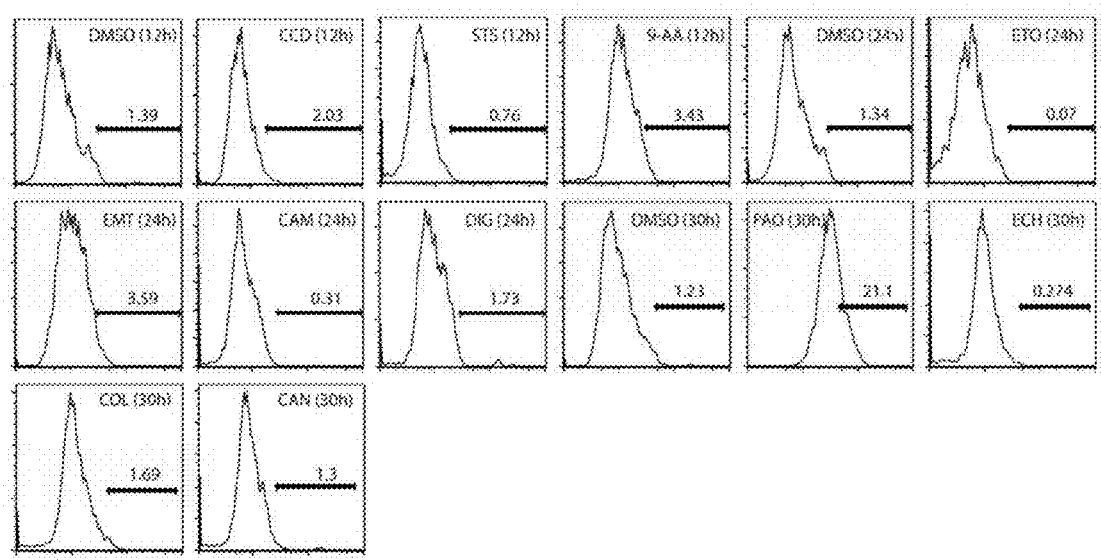

BJeLR cells treated with the 10 additional RSL compounds exhibited an increase in BODIPY-C11 fluorescence, indicating that lipid peroxides were generated (FIG. 11). 11 non-RSL lethal compounds with diverse lethal mechanisms were tested to see whether they induced lipid peroxide generation. These 11 lethal compounds were confirmed to be non-RSL compounds previously (Root et al., 2003). It was found that 10/11 of the non-RSL compounds did not generate lipid peroxides, implying a specificity of lipid peroxidation to RSL compound treatment (FIG. 11). Of note, phenylarsine oxide (PAO) increased the BODIPY-stained cell population, albeit significantly less than the RSL compounds. It is likely that the known ROS-generating activity of PAO oxidized the BODIPY-C11 dye (Fanelus, 2008).

Figure 12:
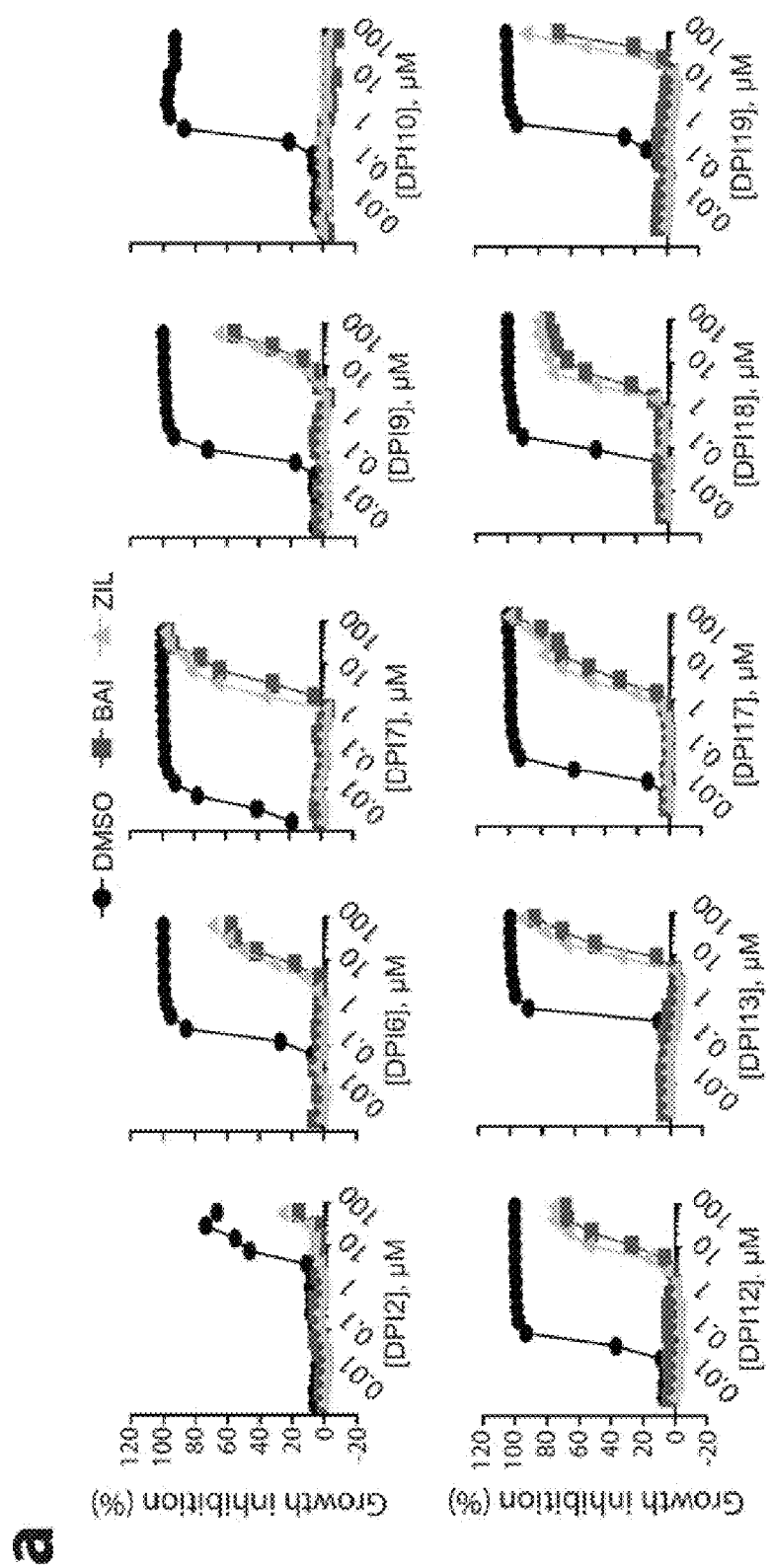
Figure 12:
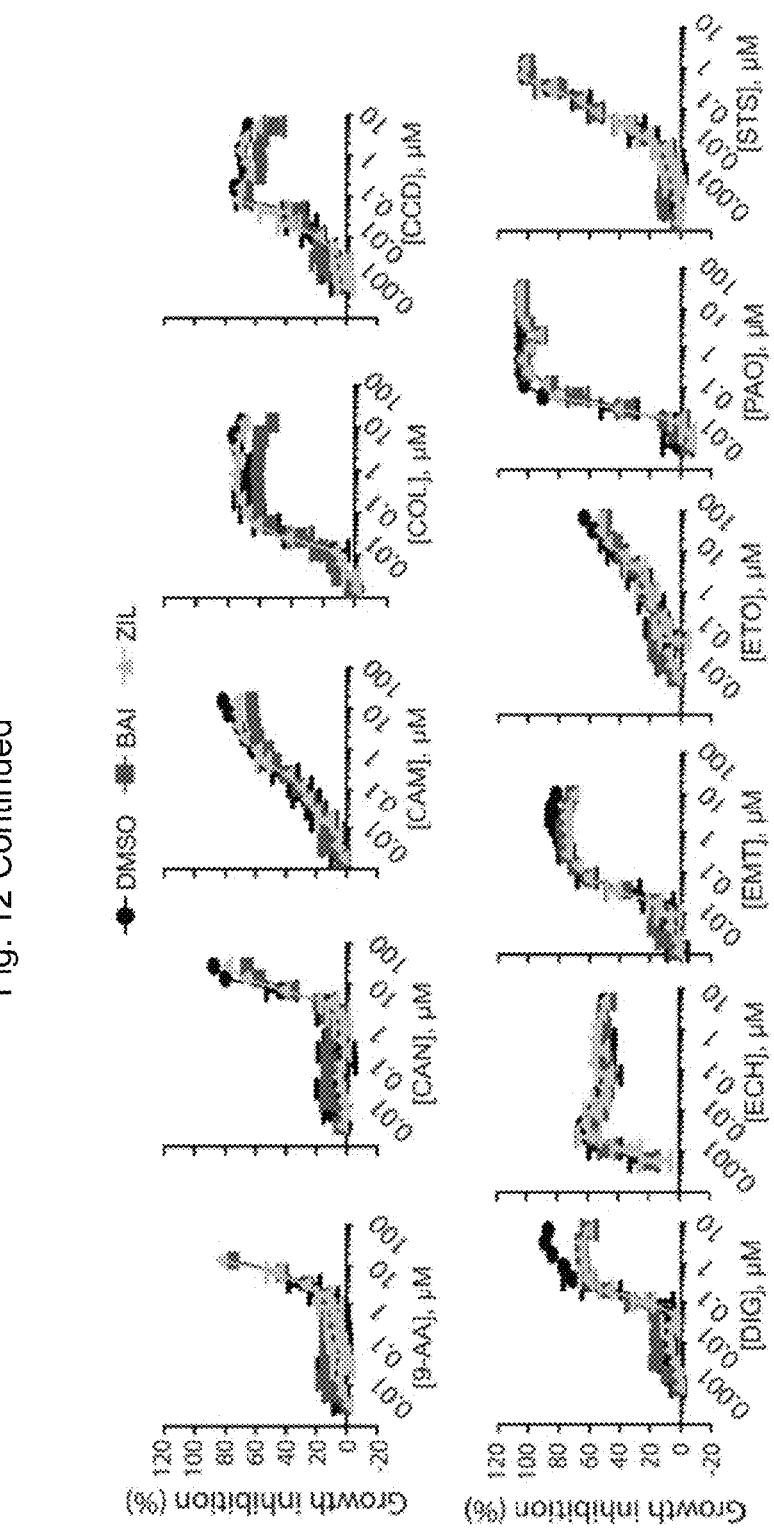

In order to examine the requirement of ALOX proteins for the lethality of each compound, HT-1080 cells were treated with each lethal compound (RSLs and non-RSLs) in the presence or absence of baicalein (BAI) or zileuton (ZIL), the two ALOX inhibitors. Both ALOX inhibitors strongly suppressed cell death induced by all RSL compounds (FIG. 12). The rescuing effect of these ALOX inhibitors was specific to RSL compounds, because the ALOX inhibitors were not able to suppress cell death induced by eleven non-RSL compounds (FIG. 8). The degree of cell death suppression was quantified by calculating the normalized differences in the AUC (Area Under the Curve) of the compound alone curve and compound with zileuton curve. Combined with the BODIPY-C11 staining data, these results revealed that all RSL compounds are mechanistically distinct from the 11 non-RSL compounds (FIG. 4a).

Figure 13:
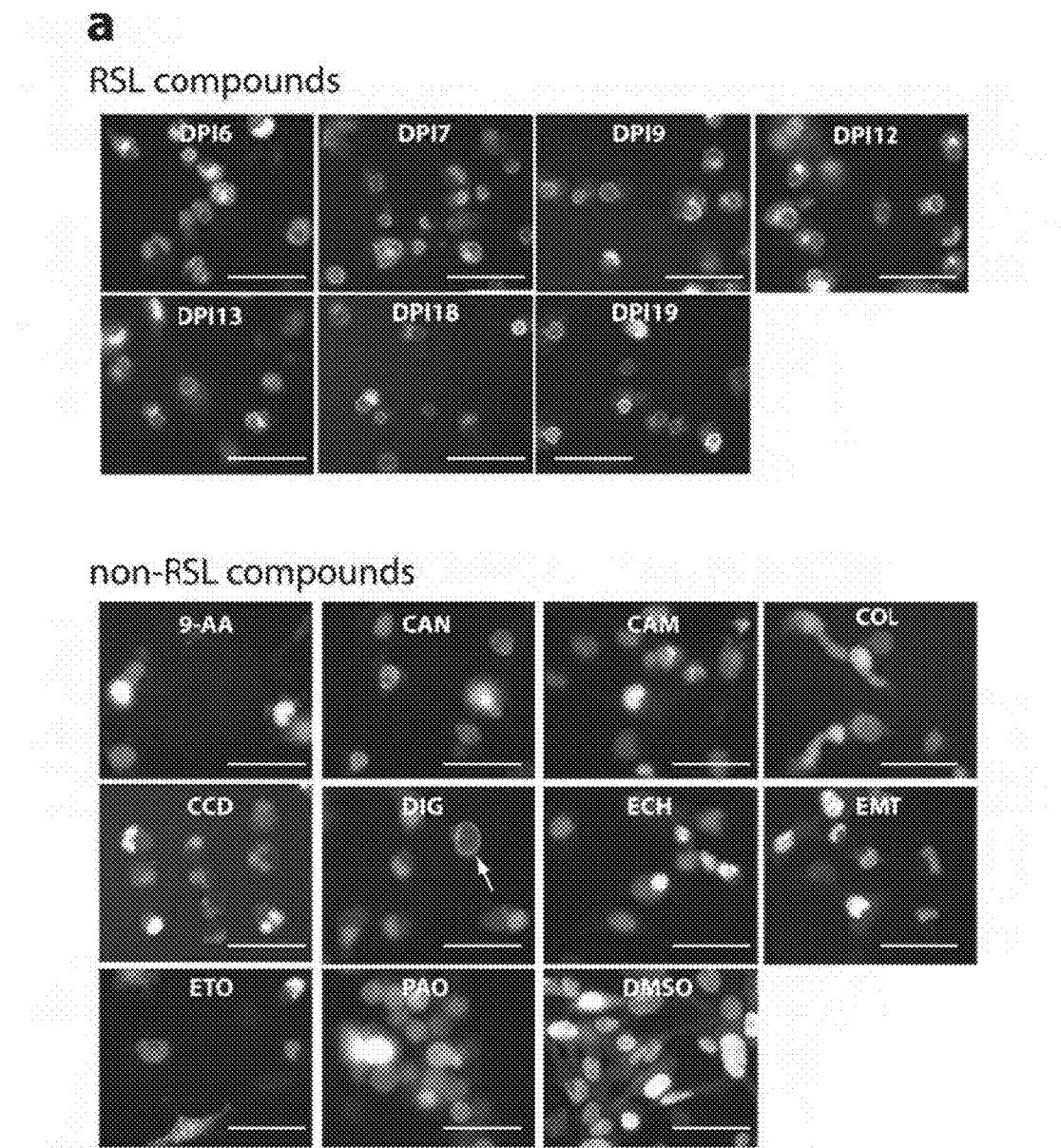
Figure 13:
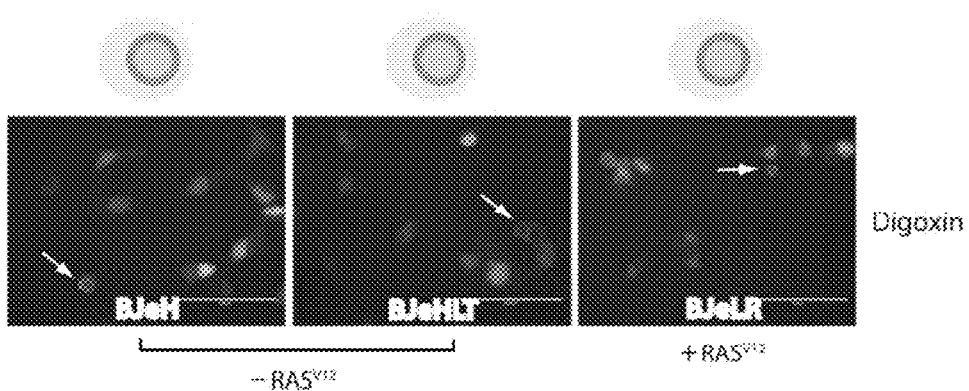

Next, GFP-ALOX5-expressing HT-1080 cells were treated with these non-RSL and RSL compounds and changes in the location of GFP-ALOX5 were monitored as a measure of ALOX protein activation. All RSL compounds induced translocation of GFP-ALOX5 to the nuclear membrane, whereas of the eleven different non-RSL compounds, only digoxin induced GFP-ALOX5 translocation (FIG. 4b and FIG. 13). Digoxin is known to elevate intracellular calcium (McGarry et al., 1993), which is likely to cause the translocation of GFP-ALOX5, similar to ionomycin. Note that ionomycin and digoxin are not RSL compounds and induce translocation of GFP-ALOX5 non-specifically in the BJ-derived cell lines (FIGS. 7 and 13). The results highlight the importance of selective ALOX activation for the induction of the RSL phenotype.

The suppression of RSL-induced cell death by lipoxygenase inhibitors implied that knocking down ALOX expression using RNA interference (RNAi) might rescue cells from RSL-induced cell death, if there is a lack of functional redundancy among ALOX genes. There are six ALOX genes in humans—ALOX5, ALOX12, ALOX12B, ALOX15, ALOX15B, and ALOXE3. These genes have different expression patterns among different tissues; therefore, which ALOX genes were expressed in the BJ cell lines and in HT-1080 cells were examined using qPCR. Of the six isoforms, ALOX15B and ALOXE3 were consistently expressed in these cell lines, whereas ALOX5, ALOX12, ALOX12B, and ALOX15 did not show consistent expression in the qPCR analysis (FIG. 14a). Accordingly, pools of small interfering RNAs (siRNAs) targeting ALOX15B and ALOXE3 were prepared, and the effect of each siRNA pool on the lethality of the RSL compounds was tested. The siRNA pools targeting ALOX15B and ALOXE3 were able to decrease their target mRNA levels by greater than 6-fold and 20-fold, respectively (FIG. 14b). Knocking down ALOX15B prevented erastin-induced cell death, but sensitized cells to RSL3-induced cell death (FIG. 4c). On the other hand, knockdown of ALOXE3 suppressed both erastin and RSL3-induced cell death (FIG. 4c). When the experiment was expanded to 10 additional RSL compounds, siRNAs targeting ALOXE3 consistently suppressed cell death induced by all RSLs, demonstrating a critical role for ALOXE3 in inducing the RSL phenotype (FIG. 4c and FIG. 15). Moreover, ALOXE3 knockdown exerted minimal effect on cell death induced by 10 non-RSL compounds (FIG. 4c and FIG. 15). The effect of ALOXE3 knockdown was not as specific to RSL compounds as small molecule ALOX inhibitors. The differences in isoform specificity, and the different mechanisms of RNAi and small molecules, may explain these differences (Luo et al., 2012; Weiss et al., 2007; Yang et al., 2012).

Example 7

PE (Compound 30), an Improved Analog of Erastin, Shows Efficacy in a Mouse Xenograph Study Whether ferroptosis could be utilized to suppress the growth of tumors harboring oncogenic RAS proteins in a xenograft mouse model was investigated. Because erastin itself was not optimal for testing in mice, a more soluble and stable analog of erastin, piperazineerastin (PE), was developed. PE exhibited the RSL phenotype (FIG. 16a). The improved metabolic stability and solubility of PE was confirmed using liquid chromatography-mass spectrometry (LC-MS) and nephelometry, respectively (FIG. 4d and FIG. 16b). PE was affected similarly by cell death modulators as erastin and displayed a distinct pattern from other non-RSL compounds, indicating that PE induced a similar form of cell death as erastin (FIG. 4e; Spearman correlation coefficient=0.9291, P<0.0001). Moreover, knocking down VDAC3, a target of erastin, suppressed PE-induced cell death, further substantiating that erastin and PE act through the same mechanism (FIG. 16c).

Both erastin and PE were evaluated in nude mice into which HT-1080 cells had been injected into their flank. Mice were treated with either erastin or PE by subcutaneous injection (40 mg/kg) or vehicle control (FIG. 4f). Erastin was not able to inhibit tumor growth, due to its poor solubility and metabolic instability. However, a significant delay in tumor growth in the PE-treated group compared to the vehicle-treated group was observed (FIG. 4f). These results suggest that RSL compounds with suitable pharmacological properties, such as PE, can reduce tumor growth in an in vivo context.

The data establish that a GSH/GPX4/ALOX-regulated pathway is responsible for inducing oncogenic-RAS selective lethality by multiple compounds (FIG. 4g), leading to an iron-dependent, oxidative, non-apoptotic form of cell death termed ferroptosis (Dixon et al., 2012). The executioners of ferroptosis have been enigmatic until now. Without wishing to be bound by a particular theory, the data presented herein appear to show that lipoxygenases may function as the key effectors of ferroptosis, much the way that caspases function as the key effectors of apoptosis.

Physiologically, components of this lipoxygenase cell death pathway have been implicated in several forms of neurotoxicity such as glutamate-induced excitotoxicity (Li et al., 1997), ischemia/reperfusion injury (Patel et al., 2004), and amyloid toxicity (Lebeau et al., 2004). ALOX15 has been reported to play critical roles in these disease models, inducing non-apoptotic cell death (Dixon et al., 2012; Seiler et al., 2008). HT-1080 cells and BJeLR cells lacked ALOX15 expression and required ALOXE3 to induce ferroptotic cell death by RSL compounds. ALOXE3 is a distantly related lipoxygenase that, unlike other lipoxygenases, does not use arachidonic acid as its substrate (Yu et al., 2003). The results show that ALOXE3 is critical for mediating the oncogenic-RAS-selective lethality in HT-1080 and BJeLR tumor cells.

There is evidence that activation of RAS signaling can interact synergistically with aspects of this GSH/GPX4/ALOX cell death pathway. First, it was reported that overexpression of HRAS in A431 cells is able to activate transcription of ALOX12 (Chen et al., 1997). This RAS-mediated regulation of ALOX gene expression may be broader than previously suspected. Second, PD 098059, a MEK1/2 inhibitor, suppressed ALOX5 translocation to the nuclear membrane and subsequent 5-HETE productions, which suggests that MEK can regulate ALOX activity at the post-translational level (Boden et al., 2000). Third, RAS signaling is known to enhance unsaturated fatty acid production, including arachidonic acid (Boden et al., 2000; Kamphorst et al., 2011; Price et al., 1989). Cells with increased arachidonic acid levels should produce more lipid peroxides through the oxidation of unsaturated fatty acids by ALOXs. Finally, cells with oncogenic RAS have increased basal ROS (Irani et al., 1997), which lowers the threshold to initiate oxidative cell death.

The optimized RSL compound PE (Compound 30) showed efficacy in a human tumor xenograft model, establishing the plausibility of targeting the GSH/GPX4/ALOX pathway for anti-cancer drug discovery. Until now, to the best of our knowledge, no attempt has been reported to exploit lipid-peroxide-mediated cell death to develop anti-cancer drugs.

Example 8

Evaluation of Pharmacokinetic Profiles and Blood-Brain Barrier (BBB) Penetration of PE (Compound 30) in Male C57BL6/j Mice Following Single Intravenous and Oral Administration Test Article Preparation 58.5 mg of the test article, PE (compound 30), was dissolved in 10% NMP/90% PEG-400 (a volume of 2.9 mL) to yield a final concentration of 20 mg/mL for intravenous and oral administration. The resulting solution was stored at room temperature until dosing (about 14 hours and 30 minutes).

Analysis of Dose Formulations

All analytical work was conducted by Analytical Sciences Division of Medicilon Preclinical Research (Shanghai) LLC.

Animal Acquisition and Assignment to Study

A total of 60 male C57BL6/j mice, approximately 8-9 weeks of age at receipt, were received from Shanghai SLAC Laboratory Animal, Inc., and 42 of those animals weighing between 18.0 and 24.9 grams were placed on study.

Dose Administration

The test article, PE (compound 30), was administered via a single IV bolus injection or a single PO gavage. Dose administration information is presented in Table 6.

TABLE 6

Dose Administration of PE

| Compound | Animal Number | Group Number | Sex | Dose Level (mg/kg) | Dose Concentration (mg/mL) | Dose Volume (mL/kg) | Dose Route |
|---|---|---|---|---|---|---|---|
| PE | 101-121 | 1 | Male | 20 | 20 | 1 | IV |
| PE | 201-221 | 2 | Male | 20 | 20 | 1 | PO |

Sample Collection and Bioanalysis

Three mice in each group were used for blood collection at each time point. Blood samples (approximately 400 µL) were collected after euthanasia using carbon dioxide inhalation via cardiac puncture pre-dose and 30 minutes, 1 hour, 2 hours, 4 hours, 8 hours and 12 hours post-dose. Blood samples were placed into tubes containing sodium heparin and centrifuged at 8000 rpm for 6 minutes at 4° C. to separate plasma from the blood samples. Following centrifugation, the resulting plasma was transferred to clean tubes and stored frozen at −80° C. until bioanalysis by the Testing Facility.

The whole brain from each animal was collected right after the blood collection. The whole brain was harvested, excised and rinsed by saline, dried by filter paper, and then placed into a separate tube for every animal. All samples were stored frozen at −80° C. pending bioanalysis.

In addition, extra animals obtained for the study, but not placed on study were used for collection of blank plasma (500 µL from each animal) and brain. The blank plasma and brain were used as controls in this study.

Bioanalytical Method and Sample Analysis

The concentrations of PE in plasma and brain were determined using a high performance liquid chromatography/mass spectrometry (HPLC/MS/MS) method.

LC-MS/MS Apparatus

The liquid chromatography (LC) system included an Agilent (Agilent Technologies Inc., USA) liquid chromatograph equipped with an isocratic pump (1100 series), an autosampler (1100 series), and a degasser (1100 series). Mass spectrometric analysis was performed using a 6410B instrument from Aglient with an ESI interface. The data acquisition and control system were created using Analyst 1.4.2 software from AB Inc. (Canada). Other equipments included a XW-80A Vortex mixer (Shanghai); a TGL-16B high speed centrifuge (Shanghai), and a Millipore Academic Ultrapure-water generating system. Methanol (Burdick & Jackson Laboratories, Inc., Honeywell Inc., Morristown, N.J.) was HPLC grade. All other solvents and chemicals were analytical grade or better.

LC-MS/MS Conditions

The column used for HPLC (high performance liquid chromatography) was Ascentis Express, 2.7 µm, C18, 30*2.10 mm. The conditions used for the mobile phase are listed in Table 7 below.

TABLE 7

Mobile Phase of HPLC

| Time (min) | A (%) | B (%) |
|---|---|---|
| 0.00 | 60 | 40 |
| 0.50 | 5 | 95 |
| 1.20 | 5 | 95 |
| 1.21 | 60 | 40 |
| 6.00 | 60 | 40 |

A: 0.1% Formic acid in water; B: 0.1% Formic acid in MeOH; Flow rate: 400 µL/min; Column temperature: 40° C., Injection volume: 5 µL.

Mass Spectrometry

As noted above, an Aglient 6410B was used for mass spectrometry, with an ESI Ion source. The nebulizer pressure used was 40 psi, gas flow was 8 L/min, voltage applied to the tip of the capillary was 4000 v, and the gas temperature was 350° C. Other parameters are listed in Table 8 below.

TABLE 8

Additional mass spectrometry parameters

| Analyte | Q1 (amu) | MS1 Res | Q3 (amu) | MS2 Res | Dwell time (ms) | Fragmentor (v) | CE (v) | polarity |
|---|---|---|---|---|---|---|---|---|
| PE | 645.3 | Wide | 517.2 | Wide | 200 | 200 | 29 | Positive |
| Tolbutamide (IS) | 271.1 | Wide | 91.1 | Unit | 200 | 100 | 37 | Positive |

Preparation of Standard Stock Solution for Plasma Samples

For plasma samples, a stock solution of PE was prepared by dissolving the drug in methanol to yield a final concentration of 764,000 ng/mL. An aliquot of this solution was diluted using methanol to prepare a series of working solutions of 100, 200, 400, 2,000, 4,000, 20,000 and 40,000 ng/mL. Seven calibration standard samples containing 2.5, 5, 10, 50, 100, 500, 1,000 ng/mL were obtained by adding 5 μL working solution prepared above into seven Eppendorff tubes containing 195 μL blank plasma. QC samples were prepared by spiking 195 μL blank plasma with 5 μL working solutions of 300, 8,000, 32,000, 200,000 ng/mL to yield final concentrations of 7.5, 200, 800, 5000 ng/mL. (Table 9).

TABLE 9

Preparation of Calibration Standard Solution and QC Samples for Plasma

| Sample | Blank plasma (μL) | Amount (ng) of test article added (dissolved in 5 μL methanol) | Working solution conc. (ng/mL) | Final volume of plasma (μL) | Final conc. (ng/mL) in plasma |
|---|---|---|---|---|---|
| STD samples |||||||
| STD-1 | 195 | 0.5 | 100 | 200 | 2.5 |
| STD-2 | 195 | 1 | 200 | 200 | 5 |
| STD-3 | 195 | 2 | 400 | 200 | 10 |
| STD-4 | 195 | 10 | 2,000 | 200 | 50 |
| STD-5 | 195 | 20 | 4,000 | 200 | 100 |
| STD-6 | 195 | 100 | 20,000 | 200 | 500 |
| STD-7 | 195 | 200 | 40,000 | 200 | 1,000 |
| QC samples |||||||
| QCL | 195 | 0.5 | 100 | 200 | 2.5 |
| QCM | 195 | 40 | 8,000 | 200 | 200 |
| QCH | 195 | 160 | 32,000 | 200 | 800 |
| DQC | 195 | 1000 | 200,000 | 200 | 5000 |

Preparation of Standard Stock Solution for Brain Samples

For brain samples, stock solution of PE was prepared by dissolving the drug in methanol to yield a final concentration of 764,000 ng/mL. An aliquot of this solution was diluted using methanol to get a series of working solutions of ⅙ the concentration used for plasma samples, or 200000/6, 40000/6, 20000/6, 4000/6, 2000/6, 400/6, 200/6 ng/mL. Seven calibration standard samples containing 5, 10, 50, 100, 500, 1000, 5000 ng/G were obtained by adding 5 μL working solution prepared above into seven centrifuge tubes containing 195 μL blank brain homogenate. QC samples were prepared by spiking 195 μL blank brain homogenate with 5 μL working solutions of 600/6, 32000/6, 160000/6 ng/mL to yield final concentration of 15, 800, 4000 ng/G. Information on the preparation of the standard solution and quality control samples is presented in Table 10.

TABLE 10

Preparation of Calibration Standard Solution and QC Samples for Brain

| Sample | Blank brain (μl) | Amount (ng) of test article added (dissolved in 5 μl methanole) | Working solution conc. (ng/mL) | Final volume of brain (μl) | Final conc. (ng/G) in brain |
|---|---|---|---|---|---|
| STD samples |||||||
| STD-1 | 195 | 1/6 | 200/6 | 200 | 5 |
| STD-2 | 195 | 2/6 | 400/6 | 200 | 10 |
| STD-3 | 195 | 10/6 | 2,000/6 | 200 | 50 |
| STD-4 | 195 | 20/6 | 4,000/6 | 200 | 100 |
| STD-5 | 195 | 100/6 | 20,000/6 | 200 | 500 |
| STD-6 | 195 | 200/6 | 40,000/6 | 200 | 1000 |
| STD-7 | 195 | 1000/6 | 200,000/6 | 200 | 5000 |
| QC samples |||||||
| QCL | 195 | 3/6 | 600/6 | 200 | 15 |
| QCM | 195 | 160/6 | 32,000/6 | 200 | 800 |
| QCH | 195 | 800/6 | 160,000/6 | 200 | 4000 |

Preparation of Standard Stock Solution for Internal Standard

A stock solution of tolbutamide (internal standard, IS) was prepared by dissolving the drug in methanol to yield a final concentration of 395,000 ng/mL. This solution was diluted with methanol to yield a final concentration of 200 ng/mL.

Plasma Sample Processing

Plasma samples (0.05 mL) were transferred to Eppendorff tubes, and then 250 μL IS solution (200 ng/mL Tolbutamide) was added. After vortexing for 1 minute and centrifuging for 5 minutes at 15,000 rpm, 200 μL aliquots of supernatant were transferred to a 96-well plate for injection.

Brain Sample Processing

Brain samples were homogenized with saline first (weigh:volume=1 g: 5 mL). Brain samples (0.05 mL) were transferred to Eppendorff tubes, then 250 μL IS solution (200 ng/mL Tolbutamide) was added. After vortexing for 1 minute and centrifuging for 5 minutes at 15000 rpm, 200 μL aliquots of supernatant were transferred to a 96-well plate for injection.

Pharmacokinetic Analysis

Any BLQs (below limit of quantitation) (LLOQ (lower limit of quantitation)=2.5 ng/mL for plasma samples; LLOQ=5 ng/g for brain samples) were replaced with a value of "0", and the mean value and its standard deviation (SD) were calculated with these replaced values. Any concentrations that were BLQ were omitted from the calculation of PK parameters in individual animals. The bioavailability was calculated as F (%)=(Dose$_{iv}$×AUC$_{oral(0-\infty)}$)/(Dose$_{oral}$×AUC$_{iv(0-\infty)}$)×100%.

Specificity

The chromatographic conditions showed that the blank plasma/brain had no interference on the PE and IS determination. (See FIG. 17 for plasma, FIG. 20 for brain).

Calibration Curve for Plasma

For plasma analysis, the calibration curve of PE was constructed using seven nonzero standards ranging from 2.5 to 1000 ng/mL, respectively. A blank sample (matrix sample processed without internal standard) was used to exclude contamination. The linear regression analysis of PE was performed by plotting the peak area ratio of PE over IS (y) against the PE concentration (x) in ng/mL. The linearity of the relationship between peak area ratio and concentration was demonstrated by the correlation coefficients (R) obtained for the linear regression of PE. (FIG. 18).

Calibration Curve for Brain

For analysis of the brains, the calibration curve of PE was constructed using seven nonzero standards ranging from 5 to 5000 ng/mL. A blank sample (matrix sample processed without internal standard) was used to exclude contamination. The linear regression analysis of PE was performed by plotting the peak area ratio of PE over IS (y) against the PE concentration (x) in ng/mL. The linearity of the relationship between peak area ratio and concentration was demonstrated by the correlation coefficients (R) obtained for the linear regression of PE (FIG. 21).

Infra-Assay Accuracy for Plasma and Brain

The accuracies of >66.7% of the quality control samples were between 80-120% and confirmed that the method is reliable. See Table 11 for plasma, Table 12 for brain.

TABLE 11

Intra-assay precision and accuracy for plasma samples

| | Concentration (ng/mL) & Accuracy (%) | | | |
|---|---|---|---|---|
| Replicates | 7.50 | 200.00 | 800.00 | 500.00 |
| 1 | 7.33 (97.75) | 179.26 (89.63) | 721.48 (90.19) | 456.65 (91.33) |
| 2 | 6.75 (90.00) | 189.67 (94.84) | 706.01 (88.25) | 446.59 (89.32) |
| Mean ± SD | 7.04 ± 0.41 | 184.46 ± 7.36 | 713.75 ± 10.94 | 451.61 ± 7.11 |
| | (93.88 ± 5.48) | (92.23 ± 3.68) | (89.22 ± 1.37) | (90.32 ± 1.42) |
| RSD (%) | 5.89 | 3.99 | 1.53 | 1.58 |

TABLE 12

Intra-assay precision and accuracy for brain samples

| | Concentration (ng/mL) & Accuracy (%) | | |
|---|---|---|---|
| Replicates | 15 | 800 | 4000 |
| 1.00 | 15.41 (102.74) | 613.12 (76.64) | 4125.32 (103.13) |
| 2.00 | 13.01 (86.74) | 783.50 (97.94) | 3215.37 (80.38) |
| Mean ± SD | 14.21 ± 1.70 | 698.31 ± 120.47 | 3670.34 ± 643.43 |
| | (94.74 ± 11.31) | (87.29 ± 15.06) | (91.76 ± 16.09) |
| RSD (%) | 11.94 | 17.25 | 17.53 |

Predose Observations

No abnormal observations were noted.

Postdose Observations

No abnormal observations were noted.

Results—Pharmacokinetics of PE

Plasma concentrations from individual animals in Groups 1-2 are tabulated in Table 13.

TABLE 13

Plasma concentration of PE in male C57BL6/j mice following intravenous and oral administration

| Sample Collection Time | Plasma Concentration (ng/mL) Animal Number: 101-121 IV (20 mg/kg) | | | | |
|---|---|---|---|---|---|
| Point (hr) | Mouse 1 | Mouse 2 | Mouse 3 | Mean | SD |
| 0.5 | 4625.87 | 2218.81 | 2826.92 | 3223.87 | 1251.66 |
| 1 | 1548.38 | 657.50 | 1509.78 | 1238.55 | 503.58 |
| 2 | 919.51 | 1016.04 | 1054.66 | 996.74 | 69.61 |
| 4 | 200.14 | 657.19 | 379.24 | 412.19 | 230.30 |
| 8 | 146.54 | 105.57 | 148.67 | 133.59 | 24.30 |
| 12 | 34.53 | 159.78 | 96.08 | 96.80 | 62.63 |

TABLE 13-continued

Plasma concentration of PE in male C57BL6/j mice following intravenous and oral administration

| Sample Collection Time | Plasma Concentration (ng/mL) Animal Number: 101-121 IV (20 mg/kg) | | | | |
|---|---|---|---|---|---|
| Point (hr) | Mouse 1 | Mouse 2 | Mouse 3 | Mean | SD |
| | Animal Number: 201-221 PO (20 mg/kg) | | | | |
| 0.5 | 365.89 | 403.60 | 87.63 | 285.71 | 172.57 |
| 1 | 1243.77 | 1635.86 | 1288.53 | 1389.39 | 214.62 |
| 2 | 1260.55 | 527.50 | 1016.24 | 934.76 | 373.25 |
| 4 | 776.81 | 642.39 | 669.76 | 696.32 | 71.04 |
| 8 | 19.09 | 23.99 | 28.91 | 24.00 | 4.91 |
| 12 | 20.19 | 21.10 | 15.06 | 18.78 | 3.25 |

SD: Standard deviation
BLQ: Below Limit of Quantitation
NA: Not applicable, or failed to collect samples.
LLOQ = 2.5 ng/mL The estimates of the non-compartmental PK parameters are summarized in Table 14.

TABLE 14

Selected pharmacokinetics parameters of PE in male C57BL6/j mice following intravenous and oral administration (plasma)

| $t_{1/2}$ hr | $T_{max}$ hr | $C_{max}$ ug/L | $AUC_{(0-t)}$ ug/L*h | $AUC_{(0-\infty)}$ ug/L*h | $MRT_{(0-\infty)}$ hr | Vz mL/kg | CLz mL/hr/kg | F % |
|---|---|---|---|---|---|---|---|---|
| IV 20 mg/kg | | | | | | | | |
| 2.84 | 0.50 | 3223.87 | 8098.37 | 8494.43 | 2.67 | 9633.34 | 2354.48 | NA |
| PO 20 mg/kg | | | | | | | | |
| 1.57 | 1.00 | 1389.39 | 4809.56 | 4852.20 | 2.91 | NA | NA | 57.12 |

NA—Not Applicable

Log-linear plots of the plasma concentration versus time curves are presented in FIG. 19.

Brain concentrations from individual animals in Groups 1-2 are tabulated in Table 15.

TABLE 15

Brain homogenate concentration of PE in male C57BL6/j mice following intravenous and oral administration

| Sample Collection Time | Brain Concentration (ng/g) Animal Number: 101-121 IV (20 mg/kg) | | | | |
|---|---|---|---|---|---|
| Point (hr) | Mouse 1 | Mouse 2 | Mouse 3 | Mean | SD |
| 0.5* | 115.89 | 98.32 | 74.06 | 96.09 | 21.00 |
| 1* | 76.62 | 71.12 | 108.81 | 85.52 | 20.36 |
| 2* | 79.09 | 89.04 | 52.97 | 73.70 | 18.63 |

TABLE 15-continued

Brain homogenate concentration of PE in male C57BL6/j mice following intravenous and oral administration

| Sample Collection Time Point (hr) | Brain Concentration (ng/g) Animal Number: 101-121 IV (20 mg/kg) | | | | |
|---|---|---|---|---|---|
| | Mouse 1 | Mouse 2 | Mouse 3 | Mean | SD |
| 4 | 34.10 | 59.00 | 50.80 | 47.97 | 12.69 |
| 8 | 38.64 | 33.73 | 17.54 | 29.97 | 11.04 |
| 12 | 30.29 | 40.22 | 18.79 | 29.77 | 10.72 |
| | Animal Number: 201-221 PO (20 mg/kg) | | | | |
| 0.5 | BLQ | BLQ | BLQ | NA | NA |
| 1* | BLQ | 10.89 | 18.92 | 14.91 | 5.68 |
| 2* | 15.10 | BLQ | 9.49 | 12.30 | 3.96 |
| 4* | 14.15 | 20.96 | 11.55 | 15.56 | 4.86 |
| 8 | BLQ | BLQ | BLQ | NA | NA |
| 12 | BLQ | BLQ | BLQ | NA | NA |

*The brain samples at this time point were processed by 10-fold dilution
SD: Standard deviation
BLQ: Below Limit of Quantitation
NA: Not applicable, or failed to collect samples.
LLOQ = 5 ng/g Brain-Plasma concentration ratios of the test article are presented in Table 16.

TABLE 16

Brain-plasma concentration ratio of PE in male C57BL6/j mice following intravenous and oral administration

| Sample Collection Time Point (hr) | Brain-Plasma Concentration Ratio (mL/g) Animal Number: 101-121 IV (20 mg/kg) | | | | |
|---|---|---|---|---|---|
| | Mouse 1 | Mouse 2 | Mouse 3 | Mean | SD |
| 0.5 | 0.03 | 0.04 | 0.03 | 0.03 | 0.01 |
| 1 | 0.05 | 0.11 | 0.07 | 0.08 | 0.03 |
| 2 | 0.09 | 0.09 | 0.05 | 0.07 | 0.02 |
| 4 | 0.17 | 0.09 | 0.13 | 0.13 | 0.04 |
| 8 | 0.26 | 0.32 | 0.12 | 0.23 | 0.10 |
| 12 | 0.88 | 0.25 | 0.20 | 0.44 | 0.38 |
| | Animal Number: 201-221 PO (20 mg/kg) | | | | |
| 0.5 | NA | NA | NA | NA | NA |
| 1 | NA | 0.01 | 0.01 | 0.01 | 0.01 |
| 2 | 0.01 | NA | 0.01 | 0.01 | 0.00 |
| 4 | 0.02 | 0.03 | 0.02 | 0.02 | 0.01 |
| 8 | NA | NA | NA | NA | NA |
| 12 | NA | NA | NA | NA | NA |

SD: Standard deviation
NA: Not applicable

The estimates of the non-compartmental PK parameters are summarized in Table 17.

TABLE 17

Selected pharmacokinetics parameters of PE in male C57BL6/j mice following intravenous and oral administration (Brain)

| $t_{1/2}$ hr | $T_{max}$ hr | $C_{max}$ ug/kg | $AUC_{(0-t)}$ ug/kg * h | $AUC_{(0-\infty)}$ ug/kg * h | $MRT_{(0-\infty)}$ hr |
|---|---|---|---|---|---|
| IV 20 mg/kg | | | | | |
| 6.41 | 0.50 | 96.09 | 573.06 | 848.29 | 9.91 |
| PO 20 mg/kg | | | | | |
| NA | 4.00 | 15.56 | 48.92 | NA | NA |

NA: Not applicable

Log-linear plots of the brain concentration versus time curves are presented in FIGS. 22 and 23. Log-linear plots of Brain-Plasma concentration ratios versus time curves are presented in FIG. 24.

PE Plasma

Following intravenous administration of PE at a nominal dose of 20 mg/kg, the mean value of systemic clearance was 2.35 L/hr/kg and the mean of half-life ($T_{1/2}$) was 2.84 hr. The mean value of $C_{max}$ and $T_{max}$ following IV administration at a nominal dose of 20 mg/kg were 3223.87 µg/L and 0.5 hour, respectively. The mean of $AUC_{(0-t)}$ was 8098.37 hr*µg/L. The mean volume of distribution at terminal phase was 9.63 L/kg.

Following oral administration of PE at a nominal dose of 20 mg/kg, the mean values of $C_{max}$ and $T_{max}$ were 1389.39 µg/L and 1.00 hour, respectively. The mean of $AUC_{(0-t)}$ and half-life ($T_{1/2}$) were 4809.56 hr*µg/L and 1.57 hours, respectively. The mean value of bioavailability for PE was 57.12%.

PE Brain

Following intravenous administration of PE at a nominal dose of 20 mg/kg, the mean values of $C_{max}$ and $T_{max}$ were 96.09 µg/kg and 0.50 hour, respectively. The mean of $AUC_{(0-t)}$ and half-life ($T_{1/2}$) were 573.06 hr*µg/kg and 6.41 hours, respectively.

Following oral administration of PE at a nominal dose of 20 mg/kg, the mean values of $C_{max}$ and $T_{max}$ were 15.56 µg/kg and 4.00 hours, respectively. The mean of $AUC_{(0-t)}$ were 48.92 hr*µg/kg. The mean of half-life ($T_{1/2}$) was not applicable.

DOCUMENTS

Babij, C. et al. STK33 kinase activity is nonessential in KRAS-dependent cancer cells. *Cancer Res* 71, 5818-5826 (2011).

Barbie, D. A. et al. Systematic RNA interference reveals that oncogenic KRAS-driven cancers require TBK1. *Nature* 462, 108-112(2009).

Boden, S. E., Bertsche, T., Ammon, H. P. & Safayhi, H. MEK-1/2 inhibition prevents 5-lipoxygenase translocation in N-forrmylpeptide-challenged human neutrophils. *Int J Biochem Cell Biol* 32, 1069-1074 (2000).

Chen, B. K., Liu, Y. W., Yamamoto, S. & Chang, W. C. Overexpression of Ha-ras enhances the transcription of human arachidonate 12-lipoxygenase promoter in A431 cells. *Biochim Biophys Acta* 1344, 270-277 (1997).

Chen, X. S. & Funk, C. D. The N-terminal "beta-barrel" domain of 5-lipoxygenase is essential for nuclear membrane translocation. *J Biol Chem* 276, 811-818(2001).

Chuang, J. I., Chang, T. Y. & Liu, H. S. Glutathione depletion-induced apoptosis of Ha-ras-transformed NIH3T3 cells can be prevented by melatonin. *Oncogene* 22, 1349-1357(2003).

Colles, S. M. & Chisolm, G. M. Lysophosphatidylcholine-induced cellular injury in cultured fibroblasts involves oxidative events. *J Lipid Res* 41, 1188-1198 (2000).

Dixon, S. J., Costanzo, M., Baryshnikova, A., Andrews, B. & Boone, C. Systematic mapping of genetic interaction networks. *Annu Rev Genet* 43, 601-625 (2009).

Dixon, Scott J. et al. Ferroptosis: An Iron-Dependent Form of Nonapoptotic Cell Death. *Cell* 149, 1060-1072 (2012).

Dolma, S., Lessnick, S. L., Hahn, W. C. & Stockwell, B. R. Identification of genotype-selective antitumor agents using synthetic lethal chemical screening in engineered human tumor cells. *Cancer Cell* 3, 285-296 (2003).

Downward, J. Targeting RAS signalling pathways in cancer therapy. *Nat Rev Cancer* 3, 11-22 (2003).

Fanelus, I. & Desrosiers, R. R. Reactive oxygen species generated by thiol-modifying phenylarsine oxide stimulate the expression of protein L-isoaspartyl methyltransferase. *Biochem Biophys Res Commun* 371, 203-208 (2008).

Haeggstrom, J. Z. & Funk, C. D. Lipoxygenase and leukotriene pathways: biochemistry, biology, and roles in disease. *Chemical reviews* 111, 5866-5898(2011).

Hartwell, L. H., Szankasi, P., Roberts, C. J., Murray, A. W. & Friend, S. H. Integrating genetic approaches into the discovery of anticancer drugs. *Science* 278, 1064-1068 (1997).

Hussain, S. P., Hofseth, L. J. & Harris, C. C. Radical causes of cancer. *Nat Rev Cancer* 3, 276-285(2003).

Imai, H. & Nakagawa, Y. Biological significance of phospholipid hydroperoxide glutathione peroxidase (PHGPx, GPx4) in mammalian cells. *Free Radic Biol Med* 34, 145-169 (2003).

Irani, K. et al. Mitogenic signaling mediated by oxidants in Ras-transformed fibroblasts. *Science* 275, 1649-1652 (1997).

Ji, Z. et al. Chemical genetic screening of KRAS-based synthetic lethal inhibitors for pancreatic cancer. *Frontiers in bioscience: a journal and virtual library* 14, 2904-2910 (2009).

Kaelin, W. G., Jr. The concept of synthetic lethality in the context of anticancer therapy. *Nat Rev Cancer* 5, 689-698 (2005).

Kamphorst, J. J., Fan, J., Lu, W., White, E. & Rabinowitz, J. D. Liquid chromatography-high resolution mass spectrometry analysis of fatty acid metabolism. *Analytical chemistry* 83, 9114-9122 (2011).

Kang, Y. J. & Enger, M. D. Buthionine sulfoximine-induced cytostasis does not correlate with glutathione depletion. *Am J Physiol* 262, C122-127 (1992).

Kumar, M. S. et al. The GATA2 Transcriptional Network Is Requisite for RAS Oncogene-Driven Non-Small Cell Lung Cancer. *Cell* 149, 642-655 (2012).

Lebeau, A., Terro, F., Rostene, W. & Pelaprat, D. Blockade of 12-lipoxygenase expression protects cortical neurons from apoptosis induced by beta-amyloid peptide. *Cell Death Differ* 11, 875-884(2004).

Li, Y., Maher, P. & Schubert, D. A role for 12-lipoxygenase in nerve cell death caused by glutathione depletion. *Neuron* 19, 453-463 (1997).

Luo, J. et al. A genome-wide RNAi screen identifies multiple synthetic lethal interactions with the Ras oncogene. *Cell* 137, 835-848(2009).

Luo, T. et al. STK33 kinase inhibitor BRD-8899 has no effect on KRAS-dependent cancer cell viability. *Proc Natl Acad Sci USA* 109, 2860-2865, (2012).

Malumbres, M. & Barbacid, M. RAS oncogenes: the first 30 years. *Nat Rev Cancer* 3, 459-465 (2003).

McGarry, S. J. & Williams, A. J. Digoxin activates sarcoplasmic reticulum Ca(2+)-release channels: a possible role in cardiac inotropy. *Br J Pharmacol* 108, 1043-1050 (1993).

Patel, N. S. et al. Reduction of renal ischemia-reperfusion injury in 5-lipoxygenase knockout mice and by the 5-lipoxygenase inhibitor zileuton. *Mol Pharmacol* 66, 220-227(2004).

Price, B. D., Morris, J. D., Marshall, C. J. & Hall, A. Stimulation of phosphatidylcholine hydrolysis, diacylglycerol release, and arachidonic acid production by oncogenic ras is a consequence of protein kinase C activation. *J Biol Chem* 264, 16638-16643 (1989).

Ran, Q. et al. Embryonic fibroblasts from Gpx4+/− mice: a novel model for studying the role of membrane peroxidation in biological processes. *Free Radic Biol Med* 35, 1101-1109 (2003).

Root, D. E., Flaherty, S. P., Kelley, B. P. & Stockwell, B. R. Biological mechanism profiling using an annotated compound library. *Chemistry & biology* 10, 881-892 (2003).

Scholl, C. et al. Synthetic lethal interaction between oncogenic KRAS dependency and STK33 suppression in human cancer cells. *Cell* 137, 821-834(2009).

Seiler, A. et al. Glutathione peroxidase 4 senses and translates oxidative stress into 12/15-lipoxygenase dependent- and AIF-mediated cell death. *Cell Metab* 8, 237-248 (2008).

Shaw, A. T. et al. Selective killing of K-ras mutant cancer cells by small molecule inducers of oxidative stress. *Proc Natl Acad Sci USA* 108, 8773-8778 (2011).

Shornick, L. P. & Holtzman, M. J. A cryptic, microsomal-type arachidonate 12-lipoxygenase is tonically inactivated by oxidation-reduction conditions in cultured epithelial cells. *J Biol Chem* 268, 371-376 (1993).

Szatrowski, T. P. & Nathan, C. F. Production of large amounts of hydrogen peroxide by human tumor cells. *Cancer Res* 51, 794-798 (1991).

Trachootham, D. et al. Selective killing of oncogenically transformed cells through a ROS-mediated mechanism by beta-phenylethyl isothiocyanate. *Cancer Cell* 10, 241-252 (2006).

Weiss, W. A., Taylor, S. S. & Shokat, K. M. Recognizing and exploiting differences between RNAi and small-molecule inhibitors. *Nat Chem Biol* 3, 739-744(2007).

Weiwer, M. et al. Development of small-molecule probes that selectively kill cells induced to express mutant RAS. *Bioorg Med Chem Lett* 22, 1822-1826 (2012).

Wolpaw, A. J. et al. Modulatory profiling identifies mechanisms of small molecule-induced cell death. *Proc Natl Acad Sci USA* 108, E771-780(2011).

Yagoda, N. et al. RAS-RAF-MEK-dependent oxidative cell death involving voltage-dependent anion channels. *Nature* 447, 864-868 (2007).

Yang, W. S. & Stockwell, B. R. Synthetic Lethal Screening Identifies Compounds Activating Iron-Dependent, Non-apoptotic Cell Death in Oncogenic-RAS-Harboring Cancer Cells. *Chemistry & biology* 15, 234-245 (2008a).

Yang, W. S. & Stockwell, B. R. Inhibition of casein kinase 1-epsilon induces cancer-cell-selective, PERIOD2-dependent growth arrest. *Genome biology* 9, R92 (2008b).

Yang, W. S. et al. Identification of Simple Compounds with Microtubule-Binding Activity That Inhibit Cancer Cell Growth with High Potency. *ACS Med Chem Lett* 3, 35-38 (2012).

Yu, Z., Schneider, C., Boeglin, W. E., Marnett, L. J. & Brash, A. R. The lipoxygenase gene ALOXE3 implicated in skin differentiation encodes a hydroperoxide isomerase. *Proc Nati Acad Sci USA* 100, 9162-9167 (2003).

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A compound having the structure (1):

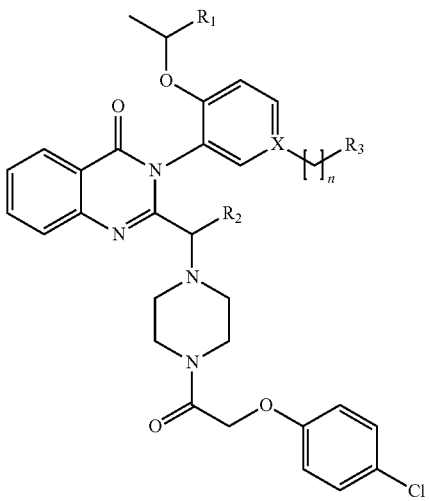

(1)

wherein
R₁ is selected from the group consisting of H, $C_{1-4}$ alkyl, $C_{1-4}$ alkoxy, hydroxy, and halogen;
R₂ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;
R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;
X is selected from the group consisting of C, N, and O; and
n is an integer from 0-6,
with the proviso that when X is C, n=0, and R₃ is nothing, R₁ cannot be H when R₂ is CH₃,
or an N-oxide, crystalline form, hydrate, or pharmaceutically acceptable salt thereof.

2. The compound according to claim 1 having the structure (10):

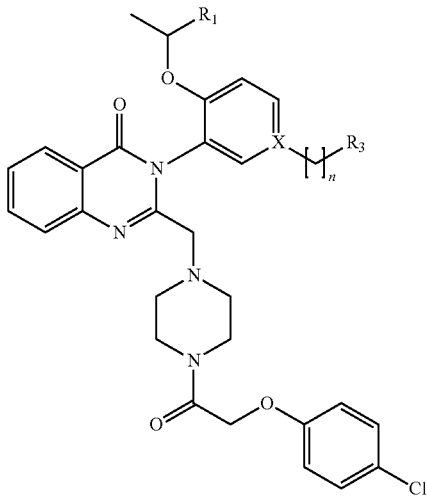

(10)

wherein
R₁ is selected from the group consisting of H, $C_{1-4}$ alkyl, $C_{1-4}$ alkoxy, hydroxy, and halogen;
R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;
X is selected from the group consisting of C, N, and O; and
n is an integer from 0-6,
or an N-oxide, crystalline form, hydrate, or pharmaceutically acceptable salt thereof.

3. The compound according to claim 1 having the structure (20):

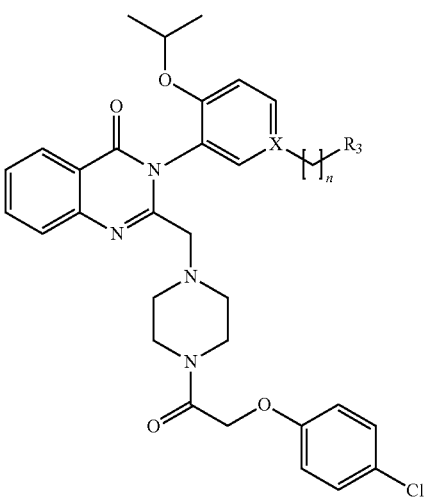

(20)

wherein
R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;
X is selected from the group consisting of C, N, and O; and
n is an integer from 0-6,
or an N-oxide, crystalline form, hydrate, or pharmaceutically acceptable salt thereof.

4. The compound according to claim 1, which is selected from the group consisting of:

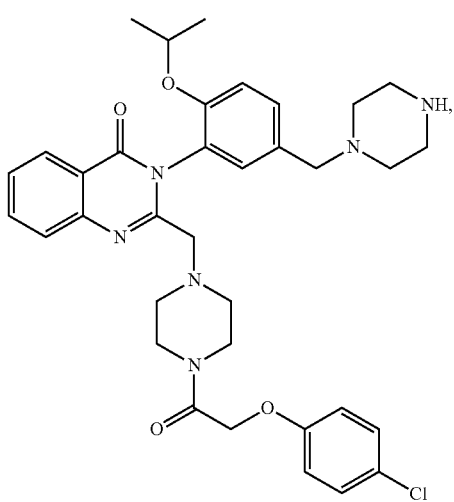

(30)

-continued

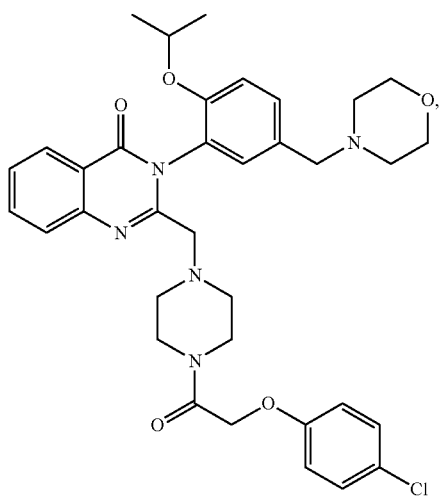

(40)

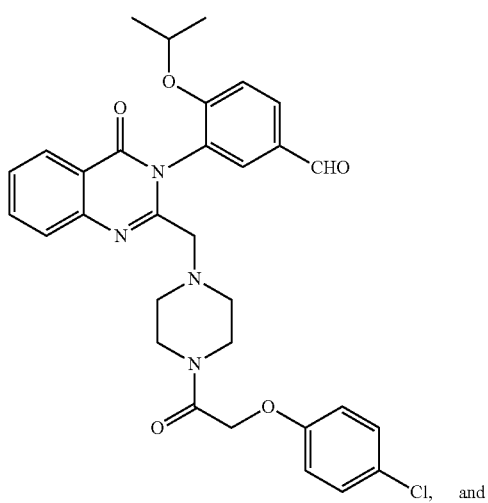

(50)

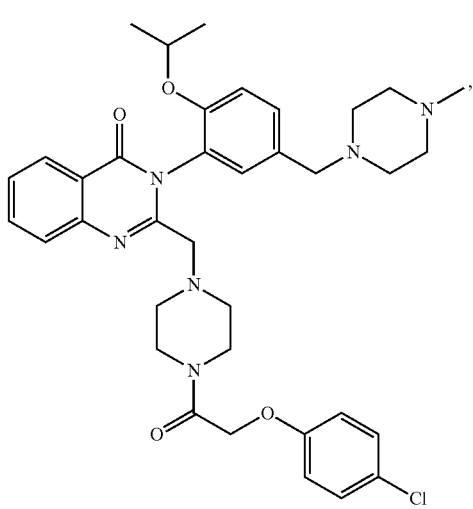

(60)

or an N-oxide, crystalline form, hydrate, or pharmaceutically acceptable salt thereof.

5. A compound having the structure (30):

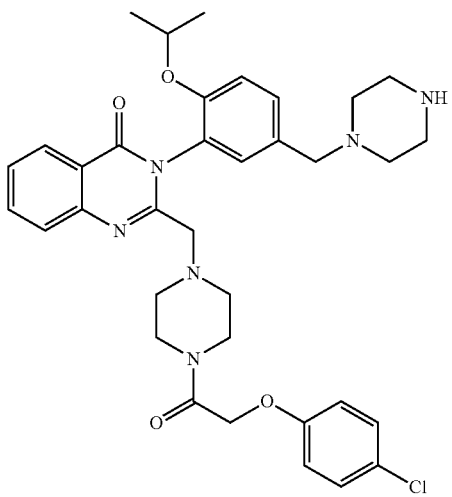

(30)

or an N-oxide, crystalline form, hydrate, or pharmaceutically acceptable salt thereof.

6. A composition comprising a pharmaceutically acceptable carrier and a compound having the structure (1):

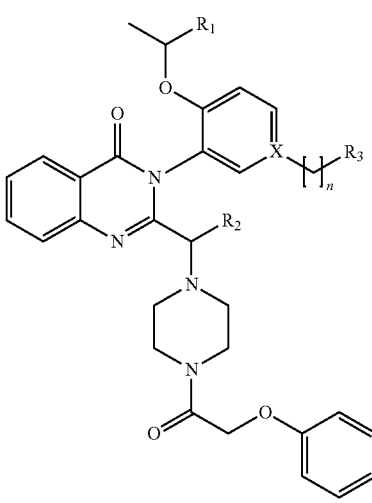

(1)

wherein
R$_1$ is selected from the group consisting of H, C$_{1-4}$ alkyl, C$_{1-4}$ alkoxy, hydroxy, and halogen;
R$_2$ is selected from the group consisting of H, C$_{1-4}$ alkyl, C$_{1-4}$ alkoxy, C$_{3-8}$ cycloalkyl, C$_{3-8}$ heterocycloalkyl, aryl, heteroaryl, C$_{1-4}$ aralkyl;
R$_3$ is selected from the group consisting of nothing, C$_{1-4}$ alkyl, C$_{1-4}$ alkoxy, carbonyl, C$_{3-8}$ cycloalkyl, and C$_{3-8}$ heterocycloalkyl;
X is selected from the group consisting of C, N, and O; and
n is an integer from 0-6,
with the proviso that when X is C, n=0, and R$_3$ is nothing, R$_1$ cannot be H when R$_2$ is CH$_3$,
or an N-oxide, crystalline form, hydrate, or pharmaceutically acceptable salt thereof.

7. A composition according to claim 6, wherein the compound has the structure (10):

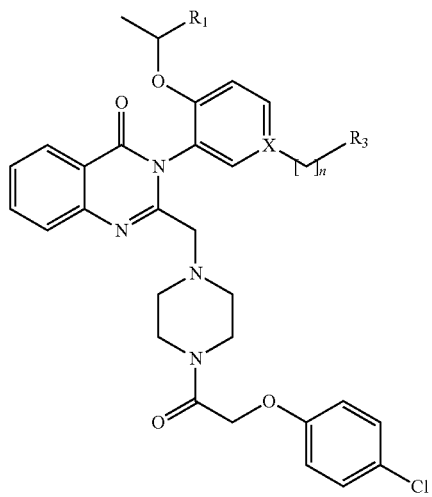

(10)

wherein
R$_1$ is selected from the group consisting of H, C$_{1-4}$ alkyl, C$_{1-4}$ alkoxy, hydroxy, and halogen
R$_3$ is selected from the group consisting of nothing, C$_{1-4}$ alkyl, C$_{1-4}$ alkoxy, carbonyl, C$_{3-8}$ cycloalkyl, and C$_{3-8}$ heterocycloalkyl;
X is selected from the group consisting of C, N, and O; and
n is an integer from 0-6,
or an N-oxide, crystalline form, hydrate, or pharmaceutically acceptable salt thereof.

8. A composition according to claim 6, wherein the compound has the structure (20):

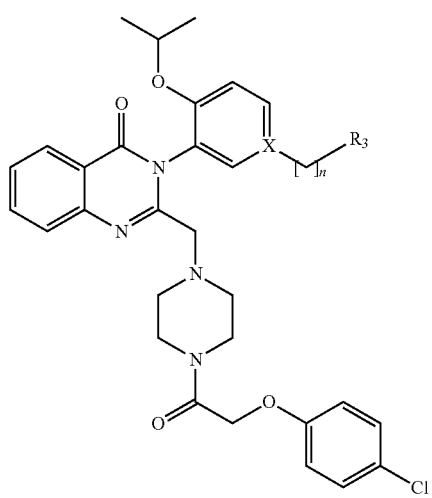

(20)

wherein
R$_3$ is selected from the group consisting nothing, C$_{1-4}$ alkyl, C$_{1-4}$ alkoxy, carbonyl, C$_{3-8}$ cycloalkyl, and C$_{3-8}$ heterocycloalkyl;
X is selected from the group consisting of C, N, and O; and
n is an integer from 0-6,
or an N-oxide, crystalline form, hydrate, or pharmaceutically acceptable salt thereof.

9. A composition according to claim 6, wherein the compound is selected from the group consisting of:

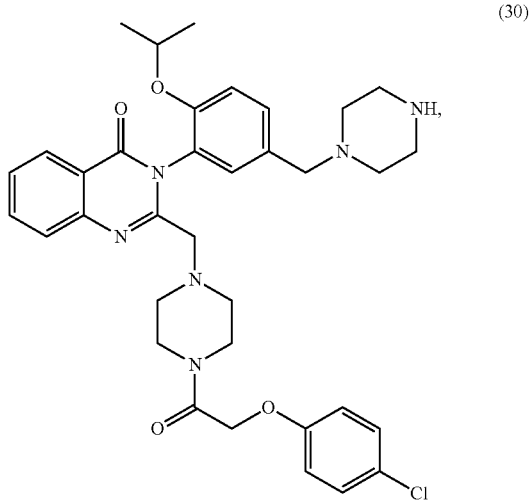

(30)

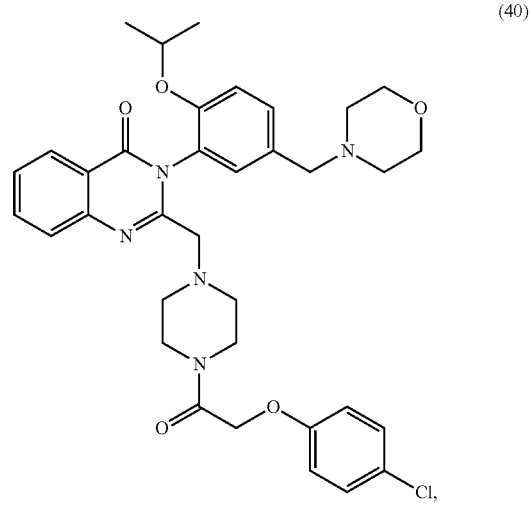

(40)

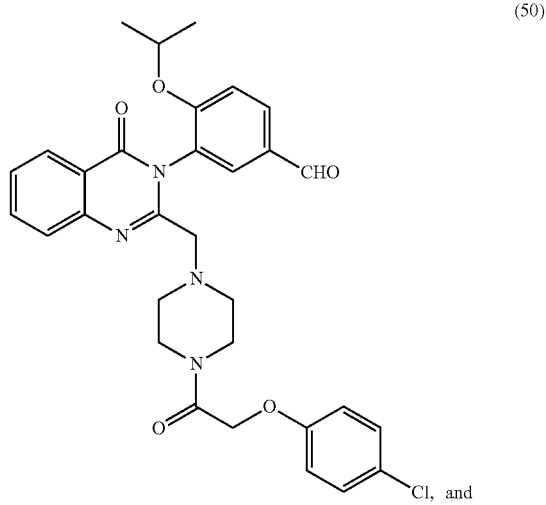

(50)

and (60)

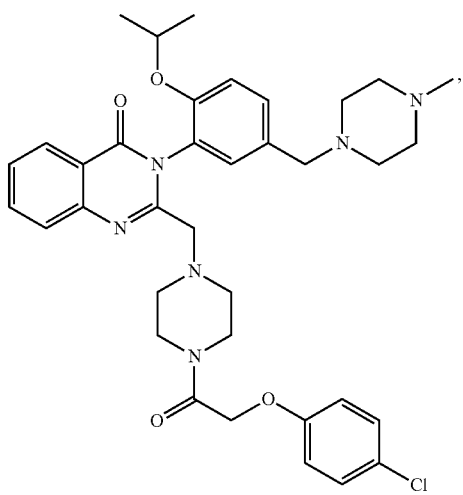

or an N-oxide, crystalline form, hydrate, or pharmaceutically acceptable salt thereof.

10. A composition comprising a pharmaceutically acceptable carrier and a compound having the structure (30):

(30)

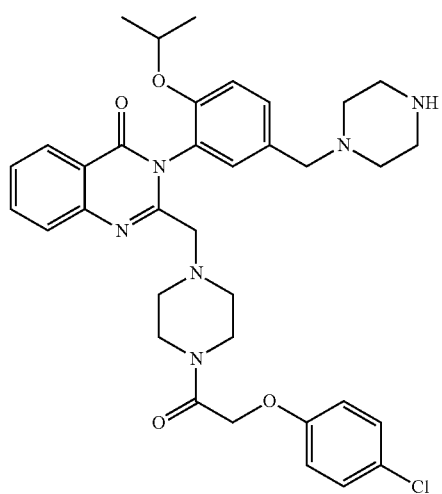

or an N-oxide, crystalline form, hydrate, or pharmaceutically acceptable salt thereof.

11. A method for modulating a lipoxygenase in a ferroptosis cell death pathway comprising administering to a cell an effective amount of a compound having the structure (1):

(1)

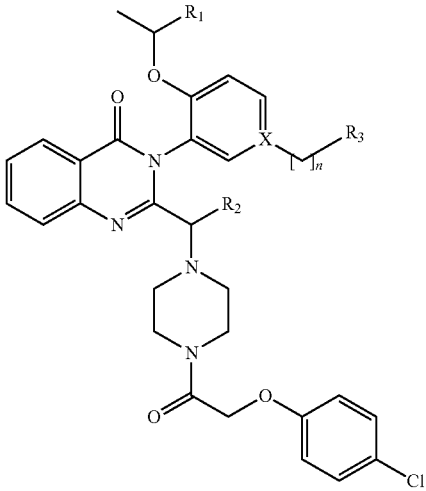

wherein
$R_1$ is selected from the group consisting of H, $C_{1-4}$ alkyl, $C_{1-4}$ alkoxy, hydroxy, and halogen;
$R_2$ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;
$R_3$ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;
X is selected from the group consisting of C, N, and O; and
n is an integer from 0-6,
with the proviso that when X is C, n=0, and $R_3$ is nothing, $R_1$ cannot be H when $R_2$ is $CH_3$,
or an N-oxide, crystalline form, hydrate, or pharmaceutically acceptable salt thereof.

12. The method according to claim 11, wherein the compound has the structure (10):

(10)

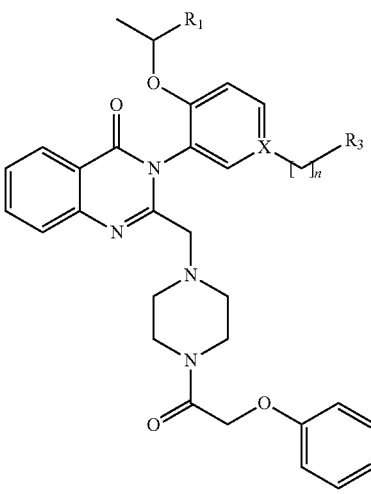

wherein
$R_1$ is selected from the group consisting of H, $C_{1-4}$ alkyl, $C_{1-4}$ alkoxy, hydroxy, and halogen R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, or an N-oxide, crystalline form, hydrate, or pharmaceutically acceptable salt thereof.

13. The method according to claim 11, wherein the compound has the structure (20):

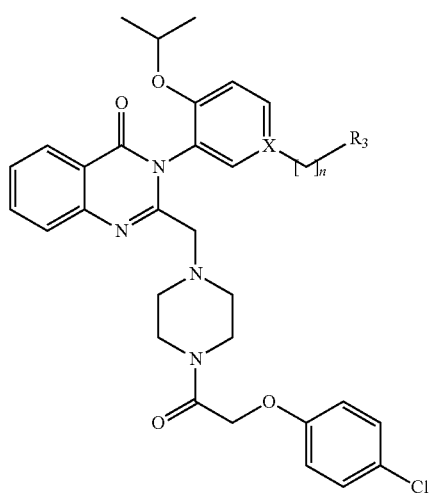

(20)

wherein

R₃ is selected from the group consisting nothing, $C_{1-4}$ alkyl, $C_{1-4}$ alkoxy, carbonyl, $C_{3-8}$ cycloalkyl, and $C_{3-8}$ heterocycloalkyl;

X is selected from the group consisting of C, N, and O; and n is an integer from 0-6, or an N-oxide, crystalline form, hydrate, or pharmaceutically acceptable salt thereof.

14. The method according to claim 11, wherein the compound is selected from the group consisting of:

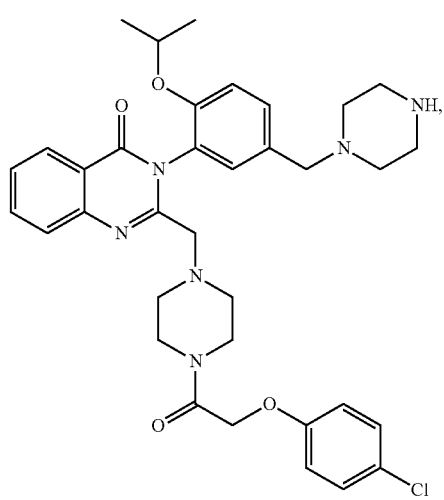

(30)

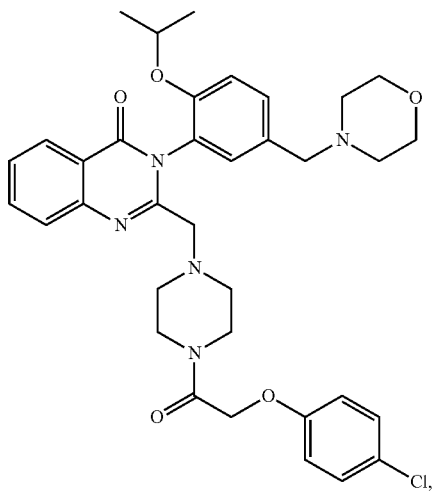

(40)

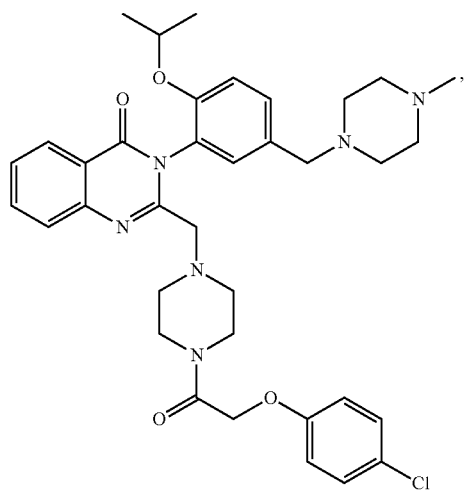

(50)

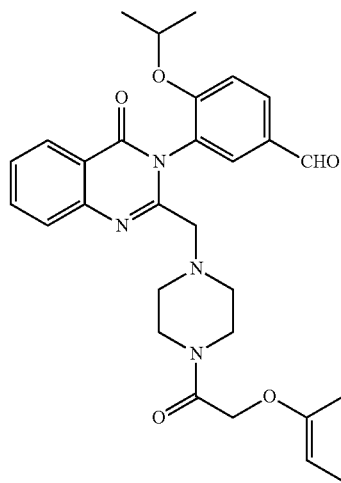

(60)

or an N-oxide, crystalline form, hydrate, or pharmaceutically acceptable salt thereof.

15. The method according to claim 11, wherein the compound has the structure (30):

(30)

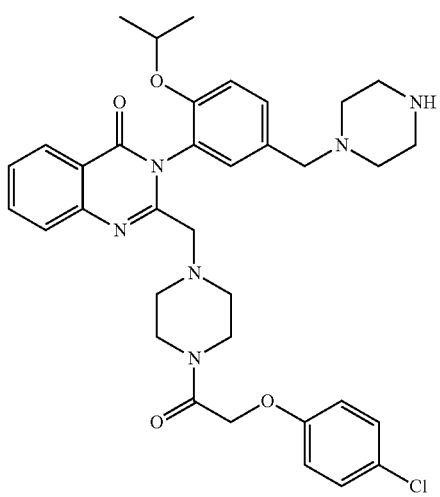

or an N-oxide, crystalline form, hydrate, or pharmaceutically acceptable salt thereof.

16. The method according to claim 11, wherein the modulation comprises activation of one or more polypeptides encoded by ALOX genes.

17. A method for depleting reduced glutathione (GSH) in a cell harboring an oncogenic RAS mutation comprising administering to the cell an effective amount of a compound having the structure (1):

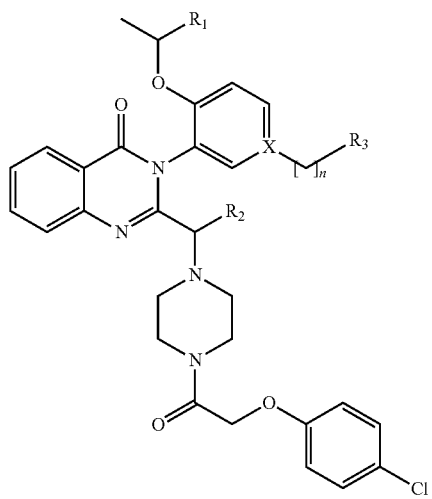

(1)

wherein
R₁ is selected from the group consisting of H, $C_{1-4}$ alkyl, $C_{1-4}$ alkoxy, hydroxy, and halogen;
R₂ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;
R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;
X is selected from the group consisting of C, N, and O; and n is an integer from 0-6,
with the proviso that when X is C, n=0, and R₃ is nothing, R₁ cannot be H when R₂ is CH₃, or an N-oxide, crystalline form, hydrate, or pharmaceutically acceptable salt thereof.

18. A compound having the structure (100):

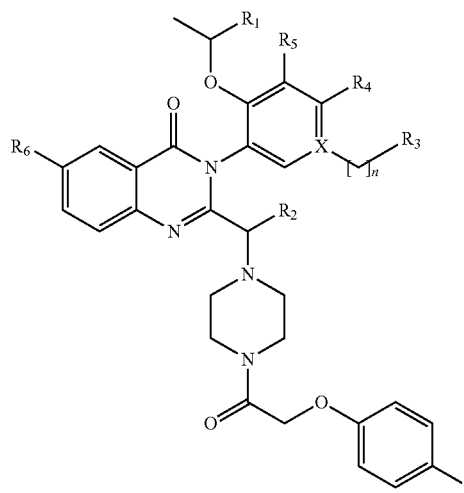

(100)

wherein
R₁ is selected from the group consisting of H, $C_{1-4}$ alkyl, $C_{1-4}$ alkoxy, hydroxy, and halogen;
R₂ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl;
R₃ is selected from the group consisting of nothing, H, $C_{1-4}$ alkyl, $C_{1-4}$ alkoxy, carbonyl, $C_{3-8}$ cycloalkyl, and $C_{3-8}$ heterocycloalkyl;
R₄ and R₅ are independently selected from the group consisting of H, $C_{3-8}$ cycloalkyl, and $C_{3-8}$ heterocycloalkyl;
R₆ is selected from the group consisting of H, —NH₂, $C_{1-4}$ alkyl, $C_{1-4}$ alkoxy, carbonyl, aryl, heteraryl, $C_{3-8}$ cycloalkyl, and $C_{3-8}$ heterocycloalkyl;
X is selected from the group consisting of C, N, and O; and n is an integer from 0-6,
with the proviso that when X is C, n=0, and R₃ is nothing, R₁ cannot be H when R₂ is CH₃, or an N-oxide, crystalline form, hydrate, or pharmaceutically acceptable salt thereof.

19. The compound according to claim 18 having the structure (200):

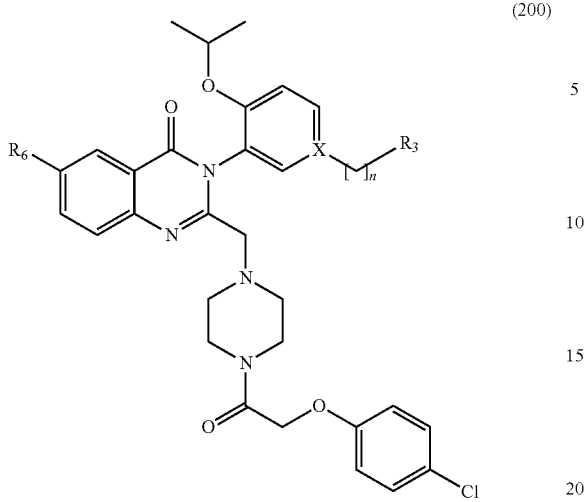

(200)

wherein
R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;
R₆ is selected from the group consisting of H, —NH₂, $C_{1-4}$ alkyl, $C_{1-4}$ alkoxy, carbonyl, aryl, heteraryl, $C_{3-8}$ cycloalkyl, and $C_{3-8}$ heterocycloalkyl;
X is selected from the group consisting of C, N, and O; and
n is an integer from 0-6,
or an N-oxide, crystalline form, hydrate, or pharmaceutically acceptable salt thereof.

20. The compound according to claim 18 having the structure (300):

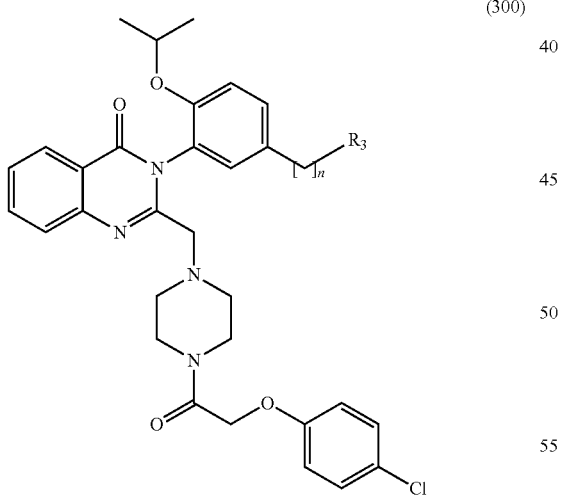

(300)

wherein
R₃ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl;
n is an integer from 0-6,
or an N-oxide, crystalline form, hydrate, or pharmaceutically acceptable salt thereof.

21. The compound according to claim 18, which is selected from the group consisting of:

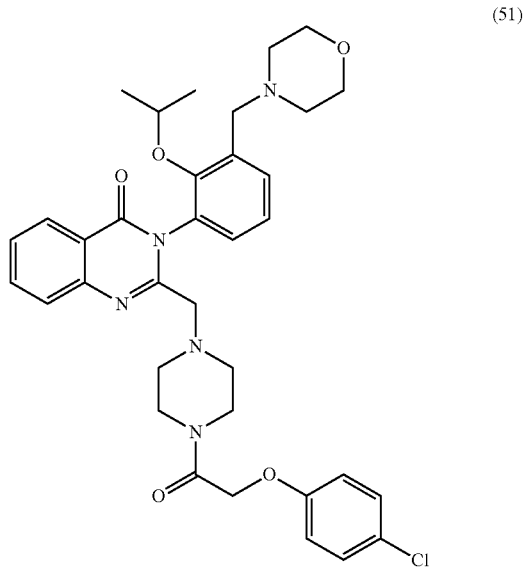

(51)

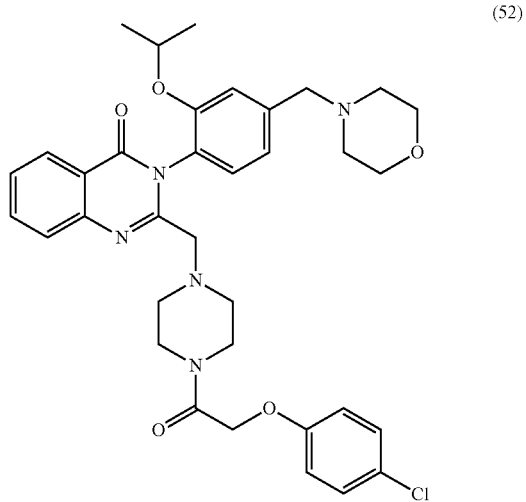

(52)

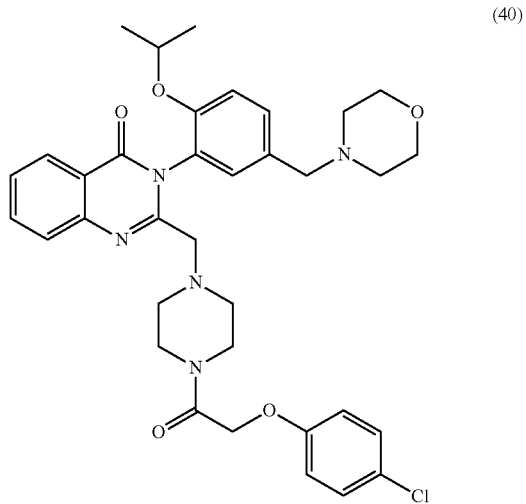

(40)

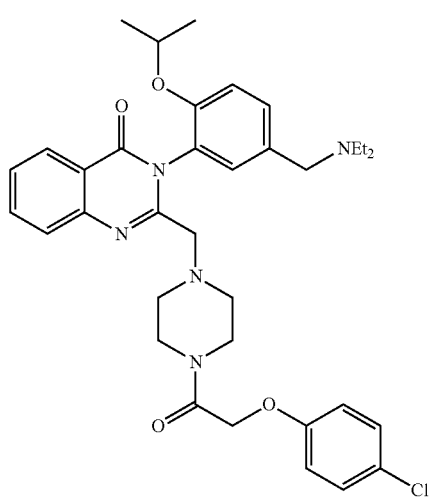
(15)
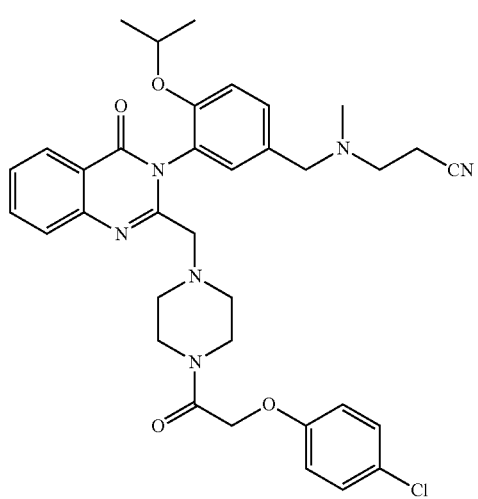
(19)
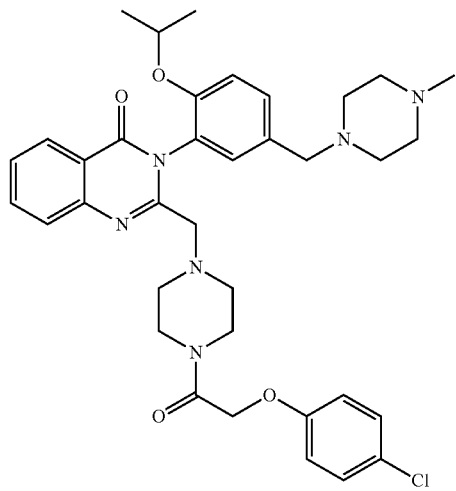
(60)
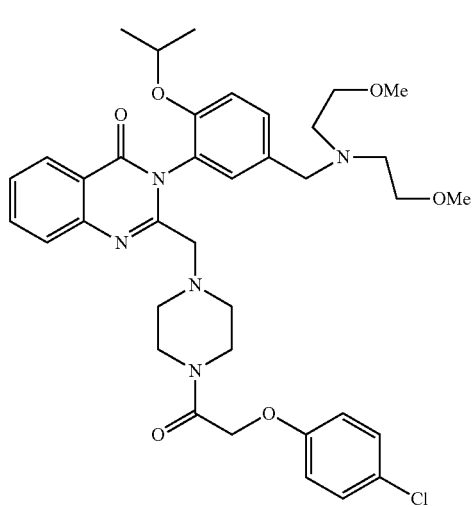
(18)
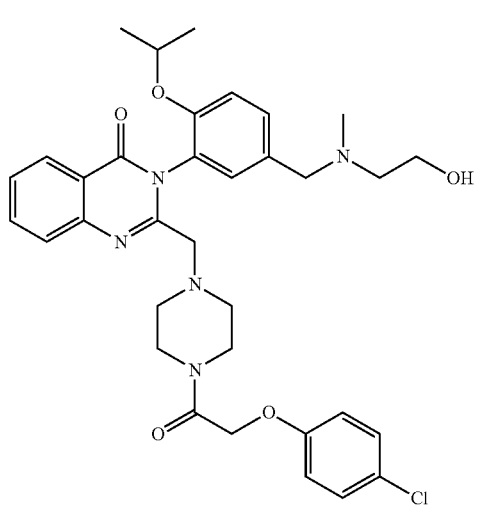
(21)

-continued
(22)
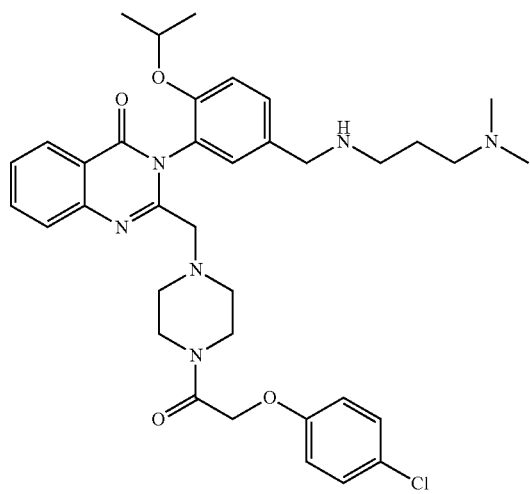
(1a)
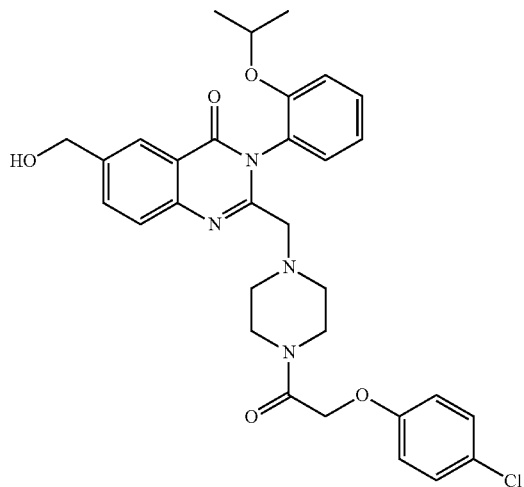
(23)
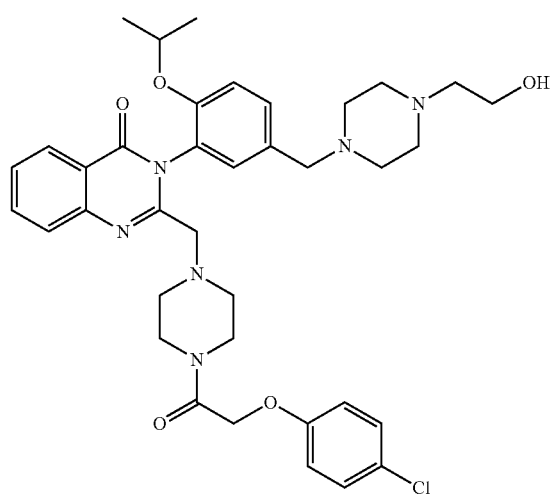
(2)
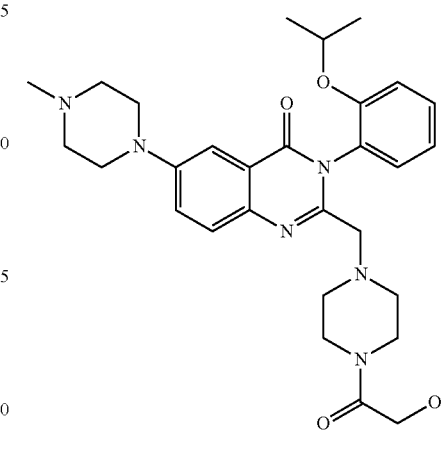
(24)
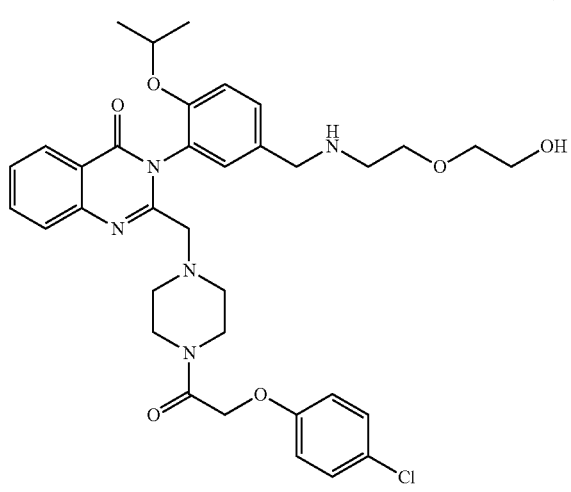
(3)
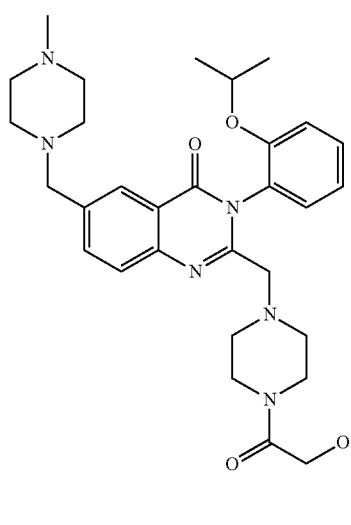

(4)
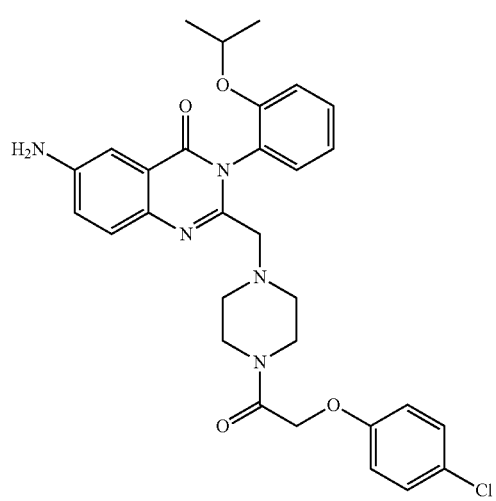
(5)
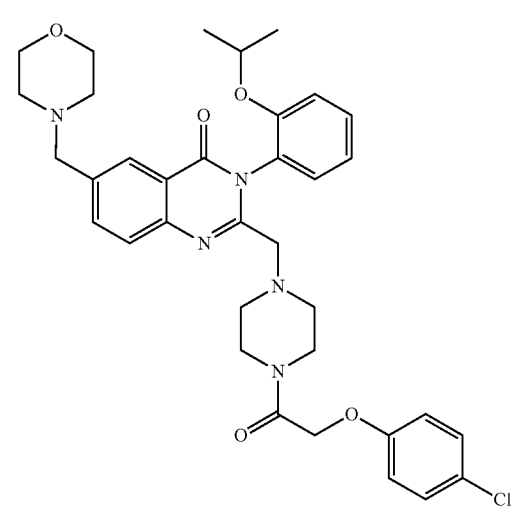
(6)
(7)
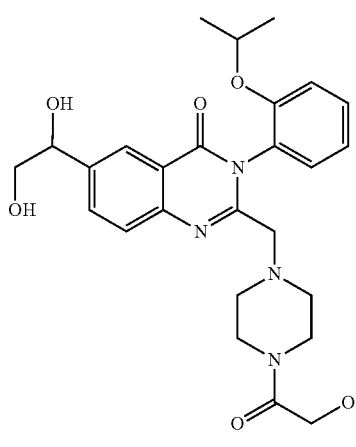
(8)
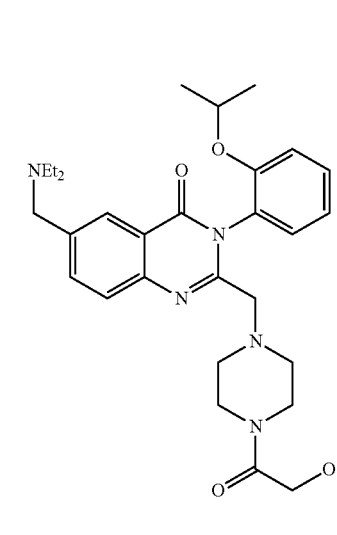
(9)
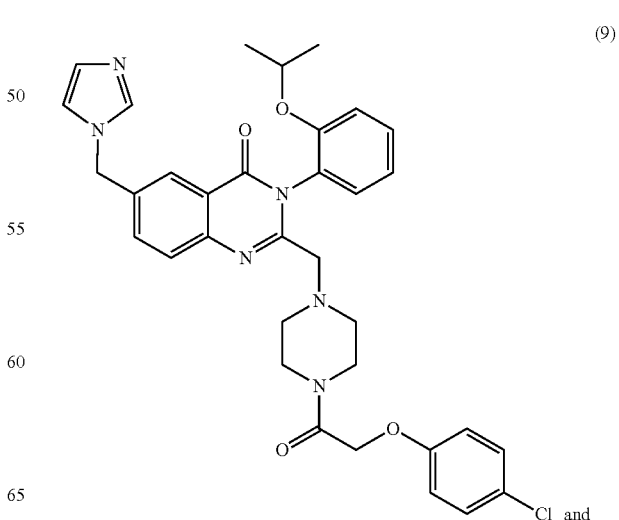
and (11)

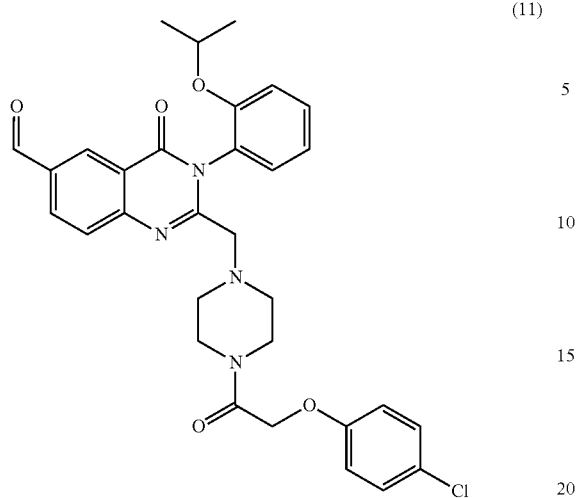

or an N-oxide, crystalline form, hydrate, or pharmaceutically acceptable salt thereof.

22. A composition comprising a pharmaceutically acceptable carrier and a compound according to claim 18.

23. A method for modulating a lipoxygenase in a ferroptosis cell death pathway comprising administering to a cell an effective amount of a compound according to claim 18.

24. The method according to claim 23, wherein the modulation comprises activation of one or more polypeptides encoded by ALOX genes.

25. A method for modulating a lipoxygenase in a ferroptosis cell death pathway comprising administering to a cell an effective amount of a compound selected from the group consisting of:

(DPI2)

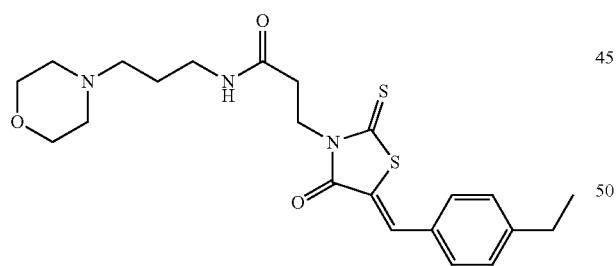

(DPI3)

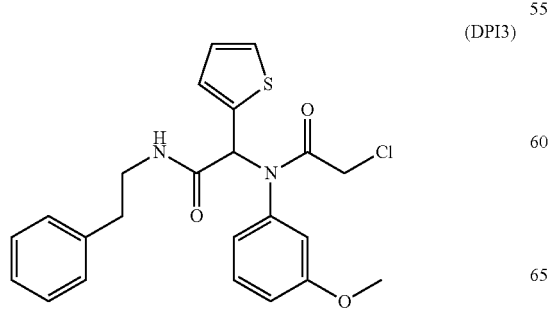

(DPI4)

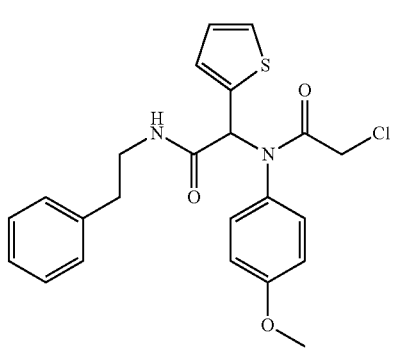

(DPI6)

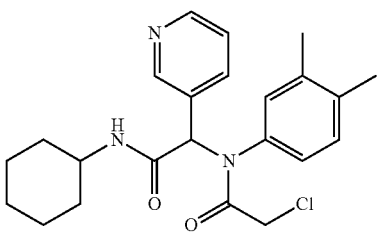

(DPI7)

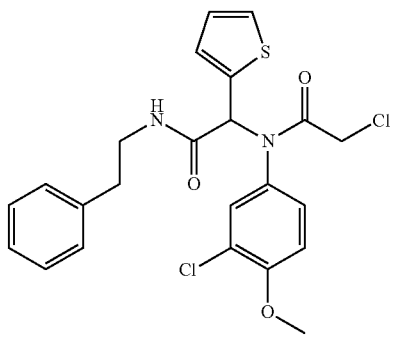

(DPI8)

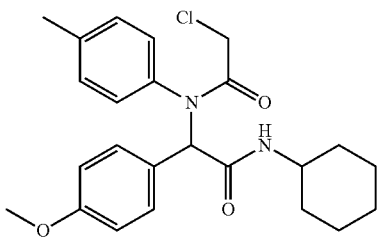

(DPI9)

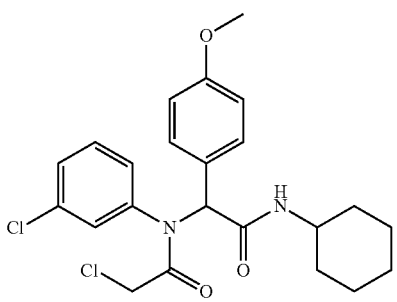

-continued
(DPI10)
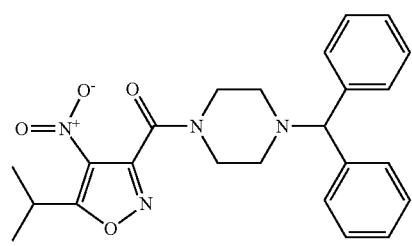
(DPI12)
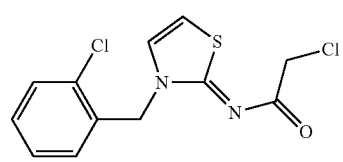
(DPI13)
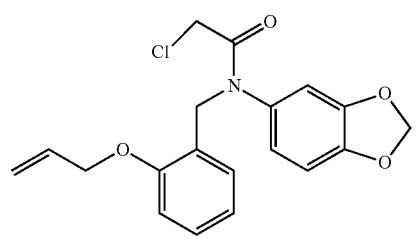
(DPI15)
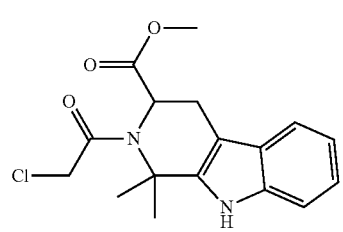
(DPI17)
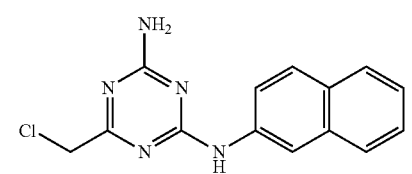
(DPI18)
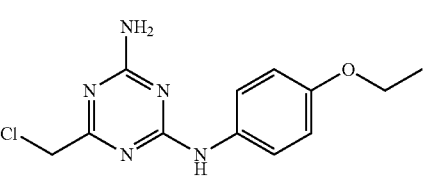
(DPI19)
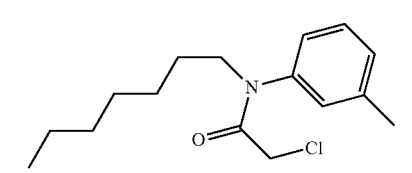
-continued
(51)
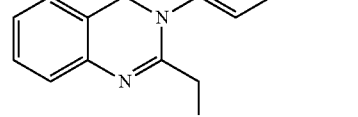
(52)
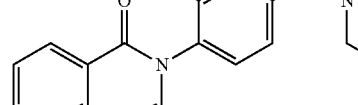
(40)
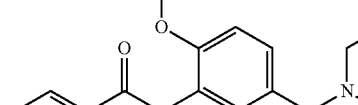

177
-continued
(15)
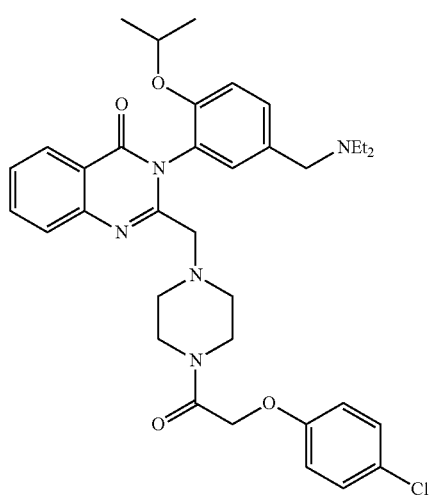
(17)
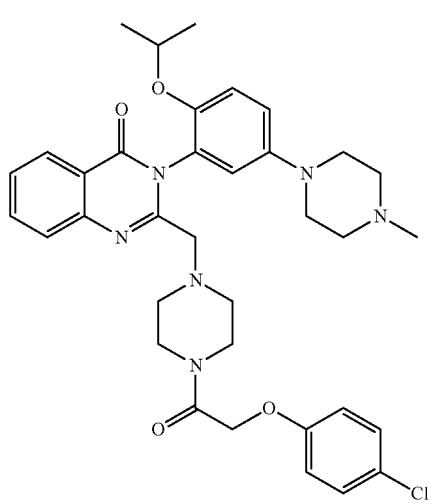
(18)
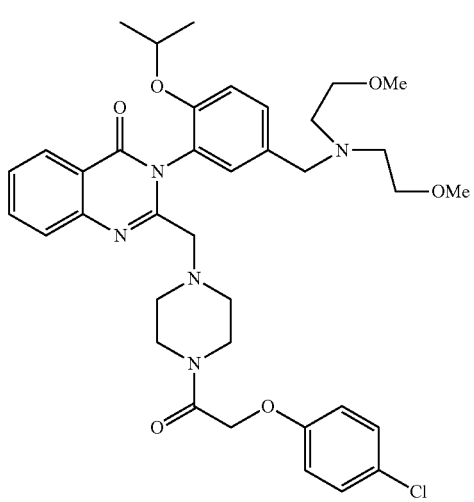
178
-continued
(19)
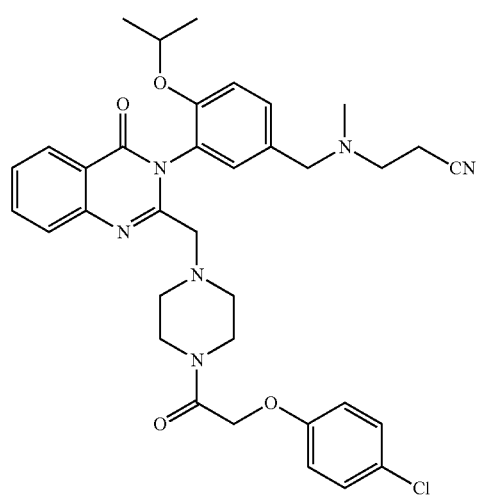
(60)
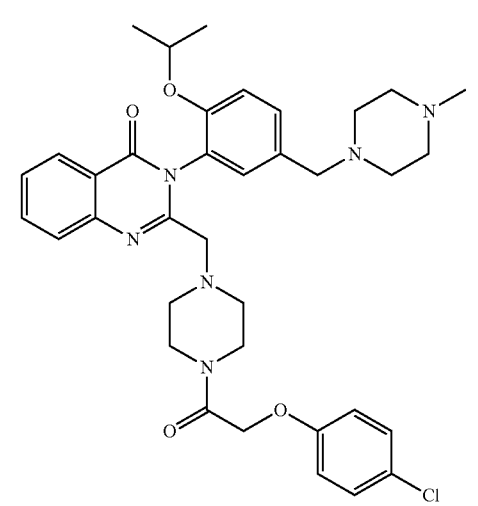
(21)
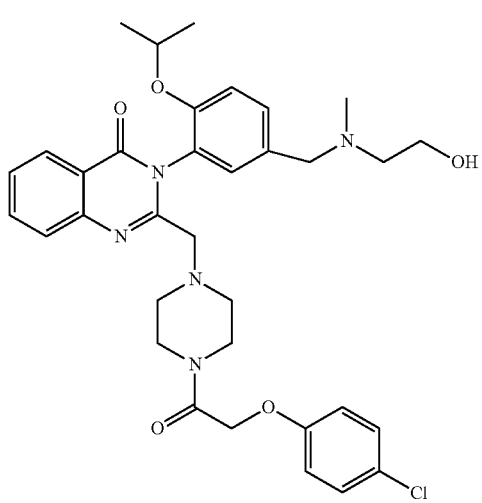

(22)
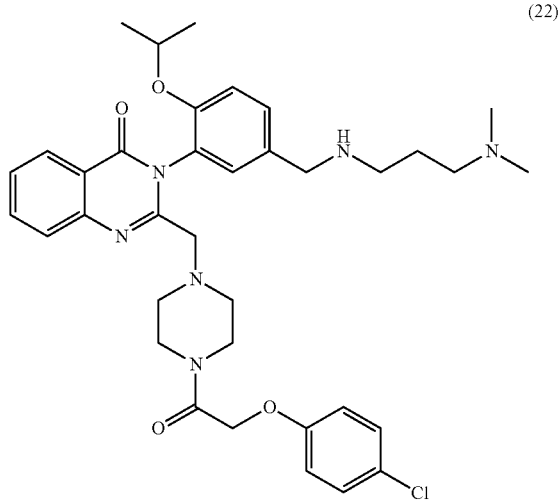
(1a)
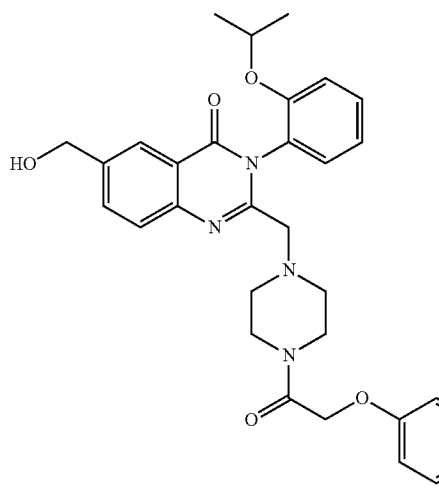
(23)
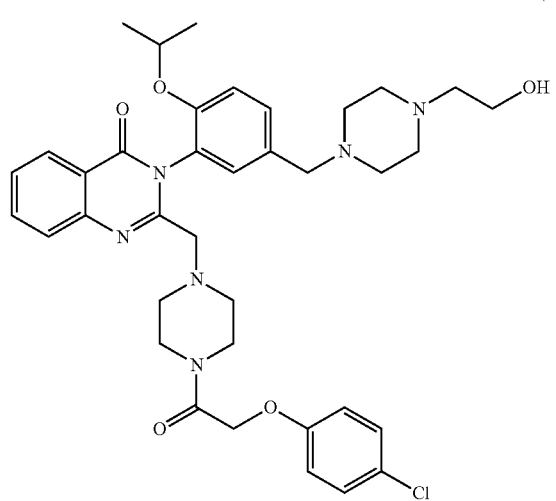
(2)
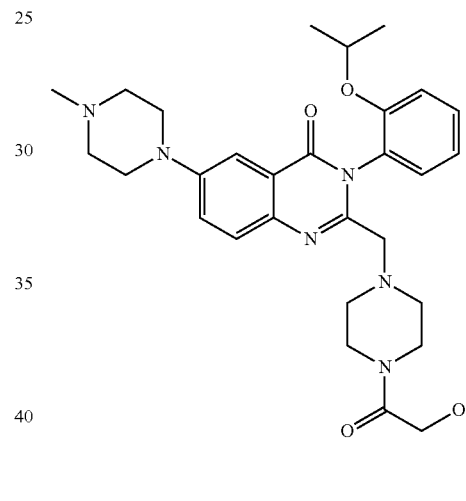
(24)
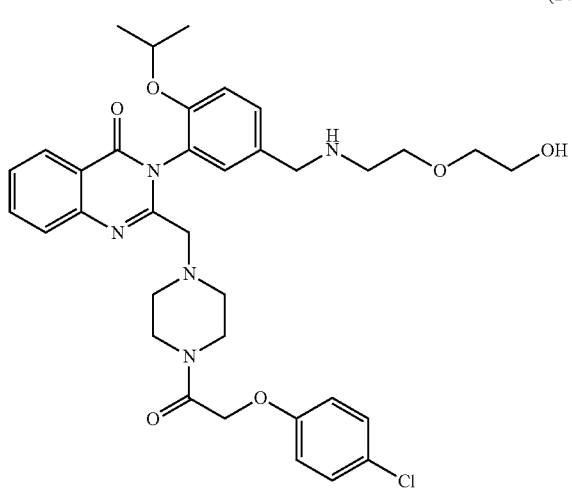
(3)
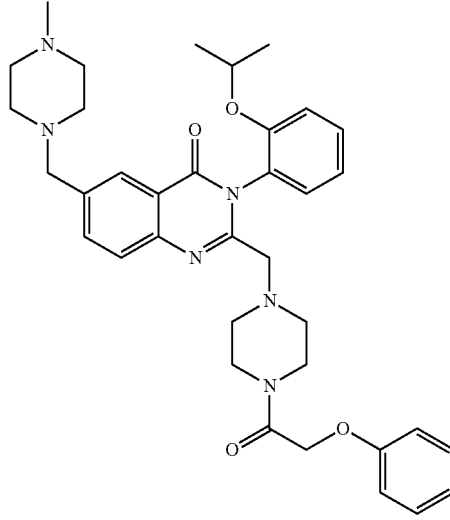

(4)
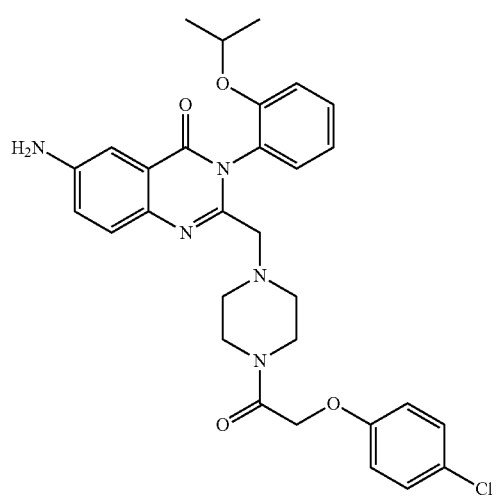
(5)
(6)
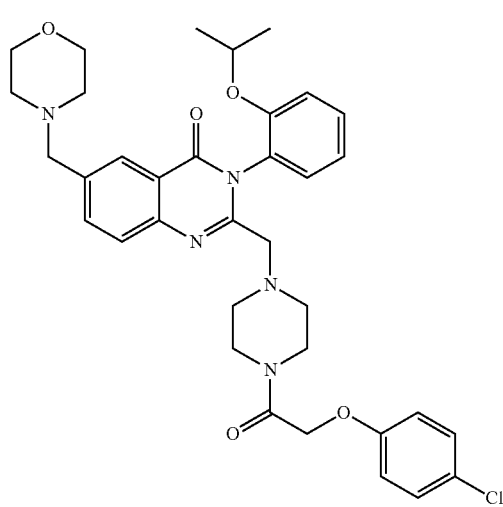
(7)
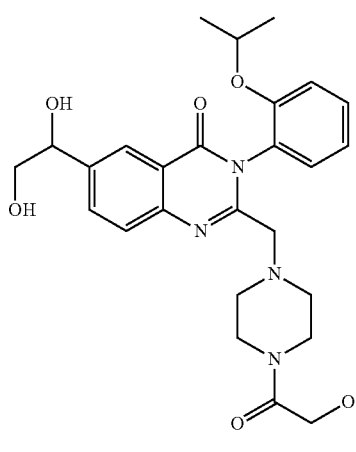
(8)
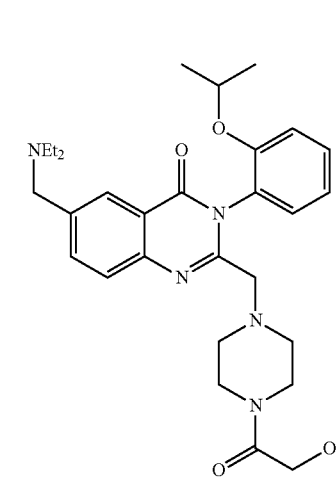
(9)
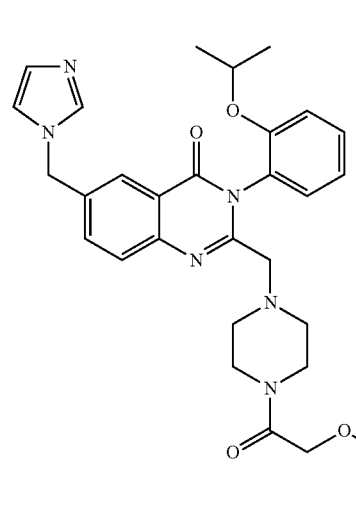

(11)

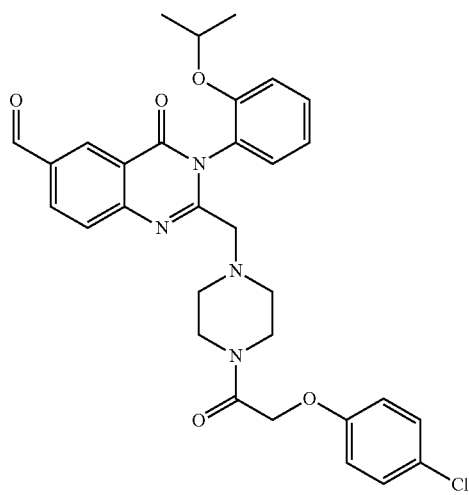

(11)

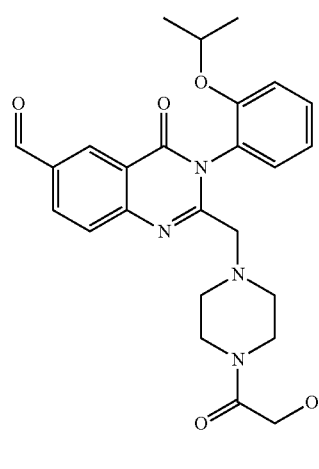

or an N-oxide, crystalline form, hydrate, or pharmaceutically acceptable salt thereof.

26. The method according to claim 25, wherein the modulation comprises activation of one or more polypeptides encoded by ALOX genes.

27. A method for depleting reduced glutathione (GSH) in a cell harboring an oncogenic RAS mutation comprising administering to the cell an effective amount of a compound according to claim 18.

28. A method for depleting reduced glutathione (GSH) in a cell harboring an oncogenic RAS mutation comprising administering to the cell an effective amount of a compound selected from the group consisting of:

(8)

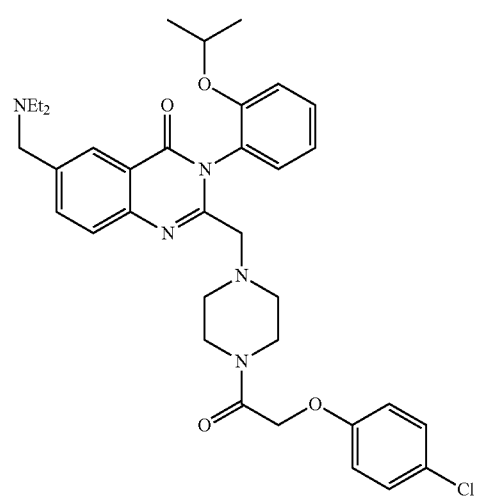

(DPI2)

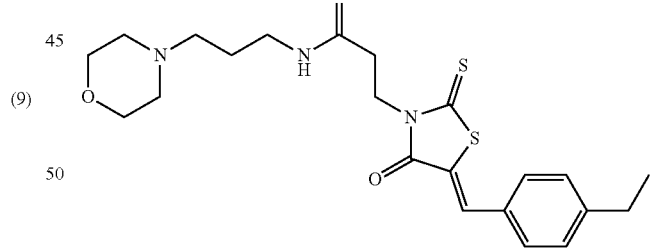

(9)

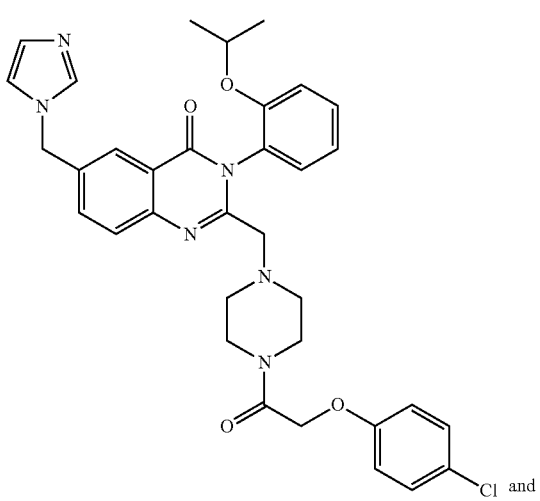

and (DPI3)

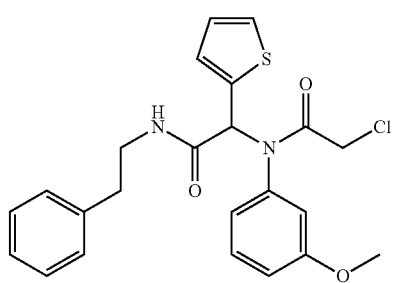

185
-continued
(DPI4)
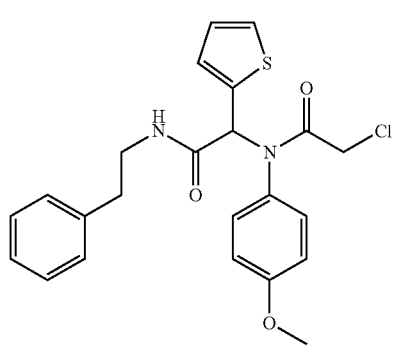
(DPI6)
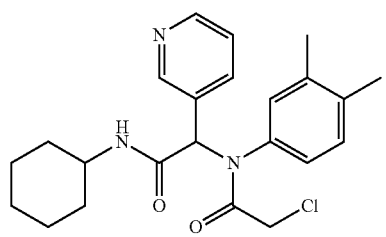
(DPI7)
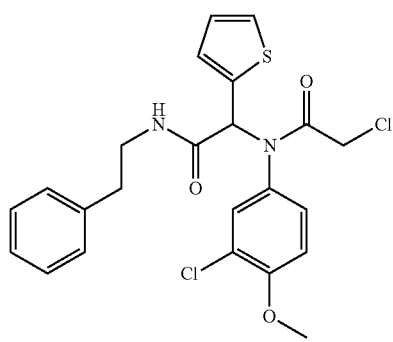
(DPI8)
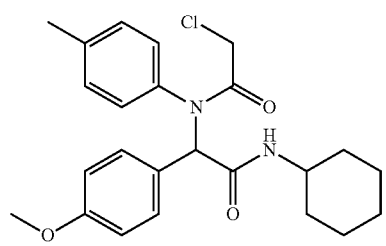
(DPI9)
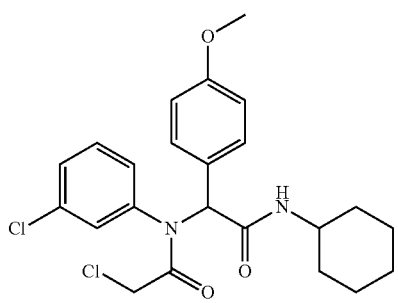
186
-continued
(DPI10)
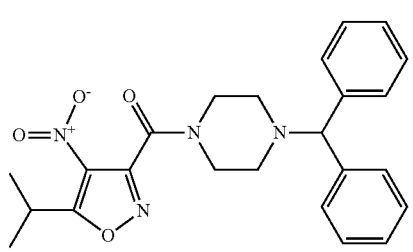
(DPI12)
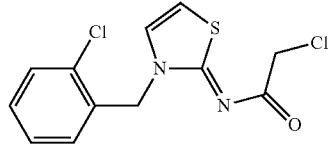
(DPI13)
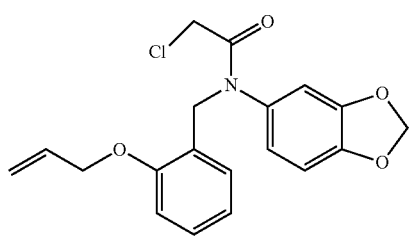
(DPI15)
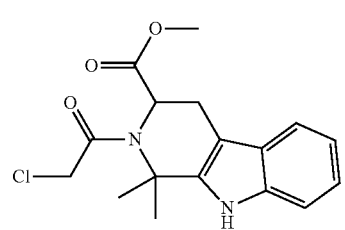
(DPI17)
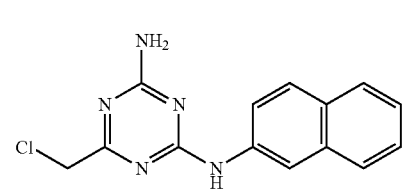
(DPI18)
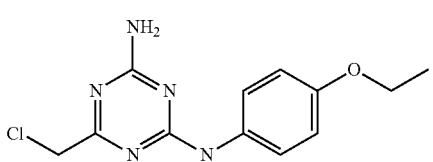
(DPI19)
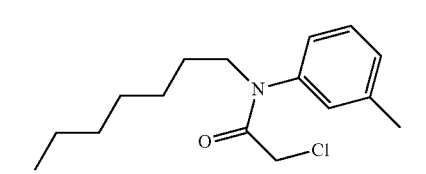

187
-continued
(51)
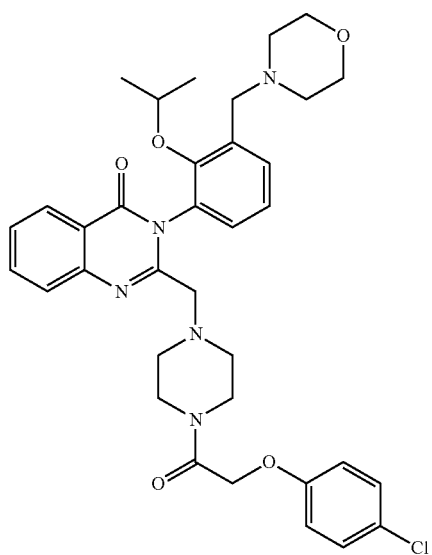
(52)
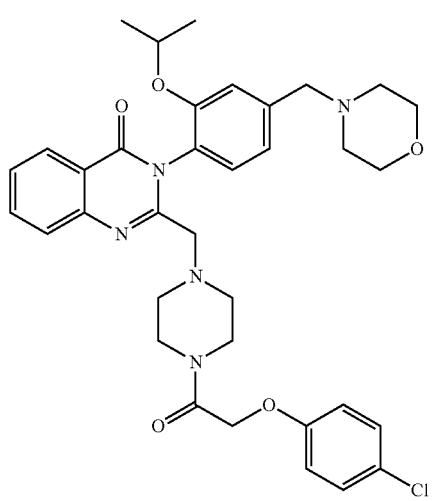
(40)
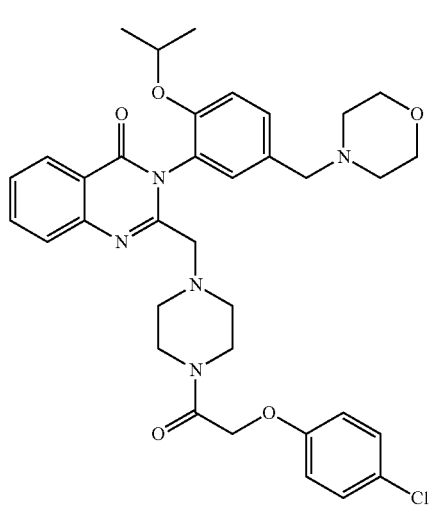
188
-continued
(15)
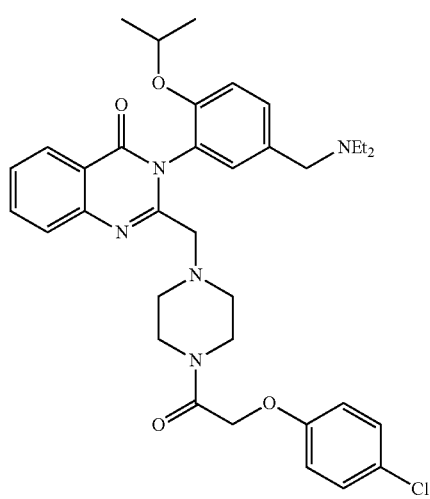
(17)
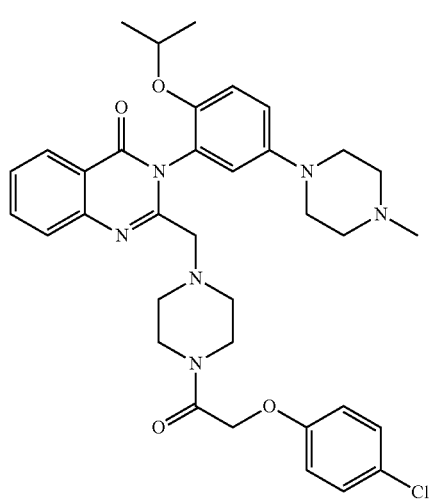
(18)
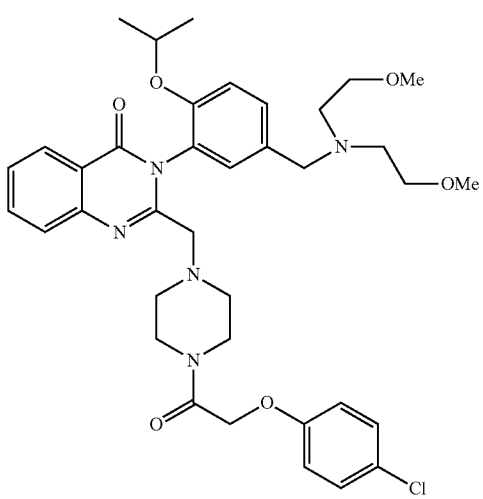

(19)
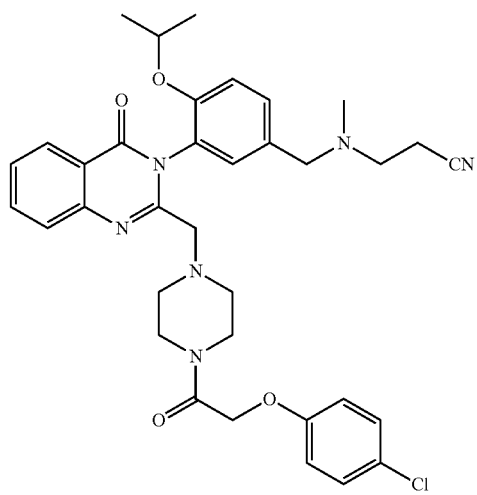
(22)
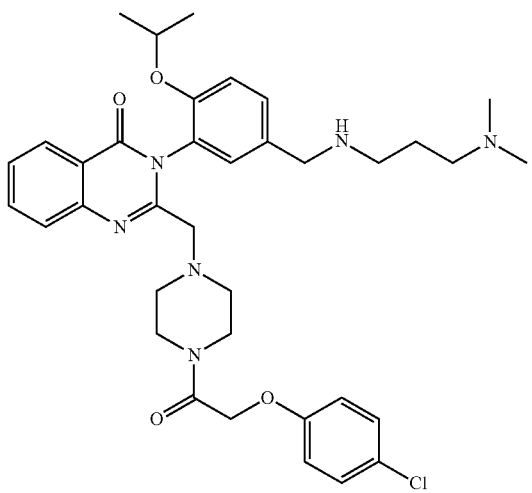
(60)
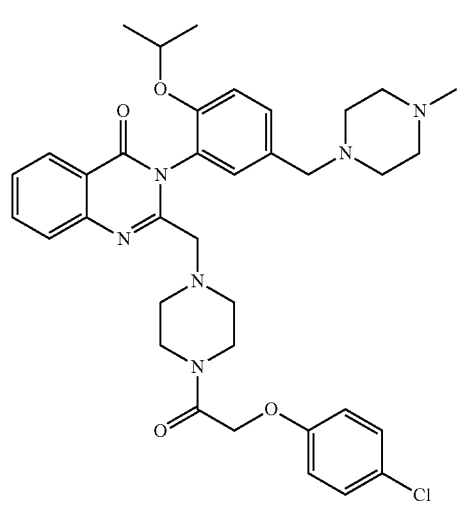
(23)
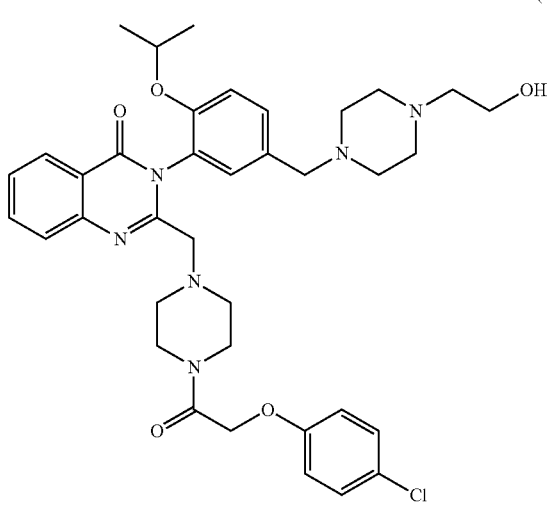
(21)
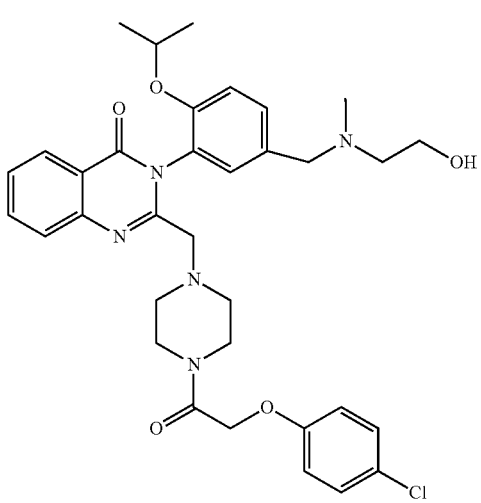
(24)
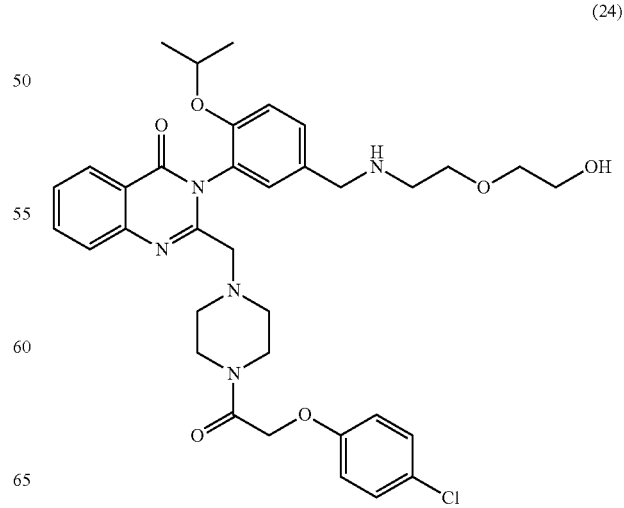

-continued
(1a)
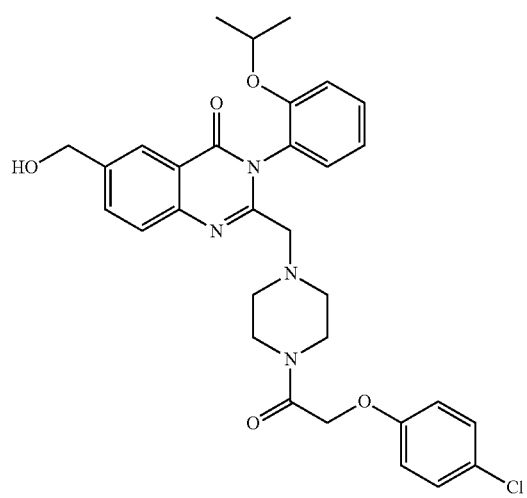
(2)
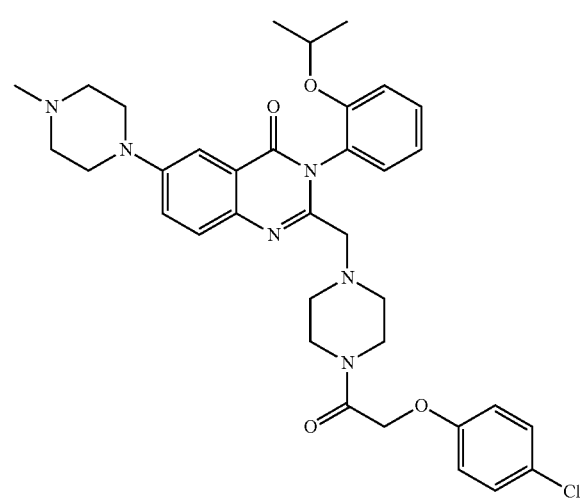
(3)
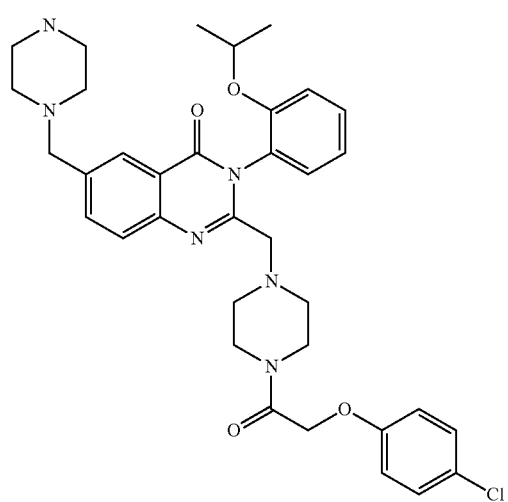
-continued
(4)
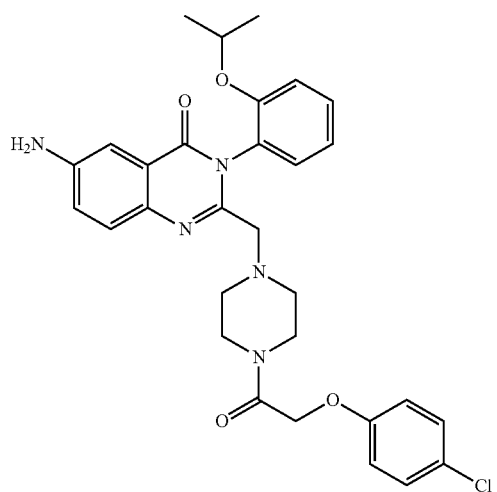
(5)
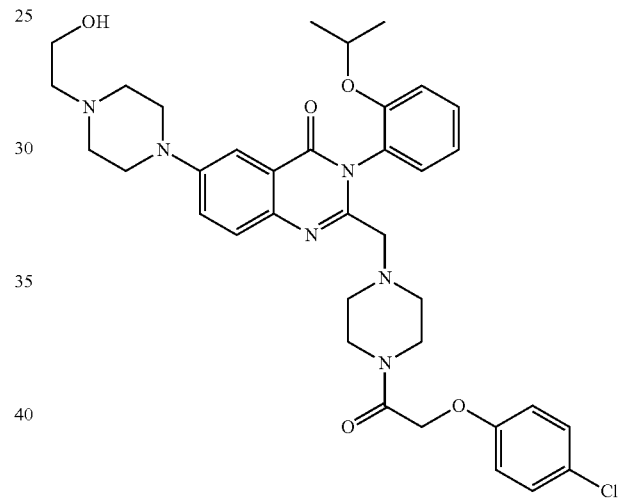
(6)
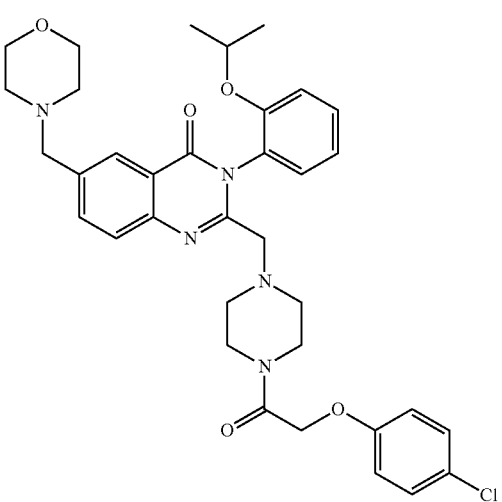

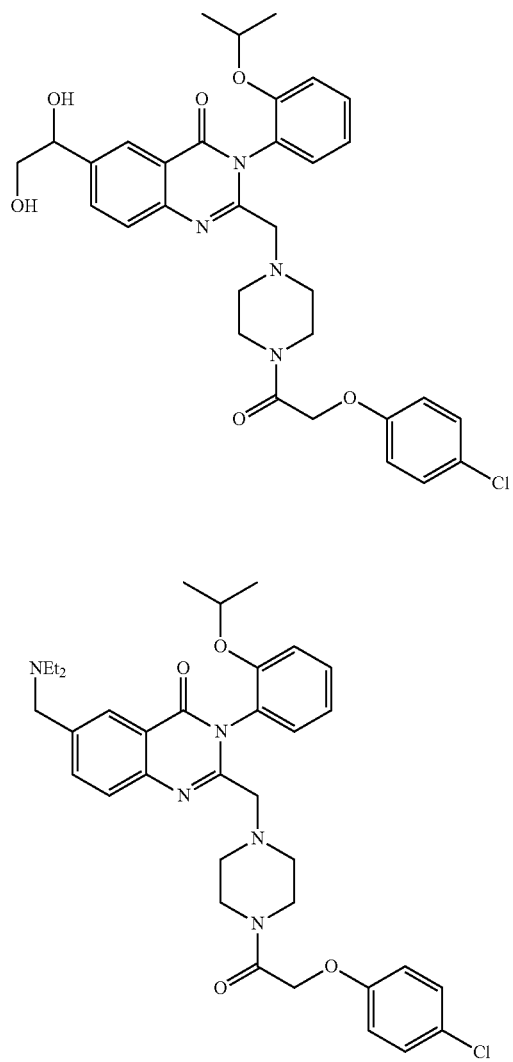
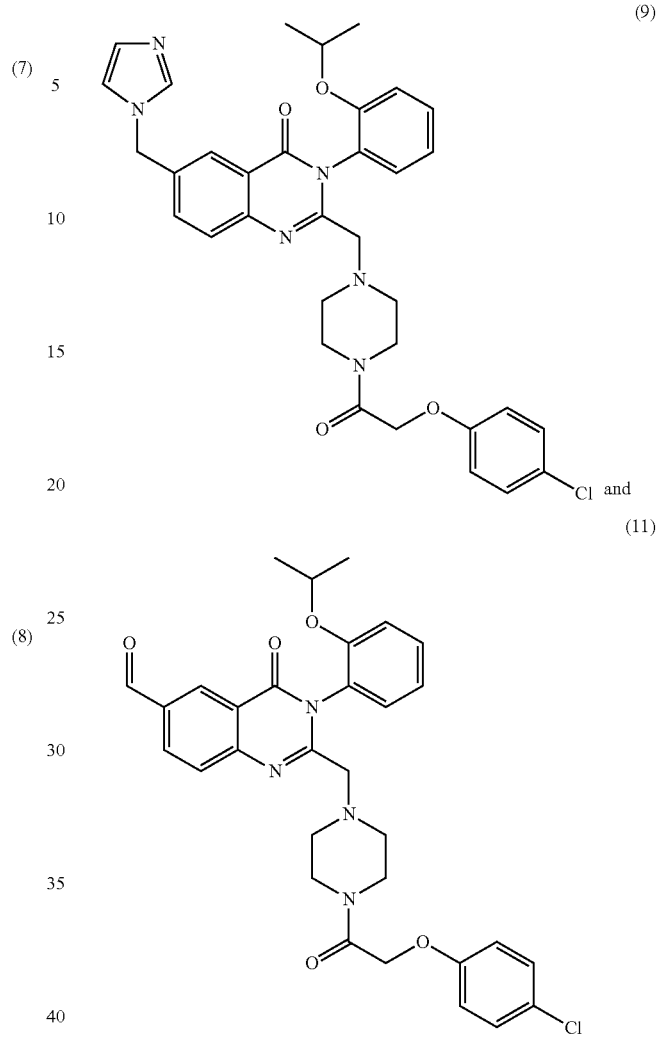
or an N-oxide, crystalline form, hydrate, or pharmaceutically acceptable salt thereof.
* * * * *

UNITED STATES PATENT AND TRADEMARK OFFICE
CERTIFICATE OF CORRECTION

PATENT NO. : 9,695,133 B2  
APPLICATION NO. : 14/414669  
DATED : July 4, 2017  
INVENTOR(S) : Brent R Stockwell et al.

Page 1 of 1

It is certified that error appears in the above-identified patent and that said Letters Patent is hereby corrected as shown below:

In Column 1, please replace the paragraph following the heading "GOVERNMENT FUNDING" and immediately before the heading "FIELD OF INVENTION" with the following:

This invention was made with government support under grant CA097061 awarded by the National Institutes of Health. The Government has certain rights in this invention.

Signed and Sealed this  
Twenty-fourth Day of October, 2017

Joseph Matal  
*Performing the Functions and Duties of the*  
*Under Secretary of Commerce for Intellectual Property and*  
*Director of the United States Patent and Trademark Office*